United States Patent
Loomis et al.

(10) Patent No.: US 12,162,936 B2
(45) Date of Patent: *Dec. 10, 2024

(54) METHODS OF TREATMENT WITH ANTI-PACAP ANTIBODIES

(71) Applicant: H. LUNDBECK A/S, Valby (DK)

(72) Inventors: Maria-Cristina Loomis, Bothell, WA (US); Leon F. Garcia-Martinez, Woodinville, WA (US); Benjamin H. Dutzar, Seattle, WA (US); Daniel S. Allison, Lake Forest Park, WA (US); Katherine Lee Hendrix, Renton, WA (US); Ethan W. Ojala, Snohomish, WA (US); Pei Fan, Bothell, WA (US); Jeffrey T. L. Smith, Dublin (IE); John A. Latham, Seattle, WA (US); Charlie Karasek, Seattle, WA (US); Jenny Mulligan, Lake Forest Park, WA (US); Michelle Scalley-Kim, Seattle, WA (US); Erica Stewart, Seattle, WA (US); Vanessa Lisbeth Rubin, Seattle, WA (US); Jens J. Billgren, Seattle, WA (US)

(73) Assignee: H. LUNDBECK A/S, Valby (DK)

( * ) Notice: Subject to any disclaimer, the term of this patent is extended or adjusted under 35 U.S.C. 154(b) by 160 days.

This patent is subject to a terminal disclaimer.

(21) Appl. No.: 17/202,790

(22) Filed: Mar. 16, 2021

(65) Prior Publication Data

US 2021/0277106 A1    Sep. 9, 2021

Related U.S. Application Data

(62) Division of application No. 16/787,294, filed on Feb. 11, 2020, now Pat. No. 10,981,985, which is a
(Continued)

(51) Int. Cl.
*A61K 39/395* (2006.01)
*A61P 25/06* (2006.01)
(Continued)

(52) U.S. Cl.
CPC .......... *C07K 16/26* (2013.01); *A61K 39/3955* (2013.01); *A61P 25/06* (2018.01); *A61K 39/39566* (2013.01); *A61K 2039/505* (2013.01); *A61K 45/06* (2013.01); *A61K 49/0004* (2013.01); *A61K 49/0008* (2013.01); *C07K 14/57536* (2013.01); *C07K 14/57563* (2013.01); *C07K 16/4241* (2013.01); *C07K 2317/21* (2013.01); *C07K 2317/24* (2013.01); *C07K 2317/33* (2013.01); *C07K 2317/34* (2013.01); *C07K 2317/40* (2013.01); *C07K 2317/50* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *G01N 33/5088* (2013.01); *G01N 33/74* (2013.01); *G01N 2333/5757* (2013.01); *Y02A 50/30* (2018.01)

(58) Field of Classification Search
CPC ...... C07K 16/26; A61K 39/3955; A61P 25/06
See application file for complete search history.

(56) References Cited

U.S. PATENT DOCUMENTS 5,198,542 A   3/1993  Onda et al.
5,486,472 A   1/1996  Suzuki et al.
(Continued)

FOREIGN PATENT DOCUMENTS

EP   0 522 159    12/2001
EP    1731168    12/2006
(Continued)

OTHER PUBLICATIONS

Ahmadzadeh V, et al. "Antibody humanization methods for development of therapeutic applications," Monoclon Antib mmunodiagn Immunother. Apr. 2014;33(2):67-73.

Alaoui-Ismaili et al. "Design of Second Generation Therapeutic Recombinant Bone Morphogenetic Proteins," Cytokine Growth Factor Rev. 2009; 20:501-507.

Almagro J, et al. "Antibody engineering: Humanization, affinity maturation, and selection techniques" Therapeutic Monoclonal Antibodies: From Bench to Clinic, Oct. 2009, Wiley, pp. 311-334.
(Continued)

*Primary Examiner* — Zachary C Howard
(74) *Attorney, Agent, or Firm* — Robin L. Teskin; Baker, Donelson, Bearman, Caldwell & Berkowitz PC

(57) ABSTRACT

The present invention is directed to antagonistic antibodies and antigen binding fragments thereof having binding specificity for PACAP. These antibodies inhibit, block or neutralize at least one biological effect associated with PACAP, e.g., vasodilation. In exemplary embodiments these antibodies and antigen binding fragments thereof may comprise specific $V_H$, $V_L$, and CDR polypeptides described herein. In some embodiments these antibodies and antigen binding fragments thereof bind to and/or compete for binding to specific epitope(s) on human PACAP. The invention is further directed to using these antagonistic anti-PACAP antibodies, and binding fragments thereof, for the diagnosis, assessment, and treatment of diseases and disorders associated with PACAP and conditions where antagonism of PACAP-related activities, such as vasodilation, mast cell degranulation, and/or neuronal activation, are therapeutically beneficial, e.g., headache and migraine indications.

23 Claims, 28 Drawing Sheets

Specification includes a Sequence Listing.

Related U.S. Application Data division of application No. 15/130,848, filed on Apr. 15, 2016, now Pat. No. 10,899,834.

(60) Provisional application No. 62/148,562, filed on Apr. 16, 2015, provisional application No. 62/148,596, filed on Apr. 16, 2015, provisional application No. 62/148,557, filed on Apr. 16, 2015, provisional application No. 62/148,550, filed on Apr. 16, 2015, provisional application No. 62/148,643, filed on Apr. 16, 2015, provisional application No. 62/148,640, filed on Apr. 16, 2015, provisional application No. 62/148,583, filed on Apr. 16, 2015.

(51) Int. Cl.
*C07K 16/26* (2006.01)
*A61K 39/00* (2006.01)
*A61K 45/06* (2006.01)
*A61K 49/00* (2006.01)
*C07K 14/575* (2006.01)
*C07K 16/42* (2006.01)
*G01N 33/50* (2006.01)
*G01N 33/74* (2006.01)

(56) References Cited

U.S. PATENT DOCUMENTS

| | | | |
|---|---|---|---|
| 5,858,787 | A | 1/1999 | Onda et al. |
| 5,892,004 | A | 4/1999 | Ohtaki et al. |
| 5,973,117 | A | 10/1999 | Onda et al. |
| 6,399,316 | B1 | 6/2002 | Onda et al. |
| 7,615,219 | B2 | 11/2009 | Freson et al. |
| 8,466,118 | B2 | 6/2013 | Banks et al. |
| 8,728,473 | B2 | 5/2014 | Garcia-Martinez et al. |
| 9,255,154 | B2 | 2/2016 | Feldhaus et al. |
| 9,290,567 | B2 | 3/2016 | Bohrmann et al. |
| 9,365,653 | B2 | 6/2016 | Xu |
| 9,939,449 | B2 | 4/2018 | May et al. |
| 9,989,541 | B2 | 6/2018 | Shi et al. |
| 10,202,435 | B2 | 2/2019 | Loomis et al. |
| 10,228,378 | B2 | 3/2019 | May et al. |
| 10,247,738 | B2 | 4/2019 | Shi et al. |
| 10,519,225 | B2 | 12/2019 | Patel et al. |
| 10,913,783 | B2 * | 2/2021 | Loomis ............ A61P 17/04 |
| 10,954,285 | B2 * | 3/2021 | Loomis ............ A61P 17/04 |
| 10,968,268 | B2 * | 4/2021 | Loomis ............ A61P 21/00 |
| 10,975,135 | B2 * | 4/2021 | Loomis ............ A61P 13/10 |
| 2002/0155533 | A1 | 10/2002 | Onda et al. |
| 2002/0182729 | A1 | 12/2002 | Dicicco-Bloom et al. |
| 2004/0014095 | A1 | 1/2004 | Gerber et al. |
| 2004/0038888 | A1 | 2/2004 | Mercer et al. |
| 2005/0129687 | A1 | 6/2005 | Vizzard et al. |
| 2006/0062785 | A1 | 3/2006 | Freson et al. |
| 2007/0054843 | A1 | 2/2007 | Yeomans et al. |
| 2007/0149439 | A1 | 6/2007 | Dicicco-Bloom et al. |
| 2007/0202099 | A1 | 8/2007 | Inooka et al. |
| 2008/0062785 | A1 | 3/2008 | Freson et al. |
| 2008/0070239 | A1 | 3/2008 | Wood |
| 2010/0068208 | A1 | 3/2010 | Ogi et al. |
| 2010/0104530 | A1 | 4/2010 | Freson et al. |
| 2010/0112601 | A1 | 5/2010 | Shirakawa et al. |
| 2010/0129372 | A1 | 5/2010 | Freson et al. |
| 2010/0196393 | A1 | 8/2010 | Banks et al. |
| 2011/0212464 | A1 | 9/2011 | Hagmann |
| 2011/0229423 | A1 | 9/2011 | Vogel et al. |
| 2012/0014958 | A1 | 1/2012 | Borras et al. |
| 2012/0058950 | A1 | 3/2012 | Wood et al. |
| 2012/0284802 | A1 | 11/2012 | Russo et al. |
| 2012/0294797 | A1 | 11/2012 | Kovacevich et al. |
| 2012/0294802 | A1 | 11/2012 | Russo et al. |
| 2012/0309696 | A1 | 12/2012 | Dores |
| 2013/0177568 | A1 | 7/2013 | Bhatt et al. |
| 2013/0267689 | A1 | 10/2013 | Latham et al. |
| 2013/0302399 | A1 | 11/2013 | Feldhaus et al. |
| 2013/0310541 | A1 | 11/2013 | Bohrmann et al. |
| 2014/0370019 | A1 | 12/2014 | Bruenker et al. |
| 2015/0010560 | A1 | 1/2015 | Xu et al. |
| 2015/0309050 | A1 | 10/2015 | May |
| 2016/0304604 | A1 | 10/2016 | Loomis et al. |
| 2016/0305962 | A1 | 10/2016 | Shi et al. |
| 2016/0361441 | A1 | 12/2016 | Kuburas et al. |
| 2016/0362488 | A1 | 12/2016 | Loomis et al. |
| 2016/0376363 | A1 | 12/2016 | Kuburas et al. |
| 2017/0298115 | A1 | 10/2017 | Loomis et al. |
| 2017/0298127 | A1 | 10/2017 | Loomis et al. |
| 2017/0343561 | A1 | 11/2017 | May et al. |
| 2018/0246126 | A1 | 8/2018 | Shi et al. |
| 2018/0362643 | A1 | 12/2018 | Hamburger et al. |
| 2019/0100579 | A1 | 4/2019 | Patel et al. |
| 2019/0178898 | A1 | 6/2019 | Shi et al. |
| 2019/0233498 | A1 | 8/2019 | Loomis et al. |
| 2019/0270807 | A1 | 9/2019 | Loomis et al. |
| 2020/0155533 | A9 | 5/2020 | Villarreal |

FOREIGN PATENT DOCUMENTS

| | | |
|---|---|---|
| EP | 2 009 026 | 12/2008 |
| JP | H06-500001 A | 1/1994 |
| JP | 2002-510500 A | 4/2002 |
| WO | 199114786 | 10/1991 |
| WO | WO 91/14786 | 10/1991 |
| WO | WO 1996/039439 | 12/1996 |
| WO | WO 1998/024900 | 6/1998 |
| WO | 199951762 | 10/1999 |
| WO | WO 1999/051762 | 10/1999 |
| WO | WO 2001/023420 | 4/2001 |
| WO | WO 2003/092716 | 11/2003 |
| WO | WO 2004/006839 | 1/2004 |
| WO | WO 2004/062684 | 7/2004 |
| WO | WO 2005/041757 | 5/2005 |
| WO | WO 2005/072385 | 8/2005 |
| WO | WO 2006/052468 | 5/2006 |
| WO | 2006118328 | 11/2006 |
| WO | WO 2009/000894 | 12/2008 |
| WO | WO 2009/033489 | 3/2009 |
| WO | 2010/005068 | 1/2010 |
| WO | WO 2010/007175 | 1/2010 |
| WO | WO 2012/010647 | 1/2012 |
| WO | WO 2012/106407 | 8/2012 |
| WO | WO 2015/058861 | 4/2015 |
| WO | WO 2015/127288 | 8/2015 |
| WO | WO 2016/168757 | 10/2016 |
| WO | WO 2016/168760 | 10/2016 |
| WO | WO 2016/168762 | 10/2016 |
| WO | WO 2016/168768 | 10/2016 |
| WO | WO 2017/106578 | 6/2017 |

OTHER PUBLICATIONS

Amin FM, et al. "Headache and prolonged dilatation of the middle meningeal artery by PACAP38 in healthy volunteers," Cephalalgia. Jan. 2012;32(2):140-9.

Amin FM, et al. "Investigation of the pathophysiological mechanisms of migraine attacks induced by pituitary adenylate cyclase-activating polypeptide-38," Brain. Mar. 2014;137(Pt 3):779-94.

Baun, M. et al., "Pharmacological characterization and expression of VIP and PACAP receptors in isolated cranial arteries of the rat", European Journal of Pharmacology, 2011; 670: 186-194.

Bhatt, D.K. et al., "PACAP-38 infusion causes sustained vasodilation of the middle meningeal artery in the rat: Possible involvement of mast cells", Cephalalgia, 2014; 0(0): 1-10.

Boni LJ, et al. "The in vivo effect of VIP, PACAP-38 and PACAP-27 and mRNA expression of their receptors in rat middle meningeal artery," Cephalalgia. Aug. 2009;29(8):837-47.

Botz, B. et al., "Role of pituitary Adenylate-Cyclase Activating Polypeptide and Tac1 gene derived tachykinins in sensory, motor and vascular functions under normal and neuropathic conditions", Peptides, 2013; 43: 105-112.

Bowie et al. "Deciphering the Message in Protein Sequences: Tolerance to Amino Acid Substitutions," Science. Mar. 16, 1990;247(4948):1306-10.

(56) References Cited

OTHER PUBLICATIONS

Brown M, et al. "Tolerance of single, but not multiple, amino acid replacements in antibody VH CDR 2: a means of minimizing B cell wastage from somatic hypermutation?" J Immunol. May 1, 1996;156(9):3285-91.

Burgess et al. "Possible Dissociation of the Heparin-Binding and Mitogenic Activities of Heparin-Binding (Acidic Fibroblast) Growth factor-1 From Its Receptor-Binding Activities by Site-Directed Mutagenesis of a Single Lysine Residue," J Cell Biol . Nov. 1990;111(5 Pt 1):2129-38.

Casset et al., "A Peptide Mimetic of an anti-CD4 Monoclonal Antibody by Rational Design," Biochem Biophys Res Commun . Jul. 18, 2003;307(1):198-205.

Chan, K.Y. et al., "Pharmacological characterization of VIP and PACAP receptors in the human meningeal and coronary artery", Cephalalgia, 2011; 31(2): 181-189.

Chen et al., "Selection and Analysis of an Optimized anti-VEGF Antibody: Crystal Structure of an Affinity-Matured Fab in Complex With Antigen," J Mol Biol. Nov. 5, 1999;293(4):865-81.

Chen, D. et al., "Pituitary adenylyl cyclase-activating peptide: A pivotal modulator of glutamatergic regulationofthe surachiasmatic circadian clock", PNAS, 1999; 96(23): 13468-13473.

Cochaud S, et al. "Neuropeptides of the VIP family inhibit glioblastoma cell invasion," J Neurooncol. Mar. 2015;122(1):63-73.

Csaba Z., et al. "Local effect of PACAP and VIP on testicular function in immature and adult rats," Peptides, 1997; 18 (10): 1561-7.

Dickson, L. and Finlayson, K. "VPAC and PAC receptors: From ligands to function", Pharmacology & Therapeutics, 2009; 121: 294-316.

Dodick, "Migraine," Lancet. Mar. 31, 2018;391(10127):1315-1330.

Edvinsson, L., "PACAP and its receptors in migraine pathophysiology: Commentary on Walker et al., Br J Pharmacol 171: 1521-1533", British Journal of Pharmacology, 2015; 172: 4782-4784.

Farnham, M.M.J. and Pilowsky, P.M., "The role of PACAP in central cardiorespiratory regulation", Respiratory Physiology and Neurobiology, 2010; 174: 65-75.

Fleischer N, et al. "Studies of ACTH antibodies and their reactions with inactive analogues of ACTH," Endocrinology. May 1966;78(5):1067-75.

Freson K, et al. "The pituitary adenylate cyclase-activating polypeptide is a physiological inhibitor of platelet activation," J Clin Invest. Mar. 2004;113(6):905-12.

Freson, K. et al., "PACAP and its receptor VPACl regulate megakaryocyte maturation: therapeutic implications", Blood, Feb. 15, 2008; 111(4): 1885-1893.

Grande, G. et al., "Comparison of responses to vasoactive drugs in human and rat cerebral arteries using myography and pressurized cerebral artery method", Cephalalgia, 2012; 33(3): 152-159.

Guo et al., "Protein Tolerance to Random Amino Acid Change," Proc Natl Acad Sci USA. Jun. 22, 2004;101(25):9205-10.

Harmar, A.J. et al., "Pharmacology and functions of receptors forvasoactive intestinal peptide and pituitary adenylate cyclase-activating polypeptide: IUPHAR Review I", British Journal of Pharmacology, 2012; 166: 4-17.

Holm et al., "Functional Mapping and Single Chain Construction of the Anti-Cytokeratin 8 Monoclonal Antibody TS1," Mol Immunol. Feb. 2007;44(6):1075-84.

Kaiser EA, et al. "CGRP and migraine: could PACAP play a role too?" Neuropeptides. Dec. 2013;47(6):451-61.

Khan, S. et al., "Sphenopalatine ganglion neuromodulation in migraine: What is the rationale?", Cephalalgia, 2014; 34(5): 382-391.

Kumar, S. et al., "Crystal Structure of the PACIR Extracellular Domain Unifies a Consensus Fold for Hormone Recognition by Class B G-Protein Coupled Receptors", PLOS One, 2011; 6(5): 1-11.

Maccallum et al. "Antibody-antigen Interactions: Contact Analysis and Binding Site Topography," J Mol Biol . Oct. 11, 1996;262(5):732-45.

Markovics, A. et al., "Pituitary adenylate cyclase-activating polypeptide plays a key role in nitroglycerol-induced trigeminovascular activation in mice", Neurobiology of Disease, 2012; 45: 633-644.

Moody, T.W. et al., "VIP and PACAP. Recent insights into their functions/roles in physiology and disease from molecular and genetic studies", Curr Opin Endocrinol Diabetes Obes., Feb. 2011; 18(1): 61-67.

Nair DT, et al. "Epitope recognition by diverse antibodies suggests conformational convergence in an antibody response," J Immunol. Mar. 1, 2002:168(5):2371-82.

Nassini, R. et al., "The 'headache tree' via umbellulone and TRPAI activates the trigeminovascular system", Brain, 2012; 135: 376-390.

Ng, S.Y.L. et al., "Agnathan VIP, PACAP and Their Receptors: Ancestral Origins of Today's Highly Diversified Forms", PLOS One, Sep. 2012; 7(9): 1-15.

Noseda et al., "Current Understanding of Photophobia, Visual Networks and Headaches," Cephalalgia Nov. 2019;39(13):1623-1634.

Noseda, R. et al., "A neural mechanism for exacerbation of headache by light", Nature Neuroscience, Feb. 2010; 13(2): 239-246.

Pascalis et al. "Grafting of 'Abbreviated' Complementarity-Determining Regions Containing Specificity-Determining Residues Essential for Ligand Contact to Engineer a Less Immunogenic Humanized Monoclonal Antibody," J Immunol Sep. 15, 2002;169(6):3076-84.

Pawson et al. "Assembly of Cell Regulatory Systems Through Protein Interaction Domains," Science. Apr. 18, 2003;300(5618):445-52.

Reglodi, et al. "Protective effects of PACAP in ischemia." The journal of headache and pain vol. 19,1 19. Mar. 2, 2018, doi:10.1186/s10194-018-0845-3).

Rubio-Beltran E, et al. "PACAP38 and PAC1 receptor blockade: a new target for headache?" J Headache Pain. Aug. 7, 2018;19(1):64.

Rudikoff, S. et al., "Single amino acid substitution altering antigen-binding specificity", PNAS, 1982; 79: 1979-1983.

Schmidt-choudhury, A. et al., "Mast cells contribute to PACAP-induced dermal oedema in mice", Regulatory Peptides, 1999; 82: 65-69.

Schwarzhoff, R. et al., "Specific monoclonal antibodies neutralize the action of PACAP 1-27 or PACAP 1-38 on intestinal muscle strips in vitro", Regulatory Peptides, 1995; 55: 57-66.

Schytz, H.W. et al., "Cutaneous nociception and neurogenic inflammation evoked by PACAP38 and VIP", J Headache Pain, 2010; 11: 309-316.

Schytz, H.W. et al., "PACAP38 induces migraine-like attacks in patients with migraine without aura", Brain, 2009; 132: 16-25.

Schytz, H.W. et al., "The PACAP Receptor: A Novel Target for Migraine Treatment", Neurotherapeutics, 2010; 7(2): 191-196.

Schytz, H.W. et al., "What have we learnt from triggering migraine?", Curr Opin Nemol, 2010; 23: 259-265.

Shimazaki Y, et al. "Epitope analysis using membrane-immobilized avidin and protein A," Protein Expr Purif. Jun. 2012;83(2):177-81.

Sun, C. et al., "Solution structure and mutational analysis of pituitary adenylate cyclase-activating polypeptide binding to the extracellular domain of PACI-Rs", PNAS, 2007; 104(19): 7875-7880.

Sundrum et al., "Pituitary Adenylate Cyclase-Activating Polypeptide Receptors in the Trigeminovascular System: Implications for Migraine," Br J Pharmacol. Nov. 2018;175(21):4109-4120.

Suzuki, N. et al., "Production of Immunoreactive Pituitary Adenylate Cyclase Activating Polypeptide (PACAP) by Human Neuroblastoma Cells, IMR-32: Detection and Characterization with Monoclonal and Polyclonal Antibodies against Different Epitopes of PACAP", J. Biochem., 1993; 113: 549-556.

Syed AU, et al. "Pituitary adenylate cyclase-activating polypeptide (PACAP) potently dilates middle meningeal arteries: implications for migraine," J Mol Neurosci. Nov. 2012;48(3):574-83.

Tuka, B. et al., "Alterations in PACAP-38-like immunoreactivity in the plasma during ictal and interictal periods of migraine patients", Cephalalgia, 2013; 0(0): 1-11.

(56) References Cited

OTHER PUBLICATIONS

Tuka, B. et al., "Peripheral and central alterations of pituitary adenylate cyclase activating polypeptide-like immunoreactivity in the rat in response to activation of the trigeminovascular system", Peptides, 2012; 33: 307-316.

Vajdos et al., "Comprehensive Functional Maps of the Antigen-Binding Site of an anti-ErbB2 Antibody Obtained With Shotgun Scanning Mutagenesis," J Mol Biol . Jul. 5, 2002;320(2):415-28.

Vecsei, L. et al., "Role of PACAP in migraine headaches", Brain (Scientific Commentaries) 2014; 137: 650-651.

Walter S, et al. "TEV-48125: a review of a monoclonal CGRP antibody in development for the preventive treatment of migraine," Curr Pain Headache Rep. Mar. 2015;19(3):6.

Wang, Z.-Y. et al., ""Distribution and effects of pituitary adenylate cyclase-activating peptide in the rabbit eye"", Neuroscience, 1995; 69(1): 297-308.

Warren, J.B. et al., "Pituitary Adenylate Cyclase Activating Polypeptide is a Potent Vasodilator in Humans", Journal of Cardiovascular Pharmacology, 1992; 20(1): 83-87.

Waschek JA, et al. "PACAP and migraine headache: immunomodulation of neural circuits in autonomic ganglia and brain parenchyma," J Headache Pain. Mar. 13, 2018;19(1):23.

White A, et al. "Characterisation of monoclonal antibodies to adrenocorticotrophin," J Immunol Methods. May 23, 1985;79(2):185-94.

Wu et al., "Humanization of a Murine Monoclonal Antibody by Simultaneous Optimization of Framework and CDR Residues," J Mol Biol. Nov. 19, 1999;294(1):151-62.

Wu et al., "Photophobia in Neurologic Disorders," Transl Neurodegener. Sep. 20, 2017;6:26.

Yada, T. et al., "Pituitary adenylate cyclase-activating polypeptide (PACAP) is an islet substance serving as an intra-islet amplifier of glucose-induced insulin secretion in rats", Journal of Physiology, 1997; 505.2: 319-328.

Zagami AS, et al. "Pituitary adenylate cyclase activating polypeptide and migraine," Ann Clin Transl Neurol. Dec. 2014;1(12):1036-40.

Zhang, Y. et al., "Capsaicin-evoked release of pituitary adenylate cyclase activating peptide (PACAP) and calcitonin gene-related peptide (CGRP) from rat spinal cord in vivo", Regulatory Peptides, 1997; 69: 83-87.

Ahmadzadeh V, et al. "Antibody humanization methods for development of therapeutic applications," Monocion Antib Immunodiagn Immunother. Apr. 2014;33(2):67-73.

Syed, A. et al., "Pituitary Adenylate Cyclase-Activating Polypeptide (PACAP) Potentially Dilates Middle Meningeal Arteries: Implications for Migraine", J. Mol. Neurosci., 2012; 48: 574-583.

Amin, F.M. et al., "Headache and prolonged dilation of the middle meningeal artery by PACAP 38 in healthy volunteers", Cephalalgia, 2011; 32(2): 140-149.

Amin, F.M. et al., "Investigation of the pathoshysiological mechanisms of migraine attacks induced by pituitary adenylate cyclase-activating polypeptide-38", Brain, 2014; 137: 779-794.

Boni, L.J. et al., "The in vivo effect of VIP, PACAP-38 and PACAP-27 and mRNA expression of their receptors in rat middle meningeal artery", Cephalalgia, 2009: 29: 837-847.

Botz, B. et al., "Role of pituitary Adenylate-Cyclase Activating Polypeptide and Tac1 gene derived tachykinins in sensory, motor and vascular functions under normal and neuropathic conditions", Peptides, 2013; 43: 105-112.

Freson, K. et al., "PACAP and its receptor VPAC1 regulate megakaryocyte maturation: therapeutic implications", Blood, Feb. 15, 2008; 111(4): 1885-1893.

Harmar, A.J. et al., "Pharmacology and functions of receptors for vasoactive intestinal peptide and pituitary adenylate cyclase-activating Polypeptide: IUPHAR Review 1", British Journal of Pharmacology, 2012; 166: 4-17.

Kaiser. E.A. and Russo, A.F., "CGRP and migraine: Could PACAP play a role too?", Neuropeptides, 2013; 47: 451-461.

Kumar, S. et al., "Crystal Structure of the PAC1R Extracellular Domain Unifies a Consensus Fold for Hormone Recognition by Class B G-Protein Coupled Receptors", PLOS One, 2011; 6(5): 1-11.

Nassini, R., et al., "The 'headache tree' via umbellulone and TRPA1 activates the trigeminovascular system", Brain, 2012; 135: 376-390.

Ng, S.Y.L. et al., "Agnathan VIP, PACAP and Their Recrptors: Ancestral Origins of Today's Highly Diversified Forms", PLOS One, Sep. 2012; 7(9): 1-15.

Schytz, H.W. et al., "What have we learnt from triggering migraine?", Curr Opin Neruol, 2010; 23: 259-265.

Sun, C. et al., "Solution structure and mutational analysis of pituitary adenylate cyclase-activating polypeptide binding to the extracellular domain of PAC1-$R_S$", PNAS, 2007; 104(19): 7875-7880.

Tuka, B. et al., "Alterations in PACAP-38-like imummoreactivity in the plasma during ictal and interictal periods of migraine patients", Cephalalgia, 2013; 0(0): 1-11.

Zagami, A.S. et al., "Pituitary adenylate cyclase activating polypeptide and migraine", Annals of Clinical and Translational Neurology, 2014; 1(12): 1036-1040.

Rudikoff et al. "Single amino acid substitution altering antigen-binding specificity." Proceedings of the National Academy of Sciences. Mar. 1, 1982;79(6):1979-83.

Grider, J R et al. "Regulation of the descending relaxation phase of intestinal peristalsis by PACAP." Journal of the autonomic nervous system vol. 50,2 (1994): 151-9. doi:10.1016/0165-1838(94)90005-1.

Atsuro Miyata, Structure and function of PACAP as a brain gut peptide, Journal of Clinical and Experimental Medicine, vol. 2007, vol. 223, No. 7, pp. 569 to 572.

Seeliger, Stephan et al. "Pituitary adenylate cyclase activating polypeptide: an important vascular regulator in human skin in vivo." The American journal of pathology vol. 177,5 (2010): 2563-75. doi:10.2353/ajpath.2010.090941.

\* cited by examiner

Figure 1A
Antibody Variable Heavy Chain Protein Features

| Sequence Name | FR1 | CDR1 | FR2 | CDR2 |
|---|---|---|---|---|
| Ab10 | QSVEESGGRLVTPGTPLTLTCTVSGIDLN | SYYMT | WVRQAPGKGLEWIG | FIDAGGDAYYASWAKG |
| Ab20 | QSVEESGGRLVTPGTPLTLTCTVSGIDLS | SYYMS | WVRQAPGKGLEWIG | FIDTDGSAYYATWAKG |
| Ab21 | QSVEESGGRLVTPGTPLTLTCTVSGIDLS | SYYMT | WVRQAPGKGLEWVG | FIDAGGSAYYATWAKG |
| Ab22 | QEQLVESGGGLVQPEGSLTLTCTASGFDFS | SNAMC | WVRQAPGKGLEWIG | SIYNADGKNYYAIWAKG |
| Ab23 | QSVEESGGRLVTPGTPLTLTCTVSGFSLN | NYAMS | WVRQAPGKGLEWIG | IMGVNDITYYASWAKG |

Figure 1B
Antibody Variable Heavy Chain Protein Features

| Sequence Name | FR3 | CDR3 | FR4 | |
|---|---|---|---|---|
| Ab10 | RFTISKTSTTVDLKITSPTTEDTATYFCAR | DLDL | WGQGTLVTVSS | (SEQ ID NO: 402) |
| Ab20 | RFTISKTSTTVDLKITSPTTEDTATYFCAR | DLDL | WGPGTLVTVSS | (SEQ ID NO: 442) |
| Ab21 | RFTISKASTTVDLKITSPTTEDTATYFCAR | DLDL | WGPGTLVTVSS | (SEQ ID NO: 842) |
| Ab22 | RFTISRTSSTTVTLQMTSLTAADTATYFCAR | DFDL | WGQGTLVTVSS | (SEQ ID NO: 882) |
| Ab23 | RFTISKTSTTVDLKMTSLTTEDTATYFCTR | EIRDDGDSSDKL | WGPGTLVTVSS | (SEQ ID NO: 922) |

Figure 2A
Antibody Variable Light Chain Protein Features

| Sequence Name | FR1 | CDR1 | FR2 | CDR2 |
|---|---|---|---|---|
| Ab10 | AAVLTQTPSPVSAAVGGTVTINC | QSSESVYGNYLA | WFQQKPGQPPKLLIY | EASKLES |
| Ab20 | AAVLTQTPSPVSAAVGGTVSISC | QSSESVYSNYLA | WFQQKPGQPPKFLIY | EASKLAS |
| Ab21 | AAVLTQTPSPVSAAVGGTVSISC | KSSESVYGDYLA | WFQQKPGQPPKQLIY | DASTLAS |
| Ab22 | AAVLTQTPSPVSAAVGGTVTINC | QSSQSVYDNDWLA | WFQQKPGQPPKLLIY | LTSTLAS |
| Ab23 | AIKMTQTPSSVSAAVGGTVTINC | QASEDIYTNLA | WYQQKPGQPPNLLIY | DASDLAS |

Figure 2B
Antibody Variable Light Chain Protein Features

| Sequence Name | FR3 | CDR3 | FR4 | |
|---|---|---|---|---|
| Ab10 | GVPSRFSGSGSGTQFTLTISDLQCDDAATYC | AGGDISEGVA | FGGGTEVVVKR | (SEQ ID NO: 422) |
| Ab20 | GVPSRFKGSGSGTQFTLTISDVQCDDAGTYC | AGGYSSEGVA | FGGGTEVVVKR | (SEQ ID NO: 462) |
| Ab21 | GVPSRFKGSGSGTQFTLTISGVQCDDAATYC | AGGYVSAGVA | FGGGTEVVVKR | (SEQ ID NO: 862) |
| Ab22 | GVPSRFSGSGSGTQFTLTISGVQCDDAATYC | LGGYDEDGDTHV | FGGGTEVVVKR | (SEQ ID NO: 902) |
| Ab23 | GVPSRFSGSGDGTQFTLTISAVQCEDAATYC | QGVAWSSNTGYGSA | FGGGTEVVVKR | (SEQ ID NO: 942) |

Figure 3A
Antibody Variable Heavy Chain DNA Features

| Sequence Name | FR1 |
|---|---|
| Ab10 | cagtcggtggaggagtccggggggtcacgcctggtcacgcctgtcacgcctggacactcacctgcacagtctctggaa |
| Ab20 | cagtcggtggaggagtccggggggtcacgcctgtcacgcctggacactcacctgcacagtctctggaa |
| Ab21 | cagtcggtggaggagtccggggggtcacgcctgtcacgcctggacactcacctgcacagtctctggaa |
| Ab22 | caggagcagctggtggagtccggggaggcctggtccagcctgagggatcctgacactcacctgcacagcctctg |
| Ab23 | cagtcggtggaggagtccggggggtcacgcctggtcacgcctggacactcacctgcaccgtctctggat |

Figure 3B
Antibody Variable Heavy Chain DNA Features

| Sequence Name | FR1 | CDR1 | FR2 |
|---|---|---|---|
| Ab10 | tcgacctcaat | agctactacatgacc | tgggtccgccaggctccagggaaggggctggaatggatcgga |
| Ab20 | tcgacctcagt | agctactacatgagc | tgggtccgccaggctccagggaaggggctggaatggatcgga |
| Ab21 | tcgacctcagt | agctactacatgacc | tgggtccgccaggctccagggaaggggctggaatggatcgga |
| Ab22 | gattcgacttcagt | agcaatgcaatgtgc | tgggtccgccaggctccagggaaggggctgagtggatcgga |
| Ab23 | tctccctcaat | aactatgcaatgagc | tgggtccgccaggctccagggaaggggctggaatggatcgga |

Figure 3C
Antibody Variable Heavy Chain DNA Features

| Sequence Name | CDR2 | FR3 |
|---|---|---|
| Ab10 | ttcattgatgctgtgtgacgcatactacgcgagctggggcgaaaggc | cgattcaccatctccaaaacctcga |
| Ab20 | ttcattgatactgatgcgcatactacgcgaccctgggcgaaaggc | cgattcaccatctccaaaacctcga |
| Ab21 | ttcattgatgctgtgtagcgcatactacgcgaccctgggcaaaaggc | cgattcaccatctccaaaagcctcga |
| Ab22 | tccatttataatgctgatgtaagaattattacgcgatttgggcgaaaggc | cgattcaccatctccagaacctcgt |
| Ab23 | atcatggtgttaatgatatcacatactacgcgagctggggcgaaaggc | cgattcaccatctccaaaacctcga |

Figure 3D
Antibody Variable Heavy Chain DNA Features

| Sequence Name | FR3 |
|---|---|
| Ab10 | ccacggtggatctgaaaatcaccagtccgacaaccgaggacacggccacctatttctgtgccaga |
| Ab20 | ccacggtggatctgaaaatcaccagtccgacaaccgaggacacggccacctatttctgtgccaga |
| Ab21 | ccacggtggatctgaaaatcaccagtccgacaaccgaggacacggccacctatttctgtgccaga |
| Ab22 | cgaccacggtgactctgcaaatgaccagtctgacagcccgcgacacggccacctatttctgtgcgaga |
| Ab23 | ccacggtggatctgaaaatgaccagtctgacaaccgaggacacggccacctatttctgtactaga |

Figure 3E
Antibody Variable Heavy Chain DNA Features

| Sequence Name | CDR3 | FR4 |
|---|---|---|
| Ab10 | gatctttgacttg | Tggggccagggcaccctggtcaccgtctcgagc |
| Ab20 | gatctttgacttg | tggggcccgggcaccctcgtcaccgtctcgagc |
| Ab21 | gatctttgacttg | tggggcccgggcaccctggtcaccgtctcgagc |
| Ab22 | gactttgacttg | tggggccagggcaccctcgtcaccgtctcgagc |
| Ab23 | gagatccgtgatgatggtgatagttctgataagttg | tggggcccgggcaccctcgtcaccgtctcgagc |

Figure 3F
Antibody Variable Heavy Chain DNA Features

| Sequence Name | |
|---|---|
| Ab10 | (SEQ ID NO: 412) |
| Ab20 | (SEQ ID NO: 452) |
| Ab21 | (SEQ ID NO: 852) |
| Ab22 | (SEQ ID NO: 892) |
| Ab23 | (SEQ ID NO: 932) |

Figure 4A
Antibody Variable Light Chain DNA Features
Sequence
Name      FR1
Ab10      gccgccgtgctgacccagactccatctcccgtgtctgcagctgtgggaggcacagtcaccatcaattgc
Ab20      gccgccgtgctgacccagactccatctcccgtgtctgcagctgtgggaggcacagtcagcatcagttgc
Ab21      gccgccgtgctgacccagactccatctcccgtgtctgcagctgtgggaggcacagtcagcatcagttgc
Ab22      gcagccgtgctgacccagacaccatcccgcccgtgtctgcagctgtgggaggcacagtcaccatcaattgc
Ab23      gccatcaaaatgacccagactcctccgtgtctgcagctgtgggaggcacagtcaccatcaattgc Figure 4B
Antibody Variable Light Chain DNA Features
Sequence
Name      CDR1                                        FR2
Ab10      cagtccagtgagagtgtttacgtaactacttagcc          tggtttcagcagaaaccagggcagcctcccaagctcc
Ab20      cagtccagtgagagtgtttatagtaactacttagcc         tggtttcagcagaaaccagggcagcctcctaagttct
Ab21      aagtccagtgagagcgtttatgtgtactacttagcc         tggtttcagcagaaaccagggcagcctcccaagcaac
Ab22      cagtccagtgagagtgtttatgataacgactgttagcc       tggttccagcagaaaccagggcagcctcccaagctcc
Ab23      caggccagtgaggacattaccaccaatttagcc            tggtatcagcagaaaccagggcagcctcccaacctcc Figure 4C
Antibody Variable Light Chain DNA Features
Sequence
Name      FR2          CDR2                   FR3
Ab10      tgatctac     gaagcatccaaactggaatct  ggggtcccatcgcggttcagcgcgcagtggatctgggacacagttca
Ab20      tgatctac     gaagcatccaaactggcatct  ggggtcccatcgcggttcagcgcgcagtggatctgggacacagttca
Ab21      tgatctat     gatgcatccactctggcatct  ggggtcccatcgcggttcaaaggcagtggatctgggacacagttca
Ab22      tgatctat     ctgacatccactctggcatct  ggagtcccatcgcggttcagcgcggcagtggatctgggacacagttca
Ab23      tgatctat     gatgcatccgatctggcatct  ggggtcccgtcgcgttcagcgcggcagtggagatgggacacagttca Figure 4D
Antibody Variable Light Chain DNA Features

| Sequence Name | FR3 | CDR3 | | |
|---|---|---|---|---|
| Ab10 | ctctcaccatcagcgacttgcagtgtgacgatgctgccacttactactgt | ttgct | gcaggcggtgatattagtgaaggtg | (SEQ ID NO: 432) |
| Ab20 | ctctcaccatcagcgacgtgcagtgtgacgatgctgccacttactactgt | ttgct | gcaggcggctatagtagtgaaggtg | (SEQ ID NO: 472) |
| Ab21 | ctctcaccatcagcgcggtgcagtgtgacgatgctgccacttactactgt | ttgct | gcaggcggttatgttagtgcaggtg | (SEQ ID NO: 872) |
| Ab22 | ctctcaccatcagtgtgtgcagtgtgacgatgctgccacttactactgt | atacgcatgtt | ctagccggctatgatgaagatggtg | (SEQ ID NO: 912) |
| Ab23 | ctctcaccatcagcgcgccgtgcagtgtgaagatgctgccacttactactgt | ctggttatggttccgct | caaggtgttgcttggagtagtaata | (SEQ ID NO: 952) |

Figure 4E
Antibody Variable Light Chain DNA Features

| Sequence Name | CDR3 | FR4 |
|---|---|---|
| Ab10 | ttgct | ttcggcggagggaccgaggtggtggtcaaacgt |
| Ab20 | ttgct | ttcggcggagggaccgaggtggtggtcaaacgt |
| Ab21 | ttgct | ttcggcggagggaccgaggtggtggtcaaacgt |
| Ab22 | atacgcatgtt | ttcggcggagggaccgaggtggtggtcaaacgt |
| Ab23 | ctggttatggttccgct | ttcggcggagggaccgaggtggtggtcaaacgt |

Figure 5
Antibody Heavy Chain Protein Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-109 | 402 | 30-34 | 404 | 49-64 | 406 | 95-98 | 408 |
| Ab20 | 1-109 | 442 | 30-34 | 444 | 49-64 | 446 | 95-98 | 448 |
| Ab21 | 1-109 | 842 | 30-34 | 844 | 49-64 | 846 | 95-98 | 848 |
| Ab22 | 1-112 | 882 | 31-35 | 884 | 50-66 | 886 | 98-101 | 888 |
| Ab23 | 1-117 | 922 | 30-34 | 924 | 49-64 | 926 | 95-106 | 928 |

Figure 6
Antibody Heavy Chain Protein Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-29 | 403 | 35-48 | 405 | 65-94 | 407 | 99-109 | 409 | 110-439 | 410 |
| Ab20 | 1-29 | 443 | 35-48 | 445 | 65-94 | 447 | 99-109 | 449 | 110-439 | 450 |
| Ab21 | 1-29 | 843 | 35-48 | 845 | 65-94 | 847 | 99-109 | 849 | 110-439 | 850 |
| Ab22 | 1-30 | 883 | 36-49 | 885 | 67-97 | 887 | 102-112 | 889 | 113-442 | 890 |
| Ab23 | 1-29 | 923 | 35-48 | 925 | 65-94 | 927 | 107-117 | 929 | 118-447 | 930 |

Figure 7
Antibody Light Chain Protein Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-110 | 422 | 24-35 | 424 | 51-57 | 426 | 90-99 | 428 |
| Ab20 | 1-110 | 462 | 24-35 | 464 | 51-57 | 466 | 90-99 | 468 |
| Ab21 | 1-110 | 862 | 24-35 | 864 | 51-57 | 866 | 90-99 | 868 |
| Ab22 | 1-113 | 902 | 24-36 | 904 | 52-58 | 906 | 91-102 | 908 |
| Ab23 | 1-113 | 942 | 24-34 | 944 | 50-56 | 946 | 89-102 | 948 |

Figure 8
Antibody Light Chain Protein Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-23 | 423 | 36-50 | 425 | 58-89 | 427 | 100-110 | 429 | 111-216 | 430 |
| Ab20 | 1-23 | 463 | 36-50 | 465 | 58-89 | 467 | 100-110 | 469 | 111-216 | 470 |
| Ab21 | 1-23 | 863 | 36-50 | 865 | 58-89 | 867 | 100-110 | 869 | 111-216 | 870 |
| Ab22 | 1-23 | 903 | 37-51 | 905 | 59-90 | 907 | 103-113 | 909 | 114-219 | 910 |
| Ab23 | 1-23 | 943 | 35-49 | 945 | 57-88 | 947 | 103-113 | 949 | 114-219 | 950 |

Figure 9
Antibody Heavy Chain DNA Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-327 | 412 | 88-102 | 414 | 145-192 | 416 | 283-294 | 418 |
| Ab20 | 1-327 | 452 | 88-102 | 454 | 145-192 | 456 | 283-294 | 458 |
| Ab21 | 1-327 | 852 | 88-102 | 854 | 145-192 | 856 | 283-294 | 858 |
| Ab22 | 1-336 | 892 | 91-105 | 894 | 148-198 | 896 | 292-303 | 898 |
| Ab23 | 1-351 | 932 | 88-102 | 934 | 145-192 | 936 | 283-318 | 938 |

Figure 10
Antibody Heavy Chain DNA Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-87 | 413 | 103-144 | 415 | 193-282 | 417 | 295-327 | 419 | 328-1317 | 420 |
| Ab20 | 1-87 | 453 | 103-144 | 455 | 193-282 | 457 | 295-327 | 459 | 328-1317 | 460 |
| Ab21 | 1-87 | 853 | 103-144 | 855 | 193-282 | 857 | 295-327 | 859 | 328-1317 | 860 |
| Ab22 | 1-90 | 893 | 106-147 | 895 | 199-291 | 897 | 304-336 | 899 | 337-1326 | 900 |
| Ab23 | 1-87 | 933 | 103-144 | 935 | 193-282 | 937 | 319-351 | 939 | 352-1341 | 940 |

Figure 11
Antibody Light Chain DNA Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-330 | 432 | 70-105 | 434 | 151-171 | 436 | 268-297 | 438 |
| Ab20 | 1-330 | 472 | 70-105 | 474 | 151-171 | 476 | 268-297 | 478 |
| Ab21 | 1-330 | 872 | 70-105 | 874 | 151-171 | 876 | 268-297 | 878 |
| Ab22 | 1-339 | 912 | 70-108 | 914 | 154-174 | 916 | 271-306 | 918 |
| Ab23 | 1-339 | 952 | 70-102 | 954 | 148-168 | 956 | 265-306 | 958 |

Figure 12
Antibody Light Chain DNA Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-69 | 433 | 106-150 | 435 | 172-267 | 437 | 298-330 | 439 | 331-648 | 440 |
| Ab20 | 1-69 | 473 | 106-150 | 475 | 172-267 | 477 | 298-330 | 479 | 331-648 | 480 |
| Ab21 | 1-69 | 873 | 106-150 | 875 | 172-267 | 877 | 298-330 | 879 | 331-648 | 880 |
| Ab22 | 1-69 | 913 | 109-153 | 915 | 175-270 | 917 | 307-339 | 919 | 340-657 | 920 |
| Ab23 | 1-69 | 953 | 103-147 | 955 | 169-264 | 957 | 307-339 | 959 | 340-657 | 960 |

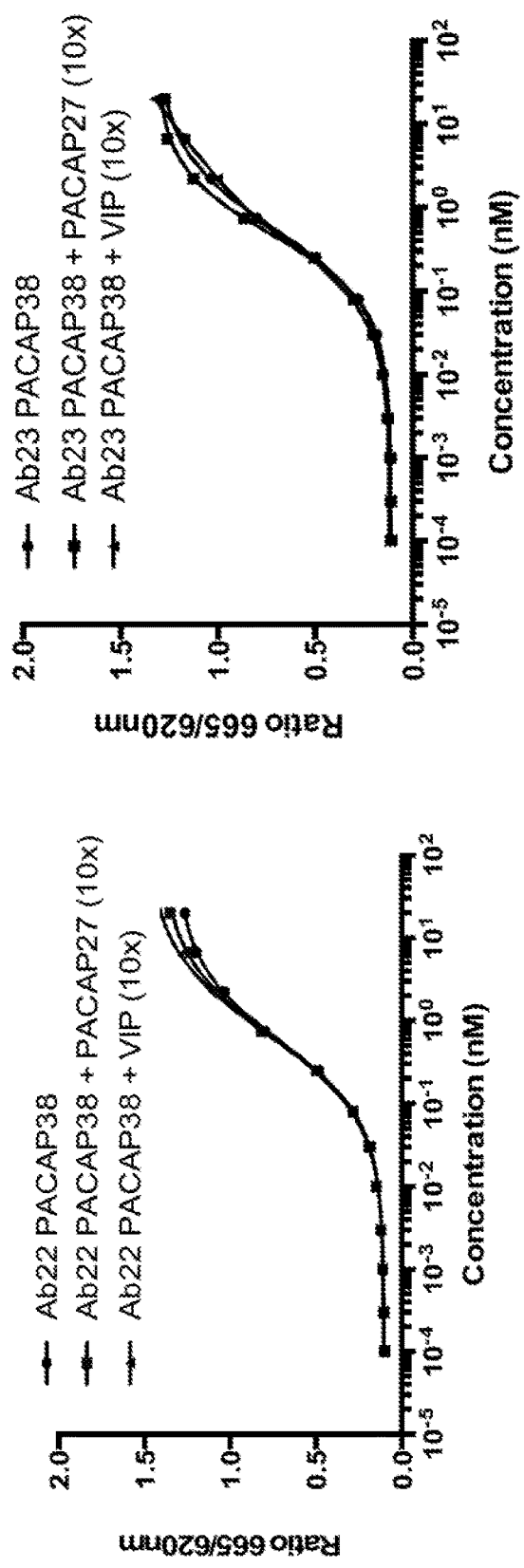
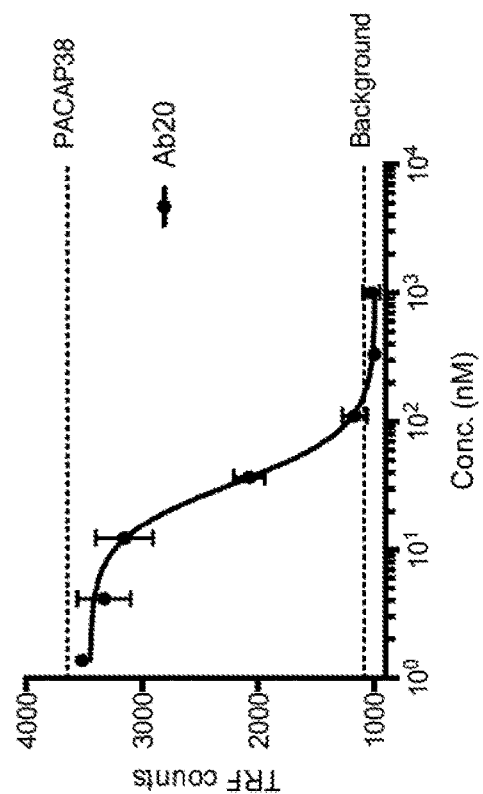
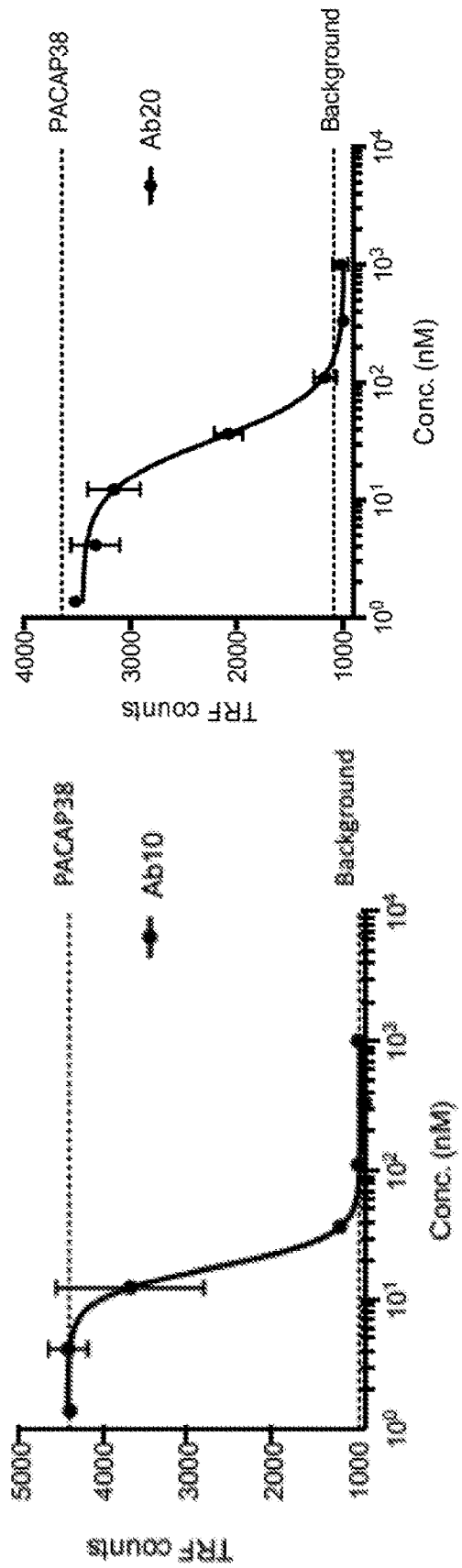

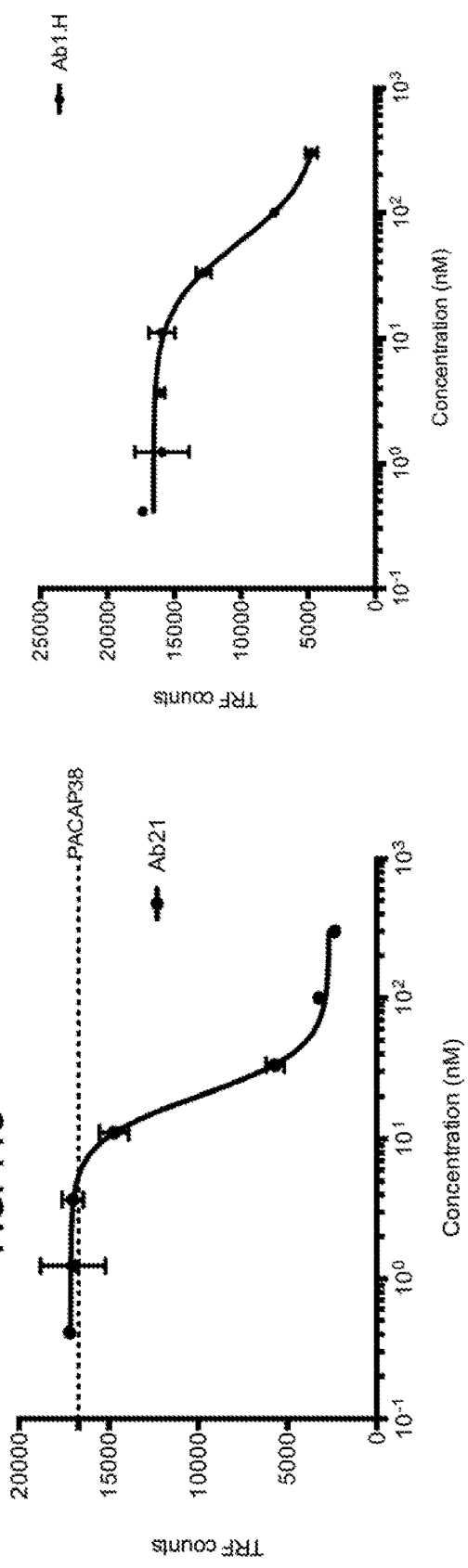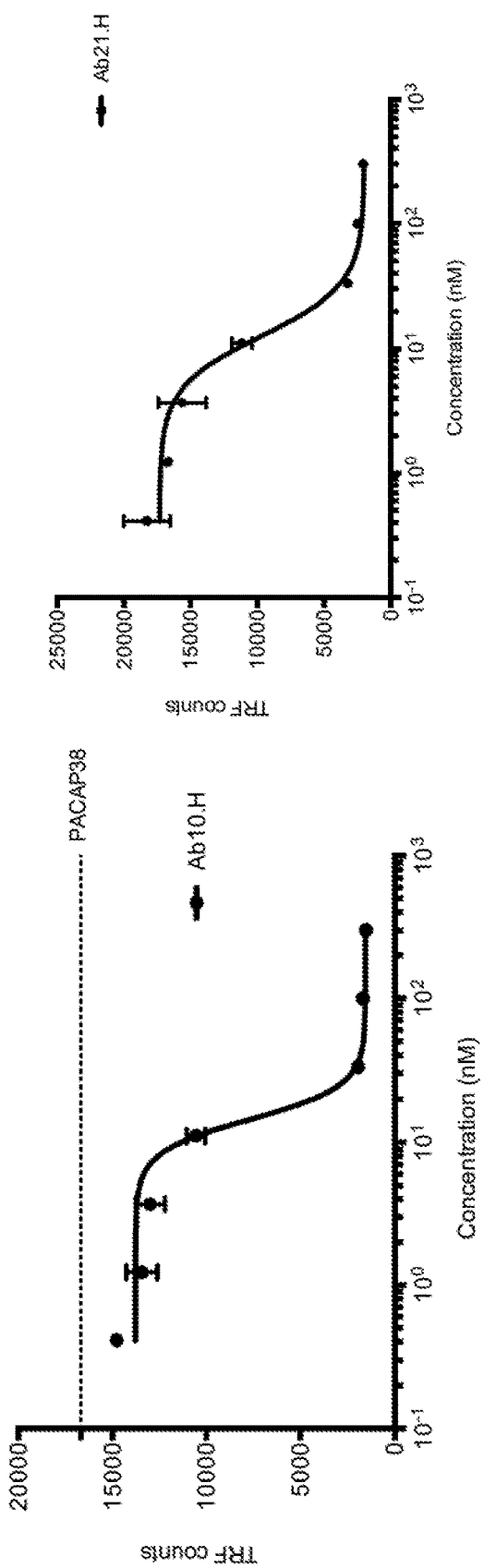

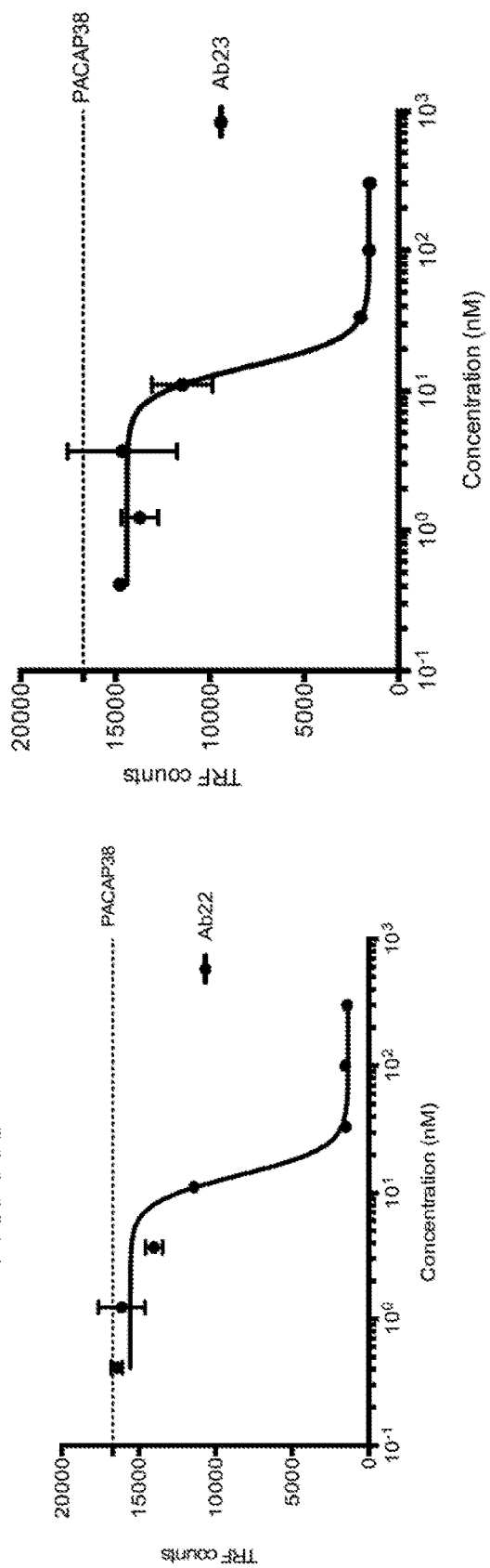
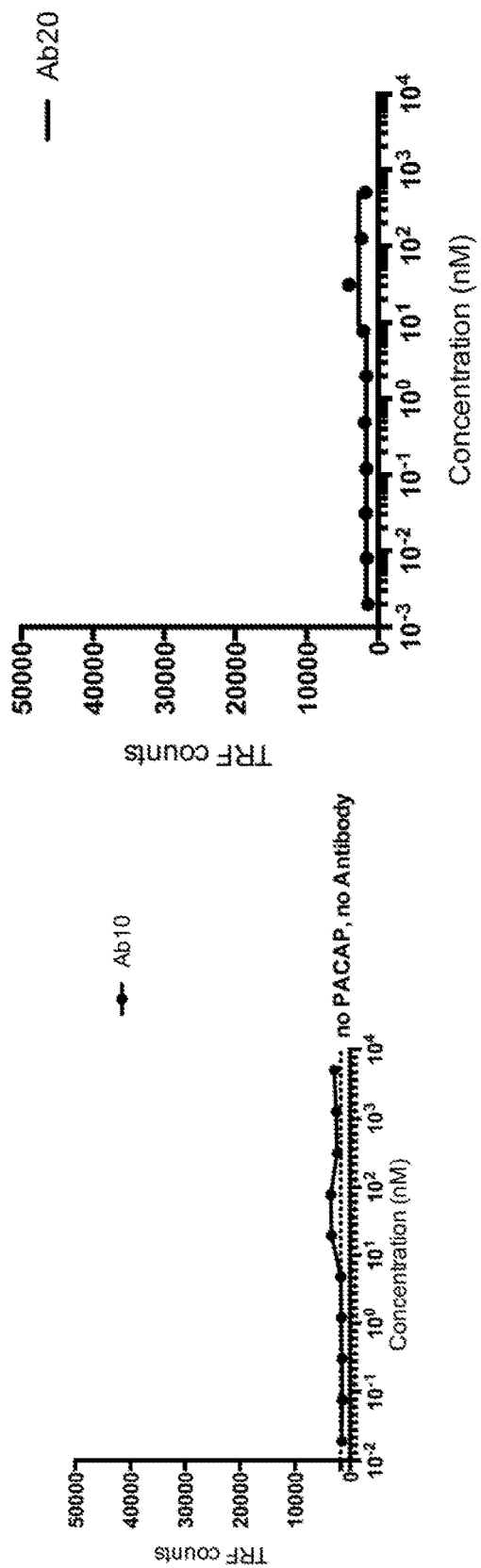

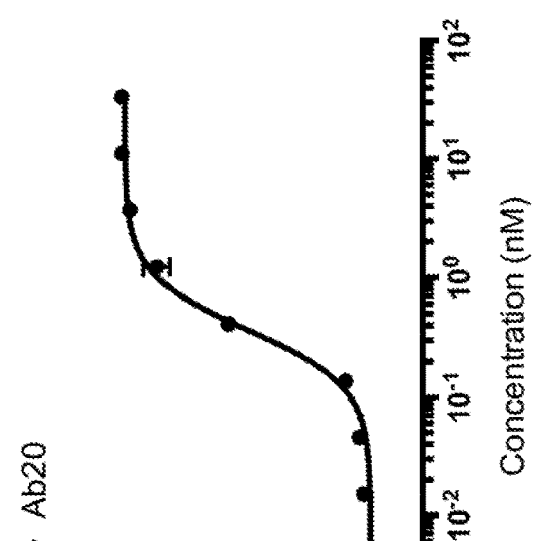
FIG. 15G
FIG. 15H
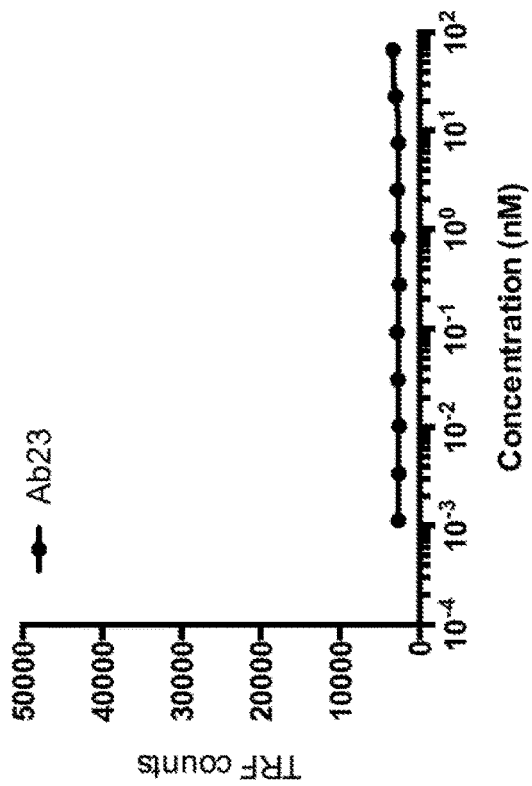
FIG. 16A
FIG. 16B
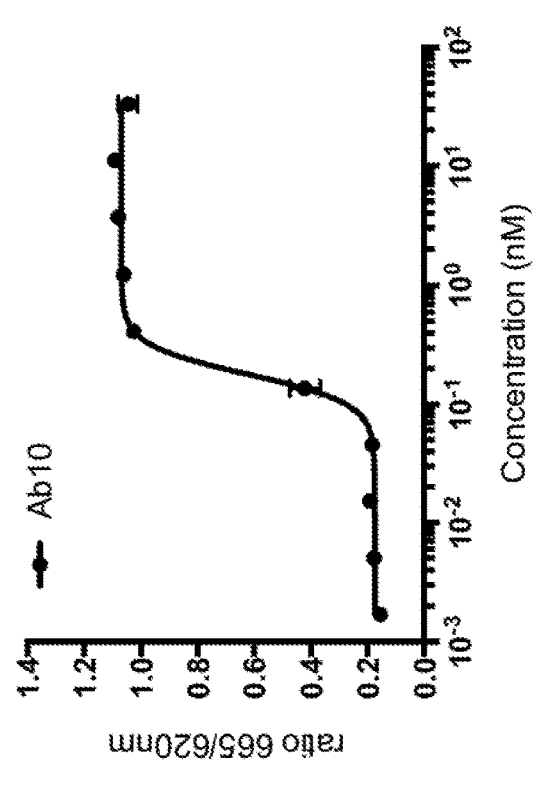

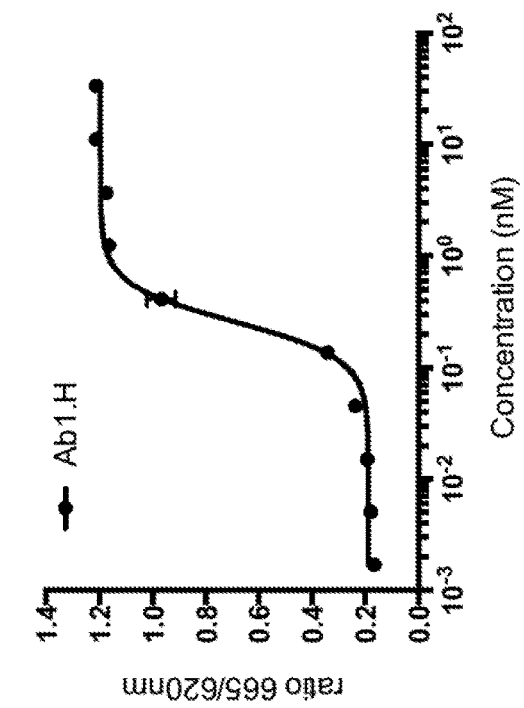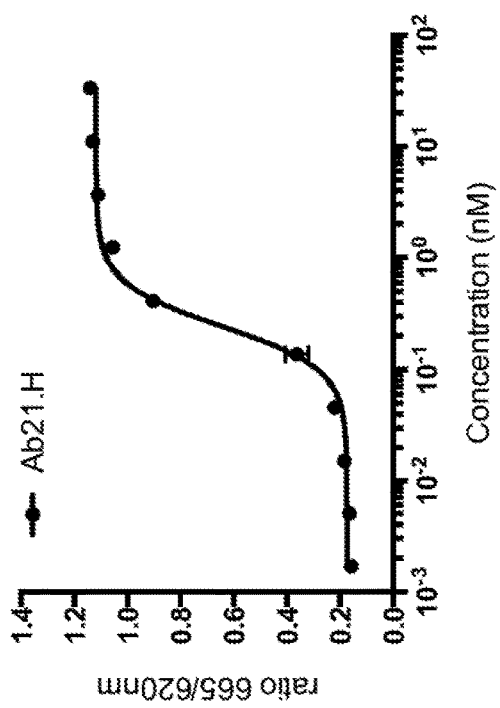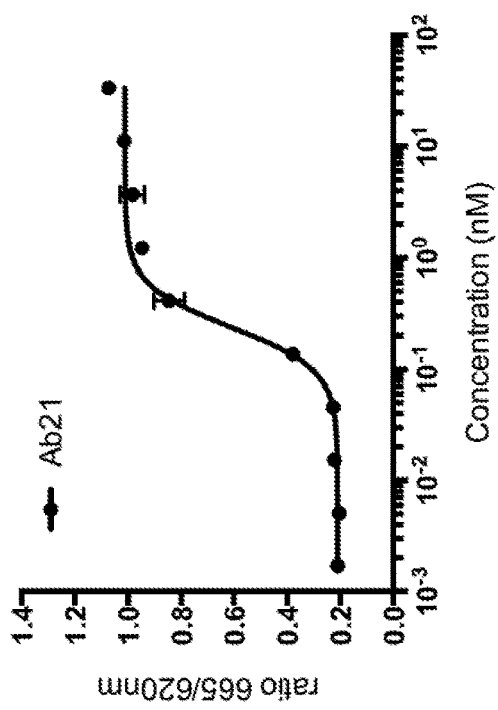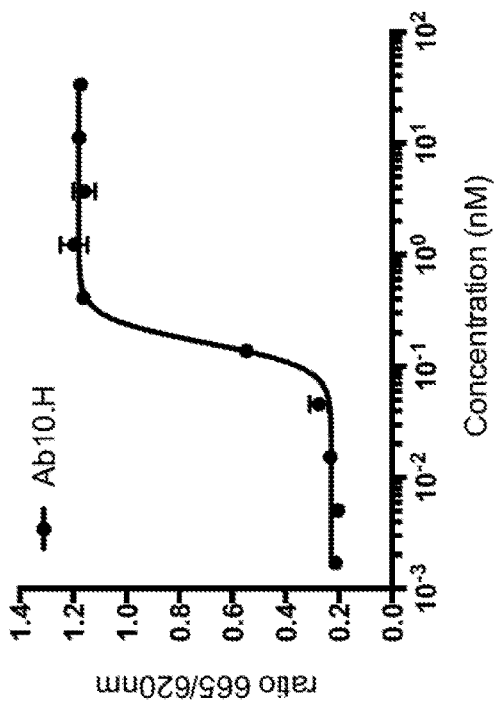

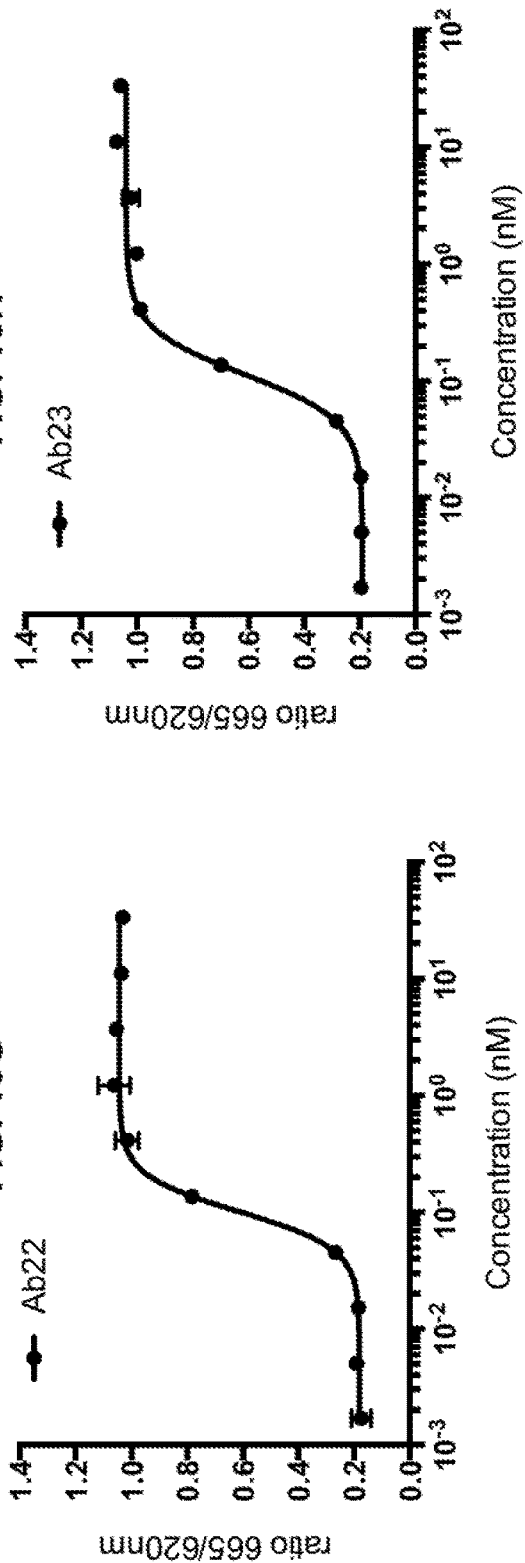
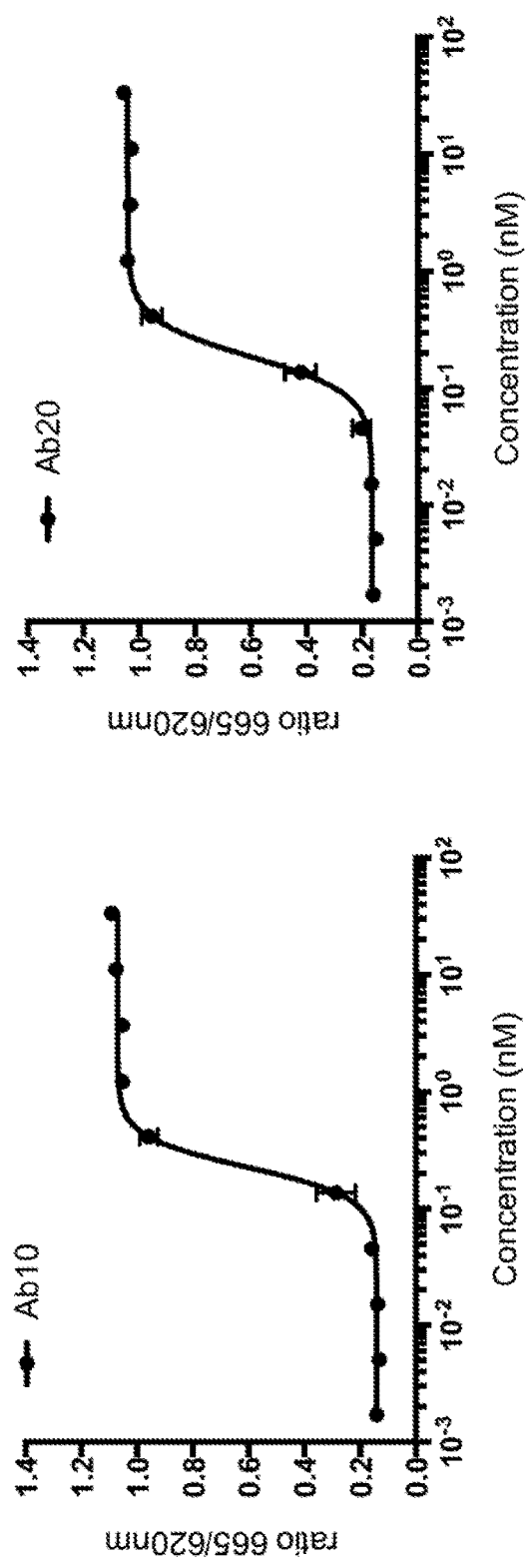

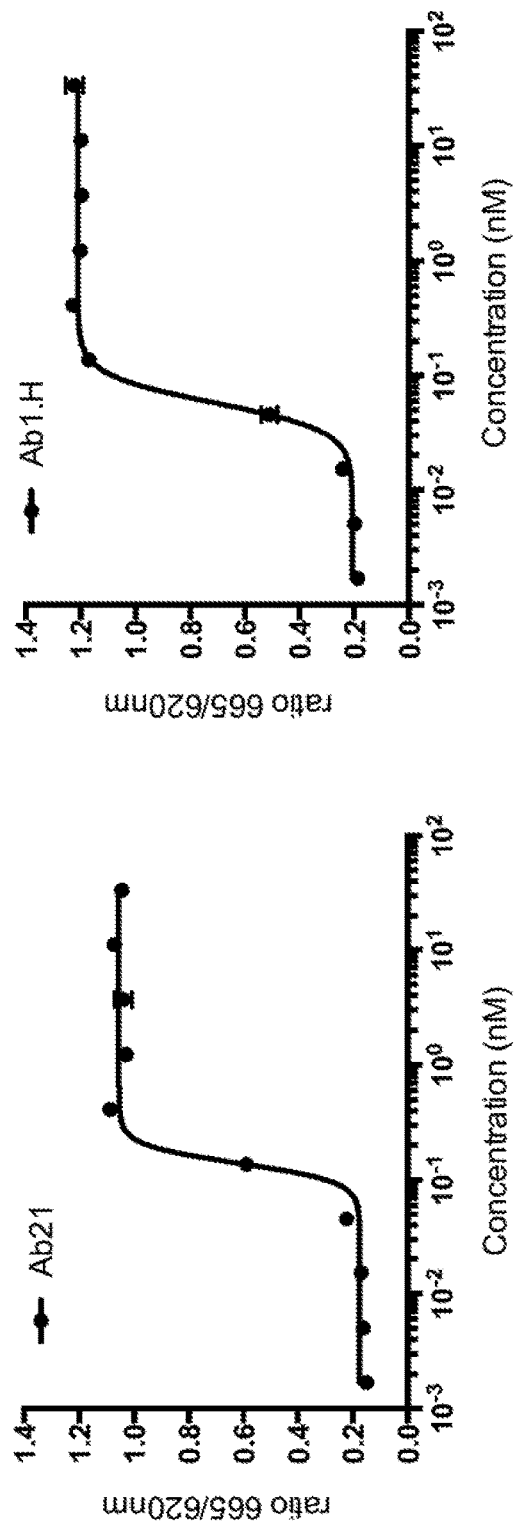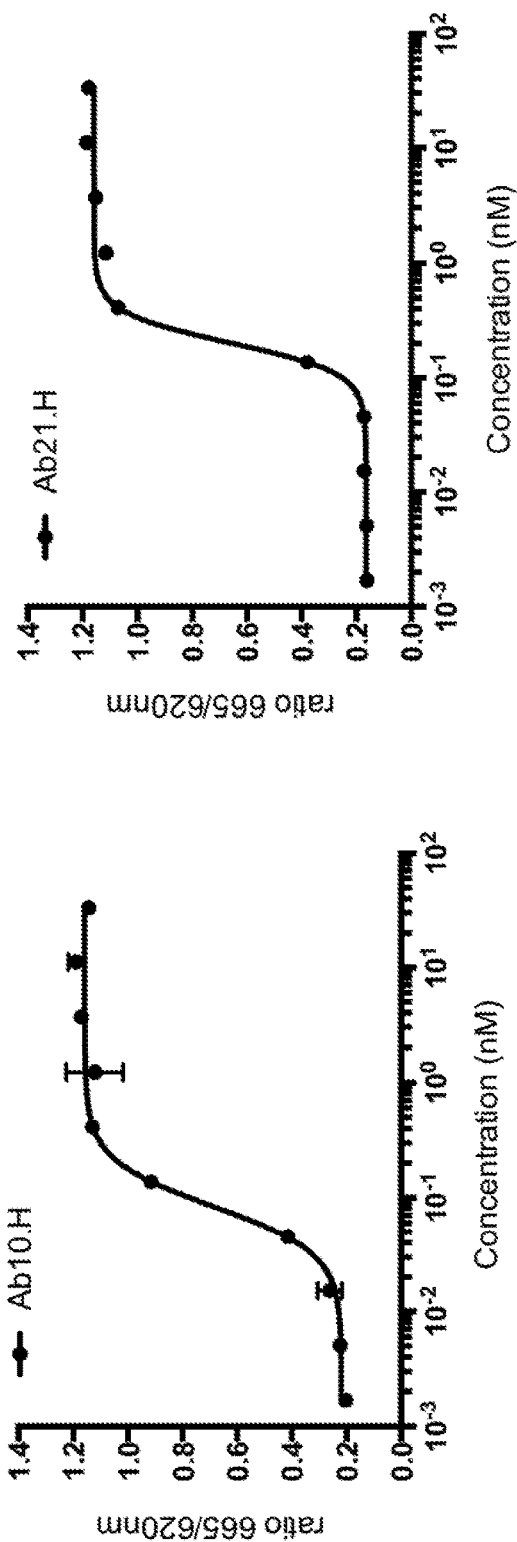

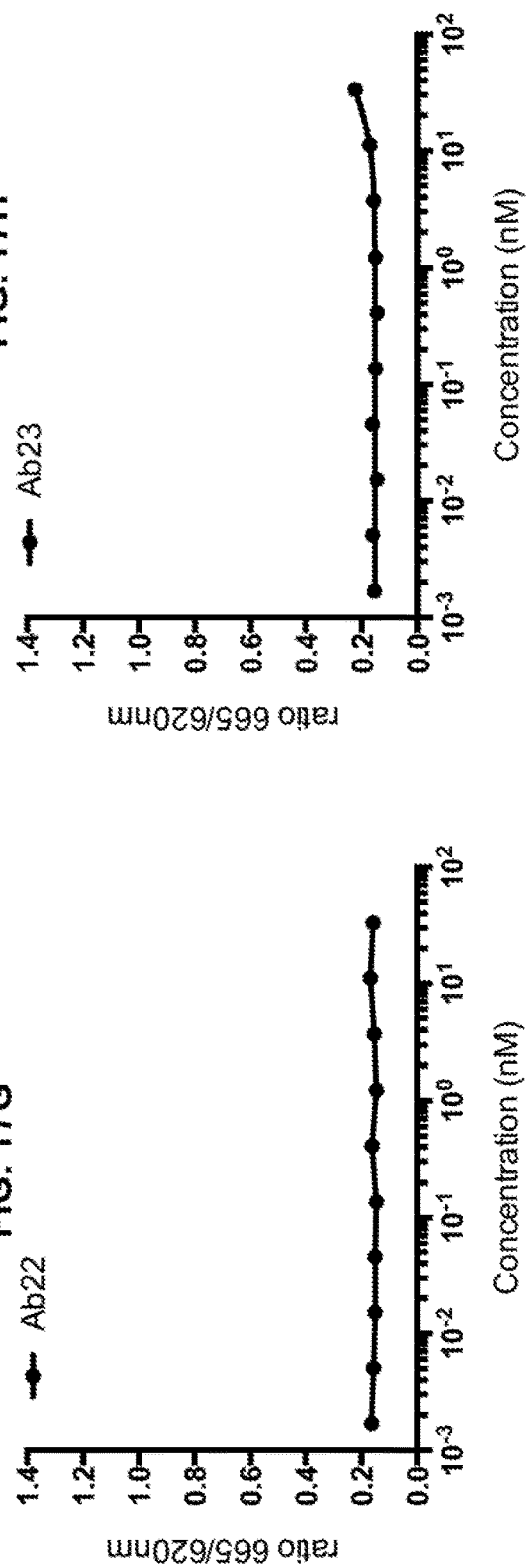
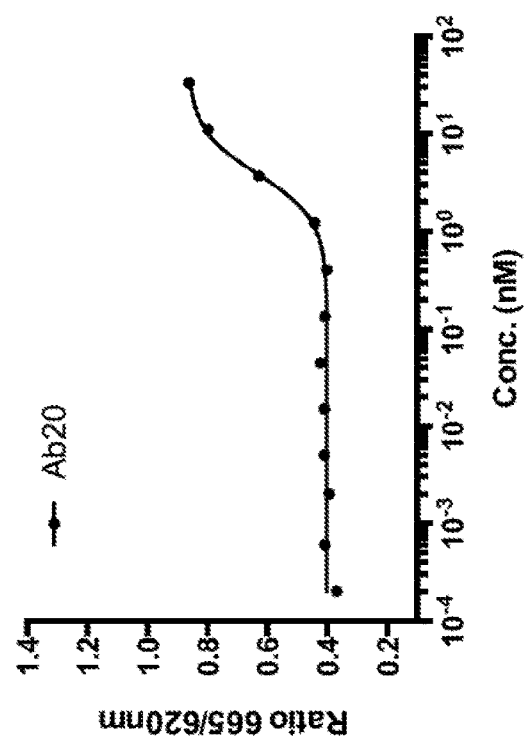
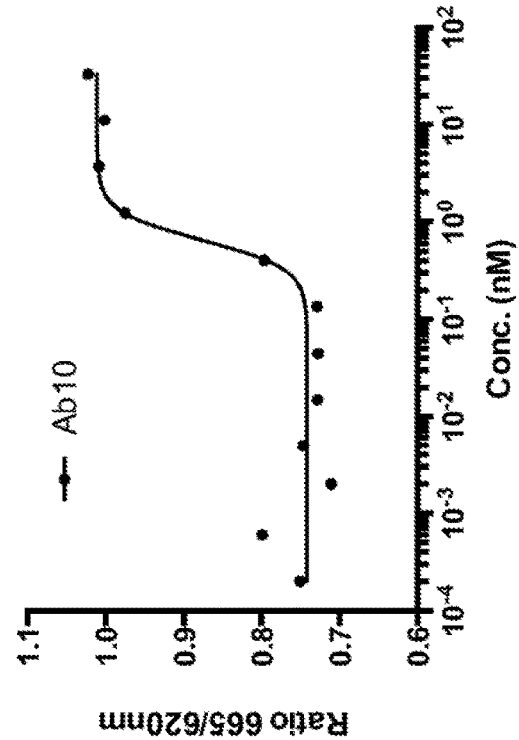

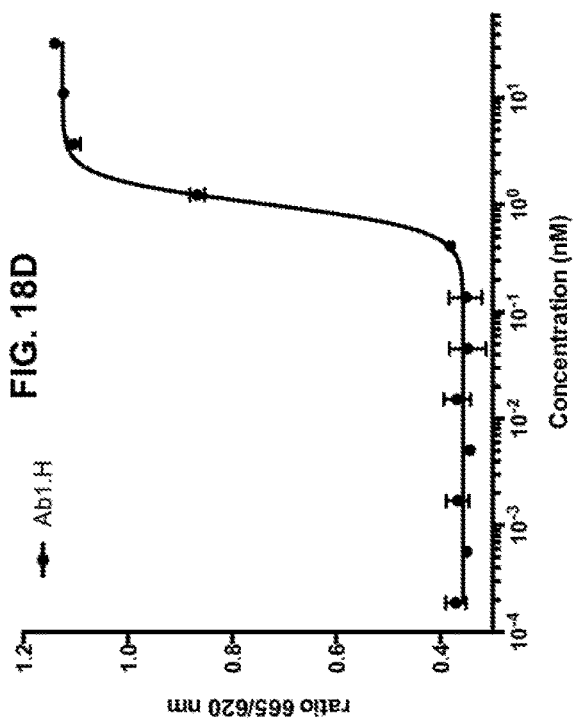
FIG. 18C
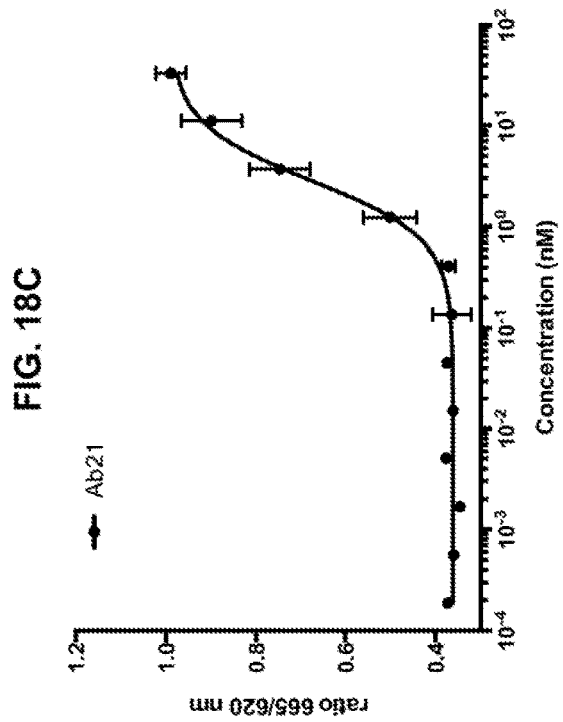
FIG. 18E
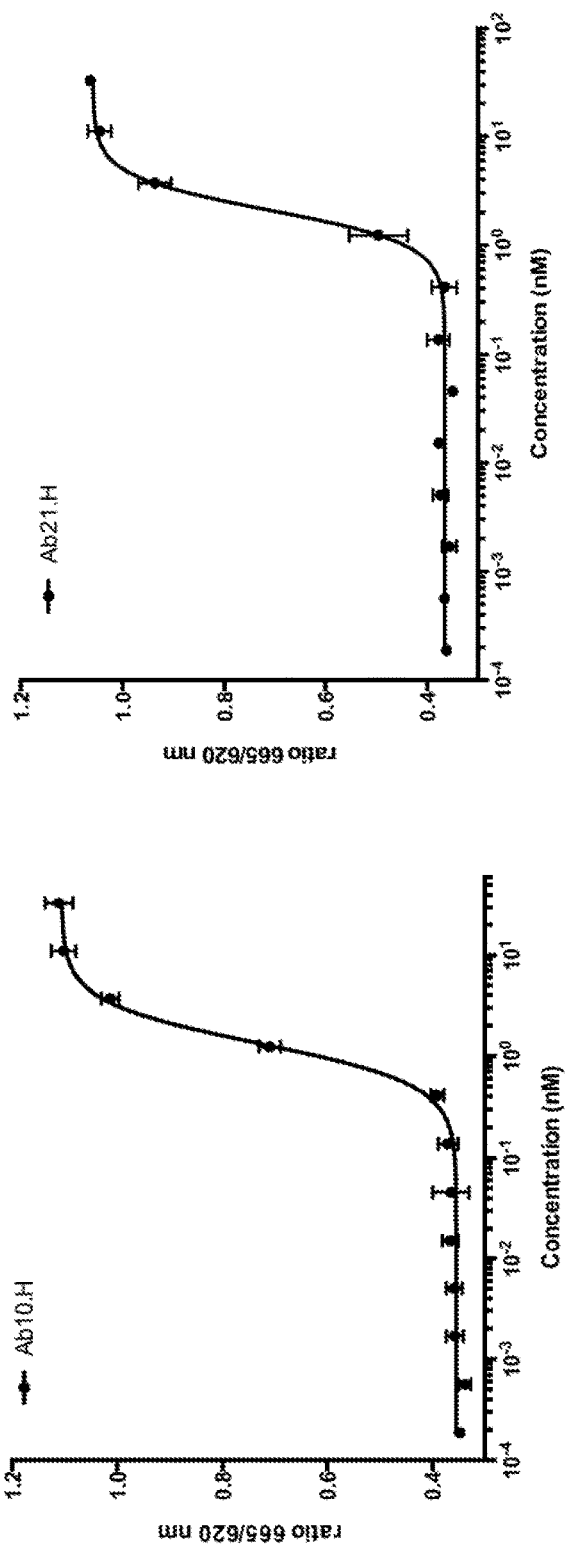
FIG. 18D
FIG. 18F

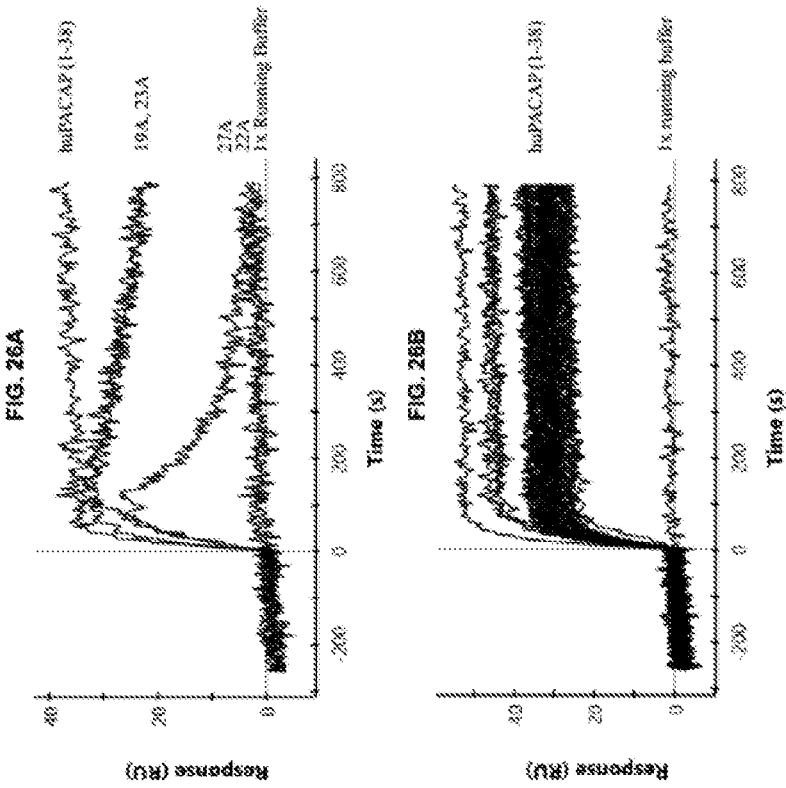
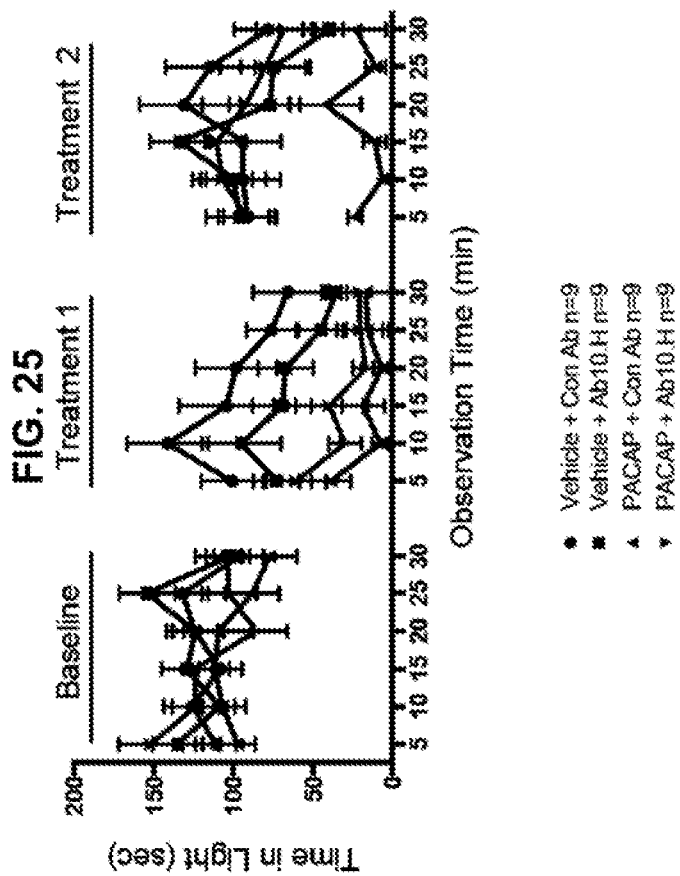

FIG. 31A. Summary of effects of PACAP alanine scanning mutants on antibody binding

| VIP | PACAP |    | Ab10 | Ab20 | Ab21 | Ab22 | Ab23 |
|-----|-------|----|------|------|------|------|------|
| H   | H     | 1  |      |      |      |      |      |
| S   | S     | 2  |      |      |      |      |      |
| D   | D     | 3  |      |      |      |      |      |
| A   | G     | 4  |      |      |      |      |      |
| V   | I     | 5  |      |      |      |      |      |
| F   | F     | 6  |      |      |      |      |      |
| T   | T     | 7  |      |      |      |      |      |
| D   | D     | 8  |      |      |      |      |      |
| N   | S     | 9  |      |      |      |      |      |
| Y   | Y     | 10 |      |      |      |      |      |
| T   | S     | 11 |      |      |      |      |      |
| R   | R     | 12 |      |      |      |      | 12A  |
| L   | Y     | 13 |      |      |      |      |      |
| R   | R     | 14 |      |      |      |      |      |
| K   | K     | 15 |      |      |      |      |      |
| Q   | Q     | 16 |      |      |      |      |      |
| M   | M     | 17 |      |      |      |      |      |
| A   | A     | 18 |      |      |      |      |      |
| V   | V     | 19 | 19A  | 19A  | 19A  |      |      |
| K   | K     | 20 |      |      |      |      | 20A  |
| K   | K     | 21 |      |      |      |      |      |
| Y   | Y     | 22 | 22A  | 22A  | 22A  | 22A  |      |
| L   | L     | 23 | 23A  | 23A  | 23A  | 23A  | 23A  |
| N   | A     | 24 |      | 24V  |      |      | 24V  |
| S   | A     | 25 |      |      |      |      |      |
| I   | V     | 26 |      |      |      |      | 26A  |
| L   | L     | 27 | 27A  | 27A  | 27A  | 27A  | 27A  |

FIG. 31B. Summary of effects of PACAP alanine scanning mutants on antibody binding

| VIP | PACAP |    | Ab10 | Ab20 | Ab21 | Ab22 | Ab23 |
|-----|-------|----|------|------|------|------|------|
| N   | G     | 28 |      |      |      | 28A  | 28A  |
|     | K     | 29 |      |      |      |      |      |
|     | R     | 30 |      |      |      |      |      |
|     | Y     | 31 |      |      |      | 31A  |      |
|     | K     | 32 |      |      |      |      |      |
|     | Q     | 33 |      |      |      |      |      |
|     | R     | 34 |      |      |      |      |      |
|     | V     | 35 |      |      |      |      |      |
|     | K     | 36 |      |      |      |      |      |
|     | N     | 37 |      |      |      |      |      |
|     | K     | 38 |      |      |      |      |      |

METHODS OF TREATMENT WITH ANTI-PACAP ANTIBODIES

CROSS-REFERENCE TO RELATED APPLICATIONS

This application is a divisional of U.S. application Ser. No. 16/787,294, filed Feb. 11, 2020, which is a divisional of U.S. application Ser. No. 15/130,848 filed Apr. 15, 2016, now U.S. Pat. No. 10,899,834, which claims the benefit of U.S. Provisional Appl. No. 62/148,550, filed Apr. 16, 2015, U.S. Provisional Appl. No. 62/148,557, filed Apr. 16, 2015, U.S. Provisional Appl. No. 62/148,562, filed Apr. 16, 2015, U.S. Provisional Appl. No. 62/148,596, filed Apr. 16, 2015, U.S. Provisional Appl. No. 62/148,643, filed Apr. 16, 2015, U.S. Provisional Appl. No. 62/148,583, filed Apr. 16, 2015, U.S. Provisional Appl. No. 62/148,640, filed Apr. 16, 2015, each of which is hereby incorporated by reference in its entirety.

SEQUENCE DISCLOSURE

This application includes as part of its disclosure an electronic sequence listing text file named "114325To005902.txt", having a size of 163,516 bytes and created on Mar. 16, 2021, which is hereby incorporated by reference in its entirety.

FIELD OF THE INVENTION

This invention generally pertains to antibodies and antigen binding fragments thereof, preferably humanized, chimerized, and human antibodies and antigen binding fragments thereof, and compositions containing such antibodies and antigen binding fragments thereof, wherein such antibodies and antigen binding fragments thereof specifically bind to Pituitary Adenylate Cyclase-Activating Polypeptide ("PACAP") and therapeutic and diagnostic uses for the antibodies, antigen binding fragments, and compositions thereof.

BACKGROUND

Pituitary Adenylate Cyclase-Activating Polypeptide ("PACAP") is a member of the secretin/vasoactive intestinal peptide ("VIP")/growth hormone-releasing hormone ("GHRH") family. PACAP is a multifunctional vasodilatory peptide that exists in two α-amidated active forms, one with 38 amino acids (PACAP38; SEQ ID NO: 1241) and the other with 27 amino acids (PACAP27; SEQ ID NO: 1242). Both peptides have the same N-terminal 27 amino acids and are synthesized from the same precursor protein, prepro-PACAP (See, Moody et al., *Curr. Opin. Endocrinol. Diabetes Obes.*, 18(1):61-67 2011). PACAP38 is the more prevalent active form, representing up to 90% of PACAP forms in mammalian tissues (See. Kaiser and Russo, *Neuropeptides*, 47:451-461 2013). The sequence of PACAP38 is identical in all mammals and differs from the avian and amphibian orthologs by only one amino acid (See, Vaudry et al., *Pharmacol. Rev.*, 52:269-324 2000). The secretin/VIP/GHRH family includes mammalian peptide histidine methioneamide ("PHM"), secretin, glucagon, glucagon-like peptide-1 ("GLP1"), glucagon-like peptide-2 ("GLP2"), glucose-dependent-insulinotrophic-polypeptide ("GIP"), and growth-hormone-releasing-factor ("GRF"). PACAP27 has 68% sequence identity to VIP at the amino acid level (See, Vaudry et al. 2000).

PACAP is widely distributed in the brain and peripheral organs, e.g., the endocrine system, gonads, sympathetic neurons, respiratory system, gastrointestinal tract, cardiovascular system, and urogenital tracts (See, Schytz et al., *Neurotherapeutics*, 7:191-196 2010). In particular, PACAP is expressed throughout the nervous system, including a presence in the trigeminovascular system, trigeminal ganglia, spinal cord, hypothalamus, and pituitary. PACAP has roles in neurodevelopment, neuroprotection, neuromodulation, neurogenic inflammation, and nociception with multiple actions (See, Kaiser and Russo 2013).

Consistent with its widespread distribution, PACAP exerts pleiotropic effects including modulation of neurotransmitter release, vasodilation, bronchodilation, and activation of intestinal motility, increase of insulin and histamine secretion, as well as stimulation of cell proliferation and/or differentiation. PACAP has been shown to act as a hormone, a neurohormone, a neurotransmitter, and a trophic factor in a number of tissues (Vaudry et al., *Pharmacological Rev.*, 52(2):269-324, 2000).

The biological effects of PACAP are mediated via three different G-protein coupled receptors: PAC1-R, vasoactive intestinal peptide receptor type 1 ("VPAC1-R"), and vasoactive intestinal peptide receptor type 2 ("VPAC2-R"). These receptors are expressed in diverse tissues. PAC1-R is particularly abundant in the nervous system (e.g., olfactory bulb, thalamus, hypothalamus, cerebellum, and spinal dorsal horn), pituitary, and adrenal glands. By contrast, VPAC1-R and VPAC2-R are expressed mainly in the lung, liver, and testis, although they have been detected in other tissues as well. VPAC1-R expression has been detected in the nervous system (e.g., cerebral cortex and hippocampus), smooth muscle cells of lung, liver, intestine, megakaryocytes, and platelets. VPAC1-R associates with receptor-associated membrane protein ("RAMP", specifically RAMP2) (See, Christopoulos et al., *J. Biol. Chem.*, 278:3293-3297, 2002). VPAC2-R expression profile includes the nervous (e.g., thalamus, hippocampus, brain stem, and dorsal root ganglia ("DRG")), cardiovascular system, gastrointestinal system, pancreas, and reproductive systems (See, Usdin et al., *Endocrin.*, 135:2662-2680, 1994; Sheward et al., *Neurosci.*, 67:409-418, 1995).

PAC1-R is selective for PACAP38 and PACAP27. In particular, PAC1-R binds to PACAP with 100-1000-fold greater affinity than VIP, i.e., $K_D$-0.5 nM for PACAP27/PACAP38 vs. $K_D$~500 nM for VIP. Conversely, VPAC1-R and VPAC2-R have equal affinities for PACAP and VIP ($K_D$~1 nM) (See, Schytz et al. 2010).

Upon activation, these receptors are all capable of causing downstream production of cyclic adenosine monophosphate ("cAMP"), and/or activation of phospholipase C ("PLC"), and/or modulation of phospholipase D ("PLD"). In particular, PAC1-R is coupled to dual signal transduction pathways acting through cAMP and $Ca^{2+}$, whereas VPAC1-R and VPAC2-R are coupled principally to adenylyl cyclase. PAC1-R is coupled to $G_s$ protein, which activates adenylyl cyclase to form cAMP that in turn activates protein kinase A. PAC1-R also couples to Gq and thereby activates PLC, which produces inositol phosphate, which increases cytosolic calcium release from intra-cellular calcium stores. There is some evidence for a role of PAC1-R in PLD activation (See, McCulloch et al., *Ann. N. Y. Acad. Sci.*, 921:175-185, 2000). Another PACAP signaling pathway results in the elevation of intra-cellular sodium levels via activation of nonselective cation channels (See, Roy et al., *American Journal of Physiology*: Regulatory, *Integrative and Comparative Physiology*, 304(12): R1070-R1084, 2013).

PACAP is hypothesized to play a role in a multitude of diseases and disorders, including but not limited to migraine, headache, and pain, though such a role for PACAP has not been clinically demonstrated. Migraines are believed to have a neurovascular component. Migraines affect approximately 10% of the adult population in the U.S. and are typically accompanied by intense headaches. Approximately 20-30% of migraine sufferers experience aura, comprising focal neurological phenomena that precede and/or accompany the event. A role for PACAP in migraine has been suggested by several observations: (1) plasma levels of PACAP are elevated during migraine attacks (ictal), as compared to interictal levels, in humans (see, Tuka et al., *Cephalalgia,* 33(13):1085-1095 2013); (2) an infusion of PACAP38 triggered headaches in healthy subjects, and headaches followed by migraine-like attacks in migraineurs (see, Schytz et al., *Brain,* 132:16-25, 2009; and Amin et al., *Brain,* 137:779-794, 2014, respectively); (3) PACAP-induced vasodilation may play a role in neurogenic inflammation (see, Kaiser and Russo, *Neuropeptides,* 47:451-461, 2013); and (4) PACAP-induced migraines are associated with photophobia, phonophobia, nausea, and respond to triptans (see, Amin et al., *Brain,* 32:140-149 2012). PACAP has also been shown to induce vasodilation, photophobia, as well as mast cell degranulation and neuronal activation (See, Markovics et al., *Neurobiology of Disease,* 45:633-644 2012; Baun et al., *Cephalalgia,* 32(4):337-345 2012; Chan et al., *Pharmacology & Therapeutics,* 129:332-351 2011).

One effective treatment for migraines is the administration of triptans, which are a family of tryptamine-based drugs, including sumatriptan and rizatriptan. Members of this family have an affinity for multiple serotonin receptors, including 5-HT$_{1B}$, 5-HT$_{1D}$, and 5-HT$_{1F}$. Members of this family of drugs selectively constrict cerebral vessels, but also cause vasoconstrictive effects on coronary vessels (See, Durham, *New Eng. J. Med.,* 350 (11):1073-75 2004). There is a theoretical risk of coronary spasm in patients with established heart disease following administration, and cardiac events after taking triptans in rare instances may occur. Accordingly, they are contraindicated for some patients with coronary vascular disease.

Similarly, pain may often be addressed through the administration of certain narcotics or non-steroidal anti-inflammatory drugs ("NSAIDs"). However, the administration of these treatments often has negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

PACAP may also be involved in diseases and disorders other than migraine, headache, and pain. For example, PACAP may correlate to or even play a causal role in anxiety disorders (WO 2012/106407); thrombocytopenia (WO 2004/062684); and inflammatory skin diseases (WO 2010/007175). PACAP and PAC1-R polymorphisms are associated with post-traumatic stress syndrome ("PTSD") in females, major depressive disorder, and generalized anxiety disorder, suggesting a role for PACAP in these conditions. Further, supporting a role for PACAP in thrombocytopenia, trisomy 18 patients have excess PACAP and exhibit defective megakaryocyte maturation (See, Schytz et al. 2010; and Moody et al., *Curr. Opin. Endocrinol. Diabetes Obes.,* 18(1):61-67, 2011).

Also, PACAP and other neuropeptides, such as Calcitonin Gene-Related Peptide ("CGRP"), substance P, neurokinin A, bradykinin, and endothelin-1, are expressed in the lower urinary tract ("LUT") (see, Arms and Vizzard, Handbook Exp. *Pharmacol.,* 202:395-423, 2011) and reportedly may play a role in LUT dysfunction and urinary tract disorders such as urinary tract infection ("UTI"), abnormal voiding, urinary urgency, nocturia, urinary incontinence, overactive bladder, and the pain associated with such conditions.

PACAP and PACAP receptors have also been suggested to modulate inflammatory and neuropathic pain and have been implicated in both pronociception and antinociception (See, Davis-Taber et al., *J. Pain,* 9(5):449-56 2008). PACAP has also been reported to be required for spinal desensitization and the induction of neuropathic pain (See, Mabuchi et al., *J. Neurosci.,* 24(33):7283-91, 2004). Additionally, morphine withdrawal behavior is reportedly modified in PACAP-receptor deficient mice further suggesting the role of PACAP in morphine withdrawal anxiolytic response (See Martin et al., *Mol. Brain Res.,* 110(1):109-18, 2003).

BRIEF SUMMARY OF THE INVENTION

In one aspect, the present invention in general relates to anti-PACAP antibodies and antigen binding fragments thereof, preferably human, humanized, or chimerized anti-PACAP antibodies and antigen binding fragments thereof, that antagonize, inhibit, neutralize, or block at least one biological effect associated with human PACAP. In certain embodiments, the anti-PACAP antibodies and antigen binding fragments thereof inhibit or neutralize at least one biological effect elicited by PACAP, which includes PACAP27 and/or PACAP38, as discussed infra. In other embodiments, the anti-PACAP antibodies and antigen binding fragments thereof neutralize or inhibit PACAP activation of at least one of PAC1-R, VPAC1-R, and/or VPAC2-R; neutralize or inhibit PACAP activation of each of PAC1-R, VPAC1-R, and VPAC2-R; and/or neutralize or inhibit PACAP activation of PAC1-R; and/or inhibits PACAP binding to the cell surface, e.g., via a glycosaminoglycan ("GAG"). In yet other embodiments, the anti-PACAP antibodies and antigen binding fragments thereof are capable of inhibiting PACAP binding to at least one of PAC1-R, VPAC1-R, and/or VPAC2-R; are capable of inhibiting PACAP binding to each of PAC1-R, VPAC1-R, and/or VPAC2-R; or are capable of inhibiting PACAP binding to PAC1-R. In other embodiments, the anti-PACAP antibodies and antigen binding fragments thereof inhibit PACAP-induced cAMP production. In yet other embodiments, the anti-PACAP antibodies and antigen binding fragments thereof, alone or in combination, when administered to a subject, e.g., a human, reduce PACAP-induced vasodilation, photophobia, mast cell degranulation, and/or neuronal activation. In related embodiments, the human or humanized anti-PACAP antibodies and antigen binding fragments thereof are suitable for treating a human subject having an acute, episodic or chronic condition associated with increased vasodilation, photophobia, mast cell degranulation, and/or neuronal activation.

In another embodiment, the method provides a eukaryotic host cell that is mammalian selected from the group consisting of baby hamster kidney ("BHK") cells; chinese hamster ovary ("CHO") cells; mouse sertoli cells ("TM4" cells); African green monkey kidney cells ("VERO-76" cells); human cervical carcinoma ("HELA") cells; canine kidney cells ("MDCK"); buffalo rat liver ("BRL") cells; human lung cells; human liver ("Hep G2") cells; mouse mammary tumor ("MMT") cells; TRI cells; MRC 5 cells;

and FS4 cells. Preferably, the mammalian host cell is a CHO cell. More preferably, the mammalian host cell is a CHO K1 cell.

In a preferred embodiment, the anti-PACAP antibodies and antigen binding fragments thereof do not substantially interact with (bind) to VIP. The present invention also encompasses the therapeutic use (as a monotherapy or combination therapy) and diagnostic use of such anti-PACAP antibodies and antigen binding fragments thereof.

More particularly, anti-PACAP antibodies and antigen binding fragments thereof according to the invention can include human, humanized, and chimerized antibodies and fragments thereof, as well as scFvs, camelbodies, shark antibodies, nanobodies, Immunoglobulin New Antigen Receptor ("IgNAR"), fragment antigen binding ("Fab") fragments, Fab' fragments, MetMab like antibodies, bispecific antibodies, monovalent antibody fragments, and F(ab')$_2$ fragments. Additionally, anti-PACAP antibodies and antigen binding fragments thereof according to the invention can substantially or entirely lack N-glycosylation and/or O-glycosylation. In one embodiment, the anti-PACAP antibodies and antigen binding fragments thereof comprise a human constant domain, e.g., that of IgG1, IgG2, IgG3, or IgG4 antibody or a fragment thereof. In another embodiment, the anti-PACAP antibodies and antigen binding fragments thereof may comprise an Fc region that has been modified to alter (enhance or impair) at least one of effector function, half-life, proteolysis, or glycosylation. For example, the Fc region may contain one or more mutations that alters or eliminates N- and/or O-glycosylation.

In some embodiments, anti-PACAP antibodies and antigen binding fragments thereof bind to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-9}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M, e.g., as determined by ELISA, bio-layer interferometry ("BLI"), Kinetic Exclusion Assay (KINEXA®, Sapidyne Instruments, Boise, ID), or SPR, e.g., at 250 or 37° C. Preferably, the human, humanized, or chimerized anti-PACAP antibodies and antigen binding fragments thereof bind to PACAP with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M. Preferably, the human, humanized, or chimerized anti-PACAP antibodies and antigen binding fragments thereof bind to PACAP with a $K_D$ that is less than about 100 nM, less than about 40 nM, less than about 1 nM, less than about 100 pM, less than about 50 pM, or less than about 25 pM. Alternatively, the anti-PACAP antibodies and antigen binding fragments thereof bind to PACAP with a $K_D$ that is between about 10 pM and about 100 pM. In another embodiment, the human, humanized, or chimerized anti-PACAP antibodies and antigen binding fragments thereof bind to PACAP with an off-rate ($k_{off}$) of less than or equal to $5\times10^{-4}$ s$^{-1}$, $10^{-4}$ s$^{-1}$, $5\times10^{-5}$ s$^{-1}$, or $10^{-5}$ s$^{-1}$.

In yet another embodiment, the anti-PACAP antibodies and antigen binding fragments thereof will specifically bind to the linear or conformational epitope(s) and/or compete for binding to the same linear or conformational epitope(s) on human PACAP as an anti-PACAP antibody selected from the group consisting of Ab10 and Ab20 (the specific amino acid sequences of the variable and constant regions of these anti-PACAP antibodies, and the nucleic acids that encode for such variable and constant regions, and the epitopes bound thereby as determined using alanine scanning methods are disclosed infra). In particular, the invention embraces anti-PACAP antibodies and antigen binding fragments thereof that specifically bind to the same linear or conformational epitope(s) on human PACAP as an anti-PACAP antibody selected from the group consisting of Ab10 and Ab20. As disclosed infra, in exemplary embodiments, the epitope(s) are determined using alanine scanning mutation strategy.

In yet another embodiment, the anti-PACAP antibodies and antigen binding fragments thereof include human, humanized or chimerized anti-PACAP antibodies or antibody fragments which bind to the identical epitopes as any one of Ab10 or Ab20 or a binding fragment of any one of the foregoing.

In yet another embodiment, the anti-PACAP antibodies and antigen binding fragments thereof include human, humanized or chimerized anti-PACAP antibodies or antibody fragments that specifically bind to an epitope on human PACAP or a fragment or variant thereof containing the corresponding amino acid residues wherein said epitope is selected from the group consisting of:
  a. at least one of residues 19, 22, 23 and 27 of human PACAP;
  b. at least one of residues 19, 22, 23, 24 and 27 of human PACAP;
  c. at least two of the residues of any one of (a)-(b);
  d. at least three of the residues of any one of (a)-(b);
  e. at least four of the residues of any one of (a)-(b);
  f. all five of the residues of (b).

In yet another embodiment, the anti-PACAP antibodies and antigen binding fragments thereof include human, humanized or chimerized anti-PACAP antibodies or antibody fragments that specifically bind to an epitope on human PACAP, or a fragment or variant thereof containing the corresponding amino acid residues that includes one or more of residues 19, 22, 23 and 27 of human PACAP.

In yet another embodiment, the anti-PACAP antibodies and antigen binding fragments thereof include human, humanized or chimerized anti-PACAP antibodies or antibody fragments that specifically bind to an epitope on human PACAP or a fragment or variant thereof containing the corresponding amino acid residues that is present in human wild-type PACAP38 but not human wild-type human PACAP27.

In yet another embodiment, the anti-PACAP antibodies and antigen binding fragments thereof include human, humanized or chimerized anti-PACAP antibodies or antibody fragments that specifically bind to an which specifically binds to an epitope on human PACAP or a fragment or variant thereof containing the corresponding amino acid residues, wherein said epitope is identified by alanine scanning, e.g., as disclosed in Example 12 or another art-recognized method.

In yet another embodiment, the anti-PACAP antibodies and antigen binding fragments thereof include human, humanized or chimerized anti-PACAP antibodies or antibody fragments that specifically bind to an epitope on human PACAP or a fragment or variant thereof containing the corresponding amino acid residues, wherein said epitope consists of the residues of (a) or (b) above.

In yet another embodiment, the anti-PACAP antibodies and antigen binding fragments thereof include human, humanized or chimerized anti-PACAP antibodies or antibody fragments which specifically binds to an epitope on human PACAP or a fragment or variant thereof containing the corresponding amino acid residues that is present in human wild-type PACAP38 and in human wild-type human PACAP27.

In yet another embodiment, the anti-PACAP antibodies and antigen binding fragments thereof include human, humanized or chimerized anti-PACAP antibodies or antibody fragments that specifically bind to human wild-type human PACAP38 but which does not bind or appreciably bind to human wild-type human PACAP27.

In yet another embodiment, the anti-PACAP antibodies and antigen binding fragments thereof include human, humanized or chimerized anti-PACAP antibodies or antibody fragments which has a $K_D$ for human PACAP38 which is at least 10 fold, 100 fold, 1,000 fold, 10,000 fold, or 100,000 fold lower (stronger) than the $K_D$ of said antibody or antibody fragment to human PACAP27.

In yet another embodiment, the anti-PACAP antibodies and antigen binding fragments thereof include human, humanized or chimerized anti-PACAP antibodies or antibody fragments which do not bind to or does not appreciably bind to human Vasoactive Intestinal Peptide ("VIP").

In yet another embodiment, the anti-PACAP antibodies and antigen binding fragments thereof include human, humanized or chimerized anti-PACAP antibodies or antibody fragments which have a $K_D$ for human PACAP which is at least 10, 100, 1,000, 10,000 or 100,000 fold less (weaker) than the $K_D$ of said antibody or antibody fragment to human VIP.

In some embodiments, the present invention provides an anti-PACAP antibodies and antigen binding fragments thereof, are preferably human, humanized, or chimerized anti-PACAP antibodies and antigen binding fragments thereof, comprising at least 2 complementarity determining regions ("CDRs"), or at least 3 CDRs, or at least 4 CDRs, or at least 5 CDRs, or all six CDRs of an anti-PACAP antibody selected from the group consisting of Ab10 and Ab20. In instances where all 6 CDRs are not present, preferably at least the $V_H$ CDR3 and $V_L$ CDR3 are present. In exemplary embodiments, the antibodies and antigen binding fragments thereof comprise the variable heavy ("$V_H$") chain and/or the variable light ("$V_L$") chain of one of Ab10 or Ab20.

In a specific embodiment, the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 404; a CDR2 sequence consisting of SEQ ID NO: 406; and a CDR3 sequence consisting of SEQ ID NO: 408; and/or (b) a variable light chain comprising a CDR1 sequence consisting of SEQ ID NO: 424; a CDR2 sequence consisting of SEQ ID NO: 426; and a CDR3 sequence consisting of SEQ ID NO: 428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 402, and/or (b) a variable light chain comprising an amino acid sequence with at least 80, 85, 90, 95, 96, 97, 98, or 99% sequence identity to SEQ ID NO: 422. In another embodiment, the anti-PACAP antibodies and antigen binding fragments thereof comprise (a) a variable heavy chain having the amino acid sequence of SEQ ID NO: 402, and/or (b) a variable light chain having the amino acid sequence of SEQ ID NO: 422. More specifically, the anti-PACAP antibodies and antigen binding fragments thereof can comprise (a) a heavy chain having the amino acid sequence of SEQ ID NO: 401, and/or (b) a light chain having the amino acid sequence of SEQ ID NO: 421.

In another specific embodiment, the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 444; a CDR2 sequence consisting of SEQ ID NO: 446; and a CDR3 sequence consisting of SEQ ID NO: 448; and/or (b) a variable light chain comprising a CDR1 sequence consisting of SEQ ID NO: 464; a CDR2 sequence consisting of SEQ ID NO: 466; and a CDR3 sequence consisting of SEQ ID NO: 468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 442, and/or (b) a variable light chain comprising an amino acid sequence with at least 80, 85, 90, 95, 96, 97, 98, or 99% sequence identity to SEQ ID NO: 462. In another embodiment, the anti-PACAP antibodies and antigen binding fragments thereof and comprise (a) a variable heavy chain having the amino acid sequence of SEQ ID NO: 442, and/or (b) a variable light chain having the amino acid sequence of SEQ ID NO: 462. More specifically, the anti-PACAP antibodies and antigen binding fragments thereof can comprise (a) a heavy chain having the amino acid sequence of SEQ ID NO: 441, and/or (b) a light chain having the amino acid sequence of SEQ ID NO: 461.

Also, in some embodiments the anti-PACAP antibodies and antigen binding fragments may comprise sequence variants of any of the disclosed antibodies which are modified by mutagenesis, e.g., affinity maturation to alter one or more properties such as binding affinity or immunogenicity.

In another embodiment, the anti-PACAP antibodies and antigen binding fragments thereof are directly or indirectly attached to another moiety, such as a detectable label or therapeutic agent.

In another embodiment, the anti-PACAP antibodies and antigen binding fragments thereof inhibit or neutralize at least one biological effect elicited by PACAP; neutralize or inhibit PACAP activation of at least one of PAC1-R, VPAC1-R, and/or VPAC2-R; neutralize or inhibit PACAP activation of each of PAC1-R, VPAC1-R, and VPAC2-R; neutralize or inhibit PACAP activation of PAC1-R; are capable of inhibiting PACAP binding to at least one of PAC1-R, VPAC1-R, and/or VPAC2-R; are capable of inhibiting PACAP binding to each of PAC1-R, VPAC1-R, and/or VPAC2-R; are capable of inhibiting PACAP binding to PAC1-R; and/or inhibits PACAP binding to the cell surface, e.g., via a GAG; inhibit PACAP-induced cAMP production; and/or when administered to a subject reduce PACAP-induced vasodilation, photophobia, mast cell degranulation, and/or neuronal activation.

In another embodiment, the human, or humanized, anti-PACAP antibodies and antigen binding fragments thereof are suitable for treating a human subject having an acute, episodic, or chronic condition associated with increased vasodilation, photophobia, mast cell degranulation, and/or neuronal activation.

In another embodiment, the anti-PACAP antibodies and antigen binding fragments thereof do not substantially interact with (i.e., bind to) VIP. Preferably, the anti-PACAP antibodies and antigen binding fragments thereof have stronger affinity for PACAP as compared to VIP, i.e., although there is some cross-reactivity, the antibodies preferentially bind to PACAP as compared to VIP. For example, the affinity of said antibodies and antigen binding fragments thereof to PACAP is at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or stronger than the affinity of said antibodies and antigen binding fragments thereof to VIP (e.g., the KD of said antibody or fragment for binding to human PACAP is 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, or 30000000-fold lower than the $K_D$ for binding to VIP).

In one embodiment, the anti-PACAP antibodies and antigen binding fragments thereof are attached to at least one effector moiety, e.g., which comprises a chemical linker. In another embodiment, the anti-PACAP antibodies and antigen binding fragments thereof are attached to one or more detectable moieties, e.g., which comprise a fluorescent dye, enzyme, substrate, bioluminescent material, radioactive material, chemiluminescent moiety, or mixtures thereof.

In one embodiment, the anti-PACAP antibodies and antigen binding fragments thereof are attached to one or more functional moieties.

The invention also contemplates antibodies, e.g., anti-idiotypic antibodies, produced against an anti-PACAP antibodies and antigen binding fragments thereof as described above. Furthermore, the invention provides a method of using the anti-idiotypic antibody to monitor the in vivo levels of said anti-PACAP antibodies and antigen binding fragments thereof in a subject or to neutralize said anti-PACAP antibody in a subject being administered said anti-PACAP antibody or antigen binding fragment thereof.

Moreover, the present invention encompasses a composition suitable for therapeutic, prophylactic, or a diagnostic use comprising a therapeutically, prophylactically, or diagnostically effective amount of at least one anti-PACAP antibody or antigen binding fragment as described herein. In particular, compositions and dosage forms containing the subject anti-PACAP antibodies or binding fragments thereof for use in treating or preventing migraine or other headache indications are provided herein. Also provided herein are dosage forms containing the subject anti-PACAP antibodies or binding fragments thereof for use in treating or preventing photophobia. The composition may be suitable for subcutaneous administration, intra-muscular administration, and/or intravenous administration. The composition may be lyophilized. In some embodiments, the composition further comprises a pharmaceutically acceptable diluent, carrier, solubilizer, emulsifier, preservative, or mixture thereof.

Additionally, in some embodiments, the composition further comprises another active agent, e.g., a chemotherapeutic, an analgesic, an anti-inflammatory, an immunosuppressant, a cytokine, an antiproliferative, and an antiemetic. Preferably, the other therapeutic agent is an analgesic, e.g., an NSAID, an opioid analgesic, an antibody (e.g., an anti-human Nerve Growth Factor ("NGF") antibody or antibody fragment; or an anti-human CGRP or anti-human CGRP-receptor antibody or antibody fragment); or a non-antibody biologic, such as an NGF or CGRP polypeptide fragment or conjugate; or BOTOX® (Botulinum toxin). Suitable NSAIDs for use in combination with the subject anti-PACAP antibodies include, but are not limited to, a cyclooxygenase 1 and/or cyclooxygenase 2 inhibitor; propionic acid derivatives including ibuprofen, naproxen, naprosyn, diclofenac, and ketoprofen; acetic acid derivatives including tolmetin and sulindac; fenamic acid derivatives including mefenamic acid and meclofenamic acid; biphenylcarboxylic acid derivatives including diflunisal and flufenisal; and oxicams including piroxim, sudoxicam, and isoxicam. Suitable opioid analgesics for use in combination with the subject anti-PACAP antibodies include, e.g., codeine, dihydrocodeine, morphine or a morphine derivative or pharmaceutically acceptable salt thereof, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, or pharmaceutically acceptable salts thereof. The combined administration of the opioid analgesic and the anti-PACAP antibody or antigen binding fragment thereof may increase the analgesic effect elicited thereby.

The present invention further contemplates an isolated nucleic acid sequence or nucleic acid sequences encoding an anti-PACAP antibody or antigen binding fragment described herein, as well as a vector or vectors containing these isolated nucleic acid sequence or sequences.

Additionally, the invention provides a host cell comprising these isolated nucleic acid sequence or sequences or the vector or set forth above. The host cell may be a eukaryotic host cell that is mammalian, selected from the group consisting of baby hamster kidney ("BHK") cells; chinese hamster ovary ("CHO") cells; mouse sertoli cells ("TM4" cells); African green monkey kidney cells ("VERO-76" cells); human cervical carcinoma ("HELA") cells; canine kidney cells ("MDCK"); buffalo rat liver ("BRL") cells; human lung cells; human liver ("Hep G2") cells; mouse mammary tumor ("MMT") cells; TRI cells; MRC 5 cells; and FS4 cells. Preferably, the mammalian host cell is a CHO cell. More preferably, the mammalian host cell is a CHO K1 cell. The host cell may be a prokaryotic cell, i.e., bacterial cell, or a eukaryotic cell, including a mammalian, fungal, yeast, avian, or insect cell. In one embodiment, the host cell is a filamentous fungus or is a yeast cell. Preferably, the yeast species is of the genus *Pichia*. Most preferably, the species of *Pichia* is selected from *Pichia pastoris, Pichia methanolica*, and *Hansenula polymorpha (Pichia angusta)*.

The invention further provides a method of expressing anti-PACAP antibodies and antigen binding fragments thereof, typically human, humanized, or chimeric antibodies and antigen binding fragments thereof, the method comprising culturing the host cell described herein under conditions that provide for expression of said antibody or antigen binding fragment thereof. The host cell may be a cell culture, such as a Chinese hamster ovary ("CHO") cell or a polyploid yeast culture that stably expresses and secretes into the culture medium at least 10-25 mg/liter of said antibody or antigen binding fragment thereof. The polyploid yeast may be made by a method that comprises: (i) introducing at least one expression vector containing one or more heterologous polynucleotides encoding said antibody operably linked to a promoter and a signal sequence into a haploid yeast cell; (ii) producing by mating or spheroplast fusion a polyploid yeast from said first and/or second haploid yeast cell; (iii) selecting polyploid yeast cells that stably express said antibody; and (iv) producing stable polyploid yeast cultures from said polyploid yeast cells that stably express said antibody into the culture medium. Preferably, the yeast species is of the genus *Pichia*.

In other embodiments, the mammalian cell culture may be made by a method that comprises: (i) introducing at least one expression vector containing one or more heterologous polynucleotides encoding said antibody operably linked to a promoter and a signal sequence into a mammalian cell; (ii) producing single cells for culturing to express one or more heterologous polynucleotides encoding said antibody; (iii) selecting a mammalian cell that stably expresses said antibody; and (iv) producing cell cultures from said mammalian cell that stably expresses said antibody into the culture medium. Preferably, the mammalian species are CHO cells.

The invention further relates to the therapeutic and diagnostic uses of anti-PACAP antibodies and antigen binding fragments thereof, preferably a human antibody, humanized antibody, or chimeric antibody, or a fragment thereof.

In one embodiment, the invention provides a method for blocking, inhibiting, or neutralizing one or more biological effects associated with PACAP in a subject comprising administering to a subject an effective amount of a human or humanized or chimerized anti-PACAP antibody or antigen binding fragment thereof that antagonizes, inhibits, neutralizes, or blocks at least one biological effect associated with human PACAP. In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In another embodiment, the invention provides a method for blocking, inhibiting, or neutralizing one or more biological effects associated with PACAP in a subject comprising administering to a subject an effective amount of a human, humanized, or chimerized anti-PACAP antibody or antigen binding fragment thereof that antagonizes, inhibits, neutralizes, or blocks at least one biological effect associated with human PACAP and that does not substantially interact with (bind) VIP, e.g., the anti-PACAP antibody or antigen binding fragment thereof has stronger affinity for PACAP as compared to VIP, i.e., although there is some cross-reactivity, the antibodies preferentially bind to PACAP as compared to VIP. For example, the affinity of said antibody or antigen binding fragment thereof to PACAP is at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or higher than the affinity of said antibody or antigen binding fragment thereof to VIP (e.g., the KD of said antibody or fragment for binding to human PACAP is 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or lower than the $K_D$ for binding to VIP). In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In yet another embodiment, the invention provides a method for blocking, inhibiting, or neutralizing one or more biological effects associated with PACAP in a subject comprising administering to a subject an effective amount of a human, humanized, or chimerized anti-PACAP antibody or antigen binding fragment thereof that inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; is capable of inhibiting PACAP binding to at least one of PAC1-R, VPAC1-R, and/or VPAC2-R; is capable of inhibiting PACAP binding to each of PAC1-R, VPAC1-R, and/or VPAC2-R; is capable of inhibiting PACAP binding to PAC1-R; and/or is capable of inhibiting PACAP binding to the cell surface, e.g., via GAG; inhibits PACAP-induced cAMP production; and/or when administered to a subject reduces PACAP-induced vasodilation, photophobia, mast cell degranulation, and/or neuronal activation. In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In another embodiment, the invention provides a method for treating or preventing the onset, frequency, severity, or duration of headache or migraine in a subject comprising administering to a subject an effective amount of a human, humanized, or chimerized anti-PACAP antibody or antigen binding fragment thereof that inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; is capable of inhibiting PACAP binding to at least one of PAC1-R, VPAC1-R, and/or VPAC2-R; is capable of inhibiting PACAP binding to each of PAC1-R, VPAC1-R, and/or VPAC2-R; is capable of inhibiting PACAP binding to PAC1-R; and/or is capable of inhibiting PACAP binding to the cell surface, e.g., via GAG; inhibits PACAP-induced cAMP production; and/or when administered to a subject reduces PACAP-induced vasodilation, photophobia, mast cell degranulation, and/or neuronal activation. In another embodiment, the invention provides a method for treating or preventing in a human subject an acute, episodic, or chronic condition associated with increased vasodilation, photophobia, mast cell degranulation, and/or neuronal activation.

In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20. The epitope can be identified using an alanine scanning mutation strategy, for example.

In a specific embodiment, the headache or migraine treated and/or prevented by administration of the subject anti-PACAP antibodies and antigen binding fragments thereof is selected from migraine with or without aura, hemiplegic migraine, cluster headache, migrainous neuralgia, chronic headache, and tension headache.

In another specific embodiment, the subject has a ocular disorder associated with photophobia selected from the group consisting of achromatopsia, aniridia, photophobia caused by an anticholinergic drug, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma iritis, optic neuritis, pigment dispersion syndrome, pupillary dilation (naturally or chemically induced), retinal detachment, scarring of the cornea or sclera, and uveitis.

In another specific embodiment, the subject has a nervous system-related or neurological condition associated with photophobia selected from the group consisting of autism spectrum disorders, chiari malformation, dyslexia, encephalitis including myalgic encephalomyelitis (also known as "chronic fatigue syndrome"), meningitis, subarachnoid hemorrhage, tumor of the posterior cranial fossa, ankylosing spondylitis, albinism, ariboflavinosis, benzodiazepines (long term use of or withdrawal from benzodiazepines), chemotherapy, chikungunya, cystinosis, Ehlers-Danlos syndrome, hangover, influenza, infectious mononucleosis, magnesium deficiency, mercury poisoning, migraine, rabies, and tyrosinemia type II (also known as "Richner-Hanhart syndrome").

In another specific embodiment, the subject has a photophobia-associated disorder selected from the group consisting of migraine (with or without aura), iritis, uveitis, meningitis, depression, bipolar disorder, cluster headache or anther trigeminal autonomic cephalalgia ("TAC") or blepharospasm, depression, agoraphobia, Post-Traumatic Stress Disorder ("PTSD"), traumatic brain injury, and bipolar disorder.

In another embodiment, the invention provides a method for neutralizing PACAP-induced PAC1-R, VPAC1-R, and/or VPAC2-R signaling, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In another embodiment, the invention provides a method for inhibiting PACAP-induced cAMP production, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In yet another embodiment, the invention provides a method for inhibiting PACAP-induced vasodilation, photophobia, mast cell degranulation, and/or neuronal activation, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20.

In yet another embodiment, the invention provides a method for treating or preventing a condition associated with elevated PACAP levels in a subject, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10 or Ab20. The epitope can be identified using an alanine scanning mutation strategy, for example.

Exemplary anti-PACAP antibodies and antigen binding fragments thereof suitable for use in this invention comprise a $V_H$ chain having an amino acid sequence with at least 80, 85, 90, 95, 96, 97, 98, 99 or 100% sequence identity to a $V_H$ chain selected from SEQ ID NO: 402 and 442, and/or a $V_L$ chain having an amino acid sequence with at least 80, 85, 90, 95, 96, 97, 98, 99, or 100% sequence identity to a $V_L$ chain selected from selected from SEQ ID NO: 422 and 462, and/or at least 2, 3, 4, 5, or all 6 CDRs comprised therein.

In one embodiment, the anti-PACAP antibody or antigen binding fragment thereof employed in the methods binds to PACAP27 and/or PACAP38 and blocks PACAP27 and/or PACAP38 binding to PAC1-R, VPAC1-R, and/or VPAC2-R.

In another embodiment, the anti-PACAP antibody or antigen binding fragment thereof employed in the methods binds to PACAP27 and/or PACAP38 and blocks PACAP27 and/or PACAP38 binding to each of PAC1-R, VPAC1-R, and VPAC2-R. Preferably, the anti-PACAP antibody or antigen binding fragment thereof binds to PACAP27 and/or PACAP38 and blocks PACAP27 and/or PACAP38 binding to PAC1-R.

More particularly, anti-PACAP antibodies and antigen binding fragments thereof employed in the methods according to the invention may include human, humanized, and chimerized antibodies and fragments thereof, as well as scFvs, camelbodies, shark antibodies, nanobodies, IgNAR, Fab fragments, Fab' fragments, MetMab like antibodies, bispecific antibodies, monovalent antibody fragments, and F(ab')$_2$ fragments. Additionally, the anti-PACAP antibody or antigen binding fragment thereof employed by the methods according to the invention may substantially or entirely lack N-glycosylation and/or O-glycosylation. In one embodiment, the anti-PACAP antibody or antigen binding fragment thereof used in the encompassed methods comprises a human constant domain, e.g., an IgG1, IgG2, IgG3, or IgG4 antibody. In another embodiment, the anti-PACAP antibody or antigen binding fragment thereof comprises an Fc region that has been modified to alter (enhance or impair) at least one of effector function, half-life, proteolysis, or glycosylation. For example, the Fc region may contain one or more mutations that alters or eliminates N- and/or O-glycosylation.

In one embodiment, the subject methods employ an anti-PACAP antibody or antigen binding fragment thereof that binds to PACAP with a $K_D$ of less than or equal to $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-9}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, or $10^{-13}$ M. Preferably, the human, humanized, or chimerized anti-PACAP antibody or antigen binding fragment thereof binds to PACAP with a $K_D$ of less than or equal to $5 \times 10^{-10}$ M, $10^{-10}$ M, $5 \times 10^{-11}$ M, $10^{-11}$ M, $5 \times 10^{-12}$ M, or $10^{-12}$ M. More preferably, the methods employ a human, humanized, or chimerized anti-PACAP antibody or antigen binding fragment thereof that binds to PACAP with a $K_D$ that is less than about 100 nM, less than about 40 nM, less than about 1 nM, less than about 100 pM, less than about 50 pM, or less than about 25 pM. Alternatively, the anti-PACAP antibody or antigen binding fragment thereof binds to PACAP with a $K_D$ that is between about 10 pM and about 100 pM. In another embodiment, the human, humanized or chimerized anti-PACAP antibody or antigen binding fragment thereof binds to PACAP with an off-rate ($k_{off}$) of less than or equal to $5 \times 10^{-4}$ s$^{-1}$, $10^{-4}$ s$^{-1}$, $5 \times 10^{-5}$ s$^{-1}$, or $10^{-5}$ s$^{-1}$.

In another embodiment, the anti-PACAP antibody or antigen binding fragment thereof used in the subject methods is directly or indirectly attached to another moiety, such as a detectable label or therapeutic agent; is attached to at least one effector moiety, e.g., which comprises a chemical linker; and/or is attached to one or more detectable moieties, e.g., which comprises a fluorescent dye, enzyme, substrate, bioluminescent material, radioactive material, chemiluminescent moiety, or mixtures thereof; and/or is attached to one or more functional moieties.

In another embodiment, the method further comprises administering separately or co-administering another agent, e.g., selected from a chemotherapeutic, an analgesic, an anti-inflammatory, an immunosuppressant, a cytokine, an antiproliferative, and an antiemetic. Preferably, the other therapeutic agent is an analgesic, e.g., an NSAID (such as a cyclooxygenase 1 and/or cyclooxygenase 2 inhibitor; propionic acid derivatives including ibuprofen, naproxen, naprosyn, diclofenac, and ketoprofen; acetic acid derivatives including tolmetin and sulindac; fenamic acid derivatives including mefenamic acid and meclofenamic acid; biphenylcarboxylic acid derivatives including diflunisal and flufenisal; and oxicams including piroxim, sudoxicam, and isoxicam), an opioid analgesic (such as morphine or a morphine derivative or pharmaceutically acceptable salt thereof; codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene and pentazocine or pharmaceutically acceptable salts thereof), another antibody (such as an anti-NGF antibody or antibody fragment or an anti-CGRP or anti-CGRP receptor ("anti-CGRP-R") antibody or antibody fragment), or a non-antibody biologic, e.g., BOTOX®.

In one embodiment, the combined administration of the opioid analgesic and the anti-PACAP antibody or antigen binding fragment thereof increase the analgesic effect as compared to either the opioid analgesic or the anti-PACAP antibody or antigen binding fragment thereof administered alone.

In another embodiment, the subject has previously been treated ("a treated subject") and received an anti-CGRP or anti-CGRP-R antibody or antibody fragment thereof. The treated subject may be a migraineur who did not adequately respond to anti-CGRP or anti-CGRP-R antibody treatment ("poor responder"). Alternatively, the treated subject may have previously received at least one anti-CGRP or anti-CGRP-R antibody or antibody fragment thereof administration, and has elicited an immune response to said antibody or antibody fragment thereof. Exemplary anti-CGRP and anti-CGRP-R antibodies and antibody fragments thereof are disclosed in U.S. Pat. Nos. 9,102,731; 9,115,194; 8,734,802; 8,623,366; 8,597,649; and 8,586,045; and U.S. Patent Application Publication Nos. 20120294822, 20120294802, and 20120294797, the contents of each which are incorporated by reference in their entireties herein.

An aspect of the present invention in general relates to anti-PACAP antibodies and antigen binding fragments thereof, preferably human, humanized, or chimerized anti-human PACAP antibodies or antibody fragments thereof that may antagonize, inhibit, neutralize or block at least one biological effect associated with human PACAP.

Moreover, the invention pertains to anti-PACAP antibodies and antigen binding fragments thereof that may include human, humanized or chimerized anti-PACAP antibodies or antibody fragments thereof that specifically compete for binding to human PACAP with an antibody that may be selected from the group consisting of Ab10 and Ab20, or an antigen-binding fragment thereof.

Additionally, the anti-PACAP antibodies and antigen binding fragments of the invention may include human, humanized or chimerized anti-PACAP antibodies or antibody fragments that may specifically bind to at least one linear or conformational epitope bound by an anti-PACAP antibody that may be selected from the group consisting of Ab10 and Ab20, or an antigen-binding fragment thereof. The epitope may be identified by alanine scanning, e.g., as disclosed in Example 12 or another art-recognized method.

Also, in another embodiment, the anti-PACAP antibodies and antigen binding fragments thereof of the invention may include human, humanized or chimerized anti-PACAP antibodies or antibody fragments thereof which bind to the identical epitopes as any one of Ab10 or Ab20, or an antigen-binding fragment thereof. The epitope may be identified by alanine scanning, e.g., as disclosed in Example 12 or another art-recognized method.

In a further embodiment of the invention, the anti-PACAP antibodies or antigen binding fragments thereof of the invention may include human, humanized or chimerized anti-PACAP antibodies or antibody fragments which may specifically bind to an epitope on human PACAP or a fragment or variant thereof containing the corresponding amino acid residues wherein said epitope includes one or more of the following:
  (i) at least one of residues 19, 22, 23 and 27 of human PACAP;
  (ii) at least one of residues 19, 22, 23, 24 and 27 of human PACAP;
  (iii) at least two of the residues of any one of (i)-(ii);
  (iv) at least three of the residues of any one of (i)-(ii);
  (v) at least four of the residues of any one of (i)-(ii); and
  (v) all five of the residues of (ii).

In a specific embodiment of the invention, anti-PACAP antibodies or antigen binding fragments thereof of the invention may include human, humanized or chimerized anti-PACAP antibodies or antibody fragments which specifically bind to an epitope on human PACAP, or a fragment or variant thereof that may contain the corresponding amino acid residues that may include residues 19, 22, 23 and 27 of human PACAP. Also, in another embodiment of the invention, the anti-PACAP antibodies or antigen binding fragments thereof may include human, humanized or chimerized anti-PACAP antibodies or antibody fragments thereof, whichspecifically bind to an epitope on human PACAP (or a fragment or variant thereof that may contain the corresponding amino acid residues that may be present in human wild-type PACAP38) but not human wild-type human PACAP27. The epitope may be identified by alanine scanning, e.g., as disclosed in Example 12 or another art-recognized method.

In an additional embodiment of the invention, anti-PACAP antibodies or antigen binding fragments thereof of the invention may include human, humanized or chimerized anti-PACAP antibodies or antibody fragments thereof which may specifically bind to an epitope on human PACAP or a fragment or variant thereof that contain the corresponding amino acid residues, wherein said epitope may consist of the residues of (i)-(ii) as described above. The epitope may be identified by alanine scanning, e.g., as disclosed in Example 12 or another art-recognized method.

Another aspect of the invention also embraces anti-PACAP antibodies or antigen binding fragments thereof that may include human, humanized or chimerized anti-PACAP antibodies or antibody fragment which specifically bind to an epitope on human PACAP (or a fragment or variant thereof containing the corresponding amino acid residues) that may be present in human wild-type PACAP38 and in human wild-type human PACAP27.

Additionally, the anti-PACAP antibodies or antigen binding fragments thereof may include human, humanized or chimerized anti-PACAP antibodies or antibody fragments thereof, which may specifically bind to human wild-type human PACAP38 but which may not bind or appreciably bind to human wild-type human PACAP27. In another embodiment of the invention, the anti-PACAP antibodies and antigen binding fragments thereof of the invention may include human, humanized or chimerized anti-PACAP antibodies or antibody fragments thereof which may have a $K_D$ for human PACAP38 which may be at least 10, 100, 1000, 10,000 or 100,000 fold lower (stronger) than the $K_D$ of said antibody or antibody fragment to human PACAP27.

In another embodiment, the anti-PACAP antibodies and antigen binding fragments thereof of the invention may include human, humanized or chimerized anti-PACAP antibodies or antibody fragments thereof which do not bind to or do not appreciably bind to human Vasoactive Intestinal Peptide ("VIP"). Said anti-PACAP antibodies or antibody fragments thereof may have a $K_D$ for human PACAP which may be at least 10, 100, 1000, 10,000 or 100,000 fold lower (stronger) than the $K_D$ of said antibody or antibody fragment to human VIP.

In embodiments of the invention, the human, humanized or chimerized anti-PACAP antibody or antibody fragment as disclosed herein, may inhibit or neutralize at least one biological effect elicited by human PACAP.

In another embodiment, the anti-PACAP antibodies and antigen binding fragments thereof of the invention may include human, humanized or chimerized anti-PACAP antibodies or antibody fragments thereof that may comprise one or more of the following properties: (a) inhibit, block or prevent PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (b) inhibit, block or prevent PACAP activation of each of PAC1-R, VPAC1-R, and VPAC2-R; (c) inhibit, block or prevent PACAP activation of PAC1-R; (d) capable of inhibiting PACAP binding to at least one of PAC1-R, VPAC1-R, and/or VPAC2-R; (e) are capable of inhibiting PACAP binding to each of PAC1-R, VPAC1-R, and/or VPAC2-R; (f) are capable of inhibiting PACAP binding to PAC1-R-expressing cells; (g) are capable of inhibiting PACAP binding to VPAC1-R-expressing cells; (h) may be capable of inhibiting PACAP binding to VPAC2-R-expressing cells; (i) inhibit PACAP binding to the cell surface, e.g. via a glycosaminoglycan ("GAG"); (j) do not inhibit PACAP-mediated binding of such antibody to the cell surface, e.g., via a GAG; (k) inhibit PACAP-mediated binding of such antibody to the cell surface, e.g., via a glycosaminoglycan ("GAG"); (l) inhibit, block or prevent PACAP-induced cAMP production; (m) when administered to a subject reduce PACAP-induced vasodilation; and/or (n) when administered to a subject reduces PACAP-induced photophobia, mast cell degranulation and/or neuronal activation.

The invention may also pertain to anti-PACAP antibodies and antigen binding fragments thereof that may be preferably human, humanized or chimerized anti-PACAP antibodies or antibody fragments which may be substantially non-immunogenic in human subjects. The invention may also relates to anti-PACAP antibodies and antigen binding fragments thereof that may be preferably human, humanized or chimerized anti-PACAP antibodies or antibody fragments, which may be suitable for treating a human subject having an acute, episodic or chronic condition associated with increased vasodilation, photophobia, mast cell degranulation and/or neuronal activation.

Another embodiment of the invention relates to anti-PACAP antibodies and antigen binding fragments thereof that may be preferably human, humanized or chimerized anti-PACAP antibodies or antibody fragments that specifically bind to the same or overlapping linear or conformational epitope(s) and/or may compete for binding to the same or overlapping linear or conformational epitope(s) on human PACAP as an anti-PACAP antibody that may be selected from Ab10 or Ab20. Yet another embodiment of the invention relates to anti-PACAP antibodies and antigen binding fragments thereof, preferably human, humanized or chimerized anti-PACAP antibodies or antibody fragments, that may specifically bind to the same or overlapping linear or conformational epitope(s) on human PACAP as an anti-PACAP antibody that may be selected from Ab10 or Ab20. Said epitope as described herein bound by said antibody or antibody fragment of the invention may be identified by alanine scanning, e.g., as disclosed in Example 12 or another art-recognized method.

The invention may also embody anti-PACAP antibodies and antigen binding fragments thereof that may be preferably human, humanized or chimerized anti-PACAP antibodies or antibody fragments that may comprise at least 2 complementarity determining regions ("CDRs") of an anti-PACAP antibody that may be selected from Ab10 or Ab20, preferably including the $V_H$ CDR3 and/or the $V_L$ CDR3. Another additional embodiment of the invention may include anti-PACAP antibodies and antigen binding fragments thereof that may be preferably human, humanized or chimerized anti-PACAP antibodies or antibody fragments that may comprise at least 3, at least 4, at least 5, or all 6 CDRS of an anti-PACAP antibody that may be selected from Ab10 or Ab20. In instances where all 6 CDRs may not be present, preferably at least the $V_H$ CDR3 and the $V_L$ CDR3 may be present.

In another embodiment of the invention, anti-PACAP antibodies and antigen binding fragments thereof, preferably human, humanized or chimerized anti-PACAP antibodies or antibody fragments thereof, may comprise a sequence variant of any of the antibodies or antibody fragments of the invention that may contain one or more modifications that may putatively alter binding affinity or immunogenicity.

In a specific embodiment, the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 404; a CDR2 sequence consisting of SEQ ID NO: 406; and a CDR3 sequence consisting of SEQ ID NO: 408; and/or (b) a variable light chain comprising a CDR1 sequence consisting of SEQ ID NO: 424; a CDR2 sequence consisting of SEQ ID NO: 426; and a CDR3 sequence consisting of SEQ ID NO: 428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 402, and/or (b) a variable light chain comprising an amino acid sequence with at least 80, 85, 90, 95, 96, 97, 98, or 99% sequence identity to SEQ ID NO: 422. In another embodiment, the anti-PACAP antibodies and antigen binding fragments thereof comprise (a) a variable heavy chain having the amino acid sequence of SEQ ID NO: 402, and/or (b) a variable light chain having the amino acid sequence of SEQ ID NO: 422. More specifically, the anti-PACAP antibodies and antigen binding fragments thereof can comprise (a) a heavy chain having the amino acid sequence of SEQ ID NO: 401, and/or (b) a light chain having the amino acid sequence of SEQ ID NO: 421.

In another specific embodiment, the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 444; a CDR2 sequence consisting of SEQ ID NO: 446; and a CDR3 sequence consisting of SEQ ID NO: 448; and/or (b) a variable light chain comprising a CDR1 sequence consisting of SEQ ID NO: 464; a CDR2 sequence consisting of SEQ ID NO: 466; and a CDR3 sequence consisting of SEQ ID NO: 468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 442, and/or (b) a variable light chain comprising an amino acid sequence with at least 80, 85, 90, 95, 96, 97, 98, or 99% sequence identity to SEQ ID NO: 462. In another embodiment, the anti-PACAP antibodies and antigen binding fragments thereof and comprise (a) a variable heavy chain having the amino acid sequence of SEQ ID NO: 442, and/or (b) a variable light chain having the amino acid sequence of SEQ ID NO: 462. More specifically, the anti-PACAP antibodies and antigen binding fragments thereof can comprise (a) a heavy chain having the amino acid sequence of SEQ ID NO: 441, and/or (b) a light chain having the amino acid sequence of SEQ ID NO: 461.

Additionally, the anti-PACAP antibodies and antigen binding fragments of the invention may include human, humanized or chimerized anti-PACAP antibodies or antibody fragments wherein the antibodies or antibody fragments may be selected from the group consisting of scFvs, camelbodies, nanobodies, Immunoglobulin New Antigen Receptor ("IgNAR"), fragment antigen binding ("Fab") fragments, Fab' fragments, MetMab like antibodies, monovalent antibody fragments, and F(ab')$_2$ fragments. In another embodiment, the anti-PACAP antibodies and antigen binding fragments of the invention, preferably human, humanized or chimerized anti-PACAP antibodies or antibody fragments, may substantially or entirely lack N-glycosylation and/or O-glycosylation. Also, the invention embraces an embodiment of the invention wherein the anti-PACAP antibodies and antigen binding fragments of the invention, preferably human, humanized or chimerized anti-PACAP antibodies or antibody fragments, may comprise a human constant domain, e.g. that of an IgG1, IgG2, IgG3, or IgG4 antibody or fragment thereof.

An additional embodiment of the invention relates to anti-PACAP antibodies and antigen binding fragments, preferably human, humanized or chimerized anti-PACAP antibodies or antibody fragments, wherein said antibodies or antibody fragments may comprise an Fc region that may have been modified to alter at least one of effector function, half-life, proteolysis, or glycosylation, e.g., wherein the Fc region may contain one or more mutations that may alter or eliminate N- and/or O-glycosylation.

In yet another embodiment of the invention, anti-PACAP antibodies and antigen binding fragments, preferably human, humanized or chimerized anti-PACAP antibodies or antibody fragments, may bind to PACAP with a binding affinity ($K_D$) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M, e.g., as may be determined by ELISA, bio-layer interferometry ("BLI"), KINEXA or surface plasmon resonance at 250 or 37° C. Also, another embodiment of the invention pertains to anti-PACAP antibodies and antigen binding fragments, preferably human, humanized or chimerized anti-PACAP antibodies or antibody fragments, wherein said antibodies or antibody fragments may bind to PACAP with a binding affinity ($K_D$) of less than or equal to $5\times10^{-10}$ M, $10^{-10}$ M, $5\times10^{-11}$ M, $10^{-11}$ M, $5\times10^{-12}$ M, or $10^{-12}$ M. Additionally, the anti-PACAP antibodies and antigen binding fragments, preferably human, humanized or chimerized anti-PACAP antibodies or antibody fragments, of the invention may include anti-PACAP antibodies or antibody fragments which may bind to PACAP with an off-rate ($k_{off}$) of less than or equal to $5\times10^{-4}$ s$^{-1}$, $10^{-4}$ s$^{-1}$, $5\times10^{-5}$ s$^{-1}$, or $10^{-5}$ s$^{-1}$.

Another embodiment of the invention relates to anti-PACAP antibodies and antigen binding fragments, preferably human, humanized or chimerized anti-PACAP antibodies or antibody fragments, wherein said antibodies and antibody fragments may be directly or indirectly attached to a detectable label or therapeutic agent. An additional embodiment of the invention pertains to anti-PACAP antibodies and antigen binding fragments, preferably human, humanized or chimerized anti-PACAP antibodies or antibody fragments that when administered to a subject may inhibit or neutralize at least one biological effect elicited by PACAP. The anti-PACAP antibodies and antigen binding fragments, preferably human, humanized or chimerized anti-PACAP antibodies or antibody fragments, of the invention may bind to PACAP27 and/or PACAP38 and may block PACAP27 and/or PACAP38 binding to PAC1-R, VPAC1-R, and/or VPAC2-R; may bind to PACAP27 and/or PACAP38 and may block PACAP27 and/or PACAP38 binding to each of PAC1-R, VPAC1-R, and VPAC2-R; and/or may bind to PACAP27 and/or PACAP38 and may block PACAP27 and/or PACAP38 binding to PAC1-R-expressing cells, VPAC1-R-expressing cells, and/or VPAC2-R-expressing cells.

In another embodiment of the invention, the anti-PACAP antibodies and antigen binding fragments, preferably human, humanized or chimerized anti-PACAP antibodies or antibody fragments, of the invention may neutralize or inhibit PACAP activation of at least one of PAC1-R, VPAC1-R, or VPAC2-R; may neutralize or inhibit PACAP activation of each of PAC1-R, VPAC1-R, and VPAC2-R; may neutralize or inhibit PACAP activation of PAC1-R; may be capable of inhibiting or preventing PACAP binding to at least one of PAC1-R, VPAC1-R, or VPAC2-R; may be capable of inhibiting or preventing PACAP binding to each of PAC1-R, VPAC1-R, and VPAC2-R; may be capable of inhibiting or preventing PACAP binding to PAC1-R-expressing cells, VPAC1-R-expressing cells, and/or VPAC2-R-expressing cells; may inhibit or block PACAP-induced cAMP production; may, when administered to a subject, reduce PACAP-induced vasodilation, photophobia, mast cell degranulation and/or neuronal activation.

In yet another embodiment of the invention, anti-PACAP antibodies and antigen binding fragments, preferably human, humanized or chimerized anti-PACAP antibodies or antibody fragments, may bind to PACAP with a $K_D$ that may be less than about 100 nM; with a $K_D$ that may be less than about 40 nM; with a $K_D$ that may be less than about 100 pM; with a $K_D$ that may be less than about 50 pM; with a $K_D$ that may be less than about 25 pM; or with a $K_D$ that may be between about 10 pM and about 100 pM. The invention also embraces anti-PACAP antibodies and antigen binding fragments, preferably human, humanized or chimerized anti-PACAP antibodies or antibody fragments, that may have stronger binding affinity for PACAP as compared to VIP and/or that may not bind to VIP, e.g., wherein said antibodies or antibody fragments thereof may have an affinity to PACAP that may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said antibody or antibody fragment to VIP.

In another embodiment, the invention pertains to anti-PACAP antibodies and antigen binding fragments, preferably human, humanized or chimerized anti-PACAP antibodies or antibody fragments, that may be attached to at least one effector moiety, e.g., wherein said effector moiety may comprise a chemical linker. In another embodiment, the invention pertains to anti-PACAP antibodies and antigen binding fragments, preferably human, humanized or chimerized anti-PACAP antibodies or antibody fragments that may be attached to one or more detectable moieties, e.g., wherein said detectable moieties may comprise a fluorescent dye, enzyme, substrate, bioluminescent material, radioactive material, chemiluminescent moiety, and/or mixtures thereof. Also, the anti-PACAP antibodies and antigen binding fragments of the invention, preferably human, humanized or chimerized anti-PACAP antibodies or antibody fragments, may be attached to one or more functional moieties.

Another embodiment of the invention relates to anti-idiotypic antibodies that may be produced against anti-PACAP antibodies or antibody fragments, wherein said anti-idiotypic antibodies optionally may neutralize one or more biological effects of the anti-PACAP antibody to which it may bind. Said embodiment of the invention may also be related to a method of using said anti-idiotypic antibody to monitor the in vivo levels of said anti-PACAP antibody or antibody fragment in a subject or to neutralize the in vivo effects of said anti-PACAP antibody in a subject.

In yet another embodiment, the invention pertains to a composition that may be suitable for therapeutic, prophylactic, or a diagnostic use, whereby the composition may comprise a therapeutically, prophylactically or diagnostically effective amount of at least one anti-PACAP antibody or antibody fragment or anti-idiotypic antibody, e.g., wherein the composition may be suitable for administration via injection, topical, oral, inhalation or transdermal; may be suitable for subcutaneous, intravenous, intramuscular, topical, oral, inhalatory, intranasal, intrabuccal, vaginal, anal, transdermal, intraperitoneal, or intrathecal administration; and/or wherein the composition may be suitable for subcutaneous intravenous or intramuscular administration. The invention also embraces an embodiment of the invention wherein said composition of at least one anti-PACAP antibody or antibody fragment or anti-idiotypic antibody may be lyophilized; and/or wherein said composition may comprise a pharmaceutically acceptable diluent, carrier, solubilizer, emulsifier, preservative, or mixture thereof. Said composition of the invention may further comprise at least one other active agent, e.g., wherein the other active agent may be selected from the group consisting of a chemotherapeutic, an analgesic, an anti-inflammatory, an immunosuppressant, a cytokine, an antiproliferative, an antiemetic and/or a cytotoxin. Said composition may also be lyophilized, stabilized, and/or formulated for administration by injection.

A further embodiment of the invention embraces an isolated nucleic acid sequence or nucleic acid sequences that may encode an anti-PACAP antibody or antibody fragment or anti-idiotypic antibody, and wherein said isolated nucleic acid sequence or nucleic acid sequences may be contained within a vector or vectors. Additionally, in an embodiment of the invention, a host cell may comprise said isolated nucleic acid sequence or sequences, wherein said host cell may be a mammalian, bacterial, fungal, yeast, avian, amphibian, plant or insect cell; and/or said host cell may be a filamentous fungus or a yeast. Wherein said host cell may be a yeast cell, the yeast may be selected from the following genera: *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis;* and *Zygosaccharomyces;* or the yeast may be genus *Pichia*. In an embodiment of the invention, the yeast host cell may be selected from *Pichia pastoris, Pichia methanolica* and *Hansenula polymorpha* (*Pichia angusta*). Additionally, said host cell may be a filamentous fungus or a yeast or may be a CHO cell.

The invention also relates to a method of expressing an anti-PACAP antibody or antibody fragment that may comprise culturing any of but not limited to the host cells disclosed herein under conditions that may provide for expression of said antibody or antibody fragment. Additionally, the invention pertains to said method wherein the host cell may be a yeast cell or CHO cell that may stably express and secrete said antibody or antibody fragment. For example, said yeast cell may be a polyploid yeast that may be made by a method that may comprise: (i) introducing at least one expression vector containing one or more heterologous polynucleotides encoding said antibody operably linked to a promoter and a signal sequence into a haploid yeast cell; (ii) producing by mating or spheroplast fusion a polyploid yeast from said first and/or second haploid yeast cell; (iii) selecting polyploid yeast cells that stably express said antibody; and (iv) producing stable polyploid yeast cultures from said polyploid yeast cells that stably express said antibody into the culture medium; and said polyploid yeast may be of the genus *Pichia*. Additionally in another embodiment, the invention embraces a method of expressing an anti-PACAP antibody or antibody fragment that may comprise culturing a host cell wherein said host cell may be a mammalian cell, e.g., a CHO cell.

Additionally, the invention pertains to a method that may block, inhibit, block or neutralize one or more biological effects associated with PACAP in a subject that may comprise administering to said subject a therapeutically or prophylactically effective amount of a human, humanized or chimerized anti-PACAP antibody or antibody fragment that may antagonize, inhibit, neutralize or block at least one biological effect associated with human PACAP. Another aspect of the invention relates to a method that may block, inhibit, or neutralize one or more biological effects associated with PACAP in a subject that may comprise administering to said subject a therapeutically or prophylactically effective amount of a human, humanized or chimerized anti-PACAP antibody or antibody fragment that may antagonize, inhibit, neutralize or block at least one biological effect associated with human PACAP and that may not substantially interact with (bind) VIP.

Another aspect of the invention generally relates to a method that may block, inhibit, or neutralize one or more biological effects, e.g., vasomotor effects, associated with PACAP in a subject that may comprise administering to a subject a therapeutically or prophylactically effective amount of a human, humanized or chimerized anti-PACAP antibody or antibody fragment that may comprise one or more of the following: inhibits, blocks or neutralizes at least one biological effect elicited by PACAP; neutralizes or inhibits PACAP activation of at least one of PAC1-R, VPAC1-R, and/or VPAC2-R; inhibits, blocks or neutralizes PACAP activation of each of PAC1-R, VPAC1-R, and VPAC2-R; neutralizes or inhibits PACAP activation of PAC1-R; inhibits PACAP binding to at least one of PAC1-R, VPAC1-R, and/or VPAC2-R; inhibits PACAP binding to each of PAC1-R, VPAC1-R, and/or VPAC2-R; inhibits PACAP binding to PAC1-R-expressing cells; inhibits PACAP binding to VPAC1-R and/or VPAC2-R-expressing cells; does not inhibit PACAP-mediated binding of such antibody to the cell surface, e.g., via a glycosaminoglycan ("GAG"); inhibits PACAP binding to the cell surface, e.g.

via a glycosaminoglycan ("GAG"); inhibits PACAP-induced cAMP production; and/or, when administered to a subject, may reduce PACAP-induced vasodilation, photophobia, mast cell degranulation and/or neuronal activation.

Another embodiment of the invention relates to method that may block, inhibit, or neutralize vasodilation, e.g., vasodilation of the dural arteries, which may be associated with or may be elicited by PACAP in a subject that may comprise administering to a subject a therapeutically or prophylactically effective amount of a human, humanized or chimerized anti-PACAP antibody or antibody fragment that may block, inhibit, or neutralize vasodilation associated with, or elicited by PACAP.

Yet another embodiment of the invention pertains to a method that may treat or prevent the onset, frequency, severity or duration of headache or migraine, e.g., wherein said headache or migraine may be selected from migraine with aura, migraine without aura, hemiplegic migraine, cluster headache, migrainous neuralgia, chronic headache, chronic migraine, medication overuse headache, and tension headache, in a subject that may comprise administering to a subject in need thereof an effective amount of a human, humanized or chimerized anti-human PACAP antibody or antibody fragment that may elicit one or more of the following effects: inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; inhibits PACAP binding to at least one of PAC1-R, VPAC1-R, and/or VPAC2-R; inhibits PACAP binding to each of PAC1-R, VPAC1-R, and/or VPAC2-R; inhibits PACAP binding to PAC1-R-expressing cells; inhibits PACAP binding to VPAC1-R and/or VPAC2-R-expressing cells; inhibits PACAP-mediated binding of such antibody to the cell surface, e.g., via a GAG; inhibits PACAP binding to the cell surface, e.g. via a glycosaminoglycan ("GAG"); inhibits PACAP-induced cyclic adenosine monophosphate ("cAMP") production; and/or, when administered to a subject, reduces PACAP-induced vasodilation, photophobia, mast cell degranulation and/or neuronal activation.

Another embodiment of the invention relates to a method of treating a human subject that may have an acute, episodic or chronic condition that may be associated with at least one of increased vasodilation, photophobia, mast cell degranulation and neuronal activation or a combination of said conditions that may comprise administering to a subject in need thereof an effective amount of an antagonistic human, humanized or chimerized anti-human PACAP antibody or antibody fragment.

In yet another embodiment, the invention relates to a method that may block, inhibit, or neutralize one or more biological effects associated with PACAP in a subject that may comprise administering to a subject in need thereof an effective amount of a human, humanized or chimerized anti-PACAP antibody or antigen binding fragment that may antagonize, inhibit, neutralize, or block at least one biological effect associated with human PACAP. Also, an embodiment of the invention encompasses a method that may block, inhibit, or neutralize one or more biological effects associated with PACAP in a subject that may comprise administering to a subject in need thereof an effective amount of a human, humanized, or chimerized anti-PACAP antibody or antigen binding fragment that may antagonize, inhibit, neutralize, or block at least one biological effect associated with human PACAP and that may not substantially interact with (bind) VIP.

In another embodiment, the invention relates to a method that may block, inhibit, or neutralize one or more biological effects associated with PACAP in a subject that may comprise administering to a subject in need thereof an effective amount of a human, humanized, or chimerized anti-PACAP antibody or antigen binding fragment that (a) inhibits or neutralizes at least one biological effect elicited by PACAP; (b) neutralizes or inhibits PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (c) neutralizes or inhibits PACAP activation of each of PAC1-R, VPAC1-R, and VPAC2-R; (d) neutralizes or inhibits PACAP activation of PAC1-R; (e) inhibits PACAP binding to at least one of PAC1-R, VPAC1-R, and/or VPAC2-R; (f) inhibits PACAP binding to each of PAC1-R, VPAC1-R, and/or VPAC2-R; (g) may be capable of inhibiting PACAP binding to PAC1-R-expressing cells; (h) inhibits PACAP binding to the cell surface, e.g., via a glycosaminoglycan ("GAG") (i) inhibits PACAP-mediated binding of such antibody to the cell surface, e.g, via a GAG; (j) inhibits PACAP-induced cyclic adenosine monophosphate ("cAMP") production; and/or (k) when administered to the subject reduces PACAP-induced vasodilation, photophobia, mast cell degranulation and/or neuronal activation.

Moreover, an embodiment of the invention pertains to a method of treating or preventing the onset, frequency, severity or duration of headache or migraine, e.g., wherein the headache or migraine may be selected from migraine with aura, migraine without aura, hemiplegic migraine, cluster headache, migrainous neuralgia, chronic headache, chronic migraine, medication overuse headache, and tension headache, in a subject that may comprise administering to a subject in need thereof an effective amount of a human, humanized, or chimerized anti-human PACAP antibody or antigen binding fragment that (a) inhibits or neutralize at least one biological effect elicited by PACAP; (b) neutralizes or inhibits PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (c) neutralizes or inhibits PACAP activation of each of PAC1-R, VPAC1-R, and VPAC2-R; (d) neutralizes or inhibits PACAP activation of PAC1-R; (e) may be capable of inhibiting PACAP binding to at least one of PAC1-R, VPAC1-R, and/or VPAC2-R; (f) inhibits PACAP binding to each of PAC1-R, VPAC1-R, and/or VPAC2-R; (g) inhibits PACAP binding to PAC1-R-expressing cells; (h) inhibits PACAP binding to the cell surface, e.g., via a glycosaminoglycan ("GAG"); (i) inhibits PACAP-mediated binding of such antibody to the cell surface, e.g, via a GAG; (j) inhibits PACAP-induced cyclic adenosine monophosphate ("cAMP") production; and/or (k) when administered to the subject reduces PACAP-induced vasodilation, photophobia, mast cell degranulation and/or neuronal activation.

A further embodiment of the invention encompasses a method of treating a human subject that may have an acute, episodic or chronic condition associated with at least one of increased vasodilation, photophobia, mast cell degranulation and neuronal activation or a combination of any of above that may comprise administering to a subject in need thereof an effective amount of an antagonistic human, humanized or chimerized anti-human PACAP antibody or antigen binding fragment.

The invention also pertains to any of the methods disclosed herein that may include the administration of anti-PACAP antibody or antigen binding fragment of the invention, and wherein said anti-PACAP antibody may be a human antibody or antigen binding fragment; and/or wherein the anti-PACAP antibody may be a humanized antibody or antigen binding fragment; and/or wherein the anti-PACAP antibody may be a chimeric antibody or antigen binding fragment.

Another embodiment of the invention also relates to a method wherein an anti-PACAP antibody or antibody fragment of the invention may bind to PACAP27 and/or PACAP38 and may block PACAP27 and/or PACAP38 binding to PAC1-R, VPAC1-R, and/or VPAC2-R. Another embodiment of the invention pertains to a method wherein said anti-PACAP antibody or antibody fragment may bind to PACAP27 and/or PACAP38 and may block PACAP27 and/or PACAP38 binding to each of PAC1-R, VPAC1-R, and VPAC2-R. Yet another embodiment of the invention relates to a method wherein said anti-PACAP antibody or antibody fragment may bind to PACAP27 and/or PACAP38 and may block PACAP27 and/or PACAP38 binding to PAC1-R-expressing cells. Additionally, said anti-PACAP antibody or antibody fragment of the invention may have an affinity to PACAP that may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said antibody or antibody fragment to VIP.

The invention embraces a method that may block, inhibit, block or neutralize one or more biological effects associated with PACAP in a subject that may comprise administering to said subject a therapeutically or prophylactically effective amount of a human, humanized or chimerized anti-PACAP antibody or antibody fragment that may antagonize, inhibit, neutralize or blocks at least one biological effect associated with human PACAP, and wherein said subject may have a condition selected from the group consisting of migraine with aura, migraine without aura, hemiplegic migraines, cluster headaches, migrainous neuralgia, chronic headaches, tension headaches, general headaches, hot flush, photophobia, chronic paroxysmal hemicrania, secondary headaches due to an underlying structural problem in the head, secondary headaches due to an underlying structural problem in the neck, cranial neuralgia, sinus headaches, headache associated with sinusitis, allergy-induced headaches, allergy-induced migraines, trigeminal neuralgia, post-herpetic neuralgia, phantom limb pain, fibromyalgia, reflex sympathetic dystrophy, pain, chronic pain, inflammatory pain, post-operative incision pain, post-surgical pain, trauma-related pain, lower back pain, eye pain, tooth pain, complex regional pain syndrome, cancer pain, primary or metastatic bone cancer pain, fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptive pain, visceral pain, menstrual pain, ovarialgia, osteoarthritis pain, rheumatoid arthritis pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder ("PTSD"), anxiety disorders, autoimmune diabetes, Sjögren's syndrome, multiple sclerosis, overactive bladder, bronchial hyperreactivity, asthma, stroke, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, endothelial dysfunction, Raynaud's syndrome, coronary heart disease ("CHD"), coronary artery disease ("CAD"), heart failure, peripheral arterial disease ("PAD"), diabetes, pulmonary hypertension ("PH"), connective tissue disorder, allergic dermatitis, psoriasis, pruritus, neurogenic cutaneous redness, erythema, sarcoidosis, shock, sepsis, opiate withdrawal syndrome, morphine tolerance, and epilepsy. Additionally, said subject may have a condition selected from the group consisting of migraine, headache and a pain associated disease or condition, wherein said headache or migraine may selected from the group consisting of migraine with aura, migraine without aura, hemiplegic migraine, cluster headache, migrainous neuralgia, chronic headache, chronic migraine, medication overuse headache, and tension headache. Also, said subject may have a ocular disorder associated with photophobia selected from the group consisting of achromatopsia, aniridia, photophobia caused by an anticholinergic drug, aphakia, buphthalmos, cataracts, cone dystrophy, congenital abnormalities of the eye, viral conjunctivitis, corneal abrasion, corneal dystrophy, corneal ulcer, disruption of the corneal epithelium, ectopia lentis, endophthalmitis, eye trauma caused by disease, eye trauma caused by injury, eye trauma caused by infection, chalazion, episcleritis, glaucoma, keratoconus, optic nerve hypoplasia, hydrophthalmos, congenital glaucoma iritis, optic neuritis, pigment dispersion syndrome, pupillary dilation, retinal detachment, scarring of the cornea, sclera and uveitis. Further, said subject may have a nervous system-related or neurological condition associated with photophobia selected from the group consisting of autism spectrum disorders, Chiari malformation, dyslexia, encephalitis, meningitis, subarachnoid hemorrhage, tumor of the posterior cranial fossa, ankylosing spondylitis, albinism, ariboflavinosis, benzodiazepines, chemotherapy, chikungunya, cystinosis, Ehlers-Danlos syndrome, hangover, influenza, infectious mononucleosis, magnesium deficiency, mercury poisoning, migraine, rabies, and tyrosinemia type II. Additionally, said subject may have a photophobia associated disorder selected from the group consisting of migraine with aura, migraine without aura, iritis, uveitis, meningitis, depression, bipolar disorder, cluster headache or anther trigeminal autonomic cephalalgia ("TAC") or blepharospasm, depression, agoraphobia and bipolar disorder.

The invention additionally embraces any of the methods disclosed herein wherein an antibody of any of the methods disclosed herein may be a human, humanized, or chimerized anti-PACAP antibody or antigen binding fragment, and/or wherein the epitope bound by said antibody of any of the methods disclosed herein may be identified by alanine scanning.

The invention also embraces any of the methods disclosed herein wherein the method relates to an antibody or antibody fragment that may be a human, humanized, or chimerized anti-PACAP antibody or antibody fragment; and/or wherein the antibody or antibody fragment may be a human, humanized, or chimerized anti-PACAP antibody or antibody fragment; and/or wherein the antibody or antibody fragment may be an anti-PACAP antibody or antibody fragment that may comprise the same CDRs as an anti-PACAP antibody that may be selected from Ab10 or Ab20.

The invention additionally embraces any of the methods disclosed herein wherein the anti-PACAP antibody or antigen binding fragment may comprise at least 3 CDRs; at least 4 CDRs; at least 5 CDRs; or all 6 CDRs of an anti-PACAP antibody that may be selected from Ab10 or Ab20.

The invention also embraces any of the methods disclosed herein wherein the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 404; a CDR2 sequence consisting of SEQ ID NO: 406; and a CDR3 sequence consisting of SEQ ID NO: 408; and/or (b) a variable light chain comprising a CDR1 sequence consisting of SEQ ID NO: 424; a CDR2 sequence consisting of SEQ ID NO: 426; and a CDR3 sequence consisting of SEQ ID NO: 428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 402, and/or (b) a variable light chain comprising an amino acid sequence with at least 80, 85, 90, 95, 96, 97, 98, or 99% sequence identity to SEQ ID NO: 422. In another embodiment, the anti-PACAP antibodies and antigen binding fragments thereof comprise (a) a variable heavy chain having the amino acid sequence of SEQ ID NO: 402, and/or (b) a variable light chain having the amino acid sequence of SEQ ID NO: 422. More specifically, the anti-PACAP antibodies and antigen binding fragments thereof can comprise (a) a heavy chain having the amino acid sequence of SEQ ID NO: 401, and/or (b) a light chain having the amino acid sequence of SEQ ID NO: 421.

The invention also embraces any of the methods disclosed herein wherein the anti-PACAP antibodies and antigen binding fragments thereof according to the invention, are human, humanized, or chimerized anti-PACAP antibodies or antigen binding fragments thereof, and comprise (a) a variable heavy chain comprising a CDR1 sequence consisting of SEQ ID NO: 444; a CDR2 sequence consisting of SEQ ID NO: 446; and a CDR3 sequence consisting of SEQ ID NO: 448; and/or (b) a variable light chain comprising a CDR1 sequence consisting of SEQ ID NO: 464; a CDR2 sequence consisting of SEQ ID NO: 466; and a CDR3 sequence consisting of SEQ ID NO: 468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 442, and/or (b) a variable light chain comprising an amino acid sequence with at least 80, 85, 90, 95, 96, 97, 98, or 99% sequence identity to SEQ ID NO: 462. In another embodiment, the anti-PACAP antibodies and antigen binding fragments thereof and comprise (a) a variable heavy chain having the amino acid sequence of SEQ ID NO: 442, and/or (b) a variable light chain having the amino acid sequence of SEQ ID NO: 462. More specifically, the anti-PACAP antibodies and antigen binding fragments thereof can comprise (a) a heavy chain having the amino acid sequence of SEQ ID NO: 441, and/or (b) a light chain having the amino acid sequence of SEQ ID NO: 461.

The invention also relates to any of the methods disclosed herein wherein the anti-PACAP antibodies or antibody fragments may be selected from the group consisting of scFvs, camelbodies, nanobodies, Immunoglobulin New Antigen Receptor ("IgNAR"), fragment antigen binding ("Fab") fragments, Fab' fragments, MetMab like antibodies, monovalent antibody fragments, and F(ab')$_2$ fragments. Additionally, the invention relates to any of the methods disclosed herein wherein the anti-PACAP antibody or antibody fragment may substantially or entirely lack N-glycosylation and/or O-glycosylation. Also, the invention pertains to any of the methods disclosed herein wherein the anti-PACAP antibody or antibody fragment may comprise a human constant domain, e.g., that of an IgG1, IgG2, IgG3, or IgG4 antibody.

Another aspect of the invention pertains to any of the methods disclosed herein wherein the anti-PACAP antibody or antibody fragment may comprise an Fc region that may have been modified to alter at least one of effector function, half-life, proteolysis, or glycosylation, e.g., the Fc region may contain one or more mutations that may alter or eliminate N- and/or O-glycosylation.

A further aspect of the invention relates to any of the methods disclosed herein wherein the anti-PACAP antibody or antibody fragment may bind to PACAP with a binding affinity ($K_D$) of less than or equal to $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, or $10^{-13}$ M. Also, said anti-PACAP antibody or antibody fragment of any of the methods disclosed herein may bind to PACAP with a binding affinity ($K_D$) of less than or equal to $5 \times 10^{10}$ M, $10^{10}$ M, $5 \times 10^{11}$ M, $10^{11}$ M, $5 \times 10^{12}$ M, or $10^{12}$ M. Another embodiment of the invention pertains any of the methods disclosed herein wherein the anti-PACAP antibody or antibody fragment may bind to PACAP with an off-rate ($k_{off}$) of less than or equal to $5 \times 10^{-4}$ s$^{-1}$, $10^{-4}$ s$^{-1}$, $5 \times 10^{-5}$ s$^{-1}$, or $10^{-5}$ s$^{-1}$.

Moreover, the invention embraces any of the methods disclosed herein wherein the anti-PACAP antibody or antibody fragment may be directly or indirectly attached to a detectable label or therapeutic agent. Also, the invention relates to any of the methods disclosed herein wherein the anti-PACAP antibody or antibody fragment may bind to PACAP with a $K_D$ that may be less than about 100 nM, less than about 40 nM, less than about 1 nM, less than about 100 pM, less than about 50 pM, or less than about 25 pM. Also, the invention embraces any of the methods disclosed herein wherein the anti-PACAP antibody or antibody fragment may bind to PACAP with a $K_D$ that may be between about 10 pM and about 100 pM. The invention further pertains to any of the methods disclosed herein wherein the method may further comprise administering separately or co-administering another agent, e.g., wherein the other agent may be selected from a chemotherapeutic, an analgesic, an anti-inflammatory, an immunosuppressant, a cytokine, an antiproliferative, an antiemetic or a cytotoxin. Also, the invention embraces any of the methods disclosed herein wherein the other therapeutic agent may be an analgesic, and said analgesic may be a non-steroidal anti-inflammatory drug ("NSAID"), an opioid analgesic, another antibody or a non-antibody biologic, and further wherein said other antibody may be an anti-NGF antibody or antibody fragment;

and/or may be an anti-Calcitonin Gene-Related Peptide ("CGRP") antibody or antibody fragment and/or an anti-CGRP receptor antibody or antibody fragment. The invention also pertains to any of the methods disclosed herein wherein said NSAID may be a cyclooxygenase 1 and/or cyclooxygenase 2 inhibitor.

In another embodiment of the invention, an anti-PACAP antibody or antibody fragment or a method as disclosed herein may inhibit the effects of PACAP on vasodilation; and/or may inhibit the effects of PACAP on cAMP production; and/or may inhibit the effects of PACAP on PLC resulting in reduced $Ca^{++}$ and PLD levels; and/or may inhibit the effects of PACAP on adenylate cyclase activity; and/or may inhibit the effects of PACAP on its binding to any or all of PAC1-R, VPAC1-R or VPAC2-R; and/or may inhibit the effects of PACAP on neurodevelopment; may inhibit the effects of PACAP on neuroprotection; and/or may inhibit the effects of PACAP on neuromodulation; and/or may inhibit the effects of PACAP on neurogenic inflammation; and/or may inhibit the effects of PACAP on nociception; and/or may modulate the interaction of PACAP with binding the cell surface, e.g. via at least one GAG, e.g., wherein at least one said GAG may comprise one or more of heparin, chondroitin, keratin, and hyaluronic acid, and further wherein said antibody or antibody fragment or method may block or inhibit receptor-independent cellular uptake of PACAP38 and/or PACAP27 and/or may inhibit or may block GAG-dependent uptake of PACAP38 and/or PACAP27 by cells.

A further embodiment of the invention relates to method of therapy or prophylaxis that may comprise the administration of an anti-PACAP antibody or antibody fragment of the invention. Additionally, the invention pertains to a composition that may be used in human therapy that may contain an anti-PACAP antibody or antibody fragment of the invention. Said composition may contain another active agent, e.g., wherein the other agent may be selected from a chemotherapeutic, an analgesic, an anti-inflammatory, an immunosuppressant, a cytokine, an antiproliferative, an anti-emetic or a cytotoxin. Wherein said other agent may be an analgesic, said analgesic may be a NSAID, an opioid analgesic, another antibody or a non-antibody biologic. When said other agent may be an analgesic that may be another antibody, the other antibody may be an anti-NGF antibody or antibody fragment, and/or the other antibody may be an anti-Calcitonin Gene-Related Peptide ("CGRP") antibody or antibody fragment and/or an anti-CGRP receptor antibody or antibody fragment. Wherein said other agent may be a NSAID, said NSAID may be a cyclooxygenase 1 and/or cyclooxygenase 2 inhibitor; and/or said NSAID may be selected from the group consisting of (1) propionic acid derivatives including ibuprofen, naproxen, naprosyn, diclofenac, and ketoprofen; (2) acetic acid derivatives including tolmetin and sulindac; (3) fenamic acid derivatives including mefenamic acid and meclofenamic acid; (4) biphenylcarboxylic acid derivatives including diflunisal and flufenisal; and (5) oxicams including piroxim, sudoxicam, and isoxicam. Wherein said other agent may be an opioid analgesic, said opioid analgesic may be selected from the group consisting of codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, pentazocine, and pharmaceutically acceptable salts thereof, and/or said opioid analgesic may be morphine or a morphine derivative or pharmaceutically acceptable salt thereof; and/or said opioid analgesic and an anti-PACAP antibody or antigen binding fragment according to the invention may increase the analgesic effect as compared to either the opioid analgesic or the anti-PACAP antibody or antigen binding fragment administered alone.

In another embodiment of the invention, an anti-PACAP antibody or fragment or composition according to the invention, wherein the anti-PACAP antibody or fragment and another active agent may be combined therewith or may be administered in combination, may elicit a synergistic or additive effect on the treatment or prevention of a PACAP associated effect, e.g., migraine or on pain. The invention additionally embraces the anti-PACAP antibody or fragment or composition according the invention that may be used in therapy or diagnosis, e.g., migraine treatment or prophylaxis. A further embodiment of the invention relates to anti-PACAP antibody or fragment or composition according to the invention that may be used for potentially treating one or more of hot flush, migraine with or without aura, hemiplegic migraine, cluster headache, migrainous neuralgia, chronic headache, chronic migraine, medication overuse headache or tension headache.

Another embodiment of the invention pertains anti-PACAP antibody or fragment or composition according to the invention that may be used for ameliorating, controlling, reducing incidence of, or delaying the development or progression of headache, e.g., migraine with or without aura, hemiplegic migraine, cluster headache, migrainous neuralgia, chronic headache, chronic migraine, medication overuse headache or tension headache. In an embodiment of the invention, the use may be for a subject who may have previously received or may be receiving an anti-CGRP antibody or antibody fragment and/or an anti-CGRP receptor antibody or antibody fragment, and further wherein said subject may be a migraineur who may not have adequately responded to anti-CGRP antibody or antibody fragment and/or anti-CGRP receptor antibody or antibody fragment treatment; and/or wherein said subject may have previously received at least one anti-CGRP antibody or antibody fragment and/or anti-CGRP receptor antibody or antibody fragment administration that may have elicited an immune response to the anti-CGRP antibody or antibody fragment and/or anti-CGRP receptor antibody or antibody fragment.

BRIEF DESCRIPTION OF THE SEVERAL VIEWS OF THE DRAWING

FIG. 1A-1B provide the polypeptide sequences of the variable heavy chain region for antibodies Ab10, Ab20, and Ab21, Ab22, and Ab23 (SEQ ID NO: 402; 442; 842; 882; and 922, respectively) aligned by their FRs and CDRs.

FIG. 2A-2B provide the polypeptide sequences of the variable light chain region for antibodies Ab10, Ab20, Ab21, Ab22, and Ab23 (SEQ ID NO: 422; 462; 862; 902; and 942, respectively) aligned by their FRs and CDRs.

FIG. 3A-3F provide the polynucleotide sequences encoding the variable heavy chain region for antibodies Ab10, Ab20, Ab21, Ab22, and Ab23 (SEQ ID NO: 412; 452; 852; 892; and 932, respectively) aligned by their FRs and CDRs.

FIG. 4A-4E provide the polynucleotide sequences encoding the variable light chain region for antibodies Ab10, Ab20, Ab21, Ab22, and Ab23 (SEQ ID NO: 432; 472; 872; 912; and 952, respectively) aligned by their FRs and CDRs.

FIG. 5 provides the polypeptide sequence coordinates for certain antibody heavy chain protein sequence features including the variable region and CDRs of the heavy chain for antibodies Ab10, Ab20, Ab21, Ab22, and Ab23.

FIG. 6 provides the polypeptide sequence coordinates for certain antibody heavy chain protein sequence features including the constant region and framework regions FRs of the heavy chain for antibodies Ab10, Ab20, Ab21, Ab22, and Ab23.

FIG. 7 provides the polypeptide sequence coordinates for certain antibody light chain protein sequence features including the variable region and CDRs of the light chain for antibodies Ab10, Ab20, Ab21, Ab22, and Ab23.

FIG. 8 provides the polypeptide sequence coordinates for certain antibody light chain protein sequence features including the constant region and framework regions FRs of the light chain for antibodies Ab10, Ab20, Ab21, Ab22, and Ab23.

FIG. 9 provides the polynucleotide sequence coordinates for certain antibody heavy chain DNA sequence features including the variable region and CDRs of the heavy chain for antibodies Ab10, Ab20, Ab21, Ab22, and Ab23.

FIG. 10 provides the polynucleotide sequence coordinates for certain antibody heavy chain DNA sequence features including the constant region and FRs of the heavy chain for antibodies Ab10, Ab20, Ab21, Ab22, and Ab23.

FIG. 11 provides the polynucleotide sequence coordinates for certain antibody light chain DNA sequence features including the variable region and CDRs of the light chain for antibodies Ab10, Ab20, Ab21, Ab22, and Ab23.

FIG. 12 provides the polynucleotide sequence coordinates for certain antibody light chain DNA sequence features including the constant region and FRs of the light chain for antibodies Ab10, Ab20, Ab21, Ab22, and Ab23.

FIG. 13A-F provides representative competitive binding data for Ab10 (FIG. 13A), Ab20 (FIG. 13B), Ab21 (FIG. 13C), Ab1.H (FIG. 13D), Ab22 (FIG. 13E), and Ab23 (FIG. 13F) obtained following the protocol in Example 1 infra.

FIG. 14A-H provides representative data showing Ab10-mediated (FIG. 14A), Ab20-mediated (FIG. 14B), Ab21-mediated (FIG. 14C), Ab1.H-mediated (FIG. 14D), Ab10.H-mediated (FIG. 14E), Ab21.H-mediated (FIG. 14F), Ab22-mediated (FIG. 14G), and Ab23-mediated (FIG. 14H) inhibition of PACAP38 binding to PAC1-R-expressing PC-12 cells obtained following the protocol in Example 5 infra.

FIG. 15A-H provides representative data showing Ab10 (FIG. 15A), Ab20 (FIG. 15B), Ab21 (FIG. 15C), Ab1.H (FIG. 15D), Ab10.H (FIG. 15E), Ab21.H (FIG. 15F), Ab22 (FIG. 15G), and Ab23 (FIG. 15H) binding to PAC1-R-expressing PC-12 cells in the presence of PACAP38 obtained following the protocol in Example 6 infra. The dashed line in FIG. 15A represents a no PACAP and no antibody control.

FIG. 16A-H provides representative data showing Ab10-mediated (FIG. 16A), Ab20-mediated (FIG. 16B), Ab21-mediated (FIG. 16C), Ab1.H-mediated (FIG. 16D), Ab10.H-mediated (FIG. 16E), Ab21.H-mediated (FIG. 16F), Ab22-mediated (FIG. 16G), and Ab23-mediated (FIG. 16H) inhibition of PACAP38-driven cAMP production via PAC1-R-expressing PC-12 cells obtained following the protocol in Example 1 infra.

FIG. 17A-H provides representative data showing Ab10-mediated (FIG. 17A), Ab20-mediated (FIG. 17B), Ab21-mediated (FIG. 17C), Ab1.H-mediated (FIG. 17D), Ab10.H-mediated (FIG. 17E), Ab21.H-mediated (FIG. 17F), Ab22-mediated (FIG. 17G), and Ab23-mediated (FIG. 17H) inhibition of PACAP27-driven cAMP production via PAC1-R-expressing PC-12 cells obtained following the protocol in Example 1 infra.

FIG. 18A-H provides representative data showing Ab10-mediated (FIG. 18A), Ab20-mediated (FIG. 18B), Ab21-mediated (FIG. 18C), Ab1.H-mediated (FIG. 18D), Ab10.H-mediated (FIG. 18E), Ab21.H (FIG. 18F) Ab22-mediated (FIG. 18G), and Ab23-mediated (FIG. 18H) inhibition of PACAP38-driven cAMP production via VPAC1-R-expressing CHO-K1 cells obtained following the protocol in Example 3 infra.

FIG. 25 provides representative data showing the in vivo effect of the administration of PACAP and an anti-PACAP antibody Ab10.H in a rodent photophobia model, which model detects the amount of time treated animals (mice) spend in the light per 5 min. interval compared to appropriate control animals obtained following the protocol in Example 11 infra.

FIG. 26A presents results of surface plasmon resonance-based binding kinetics measurements for binding of anti-PACAP antibody Ab10 to PACAP alanine scanning mutants 19A, 22A, 23A, and 27A, along with controls including wild-type PACAP (labelled huPACAP (1-38)) (positive control) and 1× running buffer (negative control) obtained following the protocol in Example 12 infra.

FIG. 26B presents results of surface plasmon resonance-based binding kinetics measurements for binding of anti-PACAP antibody Ab10 to PACAP alanine scanning mutants 1A-18A, 20A, 21A, 24V-26A, and 28A-38A, along with controls including wild-type PACAP (labelled huPACAP (1-38)) (positive control) and 1× running buffer (negative control) obtained following the protocol in Example 12 infra.

FIG. 31A presents a summary of the effects of PACAP alanine scanning mutants on antibody binding. In column 1 of FIG. 31A, VIP residues are listed in the order of their spatial arrangement along the VIP primary sequence from amino acid residues 1-27. In column 2 of FIG. 31A, PACAP residues are listed in the order of their spatial arrangement along the PACAP primary sequence from amino acid residues 1-27. Column 3 of FIG. 31A provides the number corresponding to each residue from 1-27 for both VIP and PACAP, as arranged spatially along their primary sequences. In columns 4-8 of FIG. 31A, each antibody tested during the alanine scanning studies (such as Ab10, Ab20, for example), and the PACAP residues determined to contribute to PACAP/antibody binding, (such as 5A, 6A, for example) are listed.

FIG. 31B presents a summary of the effects of PACAP alanine scanning mutants on antibody binding. In column 1 of FIG. 31B, VIP residue 28 is listed. In column 2 of FIG. 31B, PACAP residues are listed in the order of their spatial arrangement along the PACAP primary sequence from amino acid residues 28-38. Column 3 of FIG. 31B provides the number corresponding to residue 28 of VIP and each of residues 28-38 for PACAP, as arranged spatially along their primary sequences. In columns 4-8 of FIG. 31B, each antibody tested during the alanine scanning studies (such as Ab10, Ab20, for example), and the PACAP residues determined to contribute to PACAP/antibody binding, (such as 5A, 6A, for example) are listed.

DETAILED DESCRIPTION

Definitions

Figure 13A:
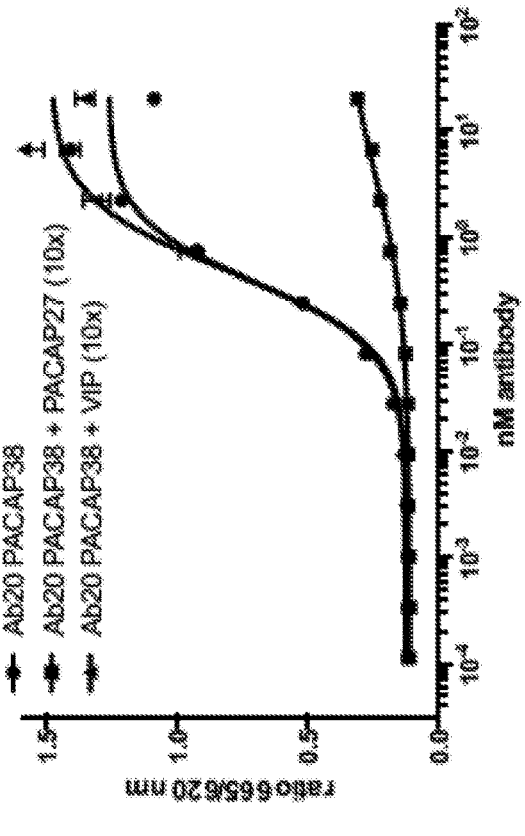
Figure 13B:
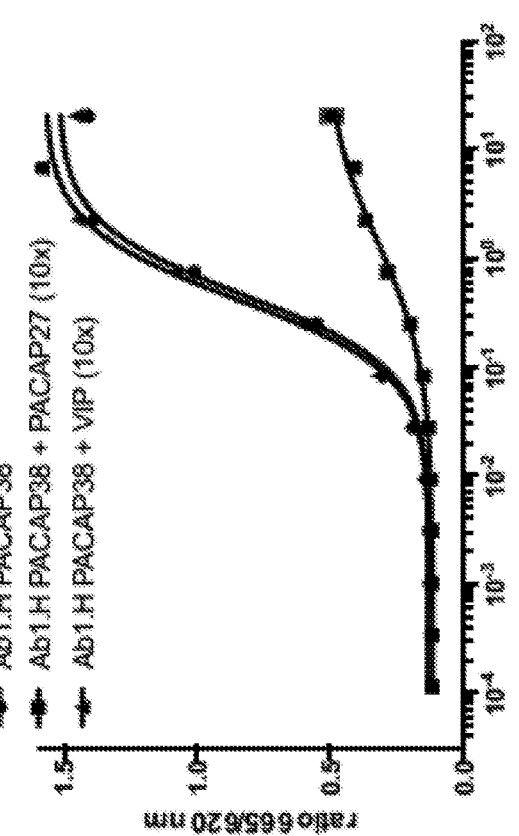
Figure 13C:
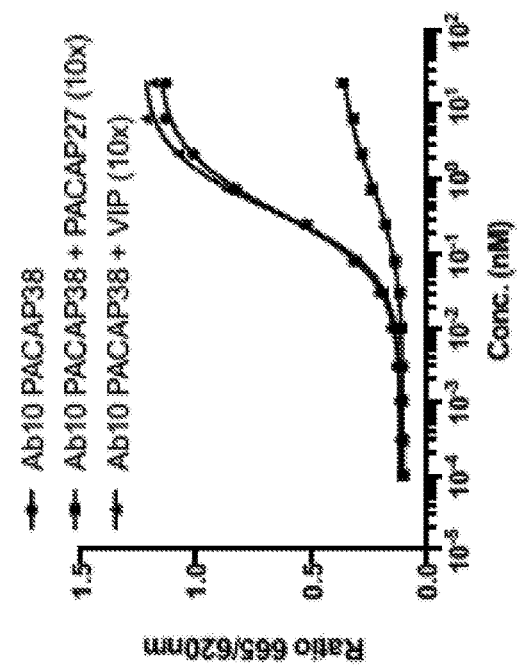
Figure 13D:
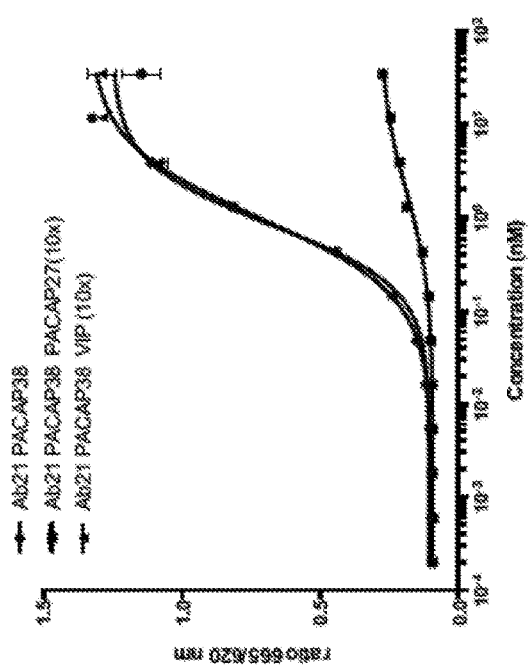
Figure 15C:
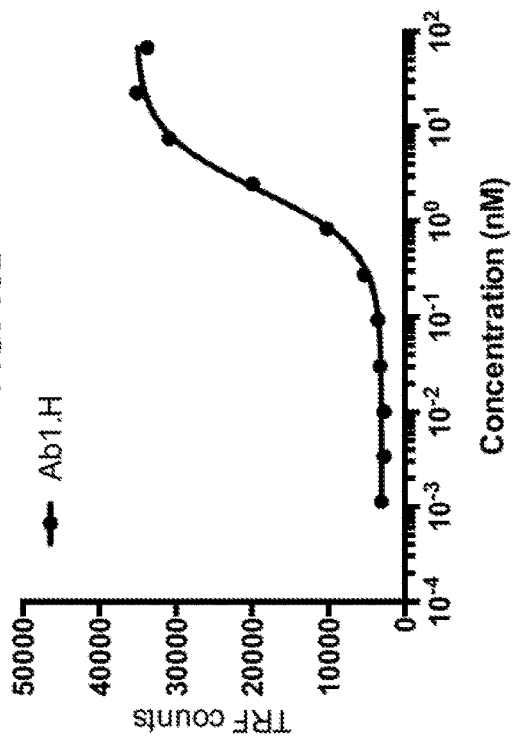
Figure 15D:
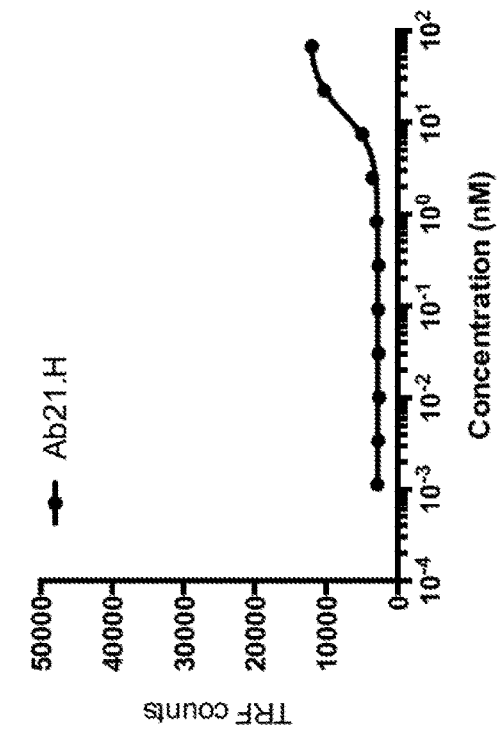
Figure 15E:
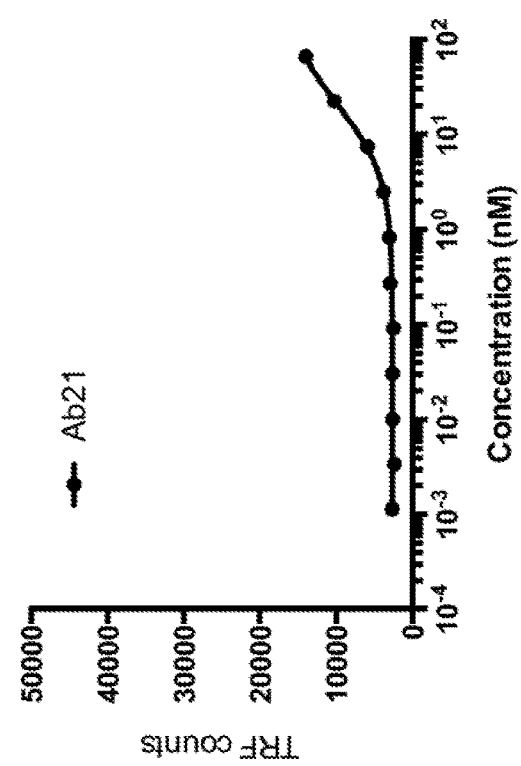
Figure 15F:
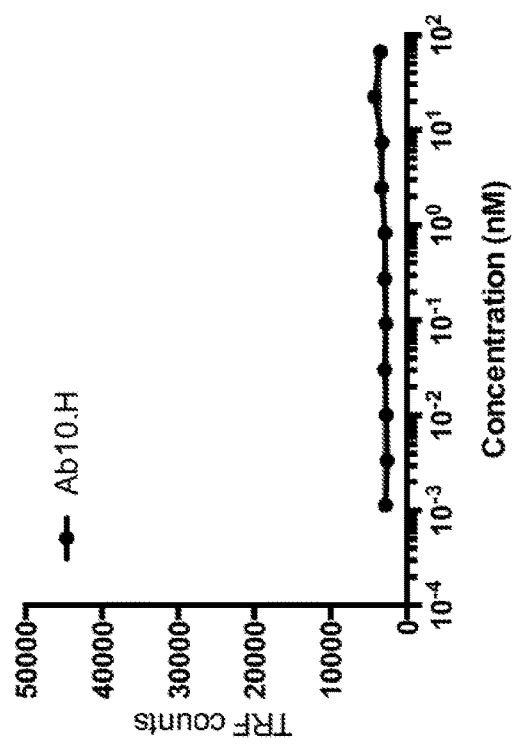
Figure 18G:
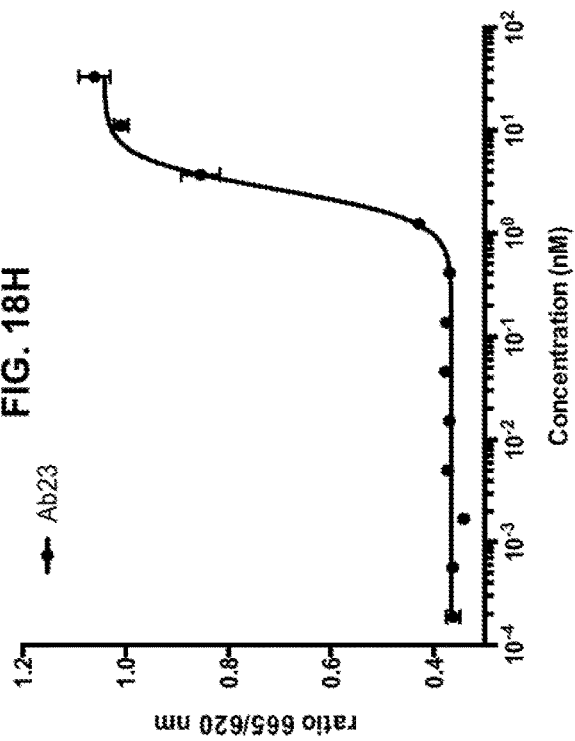
Figure 18H:
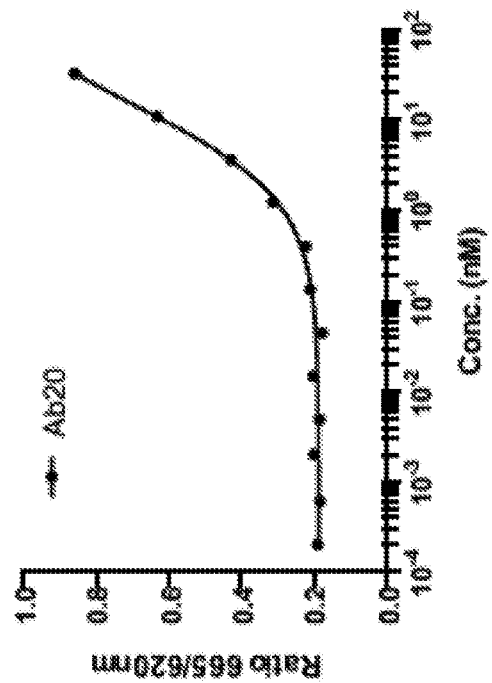
Figure 19A:
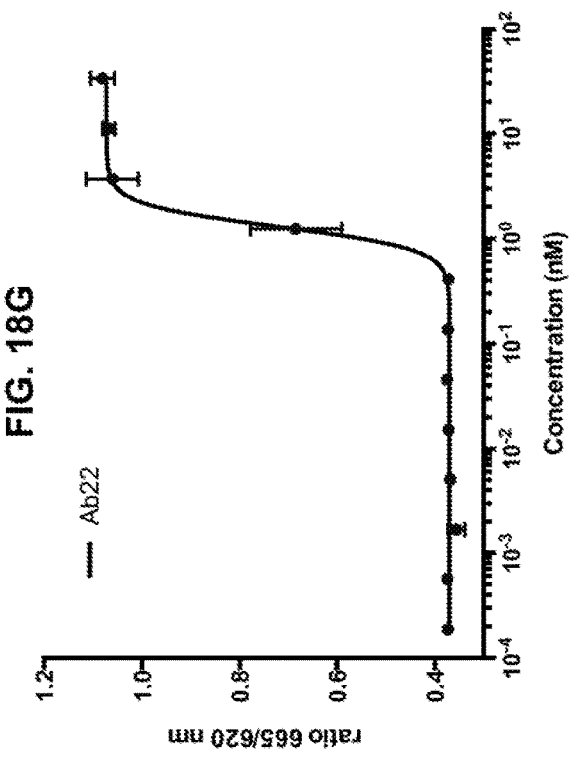
FIG. 19A-H provides representative data showing Ab10-mediated (FIG. 19A), Ab20-mediated (FIG. 19B), Ab21-mediated (FIG. 19B), Ab1.H-mediated (FIG. 19D), Ab10.H-mediated (FIG. 19E), Ab21.H (FIG. 19F), Ab22-mediated (FIG. 19G), and Ab23-mediated (FIG. 19H) inhibition of PACAP38-driven cAMP production via VPAC2-R-expressing CHO-K1 cells obtained following the protocol in Example 4 infra.
Figure 19B:
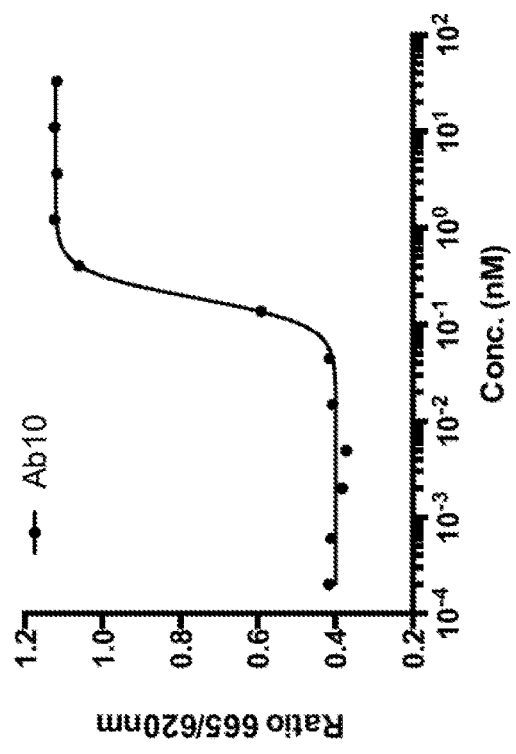
Figure 19D:
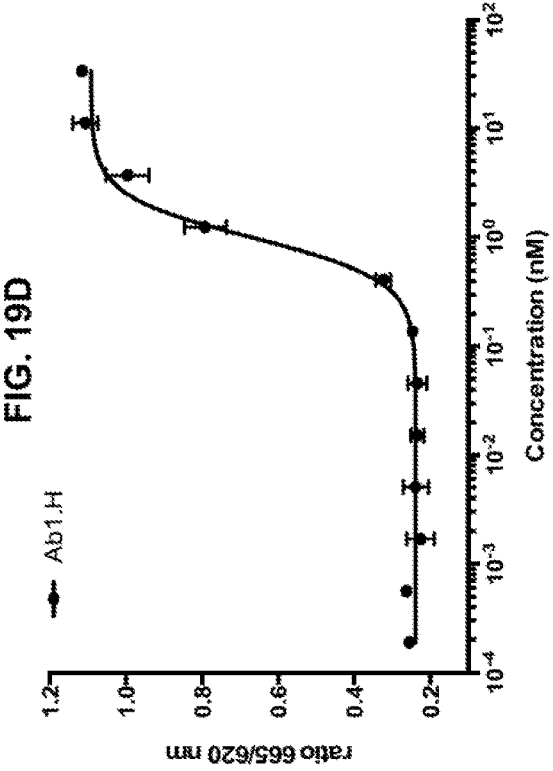
Figure 19C:
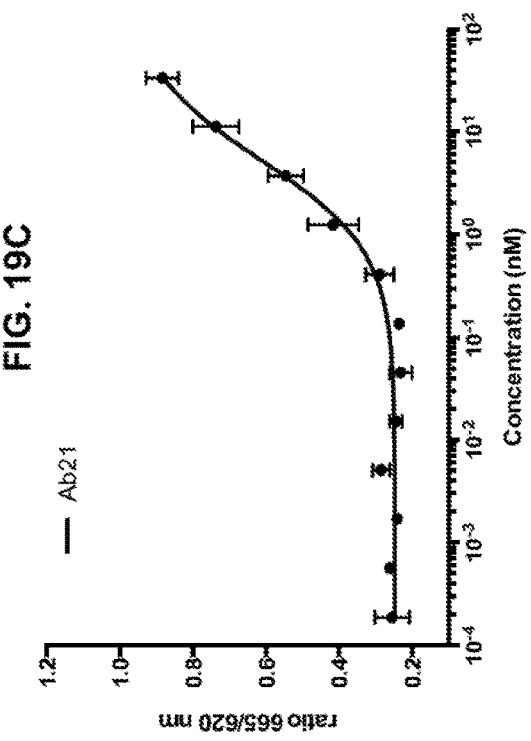
Figure 19F:
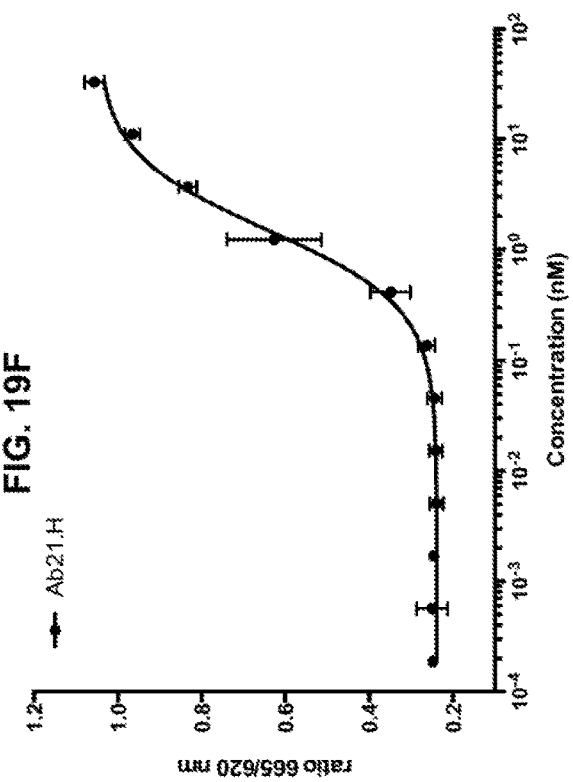
Figure 19E:
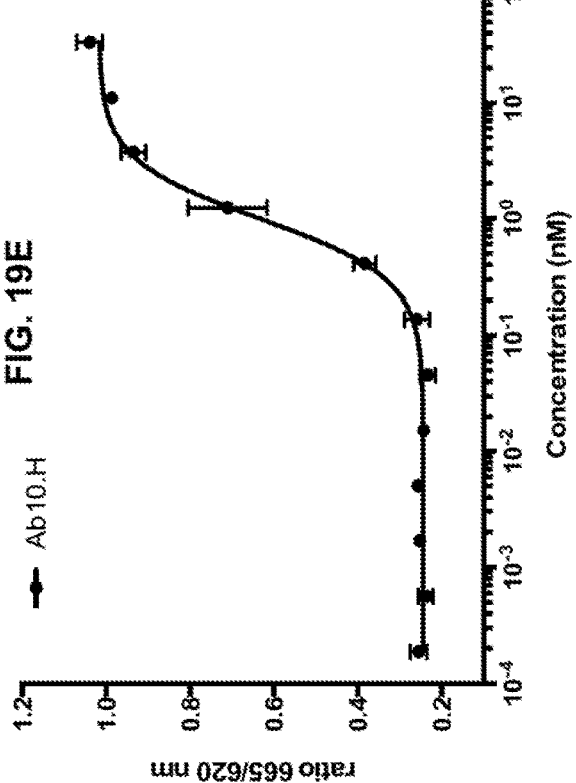
Figure 19G:
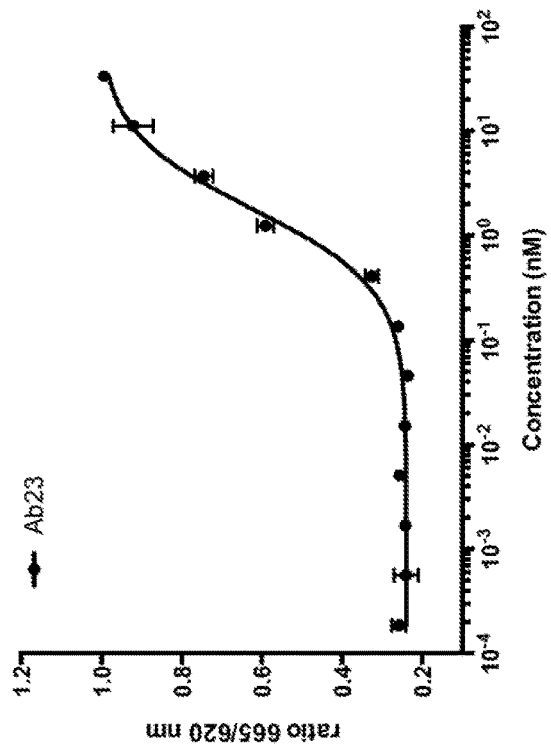
Figure 19H:
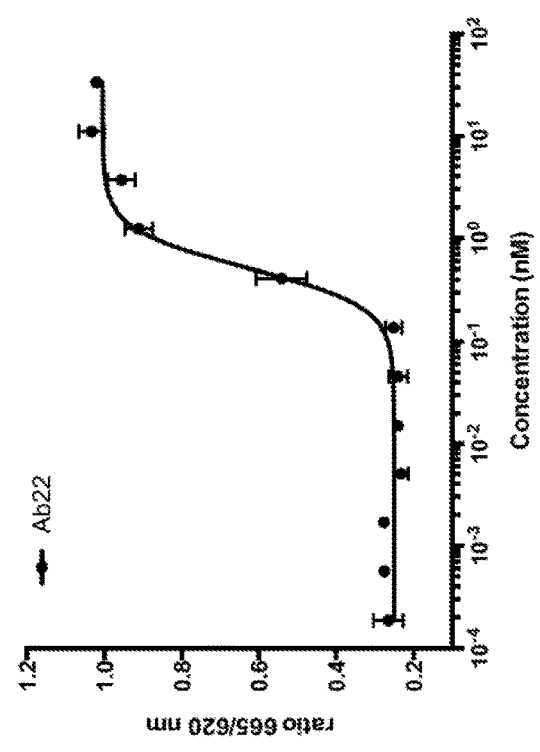

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Pituitary Adenylate Cyclase-Activating Polypeptide (PACAP): As used herein, unless stated otherwise PACAP includes any mammalian form of PACAP, and in particular encompasses the following *Homo sapiens* PACAP27 and *Homo sapiens* PACAP38 amino acid sequences:

PACAP38:
HSDGIFTDSYSRYRKQMAVKKYLAAVLGKRYKQRVKNK (SEQ ID NO: 1241), wherein the C-terminal lysine is amidated; but also any mutants, splice variants, isoforms, orthologs, homologs, and variants of this sequence.

PACAP27:
HSDGIFTDSYSRYRKQMAVKKYLAAVL (SEQ ID NO: 1242), wherein the C-terminal leucine is amidated; but also any mutants, splice variants, isoforms, orthologs, homologs, and variants of this sequence.

"Photophobia" herein refers to a symptom of abnormal intolerance to visual perception of light, sometimes additionally defined by abnormal or irrational fear of light, or by presence of actual physical photosensitivity of the eyes. In the present invention photophobia includes in particular light aversion associated with migraine, cluster headaches and other neurological causes of light aversive behavior that can trigger a migraine or cluster headache. Patients/subjects can develop photophobia as a result of several different medical conditions, related to the eye or the nervous system. Photophobia can be caused by an increased response to light starting at any step in the visual system such as: (i) too much light entering the eye, (ii) too much light can enter the eye if it is damaged, such as with corneal abrasion and retinal damage, or if a pupil(s) is unable to normally constrict (seen with damage to the oculomotor nerve), (iii) overstimulation of the photoreceptors in the retina, (iv) excessive electric impulses to the optic nerve, and (v) excessive response in the central nervous system.

"Effective treatment or prevention of photophobia" herein refers to inhibiting light aversive behavior or photophobia or inhibiting the onset of light aversive behavior or photophobia in a subject in need thereof, e.g., a subject having an active migraine attack or cluster headache or a subject prone to migraine or cluster headaches, or one of the other photophobia-associated disorders identified herein after administration of an effective amount of an anti-PACAP antibody or antigen binding fragment thereof according to the invention. The treatment may be effected as a monotherapy or in association with another active agent such as topiramate or dihydroergotamine by way of example.

The term "migraine" refers to a complex and disabling neurological disorder that may progress during four stages: prodrome, aura, headache, and postdrome. A migraine is defined by the International Headache Society as a headache that lasts for 4-72 hours and is characterized by at least two of the following: unilateral localization, pulsating quality, moderate to severe pain intensity; and aggravation by movement such as walking. In addition, the headache must be accompanied by at least one of the following: nausea and/or vomiting, photophobia, or phonophobia. A migraine may also be accompanied by aura, which typically precedes the deadline during the premonition or prodrome phase, and often results in visual changes, e.g., a scintillating scotoma that moves across the visual field. The prodrome may also be accompanied by other symptoms, e.g., fatigue, gastrointestinal issues, and mood changes. A migraineur is often incapacitated for extended periods of time. The postdrome is the final phase and occurs after the attack, during which time the migraineur may feel exhausted or mildly euphoric.

The term "headache" refers to pain in any region of the head. Headaches may occur on one or both sides of the head, be isolated to a certain location, radiate across the head from one point, or have a vise-like quality. A headache may be a sharp pain, throbbing sensation or dull ache. Headaches may appear gradually or suddenly, and they may last less than an hour or for several days.

The term "pain associated disease or condition" refers to any disease or condition defined, in whole or in part, by acute and/or chronic pain. Pain is generally defined as an unpleasant sensory and emotional experience associated with actual or potential tissue damage, or described in terms of such damage. Pain may be classified as neurogenic, neuropathic, inflammatory, or nociceptic.

The term "opioid analgesic" herein refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and sulindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described that selectively inhibit cyclooxygenase 2. COX-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

As used herein, "treatment" is an approach for obtaining beneficial or desired clinical results. For purposes of this invention, beneficial or desired clinical results include, but are not limited to, one or more of the following: improvement in any aspect of PACAP-related conditions such as migraine or headache. For example in the context of headache or migraine treatment this includes lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, rhinorrhea or nasal congestion, and red flushed face.

"Reducing incidence" or "prophylaxis" or "prevention" means any of reducing severity for a particular disease, condition, symptom, or disorder (the terms disease, condition, and disorder are used interchangeably throughout the application). Reduction in severity includes reducing drugs and/or therapies generally used for the condition by, for example, reducing the need for, amount of, and/or exposure to drugs or therapies. Reduction in severity also includes reducing the duration, and/or frequency of the particular condition, symptom, or disorder (including, for example, delaying or increasing time to next episodic attack in an individual).

"Ameliorating" headache or one or more symptoms of headache or migraine or other PACAP-related condition means a lessening or improvement of one or more symptoms of the condition, e.g., headache or migraine as compared to not administering an anti-PACAP antagonist antibody. "Ameliorating" also includes shortening or reduction in duration of a symptom.

As used herein, "controlling headache" or "controlling migraine" or "controlling" another PACAP-related condition refers to maintaining or reducing severity or duration of one or more symptoms of the condition, e.g., headache or migraine or frequency of headache or migraine attacks in an individual (as compared to the level before treatment). For example, the duration or severity of head pain, or frequency of attacks is reduced by at least about any of 10%, 20%, 30%, 40%, 50%, 60%, 70%, 80%, 90%, or 100% in the individual as compared to the level before treatment. The reduction in the duration or severity of head pain, or frequency of attacks can last for any length of time, e.g., 2 weeks, 4 weeks (1 month), 8 weeks (2 months), 16 weeks (3 months), 4 months, 5 months, 6 months, 9 months, 12 months, etc.

As used therein, "delaying" the development of a PACAP-related condition such as migraine or headache means to defer, hinder, slow, retard, stabilize, and/or postpone progression of the condition or disease. This delay can be of varying lengths of time, depending on the history of the condition or disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of a PACAP-related condition such as migraine or headache means initial manifestations and/or ensuing progression of the disorder. Development of headache or migraine can be detectable and assessed using standard clinical techniques as well known in the art. However, development also refers to progression that may be undetectable. For purpose of this invention, development, or progression refers to the biological course of the symptoms. "Development" includes occurrence, recurrence, and onset. As used herein "onset" or "occurrence" of a condition such as headache or migraine includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological, and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological, and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

A "suitable host cell" or "host cell" generally includes any cell wherein the subject anti-PACAP antibodies and antigen binding fragments thereof can be produced recombinantly using techniques and materials readily available. For example, the anti-PACAP antibodies and antigen binding fragments thereof of the present invention can be produced in genetically engineered host cells according to conventional techniques. Suitable host cells are those cell types that can be transformed or transfected with exogenous DNA and grown in culture, and include bacteria, fungal cells (e.g., yeast), and cultured higher eukaryotic cells (including cultured cells of multicellular organisms), particularly cultured mammalian cells, e.g., human or non-human mammalian cells. In an exemplary embodiment these antibodies may be expressed in CHO cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor, N.Y.: Cold Spring Harbor Laboratory Press (1989), and *Current Protocols in Molecular Biology*, Ausubel et al., editors, New York, NY: Green and Wiley and Sons (1993).

In some exemplary embodiments the antibodies may be expressed in mating competent yeast, e.g., any haploid, diploid, or tetraploid yeast that can be grown in culture. Yeast useful in fermentation expression methods may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion. By way of example, such yeast may include members of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred exemplary embodiment of the invention, the mating competent yeast used for antibody expression may comprise a member of the genus *Pichia*. In a further preferred exemplary embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris*.

A "selectable marker" herein refers to a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

An "expression vector" herein refers to DNA vectors containing elements that facilitate manipulation for the expression of a foreign protein within the target host cell, e.g., a bacterial, insect, yeast, plant, amphibian, reptile, avian, or mammalian cell, and most typically a yeast or mammalian cell, e.g., a CHO cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Steams, T., *Methods in yeast genetics: a Cold Spring Harbor Laboratory course manual*, Plainview, NY: Cold Spring Harbor Laboratory Press (2000).

Expression vectors for use in the methods of the invention may include yeast or mammalian specific sequences, including a selectable auxotrophic or drug marker for identifying transformed host strains. A drug marker may further be used to amplify copy number of the vector in a yeast host cell.

The polypeptide coding sequence of interest is operably linked to transcriptional and translational regulatory sequences that provide for expression of the polypeptide in the desired host cells, e.g., yeast or mammalian cells. These vector components may include, but are not limited to, one or more of the following: an enhancer element, a promoter, and a transcription termination sequence. Sequences for the secretion of the polypeptide may also be included, e.g. a signal sequence, and the like. An origin of replication, e.g., a yeast origin of replication, is optional, as expression vectors are often integrated into the host cell genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (GATEWAY® Technology; Invitrogen, Carlsbad California). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host cell, e.g., yeast cell, genome; alternatively, a selectable marker may be used as the site for homologous recombination. *Pichia* transformation is described in Cregg et al., *Mol. Cell. Biol.*, 5:3376-3385 (1985). Suitable promoters for use in different eukaryotic and prokaryotic cells are well known and commercially available.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell, e.g., a mammalian cell, an insect cell, or a yeast cell. Additionally, these signal peptide sequences may be engineered to provide for enhanced secretion in expression systems. Secretion signals of interest also include mammalian and yeast signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al., *Protein Eng.*, 11(2):75 (1998); and Kobayashi et. al., *Therapeutic Apheresis*, 2(4): 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion, and/or sequenced.

As an alternative to restriction and ligation of fragments, recombination methods based on specific attachment ("att") sites and recombination enzymes may be used to insert DNA sequences into a vector. Such methods are described, for example, by Landy, *Ann. Rev. Biochem.*, 58:913-949 (1989); and are known to those of skill in the art. Such methods utilize intermolecular DNA recombination that is mediated by a mixture of lambda and *E. coli*-encoded recombination proteins. Recombination occurs between att sites on the interacting DNA molecules. For a description of att sites see Weisberg and Landy, Site-Specific Recombination in Phage Lambda, in Lambda II, p. 211-250, Cold Spring Harbor, NY: Cold Spring Harbor Press (1983). The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic protein disulfide isomerase ("PDI") is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of immunoglobulin heavy chain binding protein ("BIP"); cyclophilin; and the like. In one embodiment of the invention, each of the haploid parental strains expresses a distinct folding enzyme, e.g. one strain may express BIP, and the other strain may express PDI or combinations thereof.

Cultured mammalian cells are also preferred exemplary hosts for production of the disclosed anti-PACAP antibodies and antigen binding fragments thereof. As mentioned, CHO cells are particularly suitable for expression of antibodies. Many procedures are known in the art for manufacturing monoclonal antibodies in mammalian cells. (See, Galfre, G. and Milstein, C., *Methods Enzym.*, 73:3-46, 1981; Basalp et al., *Turk. J. Biol.*, 24:189-196, 2000; Wurm, F. M., *Nat. Biotechnol.*, 22:1393-1398, 2004; and Li et al., *mAbs*, 2(5): 466-477, 2010). As mentioned in further detail infra, common host cell lines employed in mammalian monoclonal antibody manufacturing schemes include, but are not limited to, human embryonic retinoblast cell line PER.C6@ (Crucell N. V., Leiden, The Netherlands), NSO murine myeloma cells (Medical Research Council, London, UK), CV1 monkey kidney cell line, 293 human embryonic kidney cell line, BHK baby hamster kidney cell line, VERO African green monkey kidney cell line, human cervical carcinoma cell line HELA, MDCK canine kidney cells, BRL buffalo rat liver cells, W138 human lung cells, HepG2 human liver cells, MMT mouse mammary tumor cells, TRI cells, MRC5 cells, Fs4 cells, myeloma or lymphoma cells, or Chinese Hamster (*Cricetulus griseus*) Ovary (CHO) cells, and the like. Many different subclones or sub-cell lines of CHO cells known in the art that are useful and optimized for production of recombinant monoclonal antibodies, such as the DP12 (CHO K1 dhfr-) cell line, NSO cells are a non-Ig secreting, non-light chain-synthesizing subclone of NS-1 cells that are resistant to azaguanine. Other Chinese Hamster and CHO cells are commercially available (from ATCC, etc.), including CHO-DXB11 (CHO-DUKX), CHO-pro3, CHO-DG44, CHO 1-15, CHO DP-12, Lec2, M1WT3, Lec8, pgsA-745, and the like, all of which are genetically altered to optimize the cell line for various parameters. Monoclonal antibodies are commonly manufactured using a batch fed method whereby the monoclonal antibody chains are expressed in a mammalian cell line and secreted into the tissue culture medium in a bioreactor. Medium (or feed) is continuously supplied to the bioreactor to maximize recombinant protein expression. Recombinant monoclonal antibody is then purified from the collected media. In some circumstances, additional steps are needed to reassemble the antibodies through reduction of disulfide bonds, etc. Such production methods can be scaled to be as large as 10,000 L in a single batch or more. It is now routine to obtain as much as 20 pg/cell/day through the use of such cell lines and methodologies, providing titers as high as 10 g/L or more, amounting to 15 to 100 kg from bioreactors of 10 kL to 25 kL. (Li et al., 2010). Various details of this production methodology, including cloning of the polynucleotides encoding the antibodies into expression vectors, transfecting cells with these expression vectors, selecting for transfected cells, and expressing and purifying the recombinant monoclonal antibodies from these cells are provided below.

For recombinant production of an anti-PACAP antibody or antigen binding fragment in mammalian cells, nucleic acids encoding the antibody or fragment thereof are generally inserted into a replicable vector for further cloning (amplification of the DNA) or for expression. DNA encoding the antibody is readily isolated or synthesized using conventional procedures (e.g., by using oligonucleotide probes that are capable of binding specifically to DNAs encoding the heavy and light chains of the antibody). The vector components generally include, but are not limited to, one or more of the following: a signal sequence, an origin of replication, one or more marker genes, an enhancer element, a promoter, and a transcription termination sequence. Selection of promoters, terminators, selectable markers, vectors, and other elements is a matter of routine design within the level of ordinary skill in the art. Many such elements are known in the art and are available through commercial suppliers.

The antibodies of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The homologous or heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

Such expression vectors and cloning vectors will generally contain a nucleic acid sequence that enables the vector to replicate in one or more selected host cells. Typically, in cloning vectors this sequence is one that enables the vector to replicate independently of the host chromosomal DNA, and includes origins of replication or autonomously replicating sequences. Such sequences are well known for a variety of bacteria, yeast, and viruses, e.g., the origin of replication from the plasmid pBR322 is suitable for most Gram-negative bacteria, the 2mu plasmid origin is suitable for yeast, and various viral origins (Simian Virus 40 ("SV40"), polyoma, adenovirus, vesicular stomatitis virus ("VSV"), or bovine papillomavirus ("BPV") are useful for cloning vectors in mammalian cells. Generally, the origin of replication component is not needed for mammalian expression vectors (the SV40 origin may typically be used only because it contains the early promoter).

These vectors will also typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." Examples of such dominant selection use the drugs neomycin, mycophenolic acid, and hygromycin. An exemplary selectable marker is a gene encoding resistance to the antibiotic neomycin. Selection is carried out in the presence of a neomycin-type drug, such as G-418 or the like. Those cells that are successfully transformed with a heterologous gene produce a protein conferring drug resistance and thus survive the selection regimen.

Selection systems can also be used to increase the expression level of the gene of interest, a process referred to as "amplification." Amplification of transfectants typically occurs by culturing the cells in the presence of a low level of the selective agent and then increasing the amount of selective agent to select for cells that produce high levels of the products of the introduced genes. Exemplary suitable selectable markers for mammalian cells are those that enable the identification of cells competent to take up the antibody nucleic acid, such as dihydrofolate reductase ("DHFR"), thymidine kinase, metallothionein-I and -II, preferably primate metallothionein genes, adenosine deaminase, ornithine decarboxylase, etc.

For example, an amplifiable selectable marker for mammalian cells is dihydrofolate reductase, which confers resistance to methotrexate. Other drug resistance genes (e.g. hygromycin resistance, multi-drug resistance, puromycin acetyltransferase) can also be used. Cells transformed with the DHFR selection gene are first identified by culturing all of the transformants in a culture medium that contains methotrexate ("MTX"), a competitive antagonist of DHFR. An appropriate host cell when wild-type DHFR is employed is the Chinese hamster ovary ("CHO") cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase ("APH") can be selected by cell growth in medium containing a selection agent for the selectable marker such as an aminoglycosidic antibiotic, e.g., kanamycin, neomycin, or G-418. See U.S. Pat. No. 4,965,199.

These vectors may comprise an enhancer sequence that facilitates transcription of a DNA encoding the antibody. Many enhancer sequences are known from mammalian genes (for example, globin, elastase, albumin, alpha-fetoprotein, and insulin). A frequently used enhancer is one derived from a eukaryotic cell virus. Examples thereof include the SV40 enhancer on the late side of the replication origin (bp 100-270), the cytomegalovirus early promoter enhancer, the polyoma enhancer on the late side of the replication origin, and adenovirus enhancers (See, Yaniv, *Nature*, 297:17-18, 1982, on enhancing elements for activation of eukaryotic promoters). The enhancer may be spliced into the vector at a position 5' or 3' to the antibody-encoding sequence, but is preferably located at a site 5' from the promoter.

Expression and cloning vectors will also generally comprise a promoter that is recognized by the host organism and is operably linked to the antibody nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody transcription from vectors in mammalian host cells is controlled, for example, by promoters obtained from the genomes of viruses such as polyoma virus, fowlpox virus, adenovirus (such as Adenovirus 2), BPV, avian sarcoma virus, cytomegalovirus, a retrovirus, hepatitis-B virus, and most preferably SV40, from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the BPV as a vector is disclosed in U.S. Pat. No. 4,419,446. A modification of this system is described in U.S. Pat. No. 4,601,978. See also Reyes et al., *Nature,* 297:598-601 (1982) on expression of human beta-interferon cDNA in mouse cells under the control of a thymidine kinase promoter from herpes simplex virus. Alternatively, the rous sarcoma virus long terminal repeat can be used as the promoter.

Strong transcription promoters can be used, such as promoters from SV40, cytomegalovirus, or myeloproliferative sarcoma virus. See, e.g., U.S. Pat. No. 4,956,288 and U.S. Patent Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA. USA under accession numbers 98669, 98668, and PTA-5266, respectively, and derivatives of these vectors.

Expression vectors used in eukaryotic host cells (yeast, fungus, insect, plant, animal, human, or a nucleated cell from other multicellular organism) will also generally contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO 94/11026 and the expression vector disclosed therein.

Suitable host cells for cloning or expressing the subject antibodies include prokaryote, yeast, or higher eukaryote cells described above. However, interest has been greatest in vertebrate cells, and propagation of vertebrate cells in culture has become a routine procedure. Examples of useful mammalian host cell lines are monkey kidney CV1 line transformed by SV40 (COS-1 (ATCC No. CRL 1650); and COS-7, ATCC CRL 1651); human embryonic kidney line (293 or 293 cells subcloned for growth in suspension culture, (ATCC No. CRL 1573; Graham et al., *J Gen. Virol.,* 36:59-72 (1977)); baby hamster kidney cells (BHK, ATCC CCL 10, ATCC No. CRL 1632; BHK 570, ATCC No. CRL 10314); CHO cells (CHO-K1, ATCC No. CCL 61; CHO-DG44, Urlaub et al., *Proc. Natl. Acad. Sci. USA,* 77:4216-4220 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). Additional suitable cell lines are known in the art and available from public depositories such as the American Type Culture Collection, Manassas, VA.

Host cells are transformed with the above-described expression or cloning vectors for antibody production and cultured in conventional nutrient media modified as appropriate for inducing promoters, selecting transformants, or amplifying the genes encoding the desired sequences as discussed supra.

The mammalian host cells used to produce the antibody of this invention may be cultured in a variety of media. Commercially available media such as Ham's F10 (Sigma-Aldrich Corporation, St. Louis, MO), Minimal Essential Medium (("MEM" (Sigma-Aldrich Corporation, St. Louis, MO), Roswell Park Memorial Institute-1640 medium ("RPMI-1640", Sigma-Aldrich Corporation, St. Louis, MO), and Dulbecco's Modified Eagle's Medium (("DMEM" Sigma-Aldrich Corporation, St. Louis, MO) are suitable for culturing the host cells. In addition, any of the media described in Ham et al., *Meth. Enz.,* 58:44 (1979); Barnes et al., *Anal. Biochem.,* 102:255 (1980); U.S. Pat. Nos. 4,767,704; 4,657,866; 4,927,762; 4,560,655; or 5,122,469; WO 90/03430; WO 87/00195; or U.S. Pat. Reexam No. 30,985 can be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Methods of development and optimization of media and culture conditions are known in the art. (See, Gronemeyer et al., *Bioengineering,* 1(4):188-212, 2014).

After culture conditions are optimized and a preferred cell line clone is selected, these cells are cultured (either adherent cells or suspension cultures) most typically in a batch-fed process in a bioreactor (many models are commercially available) that involves continuously feeding the cell culture with medium and feed, optimized for the particular cell line chosen and selected for this purpose. (See, Butler, M., *Appl. Microbiol. Biotechnol.,* 68:283-291, 2005; and Kelley, B., *mAb,* 1(5):443-452, 2009). Perfusion systems are also available in which media and feed are continuously supplied to the culture while the same volume of media is being withdrawn from the bioreactor. (Wurm, 2004). Synthetic media, also commercially available, are available for growing cells in a batch-fed culture, avoiding the possibility of contamination from outside sources, such as with the use of animal components, such as bovine serum albumin, etc. However, animal-component-free hydrolysates are commercially available to help boost cell density, culture viability and productivity. (Li et al., 2010). Many studies have been performed in an effort to optimize cell culture media, including careful attention to head space available in roller bottles, redox potentials during growth and expression phases, presence of reducing agents to maintain disulfide bonds during production, etc. (See, for instance, Hutterer et al., mAbs, 5(4):608-613, 2013; and Mullan et al., *BMC Proceed.,* 5(Suppl 8):P110, 2011). Various methodologies have been developed to address the possibility of harmful oxidation during recombinant monoclonal antibody production. (See, for example, U.S. Pat. No. 8,574,869). Cultured cells may be grown by feeding nutrients continuously or as separately administered amounts. Often various process parameters such as cell concentration, pH, temperature, $CO_2$, $dO_2$, osmolality, amount of metabolites such as glucose, lactate, glutamine and glutamate, and the like, are monitored by the use of probes during the cell growth either on-line by direct connection to calibrated analyzers or off-line by intervention of operators. The culturing step also typically involves ensuring that the cells growing in culture maintain the transfected recombinant genes by any means known in the art for cell selection.

Following fermentation, i.e., upon reaching maximum cell growth and recombinant protein expression, the culturing step is typically followed by a harvesting step, whereby the cells are separated from the medium and a harvested cell culture media is thereby obtained. (See, Liu et al., *mAbs*, 2(5):480-499, 2010). Typically various purification steps, involving column chromatography and the like, follow culturing to separate the recombinant monoclonal antibody from cell components and cell culture media components. The exact purification steps needed for this phase of the production of recombinant monoclonal antibodies depends on the site of expression of the proteins, i.e., in the cytosol of the cells themselves, or the more commonly preferred route of protein excreted into the cell culture medium. Various cell components may be separated using techniques known in the art such as differential centrifugation techniques, gravity-based cell settling, and/or size exclusion chromatograph/filtration techniques that can include tangential flow micro-filtration or depth filtration. (See, Pollock et al., *Biotechnol. Bioeng.*, 110:206-219, 2013, and Liu et al., 2010). Centrifugation of cell components may be achieved on a large scale by use of continuous disk stack centrifuges followed by clarification using depth and membrane filters. (See, Kelley, 2009). Most often, after clarification, the recombinant protein is further purified by Protein A chromatography due to the high affinity of Protein A for the Fc domain of antibodies, and typically occurs using a low pH/acidification elution step (typically the acidification step is combined with a precautionary virus inactivation step). Flocculation and/or precipitation steps using acidic or cationic polyelectrolytes may also be employed to separate animal cells in suspension cultures from soluble proteins. (Liu et al., 2010). Lastly, anion- and cation-exchange chromatography, hydrophobic interaction chromatograph ("HIC"), hydrophobic charge induction chromatograph (HCIC), hydroxyapatite chromatography using ceramic hydroxyapatite $(Cas(PO_4)_3OH)_2$, and combinations of these techniques are typically used to polish the solution of recombinant monoclonal antibody. Final formulation and concentration of the desired monoclonal antibody may be achieved by use of ultracentrifugation techniques. Purification yields are typically 70 to 80%. (Kelley, 2009).

The terms "desired protein" or "desired antibody" are used interchangeably and refer generally to a parent antibody specific to a target, i.e., PACAP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Examples thereof include chimeric antibodies, human antibodies and other non-human mammalian antibodies, humanized antibodies, single chain antibodies (such as scFvs), camelbodies, nanobodies, IgNAR (single-chain antibodies which may be derived from sharks, for example), small-modular immunopharmaceuticals ("SMIPs"), and antibody fragments such as Fabs, Fab', F(ab')$_2$, and the like (See, Streltsov et al., *Protein Sci.*, 14(11):2901-9, 2005; Greenberg et al., *Nature*, 374(6518):168-73, 1995; Nuttall et al., *Mol. Immunol.*, 38(4):313-26, 2001; Hamers-Casterman et al., *Nature*, 363(6428):446-8, 1993; Gill et al., *Curr. Opin. Biotechnol.*, (6):653-8, 2006).

For example, antibodies or antigen binding fragments thereof may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones that co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid ("aa") substitutions, additions, or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc.). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the $V_L$ and $V_H$ regions, obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment" or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, small molecule immunopharmaceuticals ("SMIPs"), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties, and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the DNA flanking the gene usually does not flank the mammalian genomic DNA in the genome of the source organism. Another example of a heterologous region is a construct where the coding sequence itself is not found in nature (e.g., a cDNA where the genomic coding sequence contains introns or synthetic sequences having codons different than the native gene). Allelic variations or naturally-occurring mutational events do not give rise to a heterologous region of DNA as defined herein.

A "coding sequence" is an in-frame sequence of codons that correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of initiating transcription of a downstream (3' direction) coding sequence, and typically contain additional sites for binding of regulatory molecules, e.g., transcription factors, that affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

The general structure of antibodies in vertebrates now is well understood (See Edelman, G. M., *Ann. N.Y. Acad. Sci.*, 190:5 1971). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_c$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (see Kabat, E. A., Structural Concepts in Immunology and Immunochemistry, 2nd Ed., p. 413-436, New York, NY: Holt, Rinehart, Winston (1976)), and other cellular responses (see Andrews et al., *Clinical Immunology*, pp. 1-18, W. B. Sanders, Philadelphia, PA (1980); Kohl et al., *Immunology*, 48:187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B-cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions ("CDRs") found in the variable regions of light or heavy chains of an antibody (See Kabat et al., *Sequences of Proteins of Immunological Interest*, 4$^{th}$ ed., Bethesda, MD: U.S. Dept. of Health and Human Services, Public Health Service, National Institutes of Health (1987)). These expressions include the hypervariable regions as defined by Kabat et al., (*Sequences of Proteins of Immunological Interest*, NIH Publication No. 91-3242, Bethesda, MD: U.S. Dept. of Health and Human Services, National Institutes of Health (1983)) or the hypervariable loops in 3-dimensional structures of antibodies (Chothia and Lesk, *J. Mol. Biol.*, 196: 901-917 1987). The CDRs in each chain are held in close proximity by framework regions ("FRs") and, with the CDRs from the other chain, contribute to the formation of the antigen binding site. Within the CDRs there are select amino acids that have been described as the selectivity determining regions ("SDRs") that represent the critical contact residues used by the CDR in the antibody-antigen interaction (see, Kashmiri et al., *Methods*, 36(1):25-34, 2005).

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues that are effectively blocked by the specifically antigen binding peptide (in other words, the amino acid residue is within the "footprint" of the specifically antigen binding peptide). The term epitope herein includes both types of amino acid binding sites in any particular region of PACAP, i.e., PACAP38 and PACAP27, that specifically binds to an anti-PACAP antibody. PACAP may comprise a number of different epitopes, which may include, without limitation, (1) linear peptide antigenic determinants, (2) conformational antigenic determinants that consist of one or more non-contiguous amino acids located near each other in a mature PACAP conformation; and (3) post-translational antigenic determinants that consist, either in whole or part, of molecular structures covalently attached to a PACAP protein such as carbohydrate groups. In particular, the term "epitope" includes the specific residues in a protein or peptide, e.g., PACAP, which are involved in the binding of an antibody to such protein or peptide as determined by known and accepted methods such as alanine scanning techniques. Such methods are exemplified herein.

The phrase that an antibody (e.g., first antibody) binds "substantially" or "at least partially" the same epitope as another antibody (e.g., second antibody) means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody.

The phrase "binds to the same or overlapping epitope or determinant as" an antibody of interest means that an antibody "competes" with said antibody of interest for at least one, (e.g., at least 2, at least 3, at least 4, at least 5) or all residues on PACAP to which said antibody of interest specifically binds. The identification of one or more antibodies that bind(s) to substantially or essentially the same epitope as the monoclonal antibodies described herein can be readily determined using alanine scanning. Additionally, any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

For example, where the test antibodies to be examined are obtained from different source animals, or are even of a different Ig isotype, a simple competition assay may be employed in which the control antibody is mixed with the test antibody and then applied to a sample containing PACAP. Protocols based upon ELISAs, radioimmunoassays, Western blotting, and the use of BIACORE® (GE Healthcare Life Sciences, Marlborough, MA) analysis are suitable for use in such simple competition studies.

In certain embodiments, the control anti-PACAP antibody is pre-mixed with varying amounts of the test antibody (e.g., in ratios of about 1:1, 1:2, 1:10, or about 1:100) for a period of time prior to applying to the PACAP38 or PACAP27 antigen sample. In other embodiments, the control and varying amounts of test antibody can simply be added separately and admixed during exposure to the PACAP38 or PACAP27 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labeling the control antibody with a detectable label) it can be determined if the test antibody reduces the binding of the control antibody to the PACAP38 or PACAP27 antigens, indicating that the test antibody recognizes substantially the same epitope as the control anti-PACAP antibody. The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of the control antibody to PACAP38 or PACAP27 by at least about 50%, such as at least about 60%, or more preferably at least about 70% (e.g., about 65-100%), at any ratio of test antibody between about 1:1 or 1:10 and about 1:100 is considered to be an antibody that binds to substantially the same or overlapping epitope or determinant as the control antibody.

Preferably, such test antibody will reduce the binding of the control antibody to PACAP38 or PACAP27 antigen preferably at least about 50%, at least about 60%, at least about 80%, or at least about 90% (e.g., about 95%) of the binding of the control antibody observed in the absence of the test antibody.

A simple competition assay in which a test antibody is applied at saturating concentration to a surface onto which PACAP38 or PACAP27 is immobilized also may be advantageously employed. The surface in the simple competition assay is preferably a BIACORE® (GE Healthcare Life Sciences, Marlborough, MA) chip (or other media suitable for surface plasmon resonance ("SPR") analysis). The binding of a control antibody that binds PACAP38 or PACAP27 to the PACAP-coated surface is measured. This binding to the PACAP38- or PACAP27-containing surface of the control antibody alone is compared with the binding of the control antibody in the presence of a test antibody. A significant reduction in binding to the PACAP38- or PACAP27-containing surface by the control antibody in the presence of a test antibody indicates that the test antibody recognizes substantially the same epitope as the control antibody such that the test antibody "competes" with the control antibody. Any test antibody that reduces the binding of control antibody by at least about 20% or more, at least about 40%, at least about 50%, at least about 70%, or more, can be considered to be an antibody that binds to substantially the same epitope or determinant as the control antibody. Preferably, such test antibody will reduce the binding of the control antibody to PACAP38 or PACAP27 by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the "sandwich-style" binding assay exemplified in Example 9 infra is used. Alternatively, the antibody having greater affinity for PACAP38 or PACAP27 antigen is bound to the PACAP38- or PACAP27-containing surface first, as it will be expected that the decrease in binding seen for the second antibody (assuming the antibodies are competing) will be of greater magnitude. Further examples of such assays are provided in e.g., Saunal and Regenmortel, *J. Immunol. Methods,* 183:33-41 (1995), the disclosure of which is incorporated herein by reference.

In addition, whether an antibody binds the same or overlapping epitope(s) on PACAP as another antibody or the epitope bound by a test antibody may in particular be determined using a Western-blot based assay. In this assay a library of peptides corresponding to the antigen bound by the antibody, the PACAP protein, is made, that comprise overlapping portions of the protein, typically 10-25, 10-20, or 10-15 amino acids long. These different overlapping amino acid peptides encompassing the PACAP sequence are synthesized and covalently bound to a PEPSPOTS™ nitrocellulose membrane (JPT Peptide Technologies, Berlin, Germany). Blots are then prepared and probed according to the manufacturer's recommendations.

Essentially, the immunoblot assay then detects by fluorometric means what peptides in the library bind to the test antibody and thereby can identify what residues on the antigen, i.e., PACAP, interact with the test antibody. (See U.S. Pat. No. 7,935,340, incorporated by reference herein).

Various epitope mapping techniques are known in the art. By way of example, X-ray co-crystallography of the antigen and antibody; NMR; SPR (e.g., at 250 or 37° C.); array-based oligo-peptide scanning (or "pepscan analysis"); site-directed mutagenesis (e.g., alanine scanning); mutagenesis mapping; hydrogen-deuterium exchange; phage display; and limited proteolysis are all epitope mapping techniques that are well known in the art (See, e.g., *Epitope Mapping Protocols: Second Edition, Methods in Molecular Biology,* editors Mike Schutkowski and Ulrich Reineke, $2^{nd}$ Ed., New York, NY: Humana Press (2009), and *Epitope Mapping Protocols, Methods in Molecular Biology,* editor Glenn Morris, $1^{st}$ Ed., New York, NY: Humana Press (1996), both of which are herein incorporated by referenced in their entirety).

The identification of one or more antibodies that bind(s) to substantially or essentially the same epitope as the monoclonal antibodies described herein, e.g., Ab10 or Ab20, can be readily determined using any one of variety of immunological screening assays in which antibody competition can be assessed. A number of such assays are routinely practiced and well known in the art (see, e.g., U.S. Pat. No. 5,660,827, incorporated herein by reference). It will be understood that determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (one of Ab10 or Ab20, for example) is mixed with the test antibody and then applied to a sample containing either or both PACAP38 and PACAP27, each of which is known to be bound by Ab10 or Ab20. Protocols based upon ELISAs, radioimmunoassays, Western blotting, and BIACORE® (GE Healthcare Life Sciences, Marlborough, MA) analysis (as described in the Examples section herein) are suitable for use in such simple competition studies.

In certain embodiments, the method comprises pre-mixing the control antibody with varying amounts of the test antibody (e.g., in ratios of about 1:1, 1:2, 1:10, or about 1:100) for a period of time prior to applying to the PACAP antigen sample. In other embodiments, the control and varying amounts of test antibody can be added separately and admixed during exposure to the PACAP antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labelling the control antibody with a detectable label), the method can be used to determine that the test antibody reduces the binding of the control antibody to the PACAP antigen, indicating that the test antibody recognizes substantially the same epitope as the control antibody (e.g., Ab10 or Ab20). The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of Ab10 or Ab20 to both of PACAP38 and PACAP27 antigens by at least about 50%, such as at least about 60%, or more preferably at least about 70% (e.g., about 65-100%), at any ratio of control Ab10 or Ab20:test antibody, or Ab10 or Ab20:test antibody between about 1:1 or 1:10 and about 1:100 is considered to be an antibody that binds to substantially the same epitope or determinant as Ab10 or Ab20, respectively. Preferably, such test antibody will reduce the binding of Ab10 or Ab20 to at least one, preferably each, of the PACAP38 and PACAP27 antigens preferably at least about 50%, at least about 60%, at least about 80% or at least about 90% (e.g., about 95%) of the binding of Ab10 or Ab20 observed in the absence of the test antibody. These methods can be adapted to identify and/or evaluate antibodies that compete with other control antibodies.

A simple competition assay in which a test antibody is applied at saturating concentration to a surface onto which either PACAP38 or PACAP27, or both, are immobilized also may be advantageously employed. The surface in the simple competition assay is preferably of a media suitable for OCTET® and/or PROTEON®. The binding of a control antibody (e.g., Ab10 or Ab20) to the PACAP-coated surface is measured. This binding to the PACAP-containing surface of the control antibody alone is compared with the binding of the control antibody in the presence of a test antibody. A significant reduction in binding to the PACAP-containing surface by the control antibody in the presence of a test antibody indicates that the test antibody recognizes substantially the same epitope as the control antibody such that the test antibody "competes" with the control antibody. Any test antibody that reduces the binding of control antibody (such as Ab10 or Ab20) to both of PACAP38 and PACAP27 antigens by at least about 20% or more, at least about 40%, at least about 50%, at least about 70%, or more, can be considered to be an antibody that binds to substantially the same epitope or determinant as the control antibody (e.g., Ab10 or Ab20). Preferably, such test antibody will reduce the binding of the control antibody (e.g., Ab10 or Ab20) to the PACAP antigen by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for PACAP38 and PACAP27 is bound to the PACAP-containing surface first, as it will be expected that the decrease in binding seen for the second antibody (assuming the antibodies are competing) will be of greater magnitude. Further examples of such assays are provided in, e.g., Saunal and Regenmortel, *J. Immunol. Methods,* 183: 33-41 (1989), the disclosure of which is incorporated herein by reference.

Determination of whether an antibody, antigen binding fragment thereof, or antibody derivative binds within one of the epitope regions defined above can be carried out in ways known to the person skilled in the art. In another example of such mapping/characterization methods, an epitope region for an anti-PACAP antibody may be determined by epitope "footprinting" using chemical modification of the exposed amines/carboxyls in the PACAP38 and PACAP27 protein. One specific example of such a foot-printing technique is the use of hydrogen-deuterium exchange detected by mass spectrometry ("HXMS"), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry (See, e.g., Ehring H., *Anal. Biochem.,* 267(2): 252-259, 1999; and Engen, J. R. and Smith, D. L., *Anal. Chem.,* 73:256A-265A, 2001). Another example of a suitable epitope identification technique is nuclear magnetic resonance epitope mapping ("NMR"), where typically the position of the signals in two-dimensional NMR spectres of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., *Ernst Schering Res. Found. Workshop,* (44): 149-67, 2004; Huang et al., *J. Mol. Biol.,* 281(1):61-67, 1998; and Saito and Patterson, *Methods,* 9(3):516-24, 1996).

Epitope mapping/characterization also can be performed using mass spectrometry ("MS") methods (See, e.g., Downard, *J. Mass Spectrom.,* 35(4):493-503, 2000; and Kiselar and Downard, *Anal. Chem.,* 71(9):1792-801, 1999).

Protease digestion techniques also can be useful in the context of epitope mapping and identification. Antigenic determinant-relevant regions/sequences can be determined by protease digestion, e.g. by using trypsin in a ratio of about 1:50 to PACAP38 or PACAP27 overnight ("o/n") digestion at 37° C. and pH 7-8, followed by mass spectrometry ("MS") analysis for peptide identification. The peptides protected from trypsin cleavage by the anti-PACAP antibody can subsequently be identified by comparison of samples subjected to trypsin digestion and samples incubated with antibody and then subjected to digestion by e.g. trypsin (thereby revealing a footprint for the antibody). Other enzymes like chymotrypsin or pepsin can be used in similar epitope characterization methods. Moreover, enzymatic digestion can provide a quick method for analyzing whether a potential antigenic determinant sequence is within a region of PACAP in the context of a PACAP-binding polypeptide. If the polypeptide is not surface exposed, it is most likely not relevant in terms of immunogenicity/antigenicity (See, e.g., Manca, *Ann. Ist. Super. Sanita.,* 27(1):15-9, 1991, for a discussion of similar techniques).

Site-directed mutagenesis is another technique useful for characterization of a binding epitope. For example, in "alanine-scanning" site-directed mutagenesis (also known as alanine scanning, alanine scanning mutagenesis, alanine scanning mutations, combinatorial alanine scanning, or creation of alanine point mutations, for example), each residue within a protein segment is replaced with an alanine residue (or another residue such as valine where alanine is present in the wild-type sequence) through such methodologies as direct peptide or protein synthesis, site-directed mutagenesis, the GENEART™ Mutagenesis Service (Thermo Fisher Scientific, Waltham, MA U.S.A.) or shotgun mutagenesis, for example. A series of single point mutants of the molecule is thereby generated using this technique; the number of mutants generated is equivalent to the number of residues in the molecule, each residue being replaced, one at a time, by a single alanine residue. Alanine is generally used to replace native (wild-type) residues because of its non-bulky, chemically inert, methyl functional group that can mimic the secondary structure preferences that many other amino acids may possess. Subsequently, the effects replacing a native residue with an alanine has on binding affinity of an alanine scanning mutant and its binding partner can be measured using such methods as, but not limited to, SPR binding experiments. If a mutation leads to a significant reduction in binding affinity, it is most likely that the mutated residue is involved in binding. Monoclonal antibodies specific for structural epitopes (i.e., antibodies that do not bind the unfolded protein) can be used as a positive control for binding affinity experiments to verify that the alanine-replacement does not influence the overall tertiary structure of the protein (as changes to the overall fold of the protein may indirectly affect binding and thereby produce a false positive result) (See, e.g., Clackson and Wells, *Science,* 267:383-386, 1995; Weiss et al., *Proc. Natl. Acad. Sci. USA,* 97(16):8950-8954, 2000; and Wells, *Proc. Natl. Acad. Sci. USA,* 93:1-6, 1996). In Example 12 alanine scanning methods are used to identify the specific epitope or residues of PACAP which specifically interact with the anti-PACAP antibodies disclosed herein.

Electron microscopy can also be used for epitope "footprinting". For example, Wang et al., *Nature*, 355:275-278 (1992) used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include SPR (sold commercially as the BIACORE® system, GE Healthcare Life Sciences, Marlborough, MA) and reflectometric interference spectroscopy ("RifS") (See, e.g., Fagerstam et al., *J. Mol. Recog.*, 3:208-14, 1990; Nice et al., *J. Chromatogr.*, 646:159-168, 1993; Leipert et al., *Angew. Chem. Int. Ed.*, 37:3308-3311, 1998; Kroger et al., *Biosensors and Bioelectronics*, 17:937-944, 2002).

The expressions "framework region" or "FR" refer to one or more of the framework regions within the variable regions of the light and heavy chains of an antibody (See Kabat et al., *Sequences of Proteins of Immunological Interest*, 4$^{th}$ edition, Bethesda, MD: U.S. Dept. of Health and Human Services, Public Health Service, National Institutes of Health, 1987). These expressions include those amino acid sequence regions interposed between the CDRs within the variable regions of the light and heavy chains of an antibody.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat (See, Kabat et al., *Sequences of Proteins of Immunological Interest*, 5th edition, Bethesda, MD: U.S. Dept. of Health and Human Services, Public Health Service, National Institutes of Health, 1991). The Fc region of an immunoglobulin generally comprises two constant domains, CH2 and CH3.

The terms "Fc receptor" and "FcR" describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, *Ann. Rev. Immunol.*, 9:457-92 (1991); Capel et al., *Immunomethods*, 4:25-34 (1994); and de Haas et al., *J Lab. Clin. Med.*, 126:330-41 (1995). "FcR" also includes the neonatal receptor, FcRn, which is responsible for the transfer of maternal IgGs to the fetus (Guyer et al., *J. Immunol.*, 117:587, 1976; and Kim et al., *J Immunol.*, 24:249, 1994), and which primarily functions to modulate and/or extend the half-life of antibodies in circulation. To the extent that the disclosed anti-PACAP antibodies are aglycosylated, as a result of the expression system and/or sequence, the subject antibodies are expected to bind FcRn receptors, but not to bind (or to minimally bind) Fcγ receptors.

A "functional Fc region" possesses at least one effector function of a native sequence Fc region. Exemplary "effector functions" include C1q binding; complement dependent cytotoxicity ("CDC"); Fc receptor binding; antibody-dependent cell-mediated cytotoxicity ("ADCC"); phagocytosis; down-regulation of cell surface receptors (e.g. B cell receptor ("BCR")), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence that differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, or at least about 99% sequence identity therewith.

Anti-PACAP Antibodies and Binding Fragments Thereof Having Binding Activity for PACAP PACAP is a multifunctional vasodilatory peptide with expression throughout the central nervous system ("CNS") and periphery. PACAP is a member of the secretin/VIP/GRH family. PACAP exists in two α-amidated active forms, PACAP38 (SEQ ID NO: 1241) and PACAP27 (SEQ ID NO: 1242). Herein, the term "PACAP" includes either or both of PACAP38 and PACAP27 unless expressly indicated otherwise. PACAP is highly conserved between species.

In humans, PACAP is derived from a 176 amino acid precursor protein (preproPACAP) and the gene is located on chromosome 18p11, with PACAP38 encoded for by exon 5 (See, Vaudry et al., *Pharmacol. Rev.*, 61:283-357, 2009). PreproPACAP contains an N-terminal 24 amino acid signal protein, a 29 amino acid PACAP-related peptide and PACAP in the C-terminal domain. The precursor is metabolized by prohormone convertase enzymes into biologically active PACAP38 and PACAP27.

VIP (SEQ ID NO: 1243) belongs to the same protein family as PACAP and shares high homology with PACAP, i.e., VIP and PACAP27 have 68% sequence homology at the amino acid level, as well as similar overall secondary structure, i.e. long alpha-helical structures at the C-terminus.

PACAP's actions are mediated via three different G-protein coupled receptors: PAC1-R, VPAC1-R, and VPAC2-R. VPAC1-R can associate with all of the receptor-associated membrane proteins ("RAMPs", see Kaiser and Russo, *Neuropeptides*, 47:451-461, 2013). PAC1-R is selective for PACAP, whereas VPAC1-R and VPAC2-R bind to both VIP and PACAP with high affinity. PAC1-R binds to PACAP with 100-1000-fold higher affinity than VIP, i.e., $K_D$~0.5 nM for PACAP27/PACAP38 vs. $K_D$~500 nM for VIP. Conversely, VPAC1-R and VPAC2-R have equal affinities for PACAP and VIP ($K_D$~1 nM), (See, Schytz et al. 2010). All three receptors are widely expressed in both peripheral tissues and in the CNS, with PAC1-R predominantly expressed in the CNS, most abundantly in the olfactory bulb, thalamus, hypothalamus, the dentate gyrus of the hippocampus and in granule cells of the cerebellum (See, Hashimoto et al., *J. Comp. Neurol.*, 371:567-577, 1996; Shioda et al., *Neurosci. Res.*, 28:345-354, 1997).

Activation of the PAC1-R, VPAC1-R, and/or VPAC2-R results in increased adenylate cyclase activity and, thus, increased cAMP production. However, PACAP receptors can also mediate their effects through PLC, leading to increased $Ca^{2+}$ levels, and PLD.

PACAP has a wide range of biological effects, including a role in neurodevelopment, neuroprotection, neuromodulation, neurogenic inflammation, and nociception. PACAP is also reported to interact with glycosaminoglycans ("GAGs"). GAGs are long, unbranched polysaccharides composed of repeating disaccharide units, such as heparin, chondroitin, keratin, and hyaluronic acid. It has been shown that the cellular uptake of PACAP is dependent on the expression of GAG proteins and that PACAP bound to sulfated GAGs. Particularly, it was determined that PACAP38 binding to GAGs was capable of inducing receptor-independent cellular uptake of PACAP38. This study further demonstrated that a random coil-to-α-helix transition in PACAP38 was essential for GAG-dependent uptake of PACAP38, as a mutant PACAP38 that could not undergo the structural transition was not internalized by GAG-containing cell lines as efficiently as the wild-type form of PACAP38 (Neree et al., *FEBS Lett.*, 588(24):4590-4596, 2014). In a follow up study, it was determined that PACAP's ability to cluster GAGs, i.e., heparin, was directly related to its ability to function as a cell penetrating peptide ("CPP"). It is hypothesized that this activity is attributable to the heparin-binding, or Cardin-Weintraub, motif found in secretin/glucagon/GHRH family members, such as PACAP (Neree et al., *Int. J. Mol. Sci.*, 16:27391-27400, 2015). Interestingly, Neree et al. (2015) presented data demonstrating that PACAP38 was able to cluster sulfated GAGs in vitro. These data suggested that the observed clustering effect is important for the GAG-mediated cellular uptake of PACAP38, as other peptides, such as glucagon, displayed higher binding affinities for sulfated GAGs (heparin) but are not internalized by cells as efficiently as PACAP38. Further, it is reported that in in vitro studies in which cells are exposed to PACAP, cartilage formation is increased, including cartilage matrix that is rich in sulphated GAG proteins, consistent with its putative protective role expressed during various cellular stress responses (Juhisz et al., *PLoS ONE*, 9(3):e91541, 2014). Using cell types that lack PACAP-specific receptors on their plasma membranes, such as CHO-K1 cells, Doan et al. presented data demonstrating the ability of such cells to engage in receptor-independent cellular uptake of various forms of fluorescently-labeled PACAP38 and PACAP27 (Doan et al., *Biochem. Biophys. Acta*, 1823:940-949, 2012).

The present invention provides exemplary antibodies or antigen binding fragments thereof that bind PACAP, including human PACAP. Other antibodies or antigen binding fragments thereof that bind PACAP, including those having different CDRs, and epitopic specificity may be obtained using the disclosure of the present specification, and using methods that are generally known in the art. Such antibodies and antigen binding fragments thereof antagonize the biological effects of PACAP in vivo and therefore are useful in treating or preventing PACAP-related conditions including, for example, headache, migraine, pain, photophobia, hot flush, PTSD, and anxiety disorders. In preferred embodiments, the antibody or antigen binding fragment thereof according to the invention comprises one or more CDRs, a $V_L$ chain and/or $V_H$ chain of the anti-PACAP antibodies and antigen binding fragments thereof described herein.

In some embodiments, an anti-PACAP antibody or antigen binding fragment thereof according to the invention will interfere with, block, reduce, or modulate the interaction between PACAP and its receptor(s) (e.g., PAC1-R, VPAC1-R, and VPAC2-R). In some instances an anti-PACAP antibody or antigen binding fragment thereof according to the invention is "neutralizing", e.g., it totally prevents the specific interaction of PACAP with PAC1-R, VPAC1-R, and/or VPAC2-R. In some embodiments, the antibody or antigen binding fragment thereof neutralizes PACAP, e.g., by remaining bound to PACAP in a location and/or manner that prevents PACAP from specifically binding to PAC1-R, VPAC1-R, and/or VPAC2-R.

In some embodiments, the antibody or antigen binding fragment thereof according to the invention is capable of inhibiting PACAP-mediated activity (including binding to PAC1-R-expressing cells). In some embodiments, the antibody or antigen binding fragment thereof according to the invention are humanized, such as humanized rabbit antibodies to PACAP.

As mentioned, the anti-PACAP antibodies or antigen binding fragments thereof according to the invention have a variety of uses. For example, the subject antibodies and fragments can be useful in therapeutic applications, as well as diagnostically in binding assays. The subject anti-PACAP antibodies or antigen binding fragments thereof are useful for affinity purification of PACAP, in particular human PACAP or its ligands and in screening assays to identify other antagonists of PACAP activity. Some of the antibodies or antigen binding fragments thereof are useful for inhibiting binding of PACAP to PAC1-R, VPAC1-R, and/or VPAC2-R, or inhibiting PACAP-mediated activities and/or biological effects.

As used herein, the term "one or more biological effects associated with PACAP refers to any biological effect mediated, induced, or otherwise attributable to PACAP, e.g., binding properties, functional properties, and other properties of biological significance. Non-limiting exemplary biological effects of PACAP include PACAP binding to PAC1-R, VPAC1-R, and/or VPAC2-R; PACAP activating PAC1-R, VPAC1-R, and/or VPAC2-R-mediated signaling; PACAP-mediated increase in cAMP production; PACAP-mediated increase in PLC activity; PACAP-mediated increase in PLD activity; PACAP-mediated increase in $Ca^2$ levels; and PACAP-mediated vasodilation, photophobia, mast cell degranulation, and/or neuronal activation. The subject anti-PACAP antibodies are capable of inhibiting one, a combination of, or all of these exemplary PACAP biological activities. For example, the anti-PACAP antibodies and antigen binding fragments thereof provided herein are capable of inhibiting PACAP-induced vasodilation (see Example 7 and Example 8).

The antibody or antigen binding fragment thereof according to the invention can be used in a variety of therapeutic applications. For example, in some embodiments the anti-PACAP antibody or antigen binding fragment thereof are useful for treating conditions associated with PACAP, such as, but not limited to, migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, PTSD, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, LUT disorders such as urinary tract infection, abnormal voiding, urinary urgency, nocturia, urinary incontinence, overactive bladder, and for preventing or alleviating the pain associated with such LUT conditions.

Specific examples of visceral pain, i.e., pain associated with the viscera, or the internal organs of the body include pain that affects organs such as e.g., the heart, lungs, reproductive organs, bladder, ureters, the digestive organs, liver, pancreas, spleen, and kidneys. Conditions associated therewith include by way of example pancreatitis, labor, abdominal surgery associated with ileus, cystitis, menstrual period, or dysmenorrhea. Likewise, kidney pain, epigastric pain, pleural pain, and painful biliary colic, appendicitis pain may all be considered to be visceral pain. Substernal pain or pressure from early myocardial infarction is also visceral. Diseases of the stomach, duodenum or colon can cause visceral pain. Commonly encountered gastrointestinal ("GI") disorders that cause visceral pain include functional bowel disorder ("FBD") and inflammatory bowel disease ("IBD"). Such GI disorders may further include gastroesophageal reflux, dyspepsia, irritable bowel syndrome ("IBS") and functional abdominal pain syndrome ("FAPS"), and, with respect to IBD, Crohn's disease, ileitis, and ulcerative colitis.

The subject anti-PACAP antibodies and antigen binding fragments thereof may be used alone or in association with other active agents or drugs, including other biologics, to treat any subject in which blocking, inhibiting, or neutralizing the in vivo effect of PACAP or blocking or inhibiting the interaction of PACAP and its receptors, PAC1-R, VPAC1-R, and VPAC2-R, is therapeutically desirable.

Exemplary anti-PACAP antibodies and antigen binding fragments thereof according to the invention, and the specific CDRs thereof are identified in this section. For convenience, each exemplified antibody or antigen binding fragment thereof, and corresponding sequences are separately identified by a specific nomenclature, i.e., Ab10 or Ab20.

The anti-PACAP antibodies and antigen binding fragments thereof comprising the invention have binding affinity for PACAP, wherein the binding affinity comprises anti-PACAP antibodies or antigen binding fragments thereof specifically binding to PACAP38 and PACAP27, but not binding VIP, and/or antibodies or antigen binding fragments thereof specifically binding to PACAP38, but not binding to PACAP27 or VIP, and/or antibodies or antigen binding fragments thereof specifically binding to a linear and/or conformational epitope within PACAP38 and/or PACAP27. More specifically, the epitopes of PACAP38 and/or PACAP27 to which antagonistic anti-PACAP antibodies or antigen binding fragments thereof according to the invention bind will include those which are identified in Example 12 or residues thereof (as determined by use of alanine scanning) and/or other epitopic identification methods.

Anti-PACAP Antibody Polypeptide Sequences
Antibody Ab10

In one embodiment, the invention includes antibodies and antigen-binding fragments having binding specificity to PACAP that possess a heavy chain sequence comprising the sequence of SEQ ID NO: 401 which consists of the heavy chain variable region of SEQ ID NO: 402 linked to the heavy chain constant region of SEQ ID NO: 410.

In one embodiment, the invention includes antibodies and antigen-binding fragments having binding specificity to PACAP that contain a variable heavy chain sequence comprising the sequence set forth below:

(SEQ ID NO: 402)
QSVEESGGRLVTPGTPLTLTCTVSGIDLNSYYMTWVRQAPGKGLEWIGF

IDAGGDAYYASWAKGRFTISKTSTTVDLKITSPTTEDTATYFCARDLDL

WGQGTLVTVSS.

In another embodiment, the invention includes antibodies and antigen-binding fragments having binding specificity to PACAP that bind the same epitope as Ab10, and that contain a constant heavy chain sequence comprising the polypeptide of SEQ ID NO: 1244, 1245, or 1246, or comprising the sequence set forth below:

(SEQ ID NO: 410)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDARV

EPKSCDKTHTCPPCPAPELLGGPSVFLFPPKPKDTLMISRTPEVTCVVV

DVSHEDPEVKFNWYVDGVEVHNAKTKPREEQYASTYRVVSVLTVLHQDW

-continued

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 421 which consists of the light chain variable region of SEQ ID NO: 422 linked to the light chain constant region of SEQ ID NO: 430.

In another embodiment, the invention includes antibodies and antigen-binding fragments having binding specificity to PACAP that contain a variable light chain sequence comprising the sequence set forth below:

(SEQ ID NO: 422)
AAVLTQTPSPVSAAVGGTVTINCQSSESVYGNYLAWFQQKPGQPPKLLIY

EASKLESGVPSRFSGSGSGTQFTLTISDLQCDDAATYYCAGGDISEGVAF

GGGTEVVVKR.

In another embodiment, the invention includes antibodies and antigen-binding fragments having binding specificity to PACAP, that bind the same epitope as Ab10, and that contain a constant light chain sequence comprising the sequence set forth below:

(SEQ ID NO: 430)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 404; SEQ ID NO: 406; and SEQ ID NO: 408, which correspond to the CDRs (hypervariable regions) of the heavy chain sequence of SEQ ID NO: 401, or which contain the variable heavy chain sequence of SEQ ID NO: 402, and/or which further contain one, two, or three of the polypeptide sequences of SEQ ID NO: 424; SEQ ID NO: 426; and SEQ ID NO: 428, which correspond to the CDRs (hypervariable regions) of the light chain sequence of SEQ ID NO: 421, or which contain the variable light chain sequence of SEQ ID NO: 422, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 403; SEQ ID NO: 405; SEQ ID NO: 407; and SEQ ID NO: 409, which correspond to the FRs (constant regions) of the heavy chain sequence of SEQ ID NO: 401, or the variable heavy chain sequence of SEQ ID NO: 402, and/or one, two, three, or four of the polypeptide sequences of SEQ ID NO: 423; SEQ ID NO: 425; SEQ ID NO: 427; and SEQ ID NO: 429, which correspond to the FRs (constant regions) of the light chain sequence of SEQ ID NO: 421, or the variable light chain sequence of SEQ ID NO: 422, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 401, or SEQ ID NO: 402, or polypeptides that are at least 90% or 95% identical thereto. In another embodiment of the invention, the antibodies and antigen-binding fragments of the invention comprise, or alternatively consist of, the polypeptide sequence of SEQ ID NO: 421, or SEQ ID NO: 422, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 404; SEQ ID NO: 406; and SEQ ID NO: 408, which correspond to the CDRs (hypervariable regions) of the heavy chain sequence of SEQ ID NO: 401, or the variable heavy chain sequence of SEQ ID NO: 402, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 424; SEQ ID NO: 426; and SEQ ID NO: 428, which correspond to the CDRs (hypervariable regions) of the light chain sequence of SEQ ID NO: 421, or the variable light chain sequence of SEQ ID NO: 422, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 403; SEQ ID NO: 405; SEQ ID NO: 407; and SEQ ID NO: 409, which correspond to the FRs (constant regions) of the heavy chain sequence of SEQ ID NO: 401, or the variable heavy chain sequence of SEQ ID NO: 402, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 423; SEQ ID NO: 425; SEQ ID NO: 427; and SEQ ID NO: 429, which correspond to the FRs (constant regions) of the light chain sequence of SEQ ID NO: 421, or the variable light chain sequence of SEQ ID NO: 422, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 402; the variable light chain region of SEQ ID NO: 422; the complementarity determining regions (SEQ ID NO: 404; SEQ ID NO: 406; and SEQ ID NO: 408) of the variable heavy chain region of SEQ ID NO: 402; and the complementarity determining regions (SEQ ID NO: 424; SEQ ID NO: 426; and SEQ ID NO: 428) of the variable light chain region of SEQ ID NO: 422, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 402; the variable light chain region of SEQ ID NO: 422; the framework regions (SEQ ID NO: 403; SEQ ID NO: 405; SEQ ID NO: 407; and SEQ ID NO: 409) of the variable heavy chain region of SEQ ID NO: 402; and the framework regions (SEQ ID NO: 423; SEQ ID NO: 425; SEQ ID NO: 427; and SEQ ID NO: 429) of the variable light chain region of SEQ ID NO: 422, or sequences that are at least 90% or 95% identical thereto.

In another embodiment of the invention, the anti-PACAP antibody is Ab10, comprising, or alternatively consisting of, SEQ ID NO: 401 and SEQ ID NO: 421, or SEQ ID NO: 402 and SEQ ID NO: 422, or an antibody or antigen-binding fragment comprising the CDRs of Ab10 and having at least one of the biological activities set forth herein, or is an anti-PACAP antibody that competes with Ab10 in binding PACAP, preferably one containing sequences that are at least 90%, 95%, 96%, 97%, 98%, or 99% identical to that of Ab10, or an antibody that binds to the same or overlapping epitope(s) on PACAP as Ab10.

In a further embodiment of the invention, antigen-binding fragments comprise, or alternatively consist of, Fab fragments having binding specificity for PACAP. With respect to antibody Ab10, the Fab fragment preferably includes the variable heavy chain sequence of SEQ ID NO: 402 and the variable light chain sequence of SEQ ID NO: 422, or sequences that are at least 90%, 95%, 96%, 97%, 98%, or 99% identical thereto. This embodiment of the invention further includes Fabs containing additions, deletions, and variants of SEQ ID NO: 402 and/or SEQ ID NO: 422 that retain the binding specificity for PACAP.

In one embodiment of the invention described herein, Fab fragments may be produced by enzymatic digestion (e.g., papain) of Ab10. In another embodiment of the invention, anti-PACAP antibodies such as Ab10 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab10, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab20

In one embodiment, the invention includes antibodies and antigen-binding fragments having binding specificity to PACAP that possess a heavy chain sequence comprising the sequence of SEQ ID NO: 441 which consists of the heavy chain variable region of SEQ ID NO: 442 linked to the heavy chain constant region of SEQ ID NO: 450.

In one embodiment, the invention includes antibodies and antigen-binding fragments having binding specificity to PACAP that contain a variable heavy chain sequence comprising the sequence set forth below:

```
                                          (SEQ ID NO: 442)
QSVEESGGRLVTPGTPLTLTCTVSGIDLSSYYMSWVRQAPGKGLEWIGFI

DTDGSAYYATWAKGRFTISKTSTTVDLKITSPTTEDTATYFCARDLDLWG

PGTLVTVSS.
```

In another embodiment, the invention includes antibodies and antigen-binding fragments having binding specificity to PACAP that bind the same epitope as Ab20, and that contain a constant heavy chain sequence comprising the polypeptide of SEQ ID NO: 1244, 1245, or 1246, or comprising the sequence set forth below:

```
                                          (SEQ ID NO: 450)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 461 which consists of the light chain variable region of SEQ ID NO: 462 linked to the light chain constant region of SEQ ID NO: 470.

In another embodiment, the invention includes antibodies and antigen-binding fragments having binding specificity to PACAP that contain a variable light chain sequence comprising the sequence set forth below:

```
                                          (SEQ ID NO: 462)
AAVLTQTPSPVSAAVGGTVSISCQSSESVYSNYLAWFQQKPGQPPKFLIY

EASKLASGVPSRFKGSGSGTQFTLTISDVQCDDAGTYYCAGGYSSEGVAF

GGGTEVVVKR.
```

In another embodiment, the invention includes antibodies and antigen-binding fragments having binding specificity to PACAP, that bind the same epitope as Ab20, and that contain a constant light chain sequence comprising the sequence set forth below:

```
                                          (SEQ ID NO: 470)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.
```

In another embodiment, the invention includes antibodies and antigen-binding fragments having binding specificity to PACAP that contain one, two, or three of the polypeptide sequences of SEQ ID NO: 444; SEQ ID NO: 446; and SEQ ID NO: 448, which correspond to the CDRs (hypervariable regions) of the heavy chain sequence of SEQ ID NO: 441, or which contain the variable heavy chain sequence of SEQ ID NO: 442, and/or which further contain one, two, or three of the polypeptide sequences of SEQ ID NO: 464; SEQ ID NO: 466; and SEQ ID NO: 468, which correspond to the CDRs (hypervariable regions) of the light chain sequence of SEQ ID NO: 461, or which contain the variable light chain sequence of SEQ ID NO: 462, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 443; SEQ ID NO: 445; SEQ ID NO: 447; and SEQ ID NO: 449, which correspond to the FRs (constant regions) of the heavy chain sequence of SEQ ID NO: 441, or the variable heavy chain sequence of SEQ ID NO: 442, and/or one, two, three, or four of the polypeptide sequences of SEQ ID NO: 463; SEQ ID NO: 465; SEQ ID NO: 467; and SEQ ID NO: 469, which correspond to the FRs (constant regions) of the light chain sequence of SEQ ID NO: 461, or the variable light chain sequence of SEQ ID NO: 462, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 441, or SEQ ID NO: 442, or polypeptides that are at least 90% or 95% identical thereto. In another embodiment of the invention, the antibodies and antigen-binding fragments of the invention comprise, or alternatively consist of, the polypeptide sequence of SEQ ID NO: 461, or SEQ ID NO: 462, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 444; SEQ ID NO: 446; and SEQ ID NO: 448, which correspond to the CDRs (hypervariable regions) of the heavy chain sequence of SEQ ID NO: 441, or the variable heavy chain sequence of SEQ ID NO: 442, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 464; SEQ ID NO: 466; and SEQ ID NO: 468, which correspond to the CDRs (hypervariable regions) of the light chain sequence of SEQ ID NO: 461, or the variable light chain sequence of SEQ ID NO: 462, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 443; SEQ ID NO: 445; SEQ ID NO: 447; and SEQ ID NO: 449, which correspond to the FRs (constant regions) of the heavy chain sequence of SEQ ID NO: 441, or the variable heavy chain sequence of SEQ ID NO: 442, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 463; SEQ ID NO: 465; SEQ ID NO: 467; and SEQ ID NO: 469, which correspond to the FRs (constant regions) of the light chain sequence of SEQ ID NO: 461, or the variable light chain sequence of SEQ ID NO: 462, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 442; the variable light chain region of SEQ ID NO: 462; the complementarity determining regions (SEQ ID NO: 444; SEQ ID NO: 446; and SEQ ID NO: 448) of the variable heavy chain region of SEQ ID NO: 442; and the complementarity determining regions (SEQ ID NO: 464; SEQ ID NO: 466; and SEQ ID NO: 468) of the variable light chain region of SEQ ID NO: 462, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 442; the variable light chain region of SEQ ID NO: 462; the framework regions (SEQ ID NO: 443; SEQ ID NO: 445; SEQ ID NO: 447; and SEQ ID NO: 449) of the variable heavy chain region of SEQ ID NO: 442; and the framework regions (SEQ ID NO: 463; SEQ ID NO: 465; SEQ ID NO: 467; and SEQ ID NO: 469) of the variable light chain region of SEQ ID NO: 462, or sequences that are at least 90% or 95% identical thereto.

In another embodiment of the invention, the anti-PACAP antibody is Ab20, comprising, or alternatively consisting of, SEQ ID NO: 441 and SEQ ID NO: 461, or SEQ ID NO: 442 and SEQ ID NO: 462, or an antibody or antigen-binding fragment comprising the CDRs of Ab20 and having at least one of the biological activities set forth herein, or is an anti-PACAP antibody that competes with Ab20 in binding PACAP, preferably one containing sequences that are at least 90%, 95%, 96%, 97%, 98%, or 99% identical to that of Ab20, or an antibody that binds to the same or overlapping epitope(s) on PACAP as Ab20.

In a further embodiment of the invention, antigen-binding fragments comprise, or alternatively consist of, Fab fragments having binding specificity for PACAP. With respect to antibody Ab20, the Fab fragment preferably includes the variable heavy chain sequence of SEQ ID NO: 442 and the variable light chain sequence of SEQ ID NO: 462, or sequences that are at least 90%, 95%, 96%, 97%, 98%, or 99% identical thereto. This embodiment of the invention further includes Fabs containing additions, deletions, and variants of SEQ ID NO: 442 and/or SEQ ID NO: 462 that retain the binding specificity for PACAP.

In one embodiment of the invention described herein, Fab fragments may be produced by enzymatic digestion (e.g., papain) of Ab20. In another embodiment of the invention, anti-PACAP antibodies such as Ab20 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab20, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

In another embodiment, the invention contemplates an isolated anti-PACAP antibody comprising a $V_H$ polypeptide sequence selected from: SEQ ID NO: 402, SEQ ID NO: 442, or a variant thereof, and further comprising a $V_L$ polypeptide sequence selected from: SEQ ID NO: 422, SEQ ID NO: 462, or a variant thereof, wherein one or more of the framework region residues ("FR residues") and/or CDR residues in said $V_H$ or $V_L$ polypeptide has been substituted with another amino acid residue resulting in an anti-PACAP antibody that specifically binds PACAP. The invention also includes humanized and chimeric forms of these antibodies. The chimeric and humanized antibodies may include an Fc derived from IgG1, IgG2, IgG3, or IgG4 constant regions.

In one embodiment of the invention, the chimeric or humanized antibodies or fragments or $V_H$ or $V_L$ polypeptides originate or are derived from one or more rabbit antibodies, e.g., a rabbit antibody isolated from a clonal rabbit B cell population.

In some aspects, the invention provides a vector comprising a nucleic acid molecule encoding an anti-PACAP antibody or fragment thereof as disclosed herein. In some embodiments, the invention provides a host cell comprising a nucleic acid molecule encoding an anti-PACAP antibody or fragment thereof as disclosed herein.

In some aspects, the invention provides an isolated antibody or antigen binding fragment thereof that competes for binding to PACAP with an antibody or antigen binding fragment thereof disclosed herein.

In some aspects, the invention provides a nucleic acid molecule encoding an antibody or antigen binding fragment thereof as disclosed herein.

In some aspects, the invention provides a pharmaceutical or diagnostic composition comprising at least one antibody or antigen binding fragment thereof as disclosed herein.

In some aspects, the invention provides a method for treating or preventing a condition associated with elevated PACAP levels in a subject, comprising administering to a subject in need thereof an effective amount of at least one isolated antibody or antigen binding fragment thereof as disclosed herein.

In some aspects, the invention provides a method of inhibiting binding of PACAP to PAC1-R, VPAC1-R, and/or VPAC2-R in a subject comprising administering an effective amount of at least one antibody or antigen binding fragment thereof as disclosed herein.

In some aspects, the invention provides an antibody or antigen binding fragment thereof that selectively binds to PACAP, wherein the antibody or antigen binding fragment thereof binds to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M; preferably, with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M; more preferably, with a $K_D$ that is less than about 100 pM, less than about 50 pM, less than about 40 pM, less than about 25 pM, less than about 1 pM, between about 10 pM and about 100 pM, between about 1 pM and about 100 pM, or between about 1 pM and about 10 pM. Preferably, the anti-PACAP antibody or antigen binding fragment thereof has no cross-reactivity or minimal cross-reactivity with VIP.

The inventive antibodies and antigen binding fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies and antigen binding fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol, and the like. The antibodies and fragments thereof may be modified at random positions within the molecule, or at predetermined positions within the molecule and may include one, two, three, or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., *Appl. Biochem. Biotechnol.*, 56:59-72 (1996); Vorobjev et al., *Nucleosides and Nucleotides*, 18:2745-2750 (1999); and Caliceti et al., *Bioconjug. Chem.*, 10:638-646 (1999), the disclosures of each of which are incorporated herein by reference.

There are a number of attachment methods available to those skilled in the art (See e.g., EP 0 401 384, herein incorporated by reference, disclosing a method of coupling PEG to G-CSF; and Malik et al., *Exp. Hematol.,* 20:1028-1035 (1992) (reporting pegylation of GM-CSF using tresyl chloride)). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or antigen binding fragments thereof may have increased in vivo half-lives via fusion with albumin (including but not limited to recombinant human serum albumin or fragments or variants thereof (See, e.g., U.S. Pat. No. 5,876,969, EP 0 413 622, and U.S. Pat. No. 5,766,883, herein incorporated by reference in their entirety)), or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase, and luciferase. Further exemplary fluorescent materials include, but are not limited to, rhodamine, fluorescein, fluorescein isothiocyanate, umbelliferone, dichlorotriazinylamine, phycoerythrin, and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Methods are known in the art for conjugating an antibody or antigen binding fragment thereof to a detectable moiety and the like, such as for example those methods described by Hunter et al., *Nature,* 144:945 (1962); David et al., *Biochemistry,* 13:1014 (1974); Pain et al., *J. Immunol. Meth.,* 40:219 (1981); and Nygren, *J., Histochem. and Cytochem.,* 30:407 (1982).

Embodiments described herein further include variants and equivalents that are substantially homologous to the antibodies, antibody fragments, diabodies, SMIPs, camelbodies, nanobodies, IgNAR, polypeptides, variable regions, and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antigen binding fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antigen binding fragments, variable regions, and CDRs set forth herein.

Methods for determining homology between nucleic acid and amino acid sequences are well known to those of ordinary skill in the art.

In another embodiment, the invention further contemplates the above-recited polypeptide homologs of the antigen binding fragments, variable regions and CDRs set forth herein further having anti-PACAP activity. Non-limiting examples of anti-PACAP activity are set forth herein, e.g., ability to inhibit PACAP binding to PAC1-R, VPAC1-R, and/or VPAC2-R, thereby resulting in the reduced production of cAMP.

In another embodiment, the invention further contemplates the generation and use of antibodies that bind any of the foregoing sequences, including, but not limited to, anti-idiotypic antibodies. In an exemplary embodiment, such an anti-idiotypic antibody could be administered to a subject who has received an anti-PACAP antibody to modulate, reduce, or neutralize, the effect of the anti-PACAP antibody. Such antibodies could also be useful for treatment of an autoimmune disease characterized by the presence of anti-PACAP antibodies. A further exemplary use of such antibodies, e.g., anti-idiotypic antibodies, is for detection of the anti-PACAP antibodies of the present invention, for example to monitor the levels of the anti-PACAP antibodies present in a subject's blood or other bodily fluids. For example, in one embodiment, the invention provides a method of using the anti-idiotypic antibody to monitor the in vivo levels of said anti-PACAP antibody or antigen binding fragment thereof in a subject or to neutralize said anti-PACAP antibody in a subject being administered said anti-PACAP antibody or antigen binding fragment thereof.

The present invention also contemplates anti-PACAP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Exemplary Polynucleotides Encoding Anti-PACAP Antibody Polypeptides

The invention is further directed to polynucleotides encoding antibody polypeptides having binding specificity to PACAP.

Antibody Ab10

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 411 which encodes the heavy chain sequence of SEQ ID NO: 401 and which consists of the heavy chain variable region coding sequence of SEQ ID NO: 412 and the heavy chain constant region coding sequence of SEQ ID NO: 420.

In another embodiment of the invention, the polynucleotides of the invention comprise, or alternatively consist of, the following polynucleotide sequence encoding the variable heavy chain polypeptide sequence of SEQ ID NO: 402:

(SEQ ID NO: 412)
cagtcggtggaggagtccgggggtcgcctggtcacgcctgggacaccct
gacactcacctgcacagtctctggaatcgacctcaatagctactacatga
cctgggtccgccaggctccagggaaggggctggaatggatcggattcatt
gatgctggtggtgacgcatactacgcgagctgggcgaaaggccgattcac
catctccaaaacctcgaccacggtggatctgaaaatcaccagtccgacaa
ccgaggacacggccacctatttctgtgccagagatcttgacttgtgggggc
cagggcaccctggtcaccgtctcgagc.

In another embodiment of the invention, polynucleotides of the invention comprise, or alternatively consist of, the following polynucleotide sequence encoding the constant heavy chain polypeptide sequence of SEQ ID NO: 410:

(SEQ ID NO: 420)
gcctccaccaagggcccatcggtcttccccctggcaccctcctccaagag
cacctctggggggcacagcggccctgggctgcctggtcaaggactacttcc
ccgaaccggtgacggtgtcgtggaactcaggcgccctgaccagcggcgtg
cacaccttcccggctgtcctacagtcctcaggactctactccctcagcag
cgtggtgaccgtgccctccagcagcttgggcacccagacctacatctgca
acgtgaatcacaagcccagcaacaccaaggtggacgcgagagttgagccc
aaatcttgtgacaaaactcacacatgcccaccgtgcccagcacctgaact
cctgggggaccgtcagtcttcctcttccccccaaaacccaaggacaccc
tcatgatctcccggacccctgaggtcacatgcgtggtggtggacgtgagc
cacgaagaccctgaggtcaagttcaactggtacgtggacggcgtggaggt
gcataatgccaagacaaagccgcgggaggagcagtacgccagcacgtacc
gtgtggtcagcgtcctcaccgtcctgcaccaggactggctgaatggcaag
gagtacaagtgcaaggtctccaacaaagcctcccagccccatcgagaa
aaccatctccaaagccaaagggcagccccgagaaccacaggtgtacaccc
tgcccccatcccgggaggagatgaccaagaaccaggtcagcctgacctgc
ctggtcaaaggcttctatcccagcgacatcgccgtggagtgggagagcaa
tgggcagccggagaacaactacaagaccacgcctcccgtgctggactccg
acggctccttcttcctctacagcaagctcaccgtggacaagagcaggtgg
cagcaggggaacgtcttctcatgctccgtgatgcatgaggctctgcacaa
ccactacacgcagaagagcctctccctgtctccgggtaaa.

In another embodiment of the invention, polynucleotides comprise, or alternatively consist of, the polynucleotide sequence of SEQ ID NO: 431 which encodes the light chain polypeptide sequence of SEQ ID NO: 421 and which consists of the light chain variable region coding sequence of SEQ ID NO: 432 and the light chain constant region coding sequence of SEQ ID NO: 440.

In another embodiment of the invention, polynucleotides of the invention comprise, or alternatively consist of, the following polynucleotide sequence encoding the variable light chain polypeptide sequence of SEQ ID NO: 422:

(SEQ ID NO: 432)
gccgccgtgctgacccagactccatctcccgtgtctgcagctgtgggagg
cacagtcaccatcaattgccagtccagtgagagtgtttacggtaactact
tagcctggtttcagcagaaaccagggcagcctcccaagctcctgatctac
gaagcatccaaactggaatctggggtcccatcgcggttcagcggcagtgg
atctgggacacagttcactctcaccatcagcgacttgcagtgtgacgatg
ctgccacttactactgtgcaggcggtgatattagtgaaggtgttgctttc
ggcggagggaccgaggtggtggtcaaacgt.

In another embodiment of the invention, polynucleotides of the invention comprise, or alternatively consist of, the following polynucleotide sequence encoding the constant light chain polypeptide sequence of SEQ ID NO: 430:

(SEQ ID NO: 440)
acggtagcggccccatctgtcttcatcttcccgccatctgatgagcagtt
gaaatctggaactgcctctgttgtgtgcctgctgaataacttctatccca
gagaggccaaagtacagtggaaggtggataacgccctccaatcgggtaac
tcccaggagagtgtcacagagcaggacagcaaggacagcacctacagcct
cagcagcaccctgacgctgagcaaagcagactacgagaaacacaaagtct
acgcctgcgaagtcacccatcagggcctgagctcgcccgtcacaaagagc
ttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 414; SEQ ID NO: 416; and SEQ ID NO: 418, which correspond to polynucleotides encoding the CDRs (hypervariable regions) of the heavy chain sequence of SEQ ID NO: 401, or the variable heavy chain sequence of SEQ ID NO: 402, and/or one or more of the polynucleotide sequences of SEQ ID NO: 434; SEQ ID NO: 436; and SEQ ID NO: 438, which correspond to the CDRs (hypervariable regions) of the light chain sequence of SEQ ID NO: 421, or the variable light chain sequence of SEQ ID NO: 422, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 413; SEQ ID NO: 415; SEQ ID NO: 417; and SEQ ID NO: 419, which correspond to polynucleotides encoding the FRs (constant regions) of the heavy chain sequence of SEQ ID NO: 401, or the variable heavy chain sequence of SEQ ID NO: 402, and/or one or more of the polynucleotide sequences of SEQ ID NO: 433; SEQ ID NO: 435; SEQ ID NO: 437; and SEQ ID NO: 439, which correspond to the FRs (constant regions) of the light chain sequence of SEQ ID NO: 421, or the variable light chain sequence of SEQ ID NO: 422, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 411 encoding the heavy chain sequence of SEQ ID NO: 401; the polynucleotide SEQ ID NO: 412 encoding the variable heavy chain sequence of SEQ ID NO: 402; the polynucleotide SEQ ID NO: 431 encoding the light chain sequence of SEQ ID NO: 421; the polynucleotide SEQ ID NO: 432 encoding the variable light chain sequence of SEQ ID NO: 422; polynucleotides encoding the CDRs (SEQ ID NO: 414; SEQ ID NO: 416; and SEQ ID NO: 418) of the heavy chain sequence of SEQ ID NO: 401, or the variable heavy chain sequence of SEQ ID NO: 402; polynucleotides encoding the CDRs (SEQ ID NO: 434; SEQ ID NO: 436; and SEQ ID NO: 438) of the light chain sequence of SEQ ID NO: 421, or the variable light chain sequence of SEQ ID NO: 422; polynucleotides encoding the FRs (SEQ ID NO: 413; SEQ ID NO: 415; SEQ ID NO: 417; and SEQ ID NO: 419) of the heavy chain sequence of SEQ ID NO: 401, or the variable heavy chain sequence of SEQ ID NO: 402; and polynucleotides encoding the FRs (SEQ ID NO: 433; SEQ ID NO: 435; SEQ ID NO: 437; and SEQ ID NO: 439) of the light chain sequence of SEQ ID NO: 421, or the variable light chain sequence of SEQ ID NO: 422.

In another embodiment of the invention, polynucleotides of the invention comprise, or alternatively consist of, polynucleotides encoding Fab fragments having binding specificity for PACAP. With respect to antibody Ab10, the polynucleotides encoding the full length Ab10 antibody comprise, or alternatively consist of, the polynucleotide SEQ ID NO: 411 encoding the heavy chain sequence of SEQ ID NO: 401, and the polynucleotide SEQ ID NO: 431 encoding the light chain sequence of SEQ ID NO: 421.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10 following expression of the full-length polynucleotides in a suitable host. In another embodiment of the invention, anti-PACAP antibodies, such as Ab10 or Fab fragments thereof, can be produced via expression of Ab10 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab20

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 451 which encodes the heavy chain sequence of SEQ ID NO: 441 and which consists of the heavy chain variable region coding sequence of SEQ ID NO: 452 and the heavy chain constant region coding sequence of SEQ ID NO: 460.

In another embodiment of the invention, the polynucleotides of the invention comprise, or alternatively consist of, the following polynucleotide sequence encoding the variable heavy chain polypeptide sequence of SEQ ID NO: 442:

(SEQ ID NO: 452)
cagtcggtggaggagtccgggggtcgcctggtcacgcctgggacacccct gacactcacctgcacagtctctggaatcgacctcagtagctactacatga gctgggtccgccaggctccagggaaggggctggaatggatcggattcatt gatactgatggtagcgcatactacgcgacctgggcgaaaggccgattcac catctccaaaacctcgaccacggtggatctgaaaatcaccagtccgacaa ccgaggacacggccacctatttctgtgccagagatcttgacttgtgggc ccgggcaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 450:

(SEQ ID NO: 460)
gcctccaccaagggcccatcggtcttccccctggcaccctcctccaagag cacctctgggggcacagcggccctgggctgcctggtcaaggactacttcc ccgaaccggtgacggtgtcgtggaactcaggcgccctgaccagcggcgtg cacaccttcccggctgtcctacagtcctcaggactctactccctcagcag cgtggtgaccgtgccctccagcagcttgggcacccagacctacatctgca acgtgaatcacaagcccagcaacaccaaggtggacaagaaagttgagccc aaatcttgtgacaaaactcacacatgcccaccgtgcccagcacctgaact cctggggggaccgtcagtcttcctcttccccccaaaacccaaggacaccc tcatgatctcccggacccctgaggtcacatgcgtggtggtggacgtgagc cacgaagaccctgaggtcaagttcaactggtacgtggacggcgtggaggt gcataatgccaagacaaagccgcgggaggagcagtacgccagcacgtacc gtgtggtcagcgtcctcaccgtcctgcaccaggactggctgaatggcaag -continued

```
gagtacaagtgcaaggtctccaacaaagccctcccagcccccatcgagaa aaccatctccaaagccaaagggcagccccgagaaccacaggtgtacaccc tgcccccatcccgggaggagatgaccaagaaccaggtcagcctgacctgc ctggtcaaaggcttctatcccagcgacatcgccgtggagtgggagagcaa tgggcagccggagaacaactacaagaccacgcctcccgtgctggactccg acggctccttcttcctctacagcaagctcaccgtggacaagagcaggtgg cagcaggggaacgtcttctcatgctccgtgatgcatgaggctctgcacaa ccactacacgcagaagagcctctccctgtctccgggtaaa.
```

In another embodiment of the invention, polynucleotides comprise, or alternatively consist of, the polynucleotide sequence of SEQ ID NO: 471 which encodes the light chain polypeptide sequence of SEQ ID NO: 461 and which consists of the light chain variable region coding sequence of SEQ ID NO: 472 and the light chain constant region coding sequence of SEQ ID NO: 480.

In another embodiment of the invention, polynucleotides of the invention comprise, or alternatively consist of, the following polynucleotide sequence encoding the variable light chain polypeptide sequence of SEQ ID NO: 462:

```
                                      (SEQ ID NO: 472)
gccgccgtgctgacccagactccatctcccgtgtagcagagtggggaggca cagtcagcatcagttgccagtccagtgagagtgatatagtaactacttag cctggtttcagcagaaaccagggcagcctcctaagttcttgatctacgaa gcatccaaactggcatctggggtcccatcgcggttcaaaggcagtggatc tgggacacagttcactctcaccatcagcgacgtgcagtgtgacgatgctg gcacttactactgtgcaggcggctatagtagtgaaggtgttgattcggcg gagggaccgaggtggtggtcaaacgt.
```

In another embodiment of the invention, polynucleotides of the invention comprise, or alternatively consist of, the following polynucleotide sequence encoding the constant light chain polypeptide sequence of SEQ ID NO: 470:

```
                                      (SEQ ID NO: 480)
acggtagcggccccatctgtcttcatcttcccgccatctgatgagcagtt gaaatctggaactgcctctgttgtgtgcctgctgaataacttctatccca gagaggccaaagtacagtggaaggtggataacgccctccaatcgggtaac tcccaggagagtgtcacagagcaggacagcaaggacagcacctacagcct cagcagcaccctgacgctgagcaaagcagactacgagaaacacaaagtct acgcctgcgaagtcacccatcagggcctgagctcgcccgtcacaaagagc ttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 454; SEQ ID NO: 456; and SEQ ID NO: 458, which correspond to polynucleotides encoding the CDRs (hypervariable regions) of the heavy chain sequence of SEQ ID NO: 441, or the variable heavy chain sequence of SEQ ID NO: 442, and/or one or more of the polynucleotide sequences of SEQ ID NO: 474; SEQ ID NO: 476; and SEQ ID NO: 478, which correspond to the CDRs (hypervariable regions) of the light chain sequence of SEQ ID NO: 461, or the variable light chain sequence of SEQ ID NO: 462, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 453; SEQ ID NO: 455; SEQ ID NO: 457; and SEQ ID NO: 459, which correspond to polynucleotides encoding the FRs (constant regions) of the heavy chain sequence of SEQ ID NO: 441, or the variable heavy chain sequence of SEQ ID NO: 442, and/or one or more of the polynucleotide sequences of SEQ ID NO: 473; SEQ ID NO: 475; SEQ ID NO: 477; and SEQ ID NO: 479, which correspond to the FRs (constant regions) of the light chain sequence of SEQ ID NO: 461, or the variable light chain sequence of SEQ ID NO: 462, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 451 encoding the heavy chain sequence of SEQ ID NO: 441; the polynucleotide SEQ ID NO: 452 encoding the variable heavy chain sequence of SEQ ID NO: 442; the polynucleotide SEQ ID NO: 471 encoding the light chain sequence of SEQ ID NO: 461; the polynucleotide SEQ ID NO: 472 encoding the variable light chain sequence of SEQ ID NO: 462; polynucleotides encoding the CDRs (SEQ ID NO: 454; SEQ ID NO: 456; and SEQ ID NO: 458) of the heavy chain sequence of SEQ ID NO: 441, or the variable heavy chain sequence of SEQ ID NO: 442; polynucleotides encoding the CDRs (SEQ ID NO: 474; SEQ ID NO: 476; and SEQ ID NO: 478) of the light chain sequence of SEQ ID NO: 461, or the variable light chain sequence of SEQ ID NO: 462; polynucleotides encoding the FRs (SEQ ID NO: 453; SEQ ID NO: 455; SEQ ID NO: 457; and SEQ ID NO: 459) of the heavy chain sequence of SEQ ID NO: 441, or the variable heavy chain sequence of SEQ ID NO: 442; and polynucleotides encoding the FRs (SEQ ID NO: 473; SEQ ID NO: 475; SEQ ID NO: 477; and SEQ ID NO: 479) of the light chain sequence of SEQ ID NO: 461, or the variable light chain sequence of SEQ ID NO: 462.

In another embodiment of the invention, polynucleotides of the invention comprise, or alternatively consist of, polynucleotides encoding Fab fragments having binding specificity for PACAP. With respect to antibody Ab20, the polynucleotides encoding the full length Ab20 antibody comprise, or alternatively consist of, the polynucleotide SEQ ID NO: 451 encoding the heavy chain sequence of SEQ ID NO: 441, and the polynucleotide SEQ ID NO: 471 encoding the light chain sequence of SEQ ID NO: 461.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab20 following expression of the full-length polynucleotides in a suitable host. In another embodiment of the invention, anti-PACAP antibodies, such as Ab20 or Fab fragments thereof, can be produced via expression of Ab20 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Host cells and vectors comprising said polynucleotides are also contemplated.

The invention further contemplates vectors comprising the polynucleotide sequences encoding the variable heavy and light chain polypeptide sequences, as well as the individual CDRs (hypervariable regions), as set forth herein, as well as host cells comprising said vector sequences. In embodiments of the invention, the host cells are mammalian cells, such as CHO cells. In embodiments of the invention, the host cells are yeast cells, such as yeast cells of the genus *Pichia*

B-Cell Screening and Isolation

In one embodiment, the present invention contemplates the preparation and isolation of a clonal population of antigen-specific B-cells that may be used for isolating at least one PACAP antigen-specific cell, which can be used to produce a monoclonal antibody against PACAP, which is specific to a desired PACAP antigen, or a nucleic acid sequence corresponding to such an antibody. Methods of preparing and isolating said clonal population of antigen-specific B-cells are taught, for example, in U.S. Patent Publication No. 2007/0269868 to Carvalho-Jensen et al., the disclosure of which is herein incorporated by reference in its entirety. Methods of preparing and isolating said clonal population of antigen-specific B-cells are also taught herein in the examples. Methods of "enriching" a cell population by size or density are known in the art (See, e.g., U.S. Pat. No. 5,627,052). These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains that may be applied to anti-PACAP antibodies are taught, for example, in U.S. Patent Publication No. 2009/0022659 to Olson et al., and in U.S. Pat. No. 7,935,340 to Garcia-Martinez et al., the disclosures of each of which are herein incorporated by reference in their entireties.

Methods of Producing Antibodies and Fragments Thereof

In another embodiment, the present invention contemplates methods for producing anti-PACAP antibodies and fragments thereof. Methods for producing anti-PACAP antibodies and fragments thereof secreted from polyploidal, preferably diploid or tetraploid strains of mating competent yeast are taught, for example, in U.S. Patent Publication No. 2009/0022659 to Olson et al., and in U.S. Pat. No. 7,935,340 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., *Proc. Natl. Acad. Sci. U.S.A.*, 81:8651-55, 1984; Neuberger et al., *Nature*, 314:268-270, 1985; Boulianne, G. L. et al., *Nature*, 312:643-46, 1984, the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al., *Nature*, 321:522-525, 1986; Reichmann, L. et al., *Nature*, 332:323-327, 1988; Verhoeyen, M. et al., *Science*, 239:1534-36, 1988, the disclosures of each of which are herein incorporated by reference in their entireties).

Antibody polypeptides of the invention having PACAP binding specificity may also be produced by constructing, using conventional techniques well known to those of ordinary skill in the art, an expression vector containing a promoter (optionally as a component of a eukaryotic or prokaryotic operon) and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing a promoter (optionally as a component of a eukaryotic or prokaryotic operon) and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding a promoter (optionally as a component of a eukaryotic or prokaryotic operon) and a light chain-derived polypeptide and the second vector containing DNA encoding a promoter (optionally as a component of a eukaryotic or prokaryotic operon) and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as *E. coli*, or a eukaryotic cell such as *P. pastoris*. In one embodiment of the invention, a mammalian cell of a well-defined type for this purpose, such as a myeloma cell, a CHO cell line, a NSO cell line, or a HEK293 cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography, hydrophobic interaction chromatography ("HIC"), and the like.

The antibody polypeptides described herein may also be used for the design and synthesis of either peptide or non-peptide mimetics that would be useful for the same therapeutic applications as the antibody polypeptides of the invention (See, for example, Saragobi et al., *Science*, 253: 792-795, 1991, the contents of which are herein incorporated by reference in its entirety).

Screening Assays

The screening assays described here are designed to identify high affinity anti-PACAP Abs which may be useful in the treatment of diseases and disorders associated with PACAP in subjects exhibiting symptoms of a PACAP associated disease or disorder.

In some embodiments, the antibody is used as a diagnostic tool. The antibody can be used to assay the amount of PACAP present in a sample and/or subject. As will be appreciated by one of skill in the art, such antibodies need not be neutralizing antibodies. In some embodiments, the diagnostic antibody is not a neutralizing antibody. In some embodiments, the diagnostic antibody binds to a different epitope than the neutralizing antibody binds to. In some embodiments, the two antibodies do not compete with one another.

In some embodiments, the antibodies disclosed herein are used or provided in an assay kit and/or method for the detection of PACAP in mammalian tissues or cells in order to screen/diagnose for a disease or disorder associated with changes in levels of PACAP. The kit comprises an antibody that binds PACAP and means for indicating the binding of the antibody with PACAP, if present, and optionally PACAP protein levels. Various means for indicating the presence of an antibody can be used. For example, fluorophores, other molecular probes, or enzymes can be linked to the antibody and the presence of the antibody can be observed in a variety of ways. The method for screening for such disorders can involve the use of the kit, or simply the use of one of the disclosed antibodies and the determination of whether the antibody binds to PACAP in a sample. As will be appreciated by one of skill in the art, high or elevated levels of PACAP will result in larger amounts of the antibody binding to PACAP in the sample. Thus, degree of antibody binding can be used to determine how much PACAP is in a sample. Subjects or samples with an amount of PACAP that is greater than a predetermined amount (e.g., an amount or range that a person without a PACAP-related disorder would have) can be characterized as having a PACAP-mediated disorder, e.g., migraine, headache, pain, or other condition.

The present invention further provides for a kit for detecting binding of an anti-PACAP antibody of the invention to PACAP. In particular, the kit may be used to detect the presence of PACAP specifically reactive with an anti-PACAP antibody of the invention or an immunoreactive fragment thereof. The kit may also include an antibody bound to a substrate, a secondary antibody reactive with the antigen and a reagent for detecting a reaction of the secondary antibody with the antigen. Such a kit may be an ELISA kit and can comprise the substrate, primary and secondary antibodies when appropriate, and any other necessary reagents such as detectable moieties, enzyme substrates, and color reagents, for example as described herein. The diagnostic kit may also be in the form of an immunoblot kit. The diagnostic kit may also be in the form of a chemiluminescent kit (Meso Scale Discovery, Gaithersburg, MD). The diagnostic kit may also be a lanthanide-based detection kit (PerkinElmer, San Jose, CA).

A skilled clinician would understand that a biological sample includes, but is not limited to, sera, plasma, urine, saliva, mucous, pleural fluid, synovial fluid, and spinal fluid.

Methods of Ameliorating or Reducing Symptoms of, or Treating, or Preventing, Diseases and Disorders Associated with PACAP In another embodiment of the invention, anti-PACAP antibodies described herein, or antigen binding fragments thereof, are useful for ameliorating or reducing the symptoms of, or treating, or preventing, diseases and disorders associated with PACAP. Anti-PACAP antibodies described herein, or antigen binding fragments thereof, as well as combinations, can also be administered in a therapeutically effective amount to patients in need of treatment of diseases and disorders associated with PACAP in the form of a pharmaceutical composition as described in greater detail below.

In another embodiment of the invention, anti-PACAP antibodies described herein, or antigen binding fragments thereof, are useful (either alone or in combination with another agent) for ameliorating or reducing the symptoms of, or treating, or preventing a disease or condition associated with PACAP.

In another embodiment of the invention, anti-PACAP antibodies described herein, or antigen binding fragments thereof, with or without a second agent, are useful for ameliorating or reducing the symptoms of, or treating, or preventing, the following non-limiting listing of diseases and disorders: migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of metastasis in the bone, postsurgical pain, sarcomas cancer of the connective tissue, cancer of bone tissue, cancer of blood-forming cells of the bone marrow, multiple myeloma, leukemia, primary or secondary bone cancer, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, lower urinary tract ("LUT") disorders such as urinary tract infection, abnormal voiding, urinary urgency, nocturia, urinary incontinence, overactive bladder and for preventing or alleviating the pain associated with such LUT conditions. Preferably, the subject anti-PACAP antibodies and antigen binding fragments described herein are useful for ameliorating or reducing the symptoms of, treating, or preventing migraine, headache and a pain associated disease or condition.

In particular, the subject anti-PACAP antibodies and antigen binding fragments can also be useful for ameliorating or reducing the symptoms of, treating, or preventing photophobia, occurring with a headache and/or migraine as well as occurring independent of a headache and/or a migraine.

Migraineurs typically develop worsening pain and migraine symptoms when exposed to light, a phenomenon known as photophobia. Photophobia is also common in ocular disorders, such as iritis and uveitis, and intracranial disorders, such as meningitis. In the classic visual pathway, light activates rods and cones in the retina, which activate retinal ganglion cells that project via the optic nerve, to the lateral *geniculate* nucleus, superior colliculus, and then the visual cortex. This pathway includes image-forming and non-image-forming data. A new pathway (non-image-forming information) allows maintenance of normal circadian rhythms via the suprachiasmatic nucleus and is regulated by intrinsically photosensitive retinal ganglion cells (ipRGCs). These ipRGCs are independent of the rods and cones and contain melanopsin, a photopigment.

Noseda, R. et al., *Nat. Neurosci.*, 13:239-245 (2010) studied blind individuals who had migraine and correlated these findings with rat models involving tracing of ipRGC projections to areas in perception of pain from the dura. Of the blind patients with migraine, 6 had no light perception due to severe optic nerve damage or bilateral enucleation. These subjects experienced abnormal sleep patterns and poor pupillary light responses. Their migraines did not worsen with light exposure. In contrast, 14 blind subjects who were able to detect light despite minimal perception of images had normal sleep patterns and a normal pupillary light reflex. Despite widespread rod and cone degeneration, these patients had worsening migraine symptoms with light exposure during migraine attacks, suggesting that ipRGCs, and not rods and cones, are important in photophobia.

These retinal projections of non-image-forming brain areas project to the contralateral dorsocaudal region of the posterior thalamus, as demonstrated by anterograde tracing in the rat. ipRGC input to this area modulates dura-sensitive pain neurons, which also project to this region. Thalamic neurons, dually sensitive to dural pain and light input, project widely to multiple cortical regions, including the primary somatosensory cortex, the primary and secondary motor cortices, the parietal association cortex, and the primary and secondary visual cortices. These cortical projections may help explain other common migraine symptoms, in addition to photophobia, such as motor weakness or incoordination, visual disturbances, and poor concentration.

Photophobia also accompanies other less frequent but likewise disabling conditions, such as cluster headache and other trigeminal autonomic cephalalgias and blepharospasm. The mechanisms underlying photophobia involve the trigeminal system. Photophobia in blind patients suggests contributions from a nonvisual pathway. In addition, trigeminal autonomic cephalalgias, a less common group of primary headache disorders, are characterized by unilateral trigeminal-mediated pain frequently associated with ipsilateral photophobia.

Common causes of photophobia include migraine headaches, cataracts, or severe ophthalmologic diseases such as uveitis or corneal abrasion. A more extensive list of disorders associated with photophobia includes eye related causes such as achromatopsia, aniridia, anticholinergic drugs may cause photophobia by paralyzing the iris sphincter muscle, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, such as that caused by a corneal foreign body or keratitis, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma iritis, optic neuritis, pigment dispersion syndrome, pupillary dilation (naturally or chemically induced), retinal detachment, scarring of the cornea or sclera and uveitis.

In addition, photophobia has nervous-system-related or neurological causes including: autism spectrum disorders, Chiari malformation, dyslexia, encephalitis including myalgic encephalomyelitis aka chronic fatigue syndrome, meningitis, subarachnoid hemorrhage, tumor of the posterior cranial fossa, as well as other causes such as ankylosing spondylitis, albinism, ariboflavinosis, benzodiazepines (long term use of or withdrawal from benzodiazepines), chemotherapy, chikungunya, cystinosis, Ehlers-Danlos syndrome, hangover, influenza, infectious mononucleosis, magnesium deficiency, mercury poisoning, migraine, rabies, and tyrosinemia type II, also known as "Richner-Hanhart syndrome".

Additionally, it is known that photophobia is elevated in depression, bipolar disorder and agoraphobia.

The subject anti-PACAP antibodies and antigen binding fragments described herein can be effective for treating or preventing photophobia in any of these conditions, preferably, in a subject with post-traumatic stress disorder ("PTSD") or in a subject with traumatic brain injury.

Headaches may be classified by cause, as discussed below.

Primary headaches. A primary headache is caused by problems with or overactivity of pain-sensitive structures in the head. A primary headache is generally not considered to be a symptom of an underlying disease. Instead, chemical activity in the brain, the nerves or blood vessels of the head outside the skull, or muscles of the head and neck, or some combination of these factors, may play a role in primary headaches. Some people may carry genes that make them more likely to develop such headaches. Exemplary common primary headaches include, but are not limited to, cluster headache; tension headache (or tension-type headache); and trigeminal autonomic cephalalgia ("TAC"), including paroxysmal hemicrania. There are other headache patterns that may be considered types of primary headache, e.g., chronic daily headaches, cough headaches, exercise headaches, and sex headaches. These headaches are less common and have distinct features, such as an unusual duration or pain associated with a certain activity. Although these headaches are generally considered primary, each of them could be a symptom of an underlying disease. Additionally, some primary headaches can be triggered by lifestyle factors, including: alcohol; certain foods (e.g., processed meats that contain nitrates); changes in sleep or lack of sleep; poor posture; skipped meals; and stress.

Secondary headaches. A secondary headache is a symptom of a disease that can activate the pain-sensitive nerves of the head. Any number of conditions, which can vary greatly in severity, may cause secondary headaches. Exemplary sources of secondary headaches include, but are not limited to, acute sinusitis; arterial tears (carotid or vertebral dissections); venous thrombosis in the brain; brain aneurysm; brain arteriovenous malformation; carbon monoxide poisoning; Chiari malformation; concussion; dehydration; dental problems; ear infection (middle ear); encephalitis; giant cell arteritis; glaucoma; hangovers; influenza (flu); intracranial hematoma; medications to treat other disorders; meningitis; monosodium glutamate ("MSG"); overuse of pain medication; panic attacks; post-concussion syndrome; pressure from tight-fitting headgear, e.g., helmet or goggles; pseudotumor cerebri; toxoplasmosis; and trigeminal neuralgia. Specific types of secondary headaches include, but are not limited to, external compression headaches (a result of pressure-causing headgear); ice cream headaches (commonly called "brain freeze"); rebound headaches (caused by overuse of pain medication); sinus headaches (caused by inflammation and congestion in sinus cavities); spinal headaches (caused by low levels of cerebrospinal fluid, possibly the result of trauma, spinal tap or spinal anesthesia); and thunderclap headaches (a group of disorders that involves sudden, severe headaches).

Exemplary, non-limiting pain associated diseases and disorders that can be treated and/or prevented by the administration of the anti-PACAP antibodies of the present invention include, pain resulting from any condition associated with neurogenic, neuropathic, inflammatory, or nociceptive pain. Preferably, the pain-associated disorder will be associated with increased PACAP at the pain site.

In certain embodiments, the pain associated disorder to be treated is cancer pain arising from malignancy or from cancer selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of metastasis in the bone, postsurgical pain, sarcomas cancer of the connective tissue, cancer of bone tissue, cancer of blood-forming cells of the bone marrow, multiple myeloma, leukemia, primary or secondary bone cancer.

In other embodiments, the pain associated condition to be treated is associated with neuropathic pain and included, by way of example, trigeminal neuralgia, post-herpetic neuralgia, phantom limb pain, fibromyalgia, and reflex sympathetic dystrophy are preferably treated.

Further exemplary pain associated diseases or conditions, include but are not limited to, general pain, chronic pain, inflammatory pain, post-operative incision pain, post-surgical pain, trauma-related pain, lower back pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptive pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, overactive bladder, bronchial hyperreactivity, asthma, bronchitis, bronchodilation, emphysema, chronic obstructive pulmonary disease ("COPD"), inflammatory dermatitis, acne vulgaris, atopic dermatitis, urticaria, keloids, hypertrophic scars and rosacea, allergic dermatitis, psoriasis, puritus, neurogenic cutaneous redness, erythema, sarcoidosis, shock, sepsis, and opiate withdrawal syndrome.

Thus, the present invention includes methods of treating, preventing, and/or ameliorating any disease or disorder associated with PACAP activity or PACAP upregulation (including any of the above mentioned exemplary pain associated diseases, disorders and conditions) through use of the antibodies and antigen binding fragments of the invention.

Also, the subject PACAP antibodies and antigen binding fragments may be used alone or in conjunction with other active agents, e.g., opioids and non-opioid analgesics such as NSAIDs to elicit analgesia or to potentiate the efficacy of another analgesic.

The subject antibodies potentially may be combined with any opioid analgesic or NSAID or other analgesic, potentially another antibody or another biologic such as, e.g., an anti-NGF or anti-CGRP or anti-CGRP-R antibody or antibody fragment or NGF, CGRP or CGRP-R polypeptide fragment or conjugate, in order to increase or enhance pain management. This may allow for such analgesic compounds to be administered for longer duration or at reduced dosages thereby potentially alleviating adverse side effects associated therewith.

Of particular interest is the co-administration of the subject anti-PACAP antibodies and antibody fragments with an anti-CGRP antibody (e.g., ALD403) or or anti-CGRP-R antibody or antibody fragment and, moreover, the use of the subject anti-PACAP antibodies and antibody fragments to treat subjects that previously received an anti-CGRP or anti-CGRP-R antibody or antibody fragment. For example, the previously treated subject (who previously received at least one anti-CGRP or anti-CGRP-R antibody or antibody fragment administration) may be a migraineur who did not adequately respond to anti-CGRP or anti-CGRP-R antibody treatment ("poor responder") and/or has elicited an immune response to the anti-CGRP or anti-CGRP-R antibody or antibody fragment.

Likewise, the co-administration of the subject anti-PACAP antibodies and antigen binding fragments with BOTOX® (Botulinum toxin) is also of particular interest, e.g., in treating a migraineur. In some instances, the migraineur may not have adequately responded to previous treatments ("poor responder") and/or has elicited an immune response to the previous treatment.

In some embodiments, aspirin and/or acetaminophen may be taken in conjunction with the subject anti-PACAP antibody or antigen binding fragment. Aspirin is another type of non-steroidal anti-inflammatory compound.

The subject to which the pharmaceutical formulation is administered can be, e.g., any human or non-human animal that is in need of such treatment, prevention and/or amelioration, or who would otherwise benefit from the inhibition or attenuation of PACAP-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with PACAP activity (including any of the above mentioned exemplary diseases, disorders and conditions).

Administration

In one embodiment of the invention, the anti-PACAP antibodies described herein, or PACAP binding fragments thereof, as well as combinations of said antibodies or antigen binding fragments thereof, are administered to a subject at a concentration of between 0.1 mg/ml and about any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190, or 200 mg/ml, +/−10% error.

In another embodiment of the invention, the anti-PACAP antibodies and fragments thereof described herein are administered to a subject at a dose of between about 0.01 and 100.0 or 200.0 mg/kg of body weight of the recipient subject. In certain embodiments, depending on the type and severity of the PACAP-related disease, about 1 μg/kg to 50 mg/kg (e.g., 0.1-20 mg/kg) of antibody is an initial candidate dosage for administration to the patient, whether, for example, by one or more separate administrations, or by continuous infusion. In another embodiment, about 1 μg/kg to 15 mg/kg (e.g., 0.1 mg/kg-10 mg/kg) of antibody is an initial candidate dosage for administration to the patient. A typical daily dosage might range from about 1 μg/kg to 100 mg/kg or more, depending on several factors, e.g., the particular mammal being treated, the clinical condition of the individual patient, the cause of the disorder, the site of delivery of the agent, the method of administration, the scheduling of administration, and other factors known to medical practitioners. However, other dosage regimens may be useful.

For example, in addition to the relative dosages (mg/kg) discussed herein, the subject anti-PACAP antibodies and antigen binding fragments thereof can be administered to a subject at an absolute dose (mg). Accordingly, in one embodiment of the invention, the anti-PACAP antibodies and antigen binding fragments thereof described herein are administered to a subject at a dose of between about 1 microgram and about 1000 milligrams regardless of the route of administration.

In a preferred embodiment of the invention, the anti-PACAP antibodies described herein, or anti-PACAP antigen binding fragments thereof, as well as combinations of said antibodies or antigen binding fragments thereof, are administered to a recipient subject with a frequency of once every twenty-six weeks or less, such as once every sixteen weeks or less, once every eight weeks or less, once every four weeks or less, once every two weeks or less, once every week or less, or once daily or less.

According to preferred embodiments, the antibody containing medicament or pharmaceutical composition is peripherally administered to a subject via a route selected from one or more of: orally, sublingually, buccally, topically, rectally, via inhalation, transdermally, subcutaneously, intravenously, intra-arterially, or intramuscularly, via intracardiac administration, intraosseously, intradermally, intraperitoneally, transmucosally, vaginally, intravitreally, epicutaneously, intra-articularly, peri-articularly, or locally.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a continuous perfusion form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in, *Goodman & Gilman's The Pharmacological Basis of Therapeutics*, Brunton, L. L. et al. editors, 11$^{th}$ edition, New York, New York: McGraw-Hill (2006); Howland, R. D. et al., *Pharmacology, Volume 864, Lippincott's illustrated reviews.*, Philadelphia, PA: Lippincott Williams & Wilkins (2006); and Golan, D. E., *Principles of pharmacology: the pathophysiologic basis of drug therapy*, Philadelphia, PA: Lippincott Williams & Wilkins (2007).

In another embodiment of the invention, the anti-PACAP antibodies described herein, or PACAP binding fragments thereof, as well as combinations of said antibodies or antigen binding fragments thereof, are administered to a subject in a pharmaceutical formulation. In a preferred embodiment, the subject is a human.

A "pharmaceutical composition" or "medicament" refers to a chemical or biological composition suitable for administration to a subject, preferably a mammal, more preferably a human. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-PACAP antibodies described herein, or PACAP binding fragments thereof, as well as combinations of said antibodies or antigen binding fragments thereof, may be optionally administered in combination with one or more active agents. Such active agents include analgesic, anti-histamine, antipyretic, anti-inflammatory, antibiotic, antiviral, and anti-cytokine agents. Active agents include agonists, antagonists, and modulators of TNF-$\alpha$, IL-2, IL-4, IL-6, IL-10, IL-12, IL-13, IL-18, IFN-$\alpha$, IFN-$\gamma$, BAFF, CXCL13, IP-10, VEGF, EPO, EGF, HRG, Hepatocyte Growth Factor ("HGF"), Hepcidin, NGF, CGRP including antibodies reactive against any of the foregoing, and antibodies reactive against any of their receptors. Active agents also include but are not limited to 2-arylpropionic acids, aceclofenac, acemetacin, acetylsalicylic acid (aspirin), alclofenac, alminoprofen, amoxiprin, ampyrone, arylalkanoic acids, azapropazone, benorylate/benorilate, benoxaprofen, bromfenac, carprofen, celecoxib, choline magnesium salicylate, clofezone, COX-2 inhibitors, dexibuprofen, dexketoprofen, diclofenac, diflunisal, droxicam, ethenzamide, etodolac, etoricoxib, faislamine, fenamic acids, fenbufen, fenoprofen, flufenamic acid, flunoxaprofen, flurbiprofen, ibuprofen, ibuproxam, indomethacin, indoprofen, kebuzone, ketoprofen, ketorolac, lornoxicam, loxoprofen, lumiracoxib, magnesium salicylate, meclofenamic acid, mefenamic acid, meloxicam, metamizole, methyl salicylate, mofebutazone, nabumetone, naproxen, N-arylanthranilic acids, NGF, oxametacin, oxaprozin, oxicams, oxyphenbutazone, oxytocin, parecoxib, phenazone, phenylbutazone, phenylbutazone, piroxicam, pirprofen, profens, proglumetacin, pyrazolidine derivatives, rofecoxib, salicyl salicylate, salicylamide, salicylates, substance P, sulfinpyrazone, sulindac, suprofen, tenoxicam, tiaprofenic acid, tolfenamic acid, tolmetin, and valdecoxib. For instance, the selected anti-PACAP antibodies, or PACAP-binding fragments thereof, as well as combinations of these antibodies or antigen binding fragments, can be optionally administered in combination with oxytocin, for instance administered in a nasal formulation, for intranasal delivery.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratadine, methscopolamine, mizolastine, norastemizole, phenindamine, promethazine, pyrilamine, terfenadine, and tranilast.

Antibiotics include but are not limited to amikacin, aminoglycosides, amoxicillin, ampicillin, ansamycins, arsphenamine, azithromycin, azlocillin, aztreonam, bacitracin, carbacephem, carbapenems, carbenicillin, cefaclor, cefadroxil, cefalexin, cefalothin, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalosporins, chloramphenicol, cilastatin, ciprofloxacin, clarithromycin, clindamycin, cloxacillin, colistin, co-trimoxazole, dalfopristin, demeclocycline, dicloxacillin, dirithromycin, doripenem, doxycycline, enoxacin, ertapenem, erythromycin, ethambutol, flucloxacillin, fosfomycin, furazolidone, fusidic acid, gatifloxacin, geldanamycin, gentamicin, glycopeptides, herbimycin, imipenem, isoniazid, kanamycin, levofloxacin, lincomycin, linezolid, lomefloxacin, loracarbef, macrolides, mafenide, meropenem, methicillin, metronidazole, mezlocillin, minocycline, monobactams, moxifloxacin, mupirocin, nafcillin, neomycin, netilmicin, nitrofurantoin, norfloxacin, ofloxacin, oxacillin, oxytetracycline, paromomycin, penicillin, penicillins, piperacillin, platensimycin, polymyxin B, polypeptides, prontosil, pyrazinamide, quinolones, quinupristin, rifampicin, rifampin, roxithromycin, spectinomycin, streptomycin, sulfacetamide, sulfamethizole, sulfanilamide, sulfasalazine, sulfisoxazole, sulfonamides, teicoplanin, telithromycin, tetracycline, tetracyclines, ticarcillin, tinidazole, tobramycin, trimethoprim, trimethoprim-sulfamethoxazole, troleandomycin, trovafloxacin, and vancomycin.

Active agents also include aldosterone, beclomethasone, betamethasone, corticosteroids, cortisol, cortisone acetate, deoxycorticosterone acetate, dexamethasone, fludrocortisone acetate, glucocorticoids, hydrocortisone, methylprednisolone, prednisolone, prednisone, steroids, and triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in *Remington's Pharmaceutical Sciences*, Gennaro, A. editor, 19$^{th}$ edition, Philadelphia, PA: Williams and Wilkins (1995), which is incorporated by reference.

As used herein "pharmaceutically acceptable carrier" or "excipient" includes any and all solvents, dispersion media, coatings, antibacterial and antifungal agents, isotonic, and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol and sorbitol, or sodium chloride in the composition. Absorption of the injectable compositions can be prolonged by including an agent that delays absorption, for example, monostearate salts and gelatin. Moreover, the alkaline polypeptide can be formulated in a time-release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, polylactic and polyglycolic copolymers ("PLG"). Many methods for the preparation of such formulations are known to those skilled in the art.

For each of the recited embodiments, the compounds can be administered by a variety of dosage forms. Any biologically acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B-cells were disclosed in U.S. Patent Publication No. 2013/0316353, the disclosure of which is herein incorporated by reference in its entirety.

Certain teachings related to humanization of rabbit-derived monoclonal antibodies and preferred sequence modifications to maintain antigen-binding affinity were disclosed in International Publication No. WO 2008/144757, entitled Novel Rabbit Antibody Humanization Methods and Humanized Rabbit Antibodies, filed May 21, 2008, the disclosure of which is herein incorporated by reference in its entirety.

Certain teachings related to producing antibodies or fragments thereof using mating competent yeast and corresponding methods were disclosed in U.S. Patent Publication No. US2006/0270045, the disclosure of which is herein incorporated by reference in its entirety.

Certain teachings related to producing antibodies or fragments thereof in *Pichia* and preferred methods for obtaining and purifying antibodies are also disclosed in U.S. Patent Publication Nos. 2014/0288272; 2014/0287952; 2013/0055888; and 2012/0277408, the disclosures of each of which are herein incorporated by reference in their entirety.

Certain teachings related to producing antibodies or fragments thereof in CHO cells and exemplary methods for obtaining and purifying antibodies are also disclosed in U.S. Publication Nos. and U.S. Pat. Nos. 7,932,087; 2009/0285795; 9,090,672; and 2010/0221781; the disclosures of each of which are herein incorporated by reference in their entirety.

Certain anti-PACAP antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.), but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Preparation of Antibodies that Selectively Bind PACAP

By using an antibody selection protocol substantially as described herein, a panel of antibodies specific to PACAP38 and PACAP27, and a panel of antibodies specific to PACAP38 only, were produced.

Immunization Strategy

Rabbits were immunized with PACAP38 (American Peptide, Vista, CA) (SEQ ID NO: 1241). Peptides were prepared for immunization as follows. A 0.15 ml volume of 10 mg/ml keyhole limpet hemocyanin ("KLH") dissolved in Dulbecco's phosphate buffered saline ("DPBS") supplemented to 1M NaCl was combined with 1.0 ml of 1 mg/ml peptide (dissolved in deionized water). Then 1.0 ml of 40 mM carbodiimide was added prior to a 12-hour incubation at room temperature with gentle mixing. Excess carbodiimide and unconjugated peptide were removed by dialysis to DPBS prior to sterile filtration. Next unconjugated peptide equal to the initial mass of KLH was added prior to preparation for injection into rabbits. Alternatively, equal masses of sterile KLH and peptide were mixed without carbodiimide chemistry.

Immunizations were performed by diluting 200 µg of antigen to 0.5 ml with DPBS and mixing with an equal volume of complete Freund's adjuvant for subcutaneous 1 ml injection at Day 1.

Boost injections of 100 pg were performed with incomplete Freund's adjuvant at Days 21 and 42.

Antibody Selection Functional Titer Assessment

To identify antibodies that neutralize PACAP38 (SEQ ID NO: 1241) induced signaling via PAC1-R, polyclonal antibody solutions were first purified via Protein A and dialyzed into a neutral buffer. Briefly, antibody solutions were incubated with PACAP38 (SEQ ID NO: 1241) at 4× the final concentration (100 pM) for 1 hr. While the antibody/antigen complexes were incubated, PAC1-R expressing PC-12 cells (Japanese Collection of Research Bioresources Cell Bank) were washed and re-suspended at $2\times10^6$ cells per ml in cell culture media. Cells (10 µl) and antigen/antibody complex (40 µl) were transferred to a homogenous time resolved fluorescence ("HTRF") plate and shaken at room temperature for 30 min. Following the incubation, 20 µl of (1:20 diluted) $Eu^{3+}$ cryptate-labeled mAb anti-cAMP and 20 µl of (1:20 diluted) d2-labeled cAMP in lysis buffer were added, and the plate was incubated for 1 hr while shaking. Following incubation, plates were read (excitation 330 nm, emission 620/665 nm), and a ratio of 620:665 signal was determined.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 µm (Thermo Fisher Scientific, Waltham, MA) with a plunger of a 20 cc syringe. Cells were collected in phosphate buffered saline ("PBS"). Cells were then washed twice by centrifugation. After the last wash, cell density was determined by trypan blue. Cells were centrifuged at 1500 RPM for 10 minutes; the supernatant was then discarded. Cells were resuspended in the appropriate volume of 10% dimethyl sulfoxide ("DMSO", Sigma-Aldrich Co., St. Louis, MO) in fetal bovine serum ("FBS" HYCLONE™, GE Healthcare Life Sciences, Marlborough, MA) and dispensed at 1 ml/vial. Vials were stored at −70° C. in a slow freezing chamber for 24 hours and stored in liquid nitrogen.

Peripheral blood mononuclear cells ("PBMCs") were isolated by mixing whole blood with equal parts of PBS. 35 ml of the whole blood mixture was carefully layered onto 8 ml of LYMPHOLYTE® Rabbit (Cedarlane Laboratories, Burlington, Ontario) into a 45 ml conical tube (Corning, Corning, NY) and centrifuged for 30 minutes at 2500 RPM at room temperature without brakes. After centrifugation, the PBMC layers were carefully removed using a glass Pasteur pipette (VWR International, Radnor, PA), combined, and placed into a clean 50 ml vial. Cells were washed twice with PBS by centrifugation at 1500 RPM for 10 minutes at room temperature, and cell density was determined by trypan blue staining. After the last wash, cells were resuspended in an appropriate volume of 10% DMSO/FBS medium and frozen as described above.

B-Cell Selection, Enrichment, and Culture Conditions

On the day of setting up B-cell culture, PBMC, splenocyte, or lymph node vials were thawed for use. Vials were removed from liquid nitrogen tank and placed in a 37° C. water bath until thawed. Contents of vials were transferred into 15 ml conical centrifuge tube (Corning, Inc., Corning, NY) and 10 ml of modified RPMI was slowly added to the tube. Cells were centrifuged for 5 minutes at 2000 RPM, and the supernatant was discarded. Cells were resuspended in 10 ml of fresh media. Cell density and viability was determined by trypan blue.

For positive selection of anti-PACAP38 producing B-cells, biotinylated PACAP38 (SEQ ID NO: 1241) was pre-loaded onto the streptavidin beads as follows. 75 µl of streptavidin beads (Miltenyi Biotec, Auburn, CA) were mixed with N-terminally biotinylated PACAP38 (10 µg/ml final concentration) and 300 µl of PBS supplemented with 0.5% biotin free bovine serum albumin ("BSA") and 2 mM EDTA ("PBF"). This mixture was incubated at 4° C. for 30 minutes, and unbound biotinylated PACAP38 (AnaSpec, Fremont, CA) was removed using a MACS® separation column (Miltenyi Biotec, Auburn, CA) with a 1 ml rinse to remove unbound material. The bound material was plunged out by detachment from the magnet and used to resuspend cells from above in 100 µl per $1\times10^7$ cells. The mixture was then incubated at 4° C. for 30 minutes and washed once with 10 ml of PBF. After washing, the cells were resuspended in 500 µl of PBF and set aside. A MACS® MS column (Miltenyi Biotec, Auburn, CA) was pre-rinsed with 500 µl of PBF on a magnetic stand (Miltenyi Biotec, Auburn, CA). Cell suspension was applied to the column through a pre-filter, and unbound fraction was collected. The column was washed with 2.5 ml of PBF buffer. The column was removed from the magnet stand and placed onto a clean, sterile 1.5 ml EPPENDORF™ tube. 1 ml of PBF buffer was added to the top of the column, and positive selected cells were collected. The yield and viability of positive cell fraction was determined by trypan blue staining. Positive selection yielded an average of 1% of the starting cell concentration.

A pilot cell screen was established to provide information on seeding levels for the culture. Plates were seeded at 5, 10, 25, 50, 100, or 200 enriched B-cells/well. In addition, each well contained 25-50K cells/well of irradiated EL-4.B5 cells (5,000 Rads) and an appropriate level of activated rabbit T-cell supernatant (See U.S. Patent Application Publication No. 20070269868) (ranging from 1-5% depending on preparation) in high glucose modified RPMI medium at a final volume of 250 µl/well. Cultures were incubated for 5 to 7 days at 37° C. in 4% $CO_2$.

B-Cell Culture Screening by Antigen-Recognition (ELISA)

To identify wells producing anti-PACAP38 antibodies, B-cell supernatants were tested by antigen-recognition (ELISA). Briefly, NEUTRAVIDIN™-coated plates (Thermo Fisher Scientific, Waltham, MA), were coated with either N-term or C-term biotinylated PACAP38 (AnaSpec Inc., Fremont, CA) (50 µl per well; 1 µg/ml) diluted in ELISA buffer (0.5% fish skin gelatin in PBS pH 7.4) either for approximately 1 hour at room temperature or alternatively overnight at 4° C. The plates were then further blocked with ELISA buffer for one hour at room temperature and washed using PBS with 0.05% Tween 20 ("wash buffer"). B-cell supernatant samples (50 µl) were transferred onto the wells and incubated for one hour at room temperature. After this incubation, the plate was washed with wash buffer. For development, an anti-rabbit specific Fc-Horse Radish Peroxidase ("Fc-HRP") (1:5000 dilution in ELISA buffer) was added onto the wells and incubated for 45 minutes at room temperature. After a 3× wash step with wash solution, the plate was developed using 3,3',5,5'-Tetramethylbenzidine ("TMB") substrate for two minutes at room temperature, and the reaction was quenched using 0.5M HCl. The well absorbance was read at 450 nm.

To identify wells producing anti-PACAP38 antibodies that do not recognize VIP (SEQ ID NO: 1243), supernatant from wells positive for PACAP38 binding by ELISA were tested by ELISA for binding to VIP. Briefly, biotinylated VIP (AnaSpec Inc., Fremont, CA) was bound onto NEUTRA-VIDIN™ coated plates (50 pg per well, 1 µg/µl each peptide). B-cell supernatant samples (50 µl) were tested without prior dilution. Recognition in this assay may indicate cross reactivity with a closely related peptide, VIP.

Identification of Functional Activity in B-Cell Supernatants Using One or More Assays To identify wells producing anti-PACAP38 antibodies that block signaling of PACAP38 via PAC1-R, supernatant from positive wells for PACAP38 binding by ELISA were tested in a cAMP HTRF assay (Cisbio US, Bedford, MA). Supernatants (78 µl) were pre-incubated with 2 µl 5 nM PACAP38 (American Peptide Company, Sunnyvale, CA) for 1 hour at 37° C. During the incubation, PC-12 cells were prepared as described for titer assessment. Cells (10 µl) and antigen/antibody complex (40 µl) were transferred to an HTRF plate and shaken at room temperature for 30 minutes. Following the incubation, 20 µl of (1:20 diluted) $Eu^{3+}$ cryptate-labeled mAb anti-cAMP and 20 µl of (1:20 diluted) d2-labeled cAMP in lysis buffer were added, and the plate was incubated for 1 hour while shaking. Following incubation plates were read (excitation 330 nm, emission 620/665 nm), and a ratio of 620:665 signal was determined.

Isolation of Antigen-Specific B-cells

Antigen-specific B-cells were isolated (for general methods see co-owned publication no. WO 2014/146074, which is hereby incorporated by reference in its entirety). Plates containing wells of interest were removed from −70° C., and the cells from each well were recovered using five washes of 200 µl of medium (10% RPMI complete, 55 µM β-mercaptoethanol ("BME")) per well. The recovered cells were pelleted by centrifugation and the supernatant was carefully removed. Cells from each well were then re-suspended in 100 µl of medium and transferred to a 96 well plate. Cells were incubated for 90 minutes at 37° C. Following incubation, cells were pelleted by centrifugation, stained with a fluorescein isothiocyanate-labeled ("FITC-labeled") anti-rabbit IgG (final concentration 6.25 µg/ml) (Creative Diagnostics, Shirley, NY), and washed with up to 2 ml fluorescence-activated cell sorting buffer ("FACS buffer") (Dulbecco's PBS w/2% FBS) and re-suspended in 250 µl of FACS buffer.

Control wells from the same culture sets that were similar in composition to pooled wells of interest were thawed and stained alongside target wells. These samples were initially run on FACS (BD INFLUX™, Becton, Dickinson and Company, Franklin Lakes, NJ), and gates were established for IgG, viability, and physical parameters (Forward scatter ("FSC")/side scatter ("SSC")) that differentiate B-cells from the murine EL4 cells. Once gates were established, the sample of interest was run, and IgG positive, viable cells that were of a consistent physical (FSC/SSC) population were sorted individually into wells of a 96 well plate pre-loaded with RT-PCR master mix. Upwards of 8 cells per well were sorted. Sorted plates were removed from the sorter and transferred directly to thermocyclers for PCR.

Amplification and Sequence Determination of Antibody Sequences from FACS-Sorted B-Cells Antibody sequences were recovered using a combined RT-PCR based method from a single cell sorted B-cell. Primers containing restriction enzymes were designed to anneal in conserved and constant regions of the target immunoglobulin genes (heavy and light), such as rabbit immunoglobulin sequences, and a two-step nested PCR recovery was used to amplify the antibody sequence. Amplicons from each well were sequenced and analyzed. Representative antibodies from the resulting sequence clusters were selected for recombinant protein expression. The original heavy and light variable regions amplified from rabbit cells were cloned into human heavy and light chain constant region expression vectors via restriction enzyme digestion and ligation, and via Gibson method. Vectors containing subcloned DNA fragments were amplified and purified. The sequences of the subcloned heavy and light chains were verified prior to expression.

Recombinant Production of Monoclonal Antibody of Desired Antigen Specificity and/or Functional Properties To determine antigen specificity and functional properties of recovered antibodies from specific B-cells, the heavy and light chain plasmids were co-transfected to generate rabbit/human chimeric antibodies for testing. Briefly, heavy and light chimeric plasmids were transiently transfected into HEK-293 cells. Transfections were allowed to incubate for 5-7 days, and upon harvest, cells were pelleted by centrifugation. Supernatants were submitted for purification via Protein A. Resulting purified chimeric antibodies were then evaluated in a variety of assays to confirm specificity and potency.

Using the above-described methods, numerous functional (antagonistic) antibodies that bind PACAP38 and PACAP27, or that bind PACAP38 only, but which do not, or do not appreciably, bind to VIP were identified. Polypeptide and exemplary coding sequences of exemplary antagonistic anti-PACAP antibodies are contained in the included biological sequence listing.

The full-length antibodies Ab10, Ab20, Ab21, Ab22, and Ab23 used in these examples were expressed as the heavy chain polypeptides having the sequences of SEQ ID NO: 401; 441; 841; 881; and 921, respectively, and the light chain polypeptides of SEQ ID NO: 421; 461; 861; 901; and 941, respectively. The heavy chain polypeptides of antibodies Ab10, Ab20, Ab21, Ab22, and Ab23 were expressed from the polynucleotides of SEQ ID NO: 411; 451; 851; 891; and 931, respectively. The light chain polypeptides of antibodies Ab10, Ab20, Ab21, Ab22, and Ab23 were expressed from the polynucleotides of SEQ ID NO: 431; 471; 871; 911; and 951, respectively. Additional features of said antibodies are identified by SEQ ID NOS in FIGS. 1-12.

Antigen Binding Specificity of Antibodies by Competitive HTRF Binding Assay

The binding and functional properties of exemplary anti-PACAP38 and anti-PACAP27 antibodies produced according to the invention are further described below.

To identify antibodies that preferentially bind PACAP38 (SEQ ID NO: 1241) and PACAP27 (SEQ ID NO: 1242), but do not bind VIP (SEQ ID NO: 1243), or to identify antibodies that specifically bind PACAP38, but do not bind appreciably PACAP27, or do not appreciably bind VIP, etc., a competition HTRF binding assay was performed.

In parallel, 10 µl of an antibody dilution series (highest final concentration of 100 nM) were incubated with 10 µl of N-terminal or C-terminal biotinylated PACAP38 (35 nM final) alone, or in combination with either PACAP27 (350 nM final) or VIP (350 nM final), i.e., 10× PACAP27 or 10×VIP, respectively, in a HTRF plate. 20 µl of $Eu^{3+}$ cryptate labeled anti-hu Fc donor and 20 µl of d2-labeled streptavidin acceptor were added to each well and incubated for 1 hour at room temperature. Fluorescence was measured at 620 and 665 nm with a delay of 300 µsec.

FIG. 13A-D provide representative binding data for Ab10, Ab20, Ab21, and Ab1.H to PACAP38 and to PACAP27, and the inability of VIP to compete with binding of PACAP38. FIG. 13E and FIG. 13F provide representative binding data for the anti-PACAP antibodies Ab22 and Ab23 to PACAP38 and the inability of PACAP27 or VIP to compete with binding of PACAP38. The lack of effect of VIP on binding to PACAP38 indicated its inability to compete with binding of PACAP38. These results demonstrated that Ab10, Ab20, Ab21, and Ab1.H bind to PACAP38 and PACAP27, but do not bind (or do not appreciably bind) VIP. These results also demonstrated that Ab22 and Ab23 bind to PACAP38, but do not bind (or do not appreciably bind) PACAP27 or VIP.

$EC_{50}$ values, i.e. the concentration of an antibody that yields a response halfway between the baseline and the maximum value within a specified time period, were computed for each antibody based upon their binding curves and are shown in Table 1 below. The results demonstrate that Ab10, Ab20, Ab21, Ab22, and Ab23 bound to and recognized human PACAP38 with high affinity. A humanized form of antibody Ab1 identified by an appended ".H", i.e., Ab1.H also bound PACAP38 with high affinity.

TABLE 1

Binding ($EC_{50}$) of PACAP38 by anti-PACAP antibodies

| ANTIBODY | PACAP38-binding EC50 (nM) |
|---|---|
| Ab10 | 0.36 |
| Ab20 | 0.38 |
| Ab21 | 0.84 |
| Ab1.H | 0.46 |
| Ab22 | 0.57 |
| Ab23 | 0.56 |

Ability of Anti-PACAP Antibodies to Neutralize PACAP38-Induced and PACAP27-Induced cAMP Production The ability of anti-PACAP antibodies to neutralize PACAP38-induced and PACAP27-induced PAC1-R signaling was tested in a cell-based assay.

For Ab10, Ab20, Ab21, Ab1.H, Ab10.H, Ab21.H, Ab22, and Ab23 to identify antibodies that neutralized PACAP38-induced and PACAP27-induced signaling via PAC1-R, antibody solutions were incubated with either PACAP38 or with PACAP27 at 4× the final concentration (100 pM) for 1 hour. While the antibody/antigen complexes were incubated, PAC1-R expressing PC-12 cells (Japanese Collection of Research Bioresources Cell Bank) were washed and re-suspended at $2 \times 10^6$ cells per ml in cell culture media. Cells (10 µl) and antigen/antibody complex (40 µl) were transferred to an HTRF plate and shaken at room temperature for 30 minutes. Following the incubation, 20 µl of (1:20 diluted) $Eu^{3+}$ cryptate-labeled mAb anti-cAMP and 20 µl of (1:20 diluted) d2-labeled cAMP in lysis buffer were added, and the plate was incubated for 1 hour while shaking. Following incubation, plates were read (excitation 330 nm, emission 620/665 nm), and a ratio of 620:665 signal was determined. The final concentration of PACAP38 and PACAP27 in each well was 0.1 nM.

FIGS. 16A-H (PACAP38) and FIGS. 17A-H (PACAP27) show inhibition curves (for Ab10, Ab20, Ab21, Ab1.H, Ab10.H, Ab21.H, Ab22, and Ab23) that are representative of the inhibition curves that were obtained with the tested antibodies. The inhibition results were quantified for each antibody to yield an $IC_{50}$ value, which are summarized in Table 2 below. These results demonstrated that anti-PACAP antibodies Ab10, Ab20, Ab21, Ab1.H, Ab10.H, Ab21.H, Ab22, and Ab23 inhibited PACAP38-induced cAMP increase in cells expressing PAC1-R (see FIGS. 16A-H). Additionally, these results demonstrated that anti-PACAP antibodies Ab10, Ab20, Ab21, Ab1.H, Ab10.H, and Ab21.H, but not Ab22 or Ab23, inhibited PACAP27-induced cAMP increase in cells expressing PAC1-R (see FIGS. 17A-H).

TABLE 2

Inhibition ($IC_{50}$) of PACAP38-induced and PACAP27-induced cAMP increase in cells expressing PAC1-R by anti-PACAP antibodies

| ANTIBODY | Inhibition of 0.1 nM PACAP38-induced PAC1-R mediated cAMP increase $IC_{50}$ (pM) | Inhibition of 0.1 nM PACAP27-induced PAC1-R mediated cAMP increase $IC_{50}$ (pM) |
|---|---|---|
| Ab10 | 180.3 | 227.0 |
| Ab20 | 368.2 | 187.8 |
| Ab21 | 239.1 | 140.2 |
| Ab1.H | 259.6 | 57.7 |
| Ab10.H | 163.4 | 84.0 |
| Ab21.H | 246.0 | 203.6 |
| Ab22 | 101.4 | n/a * |
| Ab23 | 114.9 | n/a * |

* n/a: not active because these Abs are PACAP38 specific

Example 2: Binding Affinities of Anti-PACAP Antibodies

Binding affinities of monoclonal antibodies for human PACAP were estimated using SPR on the PROTEON™ XPR36 (Bio-Rad, Hercules, CA). Antibody was immobilized to the surface of general amine coupling ("GLC" or "GLM") Chips (Bio-Rad, Hercules, CA). A dilution series of human PACAP38 (SEQ ID NO: 1241) prepared in 1×PBST Buffer (4.3 mM Na Phosphate, 1.4 mM K Phosphate, 135 mM NaCl, 2.7 mM KCl 0.05% Polysorbate-20) purchased from Teknova (Cat #P1192, Teknova, Hollister, CA) and supplemented with 0.25 M arginine (from J.T. BAKER®), 0.2 mg/ml BSA (Jackson Immuno Research Labs, West Grove, PA), and 0.005% sodium azide (VWR International, Radnor, PA) with the pH adjusted to 7 was used to query the antibodies. Antigen (ranging from 1.23 nM to 100 nM) was typically run sequentially with association times of 2-4 minutes and dissociation times of 3-120 minutes grouped with the PROTEON™ Manager Software (v3.1.0.6 (Bio-Rad, Hercules, CA)) and fitted using a 1:1 Langmuir binding model. Surfaces were regenerated between analyte queries using 0.85% Phosphoric Acid. A single $K_D$ was calculated for each antibody with association times limited near the rate of diffusion ($1.0 \times 10^6$) and dissociation times limited to $1.5 \times 10^5$ where no discernible dissociation was observed.

The same procedure was used to determine binding affinities of antibodies for human VIP (SEQ ID NO: 1243) and PACAP27 (SEQ ID NO: 1242) though peptide concentrations ranged from 1.23 nM to 1000 nM with association times of 200 seconds and dissociation times of 3-120 minutes.

The measured antibody affinities for PACAP38 are listed in Table 3.

TABLE 3

Antibody affinity constants for PACAP38

| Antibody | ka (1/Ms) | kd (1/s) | KD (M) |
|---|---|---|---|
| Ab10 | 2.6E+05 | 2.0E−05 | 7.5E−11 |
| Ab20 | 1.2E+05 | 2.4E−05 | 2.1E−10 |
| Ab21 | 3.7E+05 | 1.0E−05 | 2.7E−11 |
| Ab22 | 3.7E+05 | 1.0E−05 | 2.7E−11 |
| Ab23 | 5.1E+05 | 3.6E−05 | 7.1E−11 |
| Ab1.H | 4.7E+05 | 1.0E−05 | 2.1E−11 |
| Ab10.H | 3.4E+05 | 1.0E−05 | 2.9E−11 |
| Ab21.H | 4.8E+05 | 1.0E−05 | 2.1E−11 |

Examples of antibody affinity constants for VIP are listed in Table 4.

TABLE 4

Antibody affinity constants for VIP

| Antibody | ka (1/Ms) | kd (1/s) | KD (M) |
|---|---|---|---|
| Ab10 | 3.7E+04 | 1.0E−02 | 2.8E−07 |
| Ab20 | 4.5E+05 | 4.8E−01 | 1.1E−06 |
| Ab21 | 1.7E+03 | 5.4E−04 | 3.1E−07 |
| Ab22 | 2.7E+05 | 1.8E−01 | 6.9E−07 |
| Ab23 | 4.3E+05 | 3.2E−01 | 7.3E−07 |
| Ab1.H | 3.8E+04 | 1.8E−01 | 4.8E−06 |
| Ab10.H | 3.8E+05 | 3.9E−02 | 1.0E−07 |
| Ab21.H | 1.4E+05 | 5.9E−02 | 4.4E−07 |

Examples of antibody affinity constants for PACAP27 are listed in Table 5.

TABLE 5

Antibody affinity constants for PACAP27

| Antibody | ka (1/Ms) | kd (1/s) | $K_D$ (M) |
|---|---|---|---|
| Ab10 | 1.0E+06 | 1.0E−05 | 1.0E−11 |
| Ab20 | 3.2E+05 | 2.2E−05 | 7.0E−11 |
| Ab21 | 7.9E+05 | 1.0E−05 | 1.3E−11 |
| Ab22 | 1.0E+00 | 1.0E−01 | 1.0E−01 |
| Ab23 | 8.9E+05 | 3.1E−02 | 3.5E−08 |
| Ab1.H | 7.6E+05 | 1.0E−05 | 1.3E−11 |
| Ab10.H | 5.3E+05 | 1.8E−05 | 3.3E−11 |
| Ab21.H | 6.3E+05 | 1.0E−05 | 1.6E−11 |

The binding affinity results of Tables 3 and 5 present data demonstrating that Ab23 weakly bound to PACAP27 as compared to its binding affinity for PACAP38. Tables 3 and 5 additionally present data demonstrating that Ab22 did not specifically recognize PACAP27, but that Ab22 specifically bound to PACAP38.

Example 3: Inhibition of PACAP38-Induced Signaling Via VPAC1-R

To identify antibodies that neutralize PACAP38-induced signaling via human VPAC1-R, CHO-K1 cells expressing human VPAC1-R were used in a cAMP HTRF cell-based assay. Antibody dilutions were incubated with PACAP38 at 4× the final concentration (5 nM) for 1 hour. While the antibody/antigen complexes were incubated for 1 hour, VPAC1-R expressing CHO-K1 cells (generated at Alder Biopharmaceuticals, by stable transfection of CHO-K1 cells (ATCC, catalog #CCL-61) with human VPAC1-R cDNA; selected clone 1 was used for in vitro cell based assays) were detached with 0.25% trypsin for 4 minutes. The cells were washed and re-suspended at 1×10$^6$ cells per ml culture media. 20 µl of Ab/antigen mixture was mixed with 20 µl of cells in HTRF plates and incubated with shaking for 30 minutes. 20 µl of Eu$^{3+}$ cryptate labeled anti-cAMP mAb (1:20 diluted) and 20 µl of (1:20 diluted) d2-labeled cAMP in lysis buffer were added to each well and incubated for 1 hour with shaking. The final concentration of PACAP38 in each well was 5 nM. Following incubation, plates were read (excitation 330 nm, emission 620/665 nm), and a ratio of 620:665 signal was determined.

FIGS. 18A-H are representative of the inhibition curves obtained by this method (results are shown for Ab10, Ab20, Ab21, Ab1.H, Ab10.H, Ab21.H, Ab22, and Ab23 respectively). The computed IC$_{50}$ values for each antibody, which are shown below in Table 6, demonstrated that Ab10, Ab20, Ab21, Ab1.H, Ab10.H, Ab21.H, Ab22, and Ab23 inhibited PACAP38-induced cAMP increase in cells expressing human VPAC1-R.

TABLE 6

Inhibition (IC$_{50}$) of PACAP38-induced cAMP increase in cells expressing human VPAC1-R by anti-PACAP antibodies

| ANTIBODY | Inhibition of 5 nM PACAP38-induced human VPAC1-R mediated cAMP increase IC50 (pM) |
|---|---|
| Ab10 | 649.1 |
| Ab20 | 3889.0 |
| Ab21 | 2846.0 |
| Ab1.H | 1021.1 |
| Ab10.H | 1336.0 |
| Ab21.H | 2105.0 |
| Ab22 | 1300.0 |
| Ab23 | 2667.0 |

Example 4: Inhibition of PACAP38-Induced Signaling Via VPAC2-R

To identify antibodies that neutralize PACAP38-induced signaling via human VPAC2-R, CHO-K1 cells expressing human VPAC2-R were used in a cAMP HTRF cell based assay. Antibody dilutions were incubated with PACAP38 at 4× the final concentration (1 nM) for 1 hr. While the antibody/antigen complexes were incubated for 1 hour, VPAC2-R expressing CHO-K1 cells (generated at Alder Biopharmaceuticals, by stable transfection of CHO-K1 cells (ATCC, catalog #CCL-61) with human VPAC2-R cDNA; selected clone 8 was used for in vitro cell based assays) were detached with 0.25% trypsin for 4 minutes. The cells were washed and re-suspended at 1×10$^6$ cells per ml culture media. 20 µl of Ab/antigen mixture was mixed with 20 µl of cells in HTRF plates and incubated with shaking for 30 minutes. 20 µl of Eu$^{3+}$ cryptate labeled anti-cAMP mAb (1:20 diluted) and 20 µl of (1:20 diluted) d2-labeled cAMP in lysis buffer were added to each well and incubated for 1 hour with shaking. The final concentration of PACAP38 in the wells was 1 nM. Following incubation, plates were read (excitation 330 nm, emission 620/665 nm) and, a ratio of 620:665 signal was determined.

FIGS. 19A-H are representative of the inhibition curves obtained by this method (results are shown for Ab10, Ab20, Ab21, Ab1.H, Ab10.H, Ab21.H, Ab22, and Ab23 respectively). The computed IC$_{50}$ values for each antibody, which are shown below in Table 7, demonstrated that Ab10, Ab20, Ab21, Ab1.H, Ab10.H, Ab21.H, Ab22, and Ab23 inhibited PACAP38-induced cAMP increase in cells expressing human VPAC2-R.

TABLE 7

Inhibition (IC$_{50}$) of PACAP38-induced cAMP increase in cells expressing human VPAC2-R by anti-PACAP antibodies

| ANTIBODY | Inhibition of 1 nM PACAP38-induced human VPAC2-R mediated cAMP increase IC$_{50}$ (pM) |
|---|---|
| Ab10 | 188.5 |
| Ab20 | 14570.0 |
| Ab21 | 5215.0 |
| Ab1.H | 983.0 |
| Ab10.H | 988.0 |
| Ab21.H | 1507.0 |
| Ab22 | 515.0 |
| Ab23 | 1789.0 |

Example 5: Inhibition of PACAP38 Binding to PAC1-R-Expressing Cells

To identify antibodies that block PACAP38 binding to PAC1-R-expressing cells, adherent PC-12 cells (ATCC, Manassas, VA) expressing PAC1-R were used in a Europium-based PAC1-R-expressing cells binding assay. Antibody solutions were incubated with N-terminal biotinylated PACAP38 at 10× the final concentration (100 nM or 30 nM) for 1 hr, then added to PC-12 cells that were plated 24 hrs prior in black clear bottom 96 well plates (COSTAR™, Corning Incorporated, Corning, NY) and further incubated for 1 hr at room temperature. After three washes, the cells were incubated with 20 µl Europium-labeled streptavidin (PerkinElmer, Waltham, MA) for 1 hr at room temperature. Cells were washed three times, then 20 µl DELFIA® Enhancement solution (PerkinElmer, Waltham, MA) was added to each well and incubated for 15 minutes with gentle shaking. Plates were read (Time Resolved Fluorescence ("TRF")) on SPECTRAMAX® (Molecular Devices, Sunnyvale, CA) plate reader.

FIGS. 14A-H are representative of the inhibition curves obtained by this method (results are shown for Ab10, Ab20, Ab21, Ab1.H, Ab10.H, Ab21.H, Ab22, and Ab23, respectively) wherein the PAC1-R expressing cells were PC-12 cells. The computed IC$_{50}$ values for each antibody, which are shown below in Table 8, demonstrated that Ab10, Ab20, Ab21, Ab1.H, Ab10.H, Ab21.H, Ab22, and Ab23 inhibited PACAP38 binding to PAC1-R expressing PC-12 cells.

TABLE 8

Inhibition (IC$_{50}$) of PACAP38 binding to PAC1-R-expressing PC-12 cells by anti-PACAP antibodies

| ANTIBODY | Inhibition of 100 nM biotinylated PACAP38 binding to PAC1-R-expressing PC-12 cells IC50 (nM) |
|---|---|
| Ab10 | 17.8 |
| Ab20 | 32.7 |

| ANTIBODY | Inhibition of 30 nM Biotinylated PACAP38 binding to PAC1-R-expressing PC-12 cells IC$_{50}$ (nM) |
|---|---|

TABLE 8-continued

Inhibition (IC$_{50}$) of PACAP38 binding to PAC1-R-expressing PC-12 cells by anti-PACAP antibodies

| Ab21 | 20.3 |
|---|---|
| Ab1.H | 56.3 |
| Ab10.H | 14.5 |
| Ab21.H | 12.7 |
| Ab22 | 13.8 |
| Ab23 | 14.9 |

Example 6: PACAP38-Mediated Binding of Anti-PACAP Antibodies to the Cell Surface of PAC1-R-Expressing Cells To identify anti-PACAP antibodies that bind, via PACAP38, to the cell surface of PAC1-R expressing cells, adherent PC-12 cells (Japanese Collection of Research Bioresources Cell Bank) expressing PAC1-R were used in a cell surface binding-based assay. To perform the binding experiment, PAC1-R expressing PC-12 cells were first seeded into Corning 96 well white solid bottom plates (Corning, Corning, NY). Cells were initially seeded at 1×10$^5$ cells/well in a solution of complete RPMI ("cRPMI": RPMI medium supplemented with 10% sterile heat-inactivated FBS and 1% sterile antibiotic/antimycotic)+10% FBS, and the plates were allowed to incubate overnight at 37° C. On the day of the binding assay, antibodies at an initial concentration of 15 µg/ml were diluted at a 1:3 ratio in DELFIA® binding buffer (50 mM Tris, 150 mM NaCl, 0.1% azide, 2% horse serum) (Perkin-Elmer, Waltham, MA) to a total volume of 60 µL in a separate 96 well round bottom plate. PACAP38 was prepared for the binding assay by diluting it in DELFIA® binding buffer to a concentration of 200 nM, and then 60 µl of the diluted PACAP38 was added to each of the antibody-containing wells to form antibody: antigen complexes. Following addition of PACAP38, the antibody:antigen complexes were incubated at room temperature on a shaker for 1 hour. Separately, the PC-12 cells were prepared for addition of antibody:antigen complexes by washing the cells two times with DELFIA® wash buffer (50 mM Tris, 150 mM NaCl, 0.1% Azide) (Perkin-Elmer, Waltham, MA). After washing the cells two times and following the 1 hour room temperature incubation of the antibody:antigen complexes, 50 µl of the antibody:antigen complex was added to each well containing cells. The mixtures of cells and antibody:antigen complexes were then incubated for 30 minutes at room temperature. Following this 30 minute incubation, each mixture was washed two times with DELFIA® wash buffer (Perkin-Elmer, Waltham, MA).

DELFIA® Europium labeled anti-human IgG detection reagent (Cat #1244-330, Perkin-Elmer, Waltham, MA) was diluted to a concentration of 300 ng/ml in DELFIA® Binding Buffer. Following dilution, 50 µl of the anti-human IgG detection reagent was added to each well containing cells, and a 30 minute incubation at room temperature followed this addition of IgG detection reagent. After completion of the 30 minute room temperature incubation, the cells were then washed two times with DELFIA® wash buffer. Next, 50 µl of DELFIA® Enhancement Solution (Cat #1244-105, Perkin-Elmer, Waltham, MA) was added to each well containing cells for a final 15 minute room temperature incubation with shaking. The plates were then read (TRF, excitation 330 nm, emission 620 nm) on a SPECTRAMAX® (Molecular Devices, Sunnyvale, CA) plate reader.

FIGS. 15A-H are representative of the binding curves obtained by this method (results are shown for Ab10, Ab20, Ab21, Ab1.H, Ab10.H, Ab21.H, Ab22, and Ab23 respectively) wherein the PAC1-R expressing cells were PC-12 cells. Ab1.H demonstrated binding to the surface of PAC1-R expressing cells in the presence of PACAP38, while Ab20, Ab21, Ab10.H, Ab21.H, Ab22, and Ab23 did not appear to appreciably bind to the surface of PAC1-R expressing cells using this assay. The binding of Ab1.H to the cell surface of PAC1-R cells was only observed in the presence of PACAP38. Without intent to be bound by theory, it is hypothesized that the binding of the antibodies to the cell surface was mediated by binding of PACAP38 to GAGs that were present on the cell surface, since binding of PACAP38 by GAGs has been previously demonstrated as a PAC1-R receptor independent mechanism of PACAP38 binding and internalization by PC-12 cells (see Doan et al., 2012; Juhisz et al., 2014; and Neree et al., 2015).

Example 7. Inhibition of PACAP38-Induced Dermal Vasodilation in Rabbits by Anti-PACAP Antibody Ab1.H Intradermal injection of PACAP38 has been shown to elicit a localized vasodilation in rabbits and humans (Warren et al., *J Cardio. Pharmacol.*, 29(1): 83-87, 1992; Seelinger et al., *Am. J. Path.*, 177(5):2563-2575, 2010). An in vivo efficacy study was conducted to determine the activity of Ab1.H to inhibit a localized dermal vasodilation induced by an intradermal injection of PACAP38 in male New Zealand White rabbits.

Groups of 4 rabbits were dosed with either 90 mg/kg of Ab1.H or with negative control vehicle (25 mM histidine, 250 mM sorbitol, pH 6.0). Injections were performed by IV (ear vein) bolus administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (Region of Interest ("ROI")) for injection were identified on the back of each animal using a SHARPIE® permanent marker. Dermal vasodilation and blood perfusion were monitored using the PeriCam PSI NR system for Laser Speckle Contrast Analysis ("LASCA") imaging (Perimed, Jarfalla, Sweden), before (baseline) and for 35 minutes after intradermal PACAP38 challenge. Intradermal PACAP38 challenge was performed as follows: each animal received single intradermal administrations (100 µl/site) of vehicle (one site or ROI) and PACAP38 at 30 pmoles/site (3 sites or 3 ROIs). The blood perfusion rates for each ROI were reported by the PeriCam PSI NR system in Perfusion units ("PU") and analyzed using PIMSoft (Ver. 1.5, Perimed, Jarfalla, Sweden).

For each treatment group, the relative % PU change following Ab1.H or negative control administration compared to baseline was calculated for each ROI (% PU change for each PACAP38 challenge site–% PU change for the vehicle site). The relative % PU change in the Ab1.H group was compared to the relative % PU change in the Negative control group by performing a two-tailed unpaired t-test statistical evaluation using GraphPad Prism (version 5.0d, GraphPad Software, La Jolla, CA) software.

Figure 20:
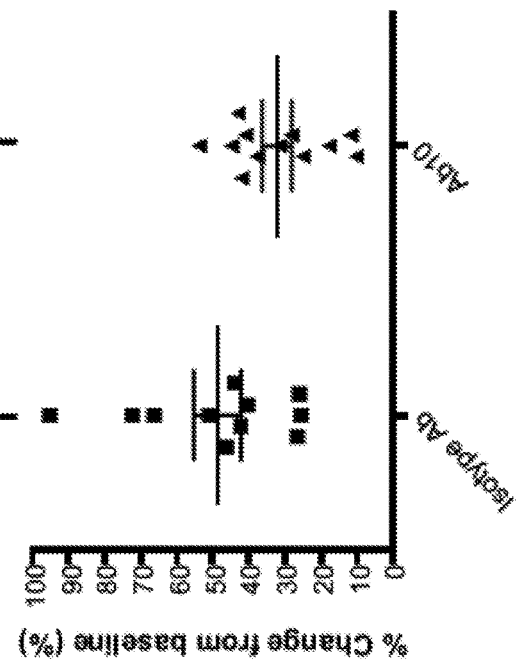
FIG. 20 provides representative data showing a reduction in vasodilation obtained by administering Ab1.H following PACAP38 administration in a rabbit model, relative to a vehicle control, obtained following the protocol in Example 7 infra.

FIG. 20 demonstrates that Ab1.H inhibited PACAP38-induced dermal vasodilation in rabbits, indicating effectiveness of the antibody at neutralizing PACAP38 activity in vivo.

Example 8: Inhibition of PACAP38-Induced Dermal Vasodilation in Rabbits by Anti-PACAP Antibody Ab10

Intradermal injection of PACAP38 has been shown to elicit a localized vasodilation in rabbits and humans (Warren et al., 1992; and Seelinger et al., 2010). An in vivo efficacy study was conducted to determine the activity of Ab10 to inhibit a localized dermal vasodilation induced by an intradermal injection of PACAP38 in male New Zealand White rabbits.

Groups of 4 rabbits were dosed with either 72 mg/kg of Ab10 or with isotype antibody control. Injections were by (ear vein) bolus intravenous administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (ROIs) for injection were identified on the back of each animal using a SHARPIE® permanent marker. Dermal vasodilation and blood perfusion were monitored using the PeriCam PSI NR system for LASCA imaging (Perimed, Jarfalla, Sweden), before (baseline) and for 35 minutes after intradermal PACAP38 challenge. Intradermal PACAP38 challenge was performed as follows: each animal received single intradermal administrations (100 µl/site) of vehicle (one site or ROI) and PACAP38 at 30 pmoles/site (3 sites or 3 ROIs). The blood perfusion rates for each ROI were reported by the PeriCam PSI NR system in PU and analyzed using PIMSoft (Ver. 1.5 (Perimed, Jarfalla, Sweden)).

For each treatment group, the relative % PU change following Ab10 or Isotype Ab control administration compared to baseline was calculated for each ROI (% PU change for each PACAP38 challenge site–% PU change for the vehicle site). The relative % PU change in the Ab10 group was compared to the relative % PU change in the Isotype Ab control group by performing a two-tailed unpaired t-test statistical evaluation using GraphPad Prism (version 5.0d, GraphPad Software, La Jolla, CA) software.

Figure 21:
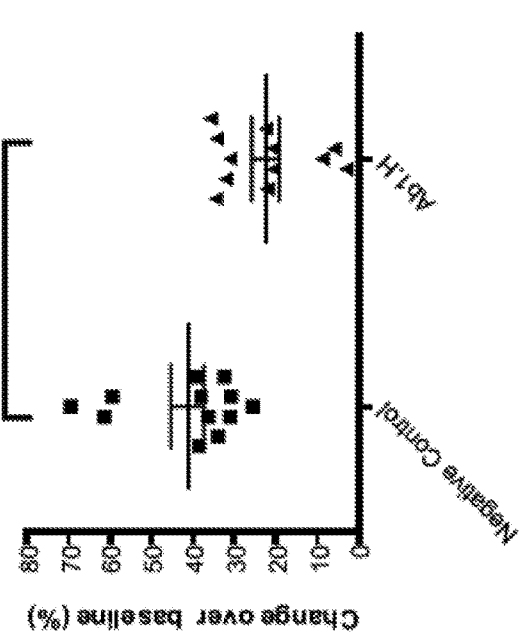
FIG. 21 provides representative data showing a reduction in vasodilation obtained by administering Ab10 following PACAP38 administration in a rabbit model, relative to an isotype antibody control, obtained following the protocol in Example 8 infra.

FIG. 21 demonstrates that Ab10 inhibited PACAP38-induced dermal vasodilation in rabbits, indicating effectiveness of the antibody at neutralizing PACAP38 activity in vivo.

Example 9: Epitope Binning of Anti-PACAP Antibodies, Ab and Ab10

Figure 22A:
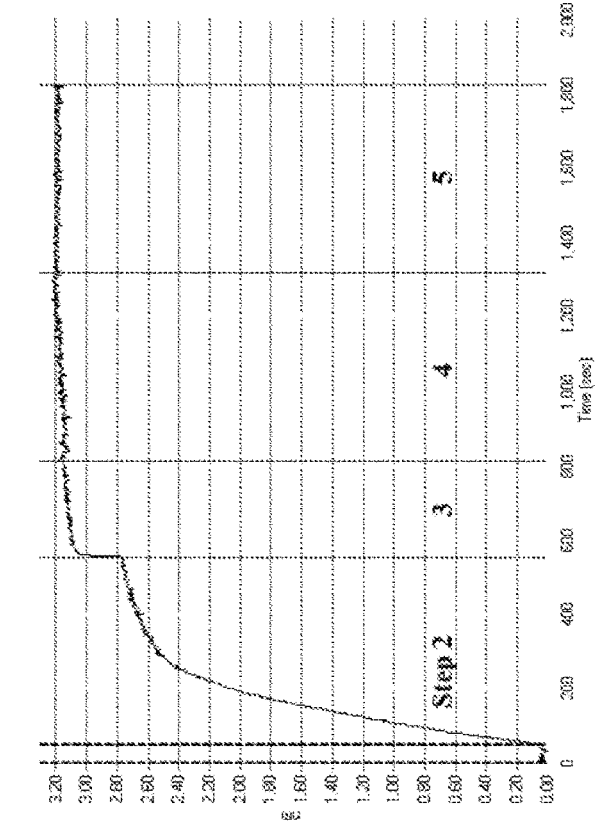
FIG. 22A provides epitope binning data for labeled Ab1 and unlabeled Ab10 obtained following the protocol in Example 9 infra.
Figure 22B:
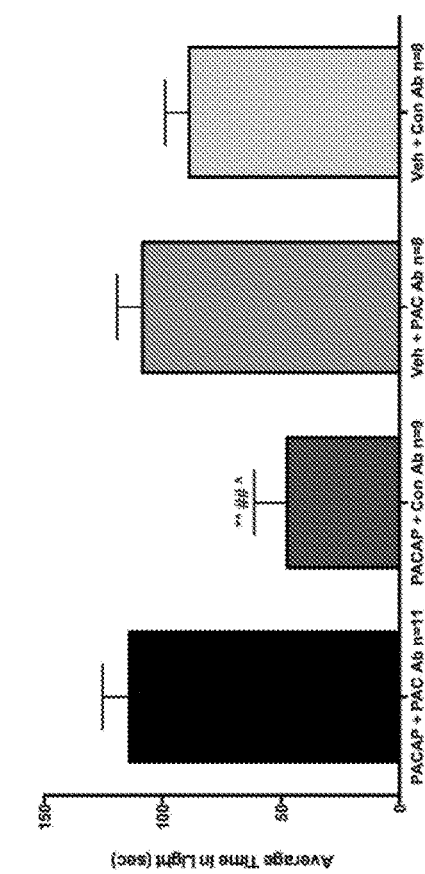
FIG. 22B provides epitope binning data for unlabeled Ab1 and labeled Ab10 obtained following the protocol in Example 9 infra.

Ab1 was biotinylated at a 10:1 molar ratio with biotin (Thermo Fisher Scientific, Waltham, MA) per manufacturer guidelines. A 5 step biolayer interferometry experiment was performed as follows: In step 1, streptavidin biosensors (Pall ForteBio LLC, Menlo Park, CA) were equilibrated for 50 seconds in 1× kinetics buffer (a 1:10 dilution in DBS of Pall ForteBio LLC, Menlo Park, CA, cat #18-5032). In step 2, a 2 µg/ml dilution of biotinylated antibody Ab1 in 1× kinetics buffer was immobilized for 500 seconds onto Streptavidin biosensors. In step 3, the antibody-functionalized biosensors were incubated in a solution of 2 µM unlabeled PACAP peptide (American Peptide Company, Sunnyvale, CA, catalog #34-0-20) in 1× kinetics buffer for 200 seconds. In step 4, the sensors were placed into 67 nM solutions of either unlabeled antibody Ab10 (FIG. 22A) or unlabeled antibody Ab1 as control (FIG. 22B) in 1× kinetics buffer for a 1000 second association step. Stability of binding was monitored during step 5 for a 1000 second dissociation in 1× kinetics buffer. In FIG. 22A, the "sandwich-style" capture of Ab10 via Ab1-captured PACAP indicates simultaneous and non-competitive binding of these two antibodies to PACAP. The control experiment in FIG. 22B shows minimal "sandwich-style" capture of Ab1 via Ab1-captured PACAP. The experiment was conducted on a ForteBio OCTET® QK instrument (Pall ForteBio LLC, Menlo Park, CA) at 30° C. and 1000 RPM.

Example 10: Inhibition of PACAP27 Binding to Human PAC1-R by Anti-PA CAP Antibodies To identify antibodies that block PACAP27 binding to PAC1-R, antibodies at an initial concentration of 30 nM were diluted in incubation buffer (50 mM Hepes pH 7.4, 1 mM $CaCl_2$, 5 mM $MgCl_2$, 0.2% BSA) and serial 1:3 dilutions were performed. Antibody dilutions (30 nM, 10 nM, 3 nM, 1 nM, 0.3 nM, 0.1 nM, 0.03 nM, 0.01 nM, 0.003 nM and 0.001 nM) were then mixed and pre-incubated at 25° C. for 30 minutes with 0.1 nM of $^{125}$I-labelled PACAP27 in incubation buffer. The antibody: $^{125}$I-labelled PACAP27 mixture was then added to 0.5 µg aliquots of cell membranes derived from Chem-1 cells expressing human recombinant PAC1-R long isoform in incubation buffer. The mixture was then incubated for 1 hour at 25° C. Following incubation, the samples were filtered and washed. Afterward, the filters were counted to quantitate $^{125}$I-labelled PACAP27. As an experimental control, non-specific binding to the cell membranes was estimated using 0.1 µM of labeled PACAP27. The results indicated that Ab1.H, Ab10.H, and Ab21.H were capable of blocking PACAP27 binding to PAC1-R, thereby demonstrating inhibition of ligand-receptor binding by the tested antibodies presented in Table 9.

TABLE 9

Inhibition ($IC_{50}$) of 0.1 nM $^{125}$I-PACAP27 binding to PAC1-R by anti-PACAP antibodies

| ANTIBODY | $IC_{50}$ (nM) |
| --- | --- |
| Ab1.H | 0.70 |
| Ab10.H | 0.22 |
| Ab21.H | 0.39 |

Example 11: Effect of Anti-PACAP Antibody on Light Aversion

To examine the effect of anti-PACAP antibodies on photophobia, a mouse model was employed in which mice were administered PACAP to trigger photophobia. Photophobia was detected using a light aversion assay using a light-dark box as described in Kaiser et al., *J. Neurosci.*, 32(44):15439-15449, 2012. Mice were then administered anti-PACAP antibodies Ab1.H or Ab10.H or an unrelated control antibody and their aversion to light quantitated. Results are reflected in FIGS. 23-25.

Light Aversion Assay

As described in Kaiser et al., the testing chambers were a plexiglas open field (27 cm wide×27 cm deep×20.3 cm high) containing three sets of 16 beam infrared arrays (two sets of perpendicular beams cross at a height of 1.0 cm to detect mouse location and locomotion, and the third beam crosses the width of the chamber at a height of 7.3 cm to detect vertical activity). The field was divided in two equal sized zones by a dark insert, which is a five-sided, black-colored plexiglas box with a top, but no floor. The use of infrared light beams allowed tracking in both zones. An opening (5.2 cm×6.8 cm) in the dark insert allowed free movement between zones. While the dark insert blocked direct light, some light could still enter through the opening. Each testing chamber was located inside a sound-attenuating cubicle (56 cm wide×38 cm deep×36 cm high) with a fan for ventilation (Med Associates, Inc.®, St. Albans, VT). A computer using Activity Monitor v6.02 (Med Associated Inc.) was used for recording data from the six chambers.

For each chamber, a LED panel was attached to the ceiling of the sound-attenuating cubicle. The LED panel contains 36 collimated 1 watt LEDs (5500k Daylight White) (LEDwholesalers.com, Burlingame, CA). To control light intensity, each LED panel was connected to a dimmable LED driver (LINEARdrive®; eldoLED America Inc., San Jose, CA) leading to a potential range of light intensity from $3.0\times10^2$ to $2.7\times10^4$ lx. Levels were further attenuated to $5.5\times10^1$ lx using wax paper placed on a clear plexiglass tray below the LEDs. Light intensity was measured with Traceable Dual-Display Light Meter (Control Company, Friendswood, TX) placed on the floor of the testing chamber. At $2.7\times10^4$ lx, LED lights generated some heat in the sound attenuating chamber with the dark zone at ~25° C. and light zone at ~27° C.

On the day of the experiment, mice were transported from animal housing and allowed to acclimate to the testing room (~22° C.) for at least 30 to 60 minutes with standard overhead fluorescent lighting (~200 lx inside the housing cage). Room lights remained on, unless noted otherwise. In addition, all sound-generating equipment were turned on during acclimation and remained on until testing was complete. There was minimal human presence in the room during acclimation. Behavioral testing was performed between 0800 CST and 1400 CST. Any abnormal physical conditions (e.g. missing eye) were noted.

Ten week old male and female CD1 mice were used in the study (strain #022, Charles River, Wilmington, MA, US). Mice were allowed to recover from shipping for one to two weeks prior to testing.

Acclimation

All mice were acclimated in the testing room at least 30 to 60 minutes prior to being placed in the light/dark chamber. The light intensity in the chamber was initially set to $2.7\times10^3$ lx. The mice were tested for thirty minutes in the chamber every day they were exposed to the light/dark chamber. Baseline time in light for each mouse was obtained by exposing the mice to the light/dark chamber twice, with a period of rest of three days between baseline measurements (FIGS. 23 and 25, "Baseline1" and "Baseline2," or "Baseline", respectively).

Treatment

Figure 23:
FIG. 23 provides representative data showing the in vivo effect of the administration of PACAP and an anti-PACAP antibody Ab1.H in a rodent photophobia model, which model detects the amount of time treated animals (mice) spend in the light per 5 min. interval compared to appropriate control animals obtained following the protocol in Example 11 infra.

The mice were administered 30 mg/kg of either anti-PACAP antibody or control IgG antibody (negative control antibody having the same framework as the tested antibodies and that recognizes digoxigenin) by i.p. injection. The mice were then returned to their home cage to rest for one day (24 hours) prior to testing. The mice were then administered 0.6 mg/kg PACAP or vehicle by i.p. injection and rested for 30 minutes. The mice were then placed in the light/dark chamber for 30 minutes (FIG. 23 and FIG. 25, "Treatment"). After each mouse was exposed to the light/dark chamber, the light/dark chamber and components were cleaned with germicidal wipes and dried. About 5 to 7 minutes after a mouse was placed in the light/dark chamber, the next mouse to be tested was injected with PACAP or vehicle, as described above. This interval was approximately the amount of time required to clean the light/dark chamber between experiments.

Motility Measurements

Motility was measured at 5 minute intervals over the 30 minute testing period as described in Kaiser et al., *J. Neurosci.*, 2012. Briefly, the number of vertical movements, such as rearing, ambulatory distance (cm, the total distance traveled during ambulatory movement status), transitions, and resting (percentage of time spent breaking no new beams), were measured by light beam. All motility parameters were normalized to the time spent in each zone to account for different amount of time spent in that zone; thus, the raw value for each parameter was divided by the time spent in that zone during the 5 min interval. Time spent in each chamber was analyzed using GraphPad Prism software (GraphPad Software, San Diego, CA), and reported as mean±standard error of the mean ("SEM"). Comparison was calculated by two-way repeated measure ANOVA, with Bonferroni's multiple-comparison test for post-hoc analysis.

Mice were excluded based on three criteria: (1) after the first two exposures to the box the baseline time in light was analyzed and any mouse that spent+/−one standard deviation of mean time in light at baseline was removed from the experiment and not given drug treatment, (2) mice were excluded from analysis if they were identified as statistical outliers (box plot, 10-90%), and (3) mice were excluded if they moved less than 10% of the time (combined light and dark).

Figure 24:
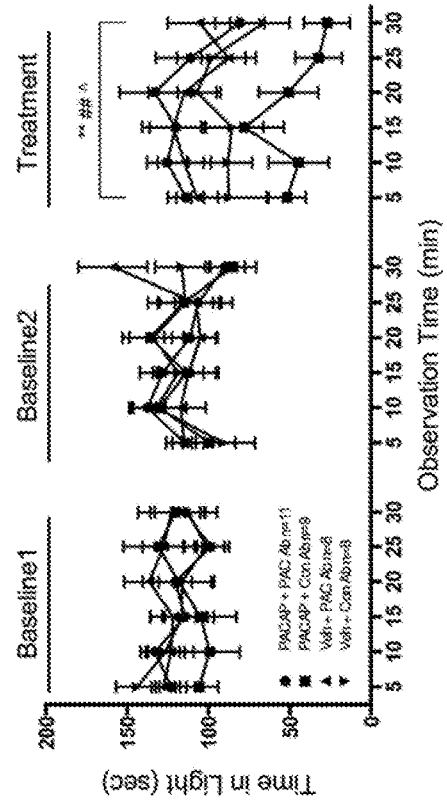
FIG. 24 provides representative data showing the in vivo effect of the administration of PACAP and anti-PACAP antibody Ab1.H in a rodent photophobia animal model, which detects the average amount of time treated animals (mice) spend in the light compared to appropriate control animals obtained following the protocol in Example 11 infra.
Figure 27A:
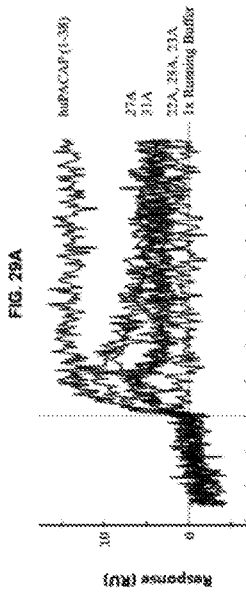
FIG. 27A presents results of surface plasmon resonance-based binding kinetics measurements for binding of anti-PACAP antibody Ab20 to PACAP alanine scanning mutants 19A, 22A, 23A, 24V, and 27A, along with controls including wild-type PACAP (labelled huPACAP (1-38)) (positive control) and 1× running buffer (negative control) obtained following the protocol in Example 12 infra.
Figure 27B:
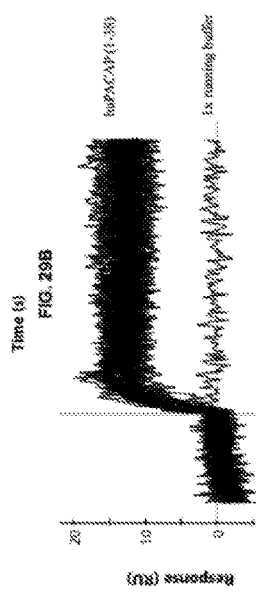
FIG. 27B presents results of surface plasmon resonance-based binding kinetics measurements for binding of anti-PACAP antibody Ab20 to PACAP alanine scanning mutants 1A-18A, 20A, 21A, 25A, 26A, and 28A-38A, along with controls including wild-type PACAP (labelled huPACAP (1-38)) (positive control) and 1× running buffer (negative control) obtained following the protocol in Example 12 infra.
Figure 28A:
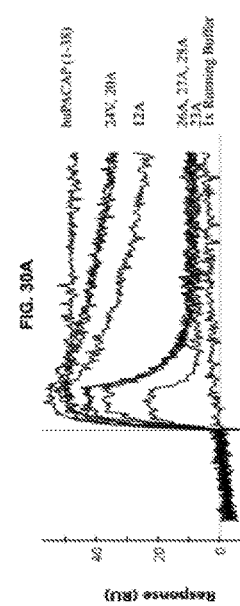
FIG. 28A presents results of surface plasmon resonance-based binding kinetics measurements for binding of anti-PACAP antibody Ab21 to PACAP alanine scanning mutants 19A, 22A, 23A, and 27A, along with controls including wild-type PACAP (labelled huPACAP (1-38)) (positive control) and 1× running buffer (negative control) obtained following the protocol in Example 12 infra.
Figure 28B:
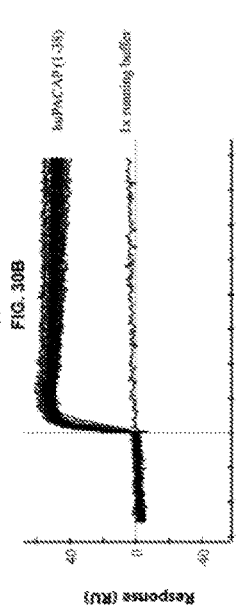
FIG. 28B presents results of binding kinetics measurements for binding of anti-PACAP antibody Ab21 to PACAP alanine scanning mutants 1A-18A, 20A, 21A, 24V-26A, and 28A-38A, along with controls including wild-type PACAP (labelled huPACAP (1-38)) (positive control) and 1× running buffer (negative control) obtained following the protocol in Example 12 infra.
Figure 29A:
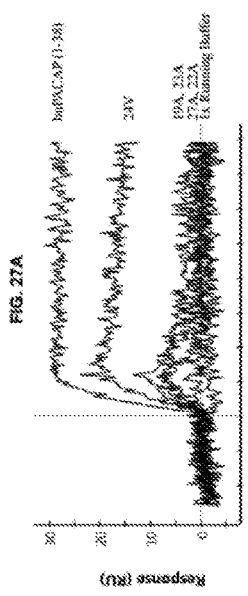
FIG. 29A presents results of surface plasmon resonance-based binding kinetics measurements for binding of anti-PACAP antibody Ab22 to PACAP alanine scanning mutants 22A, 23A, 27A, 28A, and 31A, along with controls including wild-type PACAP (labelled huPACAP (1-38)) (positive control) and 1× running buffer (negative control) obtained following the protocol in Example 12 infra.
Figure 29B:
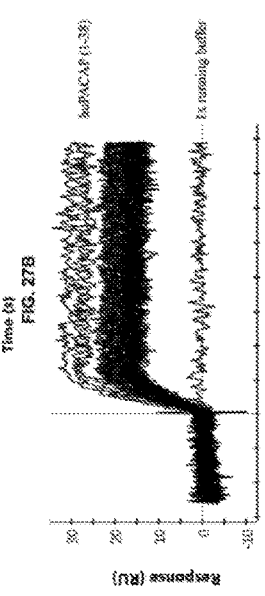
FIG. 29B presents results of surface plasmon resonance-based binding kinetics measurements for binding of anti-PACAP antibody Ab22 to PACAP alanine scanning mutants 1A-21A, 24V-26A, 29A, and 30A, along with controls including wild-type PACAP (labelled huPACAP (1-38)) (positive control) and 1× running buffer (negative control) obtained following the protocol in Example 12 infra.
Figure 30A:
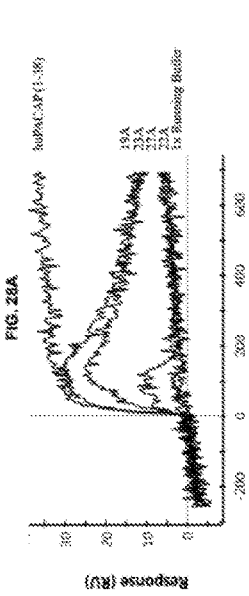
FIG. 30A presents results of surface plasmon resonance-based binding kinetics measurements for binding of anti-PACAP antibody Ab23 to PACAP alanine scanning mutants 12A, 20A, 23A, 24V, 26A, 27A, and 28A, along with controls including wild-type PACAP (labelled huPACAP (1-38)) (positive control) and 1× running buffer (negative control) obtained following the protocol in Example 12 infra.
Figure 30B:
FIG. 30B presents results of surface plasmon resonance-based binding kinetics measurements for binding of anti-PACAP antibody Ab23 to PACAP alanine scanning mutants 1A-11A, 13A-19A, 21A, 22A, 25V, and 29A-31A, along with controls including wild-type PACAP (labelled huPACAP (1-38)) (positive control) and 1× running buffer (negative control) obtained following the protocol in Example 12 infra.

In two experiments comparing the response of mice administered either antibody Ab1.H or Ab10.H to control IgG, the results indicate that mice administered either PACAP antibody Ab1.H or Ab10.H spent more time in light as compared to IgG control mice. FIG. 23 shows that mice behaved normally and similarly in both baseline measurements. On the other hand, the data provided in FIG. 23 show that mice treated with control IgG antibody and then PACAP spent statistically less time in light (squares) than mice administered anti-PACAP antibody Ab1.H and then PACAP (circles). (See, FIG. 23, "Treatment"). The data provided in FIG. 25 also show that mice behaved normally and similarly in baseline measurements. On the other hand, the data provided in FIG. 25 show that mice treated with control IgG antibody and then PACAP spent statistically less time in light (triangles) than mice administered anti-PACAP antibody Ab10.H and then PACAP (inverted triangles). (See, FIG. 25, "Treatment"). Time between each measurement was three days. The mean±SEM is provided for each 5-minute interval. Mice administered vehicle only behaved as normal controls. Data provided in FIG. 24 shows that administration of either anti-PACAP antibody Ab1.H, or control IgG, and vehicle ("Veh+PAC Ab" and "Veh+Con Ab," respectively) did not markedly alter mouse behavior. FIG. 24 also shows that the average time of the mouse in light decreased when PACAP and control IgG were administered ("PACAP+Con Ab"), whereas mice administered anti-PACAP antibody Ab1.H and PACAP exhibited normal, non-light-sensitive behavior ("PACAP+PAC Ab").

Example 12: Epitope Mapping of Anti-PACAP Antibodies

In order to determine the epitopes contained within PACAP to which the anti-PACAP antibodies and antigen binding fragments thereof of the invention bind, alanine scanning experiments were used. To perform these experiments, PACAP peptides were synthesized with a single point mutation in each position replacing the native amino acid with an Alanine ("Ala"), and the consequences of a single point mutation as it relates to binding affinity of PACAP and an antibody were measured. Since an alanine residue already occupies positions 18, 24, and 25 of wild-type PACAP, according to convention, these Ala residues were replaced with Valine ("Val") to determine the possible effects of the removal of the alanine at these positions on the binding of the subject anti-PACAP antibodies to PACAP. Per the usual convention these Ala mutants were labeled according to the position in PACAP 1-38 followed by the letter code for the substituted amino acid, e.g., 10A indicates PACAP 1-38 substituted with alanine at amino acid position 10. Binding of monoclonal antibodies for human PACAP and each mutant peptide was detected using SPR on the PROTEON™ XRP36 (Bio-Rad Laboratories, Hercules, CA). Samples and sample controls were immobilized onto a PROTEON™ GLC sensor chip (Bio-Rad Laboratories, Hercules, CA) at a single density using standard amine coupling. The running buffer used for immobilization was DPBS/modified (HYCLONE™, GE Healthcare Life Sciences, Marlborough, MA) and immobilization was conducted at 25° C. The PROTEON™ GLC sensor chip (Bio-Rad Laboratories, Hercules, CA) was initialized and pre-conditioned per the manufacturer's protocol (bi-directional injections of 0.5% SDS, 50 mM NaOH, 100 mM HCl). The immobilization process was performed step-wise to ensure a unique antibody on the spots of the PROTEON™ Chip (Bio-Rad Laboratories, Hercules, CA). The surface of the chip was activated with a 1:1 mixture of 1-ethyl-3-(3-dimethylaminopropyl)carbodiimide/N-hydroxysuccinimide ("EDAC/NHS") and flow rate of 30 μL/min×5 minutes. Antibody samples were previously dialyzed or exchanged to 10 mM HEPES 150 mM NaCl pH 7.2, and the antibody concentration was quantified using a NANODROP™2000 spectrophotometer (Thermo Fisher Scientific, Waltham, MA). The immobilization targeted 2000-3000 response units ("RU"). Antibody samples (5 μg/ml) in 10 mM sodium acetate, pH 5.5, were flowed at 30 μL/min×4 minutes. Deactivation was achieved at a flow rate of 30 μL/min for 5 minutes using 0.3 M ethanolamine concomitantly with the next activation.

Following immobilization, the running buffer was changed to 1×PBST (4.3 mM sodium phosphate, 1.4 mM potassium phosphate, 135 mM NaCl, 2.7 mM KCl, 0.05% TWEEN®) with 0.2 M arginine HCl (to reduce non-specific binding), BSA (0.2 mg/ml, as a carrier) and PROCLIN300@ (0.005% as a preservative, Sigma Aldrich, St. Louis, MO) and the chip surface was allowed to re-equilibrate with an injection of new running buffer. Stock solutions of human PACAP peptide (1-38) and alanine/valine mutant peptides (Molecular Weight(s): 4.5 kD) at a concentration of 1 mg/ml were added to the running buffer to final concentrations of 0.45 μg/ml (100 nM). These mixtures were then used to query individual spots on the chip surface with flow rates of 100 μL/min×2 minutes and allowed to dissociate for 600 seconds. Chip surfaces were regenerated between analytes by the addition of 0.85% phosphoric acid. Each of antibodies Ab10, Ab20, Ab21, Ab22, and Ab23 were examined under the same conditions as herein described.

Sensorgrams representing affinity data of mutant peptide binding to a panel of antibodies were assessed using multiple parameters. A visual inspection was first performed for each sensorgram to assess apparent maximal response ("$R_{max}$") relative to the wild-type PACAP peptide (1-38). Second, a visual inspection of the dissociation phase was performed with an emphasis on the curve shape relative to the wild-type PACAP peptide. Off-rates (dissociation rates) were calculated for wild-type PACAP peptide and the binding of each mutant peptide to the panel of antibodies. Finally, as a control experiment to confirm the integrity of each peptide variant (wild-type or mutant), the binding affinity of each member of the peptide library was individually determined for each member of a panel of antibodies that were known to bind wild-type PACAP, to ensure that each Ala mutant PACAP peptide exhibited binding affinity that was similar to the binding affinity of wild-type PACAP peptide. Collective assessment of all described parameters identified PACAP amino acid residues important for PACAP/antibody binding.

Binding and dissociation data are shown in FIGS. 26A-30B for binding of antibodies Ab10, Ab20, Ab21, Ab22, and Ab23 to wild-type PACAP and PACAP mutants. The upper panel in each figure contains the binding data for residues in PACAP that appeared to be important for antibody binding (labeled at the right end of the graph, e.g., "10A" indicates the binding data for the mutant containing alanine at position 10 of PACAP). The lower panel provides data points representing the degree of binding of the remaining PACAP alanine mutants, i.e., PACAP alanine mutants that bound to the tested antibody similar to wild-type PACAP. Based thereon, the residue was determined to likely not be important for antibody binding. As a positive control, both the upper and lower panels for each Figure also disclose the binding data obtained using wild-type PACAP (labeled huPACAP(1-38)).

FIG. 31A-B summarizes the PACAP residue positions determined to contribute to antibody binding affinity based on data obtained in these alanine scanning studies. The positions listed in each column identify the PACAP alanine scanning mutants whose mutation led to a decrease in PACAP/antibody binding affinity. The residue positions are listed in column 3 of FIG. 31A-B according to the spatial arrangement of the residues along the PACAP primary sequence (from amino acid residue 1-38). The PACAP residue positions contributing most to antibody binding were interpreted to jointly comprise the epitopes bound by each antibody. Based on data obtained in these alanine scanning studies, the epitopes bound by each antibody were concluded to comprise the following residues:
  (i) Ab10: residues 19, 22, 23, and 27 of human PACAP.
  (ii) Ab20: residues 19, 22, 23, 24, and 27 of human PACAP.
  (iii) Ab21: residues 19, 22, 23, and 27 of human PACAP.
  (iv) Ab22: residues 22, 23, 27, 28, and 31 of human PACAP.
  (v) Ab23: residues 12, 20, 23, 24, 26, 27, and 28 of human PACAP.

It was further noted based on the alanine scanning experimental results that the affinity of each of antibodies Ab10, Ab20, Ab21, Ab22, and Ab23 for PACAP involves or depends on residues 19, 22, 23, and/or 27 of human PACAP.

Additionally, it was observed that the affinity of each of antibodies Ab22 and Ab23 to PACAP involves or requires specific amino acid residues that are present in human wild-type PACAP38, but which are not present in human wild-type PACAP27, e.g., residues 28 and 31 of PACAP38.

With respect to the foregoing alanine scanning results humanized variants of the subject anti-PACAP antibodies should interact with the identical or substantially identical residues of human PACAP as humanization should not appreciably impact the specificity of the binding of the humanized anti-PACAP antibody to human PACAP compared to the parent (unhumanized) antibody. Particularly, Ab10.H should interact with the same residues on human PACAP as Ab10, and Ab21.H should interact with the same residues on human PACAP as Ab21.

Antibodies which bind to the same or overlapping epitopes on human PACAP as the subject antibodies may be produced and identified using method described herein. It is reasonable to anticipate that antibodies which bind to the same or overlapping epitope as any of the antibodies identified herein will likely possess similar biological activity absent a meaningful difference in binding kinetics. Particularly, such antibodies should antagonize one or more of the biological effects elicited by PACAP analogously to the exemplified anti-PACAP antibodies which bind these epitopes. Additionally, antibodies that bind to these same or overlapping epitopes, or a subset of residues thereof, are anticipated to mimic the binding characteristics of the subject antibodies. For example such antibodies are expected to selectively bind to PACAP and not bind or bind with much less affinity (weaker) to VIP or other peptides within this family of neuropeptides.

Having fully described and enabled the invention, the invention is further described by the claims that follow.

What is claimed is:

1. A method of blocking, inhibiting, or neutralizing one or more biological effects associated with PACAP in a subject in need thereof comprising administering to said subject a therapeutically or prophylactically effective amount of an anti-Pituitary Adenylate Cyclase-Activating Polypeptide (PACAP) antibody or antigen binding fragment thereof comprising:
   (a) a heavy chain variable region (VH) polypeptide comprising the heavy chain complementarity-determining region (CDR) 1 polypeptide of SEQ ID NO: 404, the heavy chain CDR2 polypeptide of SEQ ID NO: 406, and the heavy chain CDR3 polypeptide of SEQ ID NO: 408; and
   (b) a light chain variable region (VL) comprising the light chain CDR1 polypeptide of SEQ ID NO: 424, the light chain CDR2 polypeptide of SEQ ID NO: 426, and the light chain CDR3 polypeptide of SEQ ID NO: 428; wherein the subject has a condition associated with headache, migraine or photophobia.

2. A method of treating or preventing the onset, frequency, severity or duration of headache or migraine in a subject in need thereof comprising administering to a subject in need thereof an effective amount of an anti-Pituitary Adenylate Cyclase-Activating Polypeptide (PACAP) antibody or antigen binding fragment thereof comprising:
   (a) a heavy chain variable region (VH) polypeptide comprising the heavy chain complementarity-determining region (CDR) 1 polypeptide of SEQ ID NO: 404, the heavy chain CDR2 polypeptide of SEQ ID NO: 406, and the heavy chain CDR3 polypeptide of SEQ ID NO: 408; and
   (b) a light chain variable region (VL) comprising the light chain CDR1 polypeptide of SEQ ID NO: 424, the light chain CDR2 polypeptide of SEQ ID NO: 426, and the light chain CDR3 polypeptide of SEQ ID NO: 428.

3. The method of claim 1 or 2 wherein the anti-PACAP antibody or antigen binding fragment thereof is humanized.

4. The method of claim 1 or 2 wherein the anti-PACAP antibody or antigen binding fragment thereof is chimerized.

5. The method of claim 1 or 2 wherein the anti-PACAP antibody or antigen binding fragment thereof is a human anti-PACAP antibody or antigen binding fragment thereof.

6. The method of claim 1 or 2 wherein the VH polypeptide of the anti-PACAP antibody or antigen binding fragment thereof comprises at least 90% sequence identity to the polypeptide of SEQ ID NO: 402.

7. The method of claim 1 or 2 wherein the VL polypeptide of the anti-PACAP antibody or antigen binding fragment thereof comprises at least 90% sequence identity to SEQ ID NO: 422.

8. The method of claim 1 or 2 wherein:
   (a) the VH polypeptide of the anti-PACAP antibody or antigen binding fragment thereof comprises at least 90% sequence identity to SEQ ID NO: 402; and
   (b) the VL polypeptide of the anti-PACAP antibody or antigen binding fragment thereof comprises at least 90% sequence identity to SEQ ID NO: 422.

9. The method of claim 1 or 2 wherein the anti-PACAP antibody or antigen binding fragment thereof comprises a heavy chain polypeptide having at least 90% sequence identity to SEQ ID NO: 401.

10. The method of claim 1 or 2 wherein the anti-PACAP antibody or antigen binding fragment thereof comprises a light chain polypeptide having at least 90% sequence identity to SEQ ID NO: 421.

11. The method of claim 1 or 2 wherein the anti-PACAP antibody or antigen binding fragment thereof comprises:
   (a) a heavy chain polypeptide having at least 90% sequence identity to SEQ ID NO: 401; and
   (b) a light chain polypeptide having at least 90% sequence identity to SEQ ID NO: 421.

12. The method of claim 1 or 2 wherein the anti-PACAP antibody or antigen binding fragment thereof comprises the heavy chain polypeptide of SEQ ID NO: 401.

13. The method of claim 1 or 2 wherein the anti-PACAP antibody or antigen binding fragment thereof comprises the light chain polypeptide of SEQ ID NO: 421.

14. The method of claim 1 or 2 wherein the anti-PACAP antibody or antigen binding fragment thereof comprises a heavy chain polypeptide of SEQ ID NO: 401 and a light chain polypeptide of SEQ ID NO: 421.

15. The method of claim 1 or 2 wherein the anti-PACAP antibody or antigen binding fragment thereof is expressed from the heavy chain-encoding polynucleotide of SEQ ID NO: 411 and the light chain-encoding polynucleotide of SEQ ID NO: 431.

16. The method of claim 1 or 2 wherein the anti-PACAP antibody or antigen binding fragment thereof comprises a constant region of human IgG1, IgG2, IgG3, or IgG4.

17. The method of claim 1 or 2 wherein the anti-PACAP antibody or antigen binding fragment thereof comprises an Fc region.

18. The method of claim 17 wherein the Fc region comprises at least one mutation that alters or eliminates N- and/or O-glycosylation.

19. The method of claim 1 or 2 wherein the anti-PACAP antibody or antigen binding fragment thereof comprises a scFv, Fab, Fab', or F(ab')$_2$ antibody fragment.

20. The method of claim 1 or 2 wherein the anti-PACAP antibody or antigen binding fragment thereof is expressed in a CHO cell.

21. The method of claim 2 wherein the subject has a headache or migraine condition selected from migraine with aura, migraine without aura, hemiplegic migraine, cluster headache, migrainous neuralgia, chronic headache, chronic migraine, medication overuse headache, and tension headache.

22. The method of claim 1 wherein the subject has a headache condition selected from the group consisting of migraine with aura, migraine without aura, hemiplegic migraines, cluster headaches, migrainous neuralgia, chronic headaches, tension headaches, general headaches, chronic paroxysmal hemicrania, secondary headaches due to an underlying structural problem in the head, secondary headaches due to an underlying structural problem in the neck, cranial neuralgia, sinus headaches, headache associated with sinusitis, allergy-induced headaches, allergy-induced migraines, and trigeminal neuralgia.

23. The method of claim 1 or 2 wherein the subject has a photophobia-associated disorder selected from the group consisting of migraine with aura, migraine without aura, hot flush, erythema, neurogenic cutaneous redness, iritis, uveitis, meningitis, depression, cluster headache, another trigeminal autonomic cephalalgia ("TAC"), blepharospasm, agoraphobia, and bipolar disorder.

* * * * *

SEQUENCE LISTING

<160> NUMBER OF SEQ ID NOS: 1246

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

```
<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15
```

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

-continued

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

```
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
```

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

-continued

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

```
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
```

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

-continued

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

```
<400> SEQUENCE: 128

000

<210> SEQ ID NO 129
<400> SEQUENCE: 129

000

<210> SEQ ID NO 130
<400> SEQUENCE: 130

000

<210> SEQ ID NO 131
<400> SEQUENCE: 131

000

<210> SEQ ID NO 132
<400> SEQUENCE: 132

000

<210> SEQ ID NO 133
<400> SEQUENCE: 133

000

<210> SEQ ID NO 134
<400> SEQUENCE: 134

000

<210> SEQ ID NO 135
<400> SEQUENCE: 135

000

<210> SEQ ID NO 136
<400> SEQUENCE: 136

000

<210> SEQ ID NO 137
<400> SEQUENCE: 137

000

<210> SEQ ID NO 138
<400> SEQUENCE: 138

000

<210> SEQ ID NO 139
<400> SEQUENCE: 139
```

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

```
<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<400> SEQUENCE: 200
000

<210> SEQ ID NO 201
<400> SEQUENCE: 201
000

<210> SEQ ID NO 202
<400> SEQUENCE: 202
000

<210> SEQ ID NO 203
<400> SEQUENCE: 203
000

<210> SEQ ID NO 204
<400> SEQUENCE: 204
000

<210> SEQ ID NO 205
<400> SEQUENCE: 205
000

<210> SEQ ID NO 206
<400> SEQUENCE: 206
000

<210> SEQ ID NO 207
```

-continued

<400> SEQUENCE: 207

000

<210> SEQ ID NO 208
<400> SEQUENCE: 208

000

<210> SEQ ID NO 209
<400> SEQUENCE: 209

000

<210> SEQ ID NO 210
<400> SEQUENCE: 210

000

<210> SEQ ID NO 211
<400> SEQUENCE: 211

000

<210> SEQ ID NO 212
<400> SEQUENCE: 212

000

<210> SEQ ID NO 213
<400> SEQUENCE: 213

000

<210> SEQ ID NO 214
<400> SEQUENCE: 214

000

<210> SEQ ID NO 215
<400> SEQUENCE: 215

000

<210> SEQ ID NO 216
<400> SEQUENCE: 216

000

<210> SEQ ID NO 217
<400> SEQUENCE: 217

000

<210> SEQ ID NO 218
<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

```
<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252
```

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

```
<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
```

```
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
```

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

```
<210> SEQ ID NO 309
<400> SEQUENCE: 309
000

<210> SEQ ID NO 310
<400> SEQUENCE: 310
000

<210> SEQ ID NO 311
<400> SEQUENCE: 311
000

<210> SEQ ID NO 312
<400> SEQUENCE: 312
000

<210> SEQ ID NO 313
<400> SEQUENCE: 313
000

<210> SEQ ID NO 314
<400> SEQUENCE: 314
000

<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
```

```
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000

<210> SEQ ID NO 330
<400> SEQUENCE: 330
000

<210> SEQ ID NO 331
<400> SEQUENCE: 331
```

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

-continued

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

```
<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
```

-continued

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

```
<400> SEQUENCE: 399

000

<210> SEQ ID NO 400

<400> SEQUENCE: 400

000

<210> SEQ ID NO 401
<211> LENGTH: 439
<212> TYPE: PRT
<213> ORGANISM: Artificial
<220> FEATURE:
<223> OTHER INFORMATION: Humanized antibody sequence

<400> SEQUENCE: 401

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Tyr Tyr
            20                  25                  30

Met Thr Trp Val Arg Gln Ala Pro Gly Lys Gly Leu Glu Trp Ile Gly
        35                  40                  45

Phe Ile Asp Ala Gly Gly Asp Ala Tyr Tyr Ala Ser Trp Ala Lys Gly
50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Asp Leu
            85                  90                  95

Asp Leu Trp Gly Gln Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
            165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Ala Arg Val Glu
        195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
290                 295                 300
```

```
Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
            325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
            435
```

<210> SEQ ID NO 402
<211> LENGTH: 109
<212> TYPE: PRT
<213> ORGANISM: Artificial
<220> FEATURE:
<223> OTHER INFORMATION: Humanized antibody sequence

<400> SEQUENCE: 402

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Tyr Tyr
            20                  25                  30

Met Thr Trp Val Arg Gln Ala Pro Gly Lys Gly Leu Glu Trp Ile Gly
            35                  40                  45

Phe Ile Asp Ala Gly Gly Asp Ala Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Leu
                85                  90                  95

Asp Leu Trp Gly Gln Gly Thr Leu Val Thr Val Ser Ser
            100                 105
```

<210> SEQ ID NO 403
<211> LENGTH: 29
<212> TYPE: PRT
<213> ORGANISM: Oryctolagus cuniculus

<400> SEQUENCE: 403

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn
            20                  25
```

<210> SEQ ID NO 404
<211> LENGTH: 5
<212> TYPE: PRT
<213> ORGANISM: Oryctolagus cuniculus

<400> SEQUENCE: 404

```
Ser Tyr Tyr Met Thr
1               5

<210> SEQ ID NO 405
<211> LENGTH: 14
<212> TYPE: PRT
<213> ORGANISM: Oryctolagus cuniculus

<400> SEQUENCE: 405

Trp Val Arg Gln Ala Pro Gly Lys Gly Leu Glu Trp Ile Gly
1               5                   10

<210> SEQ ID NO 406
<211> LENGTH: 16
<212> TYPE: PRT
<213> ORGANISM: Oryctolagus cuniculus

<400> SEQUENCE: 406

Phe Ile Asp Ala Gly Gly Asp Ala Tyr Tyr Ala Ser Trp Ala Lys Gly
1               5                   10                  15

<210> SEQ ID NO 407
<211> LENGTH: 30
<212> TYPE: PRT
<213> ORGANISM: Oryctolagus cuniculus

<400> SEQUENCE: 407

Arg Phe Thr Ile Ser Lys Thr Ser Thr Thr Val Asp Leu Lys Ile Thr
1               5                   10                  15

Ser Pro Thr Thr Glu Asp Thr Ala Thr Tyr Phe Cys Ala Arg
            20                  25                  30

<210> SEQ ID NO 408
<211> LENGTH: 4
<212> TYPE: PRT
<213> ORGANISM: Oryctolagus cuniculus

<400> SEQUENCE: 408

Asp Leu Asp Leu
1

<210> SEQ ID NO 409
<211> LENGTH: 11
<212> TYPE: PRT
<213> ORGANISM: Artificial
<220> FEATURE:
<223> OTHER INFORMATION: Humanized antibody sequence

<400> SEQUENCE: 409

Trp Gly Gln Gly Thr Leu Val Thr Val Ser Ser
1               5                   10

<210> SEQ ID NO 410
<211> LENGTH: 330
<212> TYPE: PRT
<213> ORGANISM: Artificial
<220> FEATURE:
<223> OTHER INFORMATION: Humanized antibody sequence

<400> SEQUENCE: 410

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 411
<211> LENGTH: 1317
<212> TYPE: DNA
<213> ORGANISM: Artificial
<220> FEATURE:
<223> OTHER INFORMATION: Humanized antibody sequence

<400> SEQUENCE: 411
cagtcggtgg aggagtccgg gggtcgcctg gtcacgcctg gacacccct gacactcacc      60 tgcacagtct ctggaatcga cctcaatagc tactacatga cctgggtccg ccaggctcca     120 gggaagggc tggaatggat cggattcatt gatgctggtg gtgacgcata ctacgcgagc    180
tgggcgaaag gccgattcac catctccaaa acctcgacca cggtggatct gaaaatcacc    240
agtccgacaa ccgaggacac ggccacctat ttctgtgcca gagatcttga cttgtggggc    300
cagggcaccc tggtcaccgt ctcgagcgcc tccaccaagg gcccatcggt cttccccctg    360

```
gcaccctcct ccaagagcac ctctgggggc acagcggccc tgggctgcct ggtcaaggac      420
tacttccccg aaccggtgac ggtgtcgtgg aactcaggcg ccctgaccag cggcgtgcac      480
accttcccgg ctgtcctaca gtcctcagga ctctactccc tcagcagcgt ggtgaccgtg      540
ccctccagca gcttgggcac ccagacctac atctgcaacg tgaatcacaa gcccagcaac      600
accaaggtgg acgcgagagt tgagcccaaa tcttgtgaca aaactcacac atgcccaccg      660
tgcccagcac ctgaactcct ggggggaccg tcagtcttcc tcttccccc aaaacccaag       720 gacaccctca tgatctcccg gacccctgag gtcacatgcg tggtggtgga cgtgagccac      780
gaagaccctg aggtcaagtt caactggtac gtggacggcg tggaggtgca taatgccaag      840
acaaagccgc gggaggagca gtacgccagc acgtaccgtg tggtcagcgt cctcaccgtc      900
ctgcaccagg actggctgaa tggcaaggag tacaagtgca aggtctccaa caaagccctc      960
ccagccccca tcgagaaaac catctccaaa gccaagggc agccccgaga ccacaggtg      1020 tacaccctgc ccccatcccg ggaggagatg accaagaacc aggtcagcct gacctgcctg     1080
gtcaaaggct tctatcccag cgacatcgcc gtggagtggg agagcaatgg gcagccggag     1140
aacaactaca agaccacgcc tcccgtgctg gactccgacg gctccttctt cctctacagc     1200
aagctcaccg tggacaagag caggtggcag caggggaacg tcttctcatg ctccgtgatg     1260
catgaggctc tgcacaacca ctacacgcag aagagcctct ccctgtctcc gggtaaa        1317

<210> SEQ ID NO 412
<211> LENGTH: 327
<212> TYPE: DNA
<213> ORGANISM: Artificial
<220> FEATURE:
<223> OTHER INFORMATION: Humanized antibody sequence

<400> SEQUENCE: 412
cagtcggtgg aggagtccgg gggtcgcctg gtcacgcctg gacacccct gacactcacc       60 tgcacagtct ctggaatcga cctcaatagc tactacatga cctgggtccg ccaggctcca     120
gggaaggggc tggaatggat cggattcatt gatgctggtg gtgacgcata ctacgcgagc     180
tgggcgaaag gccgattcac catctccaaa acctcgacca cggtggatct gaaaatcacc     240
agtccgacaa ccgaggacac ggccacctat ttctgtgcca gagatcttga cttgtggggc     300
cagggcaccc tggtcaccgt ctcgagc                                         327

<210> SEQ ID NO 413
<211> LENGTH: 87
<212> TYPE: DNA
<213> ORGANISM: Oryctolagus cuniculus

<400> SEQUENCE: 413
cagtcggtgg aggagtccgg gggtcgcctg gtcacgcctg gacacccct gacactcacc       60 tgcacagtct ctggaatcga cctcaat                                          87

<210> SEQ ID NO 414
<211> LENGTH: 15
<212> TYPE: DNA
<213> ORGANISM: Oryctolagus cuniculus

<400> SEQUENCE: 414
agctactaca tgacc                                                       15

<210> SEQ ID NO 415
```

```
<211> LENGTH: 42
<212> TYPE: DNA
<213> ORGANISM: Oryctolagus cuniculus

<400> SEQUENCE: 415
tgggtccgcc aggctccagg aagggggctg aatggatcg ga                              42

<210> SEQ ID NO 416
<211> LENGTH: 48
<212> TYPE: DNA
<213> ORGANISM: Oryctolagus cuniculus

<400> SEQUENCE: 416
ttcattgatg ctggtggtga cgcatactac gcgagctggg cgaaaggc                       48

<210> SEQ ID NO 417
<211> LENGTH: 90
<212> TYPE: DNA
<213> ORGANISM: Oryctolagus cuniculus

<400> SEQUENCE: 417
cgattcacca tctccaaaac ctcgaccacg gtggatctga aaatcaccag tccgacaacc          60
gaggacacgg ccacctattt ctgtgccaga                                           90

<210> SEQ ID NO 418
<211> LENGTH: 12
<212> TYPE: DNA
<213> ORGANISM: Oryctolagus cuniculus

<400> SEQUENCE: 418
gatcttgact tg                                                              12

<210> SEQ ID NO 419
<211> LENGTH: 33
<212> TYPE: DNA
<213> ORGANISM: Artificial
<220> FEATURE:
<223> OTHER INFORMATION: Humanized antibody sequence

<400> SEQUENCE: 419
tggggccagg gcaccctggt caccgtctcg agc                                       33

<210> SEQ ID NO 420
<211> LENGTH: 990
<212> TYPE: DNA
<213> ORGANISM: Artificial
<220> FEATURE:
<223> OTHER INFORMATION: Humanized antibody sequence

<400> SEQUENCE: 420
gcctccacca agggcccatc ggtcttcccc ctggcaccct cctccaagag cacctctggg          60
ggcacagcgg ccctgggctg cctggtcaag gactacttcc ccgaaccggt gacggtgtcg         120
tggaactcag gcgccctgac cagcggcgtg cacaccttcc cggctgtcct acagtcctca         180
ggactctact ccctcagcag cgtggtgacc gtgccctcca gcagcttggg cacccagacc         240
tacatctgca acgtgaatca caagcccagc aacaccaagg tggacgcgag agttgagccc         300
aaatcttgtg acaaaactca cacatgccca ccgtgcccag cacctgaact cctgggggga         360
ccgtcagtct tcctcttccc cccaaaaccc aaggacaccc tcatgatctc ccggacccct         420
gaggtcacat gcgtggtggt ggacgtgagc cacgaagacc ctgaggtcaa gttcaactgg         480
tacgtggacg gcgtggaggt gcataatgcc aagacaaagc cgcgggagga gcagtacgcc         540
```

```
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag     720
atgaccaaga accaggtcag cctgacctgc ctggtcaaag gcttctatcc agcgacatc    780 gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 421
<211> LENGTH: 216
<212> TYPE: PRT
<213> ORGANISM: Artificial
<220> FEATURE:
<223> OTHER INFORMATION: Humanized antibody sequence

<400> SEQUENCE: 421

```
Ala Ala Val Leu Thr Gln Thr Pro Ser Pro Val Ser Ala Ala Val Gly
1               5                   10                  15

Gly Thr Val Thr Ile Asn Cys Gln Ser Ser Glu Ser Val Tyr Gly Asn
            20                  25                  30

Tyr Leu Ala Trp Phe Gln Gln Lys Pro Gly Gln Pro Pro Lys Leu Leu
        35                  40                  45

Ile Tyr Glu Ala Ser Lys Leu Glu Ser Gly Val Pro Ser Arg Phe Ser
    50                  55                  60

Gly Ser Gly Ser Gly Thr Gln Phe Thr Leu Thr Ile Ser Asp Leu Gln
65                  70                  75                  80

Cys Asp Asp Ala Ala Thr Tyr Tyr Cys Ala Gly Gly Asp Ile Ser Glu
                85                  90                  95

Gly Val Ala Phe Gly Gly Gly Thr Glu Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 422
<211> LENGTH: 110
<212> TYPE: PRT
<213> ORGANISM: Artificial
<220> FEATURE:
<223> OTHER INFORMATION: Humanized antibody sequence

<400> SEQUENCE: 422

```
Ala Ala Val Leu Thr Gln Thr Pro Ser Pro Val Ser Ala Ala Val Gly
1               5                   10                  15

Gly Thr Val Thr Ile Asn Cys Gln Ser Ser Glu Ser Val Tyr Gly Asn
            20                  25                  30

Tyr Leu Ala Trp Phe Gln Gln Lys Pro Gly Gln Pro Pro Lys Leu Leu
        35                  40                  45

Ile Tyr Glu Ala Ser Lys Leu Glu Ser Gly Val Pro Ser Arg Phe Ser
    50                  55                  60

Gly Ser Gly Ser Gly Thr Gln Phe Thr Leu Thr Ile Ser Asp Leu Gln
65                  70                  75                  80

Cys Asp Asp Ala Ala Thr Tyr Tyr Cys Ala Gly Gly Asp Ile Ser Glu
                85                  90                  95

Gly Val Ala Phe Gly Gly Gly Thr Glu Val Val Val Lys Arg
            100                 105                 110

<210> SEQ ID NO 423
<211> LENGTH: 23
<212> TYPE: PRT
<213> ORGANISM: Oryctolagus cuniculus

<400> SEQUENCE: 423

Ala Ala Val Leu Thr Gln Thr Pro Ser Pro Val Ser Ala Ala Val Gly
1               5                   10                  15

Gly Thr Val Thr Ile Asn Cys
            20

<210> SEQ ID NO 424
<211> LENGTH: 12
<212> TYPE: PRT
<213> ORGANISM: Oryctolagus cuniculus

<400> SEQUENCE: 424

Gln Ser Ser Glu Ser Val Tyr Gly Asn Tyr Leu Ala
1               5                   10

<210> SEQ ID NO 425
<211> LENGTH: 15
<212> TYPE: PRT
<213> ORGANISM: Oryctolagus cuniculus

<400> SEQUENCE: 425

Trp Phe Gln Gln Lys Pro Gly Gln Pro Pro Lys Leu Leu Ile Tyr
1               5                   10                  15

<210> SEQ ID NO 426
<211> LENGTH: 7
<212> TYPE: PRT
<213> ORGANISM: Oryctolagus cuniculus

<400> SEQUENCE: 426

Glu Ala Ser Lys Leu Glu Ser
1               5

<210> SEQ ID NO 427
<211> LENGTH: 32
<212> TYPE: PRT
<213> ORGANISM: Oryctolagus cuniculus

<400> SEQUENCE: 427

Gly Val Pro Ser Arg Phe Ser Gly Ser Gly Ser Gly Thr Gln Phe Thr
1               5                   10                  15
```

Leu Thr Ile Ser Asp Leu Gln Cys Asp Asp Ala Ala Thr Tyr Tyr Cys
            20                  25                  30

<210> SEQ ID NO 428
<211> LENGTH: 10
<212> TYPE: PRT
<213> ORGANISM: Oryctolagus cuniculus

<400> SEQUENCE: 428

Ala Gly Gly Asp Ile Ser Glu Gly Val Ala
1               5                   10

<210> SEQ ID NO 429
<211> LENGTH: 11
<212> TYPE: PRT
<213> ORGANISM: Artificial
<220> FEATURE:
<223> OTHER INFORMATION: Humanized antibody sequence

<400> SEQUENCE: 429

Phe Gly Gly Gly Thr Glu Val Val Val Lys Arg
1               5                   10

<210> SEQ ID NO 430
<211> LENGTH: 106
<212> TYPE: PRT
<213> ORGANISM: Artificial
<220> FEATURE:
<223> OTHER INFORMATION: Humanized antibody sequence

<400> SEQUENCE: 430

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 431
<211> LENGTH: 648
<212> TYPE: DNA
<213> ORGANISM: Artificial
<220> FEATURE:
<223> OTHER INFORMATION: Humanized antibody sequence

<400> SEQUENCE: 431
gccgccgtgc tgacccagac tccatctccc gtgtctgcag ctgtgggagg cacagtcacc      60
atcaattgcc agtccagtga gagtgtttac ggtaactact tagcctggtt tcagcagaaa     120
ccagggcagc ctcccaagct cctgatctac gaagcatcca aactggaatc tggggtccca     180
tcgcggttca gcggcagtgg atctgggaca cagttcactc tcaccatcag cgacttgcag     240
tgtgacgatg ctgccactta ctactgtgca ggcggtgata ttagtgaagg tgttgctttc     300
ggcggaggga ccgaggtggt ggtcaaacgt acggtagcgg ccccatctgt cttcatcttc     360

```
ccgccatctg atgagcagtt gaaatctgga actgcctctg ttgtgtgcct gctgaataac    420
ttctatccca gagaggccaa agtacagtgg aaggtggata cgccctcca atcgggtaac     480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648

<210> SEQ ID NO 432
<211> LENGTH: 330
<212> TYPE: DNA
<213> ORGANISM: Artificial
<220> FEATURE:
<223> OTHER INFORMATION: Humanized antibody sequence

<400> SEQUENCE: 432
gccgccgtgc tgacccagac tccatctccc gtgtctgcag ctgtgggagg cacagtcacc    60
atcaattgcc agtccagtga gagtgtttac ggtaactact tagcctggtt tcagcagaaa    120
ccagggcagc ctcccaagct cctgatctac gaagcatcca actggaatc tggggtccca    180 tcgcggttca gcggcagtgg atctgggaca cagttcactc tcaccatcag cgacttgcag    240
tgtgacgatg ctgccactta ctactgtgca ggcggtgata ttagtgaagg tgttgctttc    300
ggcggaggga ccgaggtggt ggtcaaacgt                                     330

<210> SEQ ID NO 433
<211> LENGTH: 69
<212> TYPE: DNA
<213> ORGANISM: Oryctolagus cuniculus

<400> SEQUENCE: 433
gccgccgtgc tgacccagac tccatctccc gtgtctgcag ctgtgggagg cacagtcacc    60
atcaattgc                                                            69

<210> SEQ ID NO 434
<211> LENGTH: 36
<212> TYPE: DNA
<213> ORGANISM: Oryctolagus cuniculus

<400> SEQUENCE: 434
cagtccagtg agagtgttta cggtaactac ttagcc                              36

<210> SEQ ID NO 435
<211> LENGTH: 45
<212> TYPE: DNA
<213> ORGANISM: Oryctolagus cuniculus

<400> SEQUENCE: 435
tggtttcagc agaaaccagg gcagcctccc aagctcctga tctac                    45

<210> SEQ ID NO 436
<211> LENGTH: 21
<212> TYPE: DNA
<213> ORGANISM: Oryctolagus cuniculus

<400> SEQUENCE: 436
gaagcatcca aactggaatc t                                              21

<210> SEQ ID NO 437
<211> LENGTH: 96
<212> TYPE: DNA
```

<213> ORGANISM: Oryctolagus cuniculus

<400> SEQUENCE: 437 gggtcccat cgcggttcag cggcagtgga tctgggacac agttcactct caccatcagc    60
gacttgcagt gtgacgatgc tgccacttac tactgt    96

<210> SEQ ID NO 438
<211> LENGTH: 30
<212> TYPE: DNA
<213> ORGANISM: Oryctolagus cuniculus

<400> SEQUENCE: 438
gcaggcggtg atattagtga aggtgttgct    30

<210> SEQ ID NO 439
<211> LENGTH: 33
<212> TYPE: DNA
<213> ORGANISM: Artificial
<220> FEATURE:
<223> OTHER INFORMATION: Humanized antibody sequence

<400> SEQUENCE: 439
ttcggcggag ggaccgaggt ggtggtcaaa cgt    33

<210> SEQ ID NO 440
<211> LENGTH: 318
<212> TYPE: DNA
<213> ORGANISM: Artificial
<220> FEATURE:
<223> OTHER INFORMATION: Humanized antibody sequence

<400> SEQUENCE: 440
acggtagcgg cccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgt    318

<210> SEQ ID NO 441
<211> LENGTH: 439
<212> TYPE: PRT
<213> ORGANISM: Artificial
<220> FEATURE:
<223> OTHER INFORMATION: Humanized antibody sequence

<400> SEQUENCE: 441

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Tyr
            20                  25                  30

Met Ser Trp Val Arg Gln Ala Pro Gly Lys Gly Leu Glu Trp Ile Gly
        35                  40                  45

Phe Ile Asp Thr Asp Gly Ser Ala Tyr Tyr Ala Thr Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Asp Leu
                85                  90                  95

Asp Leu Trp Gly Pro Gly Thr Leu Val Thr Val Ser Ala Ser Thr
                100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
        130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 442
<211> LENGTH: 109
<212> TYPE: PRT
<213> ORGANISM: Artificial
<220> FEATURE:
<223> OTHER INFORMATION: Humanized antibody sequence

<400> SEQUENCE: 442

Gln Ser Val Glu Glu Ser Gly Gly Arg Leu Val Thr Pro Gly Thr Pro
1               5                   10                  15

```
Leu Thr Leu Thr Cys Thr Val Ser Gly Ile Asp Leu Ser Ser Tyr Tyr
            20                  25                  30

Met Ser Trp Val Arg Gln Ala Pro Gly Lys Gly Leu Glu Trp Ile Gly
        35                  40                  45

Phe Ile Asp Thr Asp Gly Ser Ala Tyr Tyr Ala Thr Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Asp Leu
                85                  90                  95

Asp Leu Trp Gly Pro Gly Thr Leu Val Thr Val Ser Ser
            100                 105

<210> SEQ ID NO 443
<211> LENGTH: 29
<212> TYPE: PRT
<213> ORGANISM: Oryctolagus cuniculus

<400> SEQUENCE: 443

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser
            20                  25

<210> SEQ ID NO 444
<211> LENGTH: 5
<212> TYPE: PRT
<213> ORGANISM: Oryctolagus cuniculus

<400> SEQUENCE: 444

Ser Tyr Tyr Met Ser
1               5

<210> SEQ ID NO 445
<211> LENGTH: 14
<212> TYPE: PRT
<213> ORGANISM: Oryctolagus cuniculus

<400> SEQUENCE: 445

Trp Val Arg Gln Ala Pro Gly Lys Gly Leu Glu Trp Ile Gly
1               5                   10

<210> SEQ ID NO 446
<211> LENGTH: 16
<212> TYPE: PRT
<213> ORGANISM: Oryctolagus cuniculus

<400> SEQUENCE: 446

Phe Ile Asp Thr Asp Gly Ser Ala Tyr Tyr Ala Thr Trp Ala Lys Gly
1               5                   10                  15

<210> SEQ ID NO 447
<211> LENGTH: 30
<212> TYPE: PRT
<213> ORGANISM: Oryctolagus cuniculus

<400> SEQUENCE: 447

Arg Phe Thr Ile Ser Lys Thr Ser Thr Val Asp Leu Lys Ile Thr
1               5                   10                  15

Ser Pro Thr Thr Glu Asp Thr Ala Thr Tyr Phe Cys Ala Arg
            20                  25                  30
```

<210> SEQ ID NO 448
<211> LENGTH: 4
<212> TYPE: PRT
<213> ORGANISM: Oryctolagus cuniculus

<400> SEQUENCE: 448

Asp Leu Asp Leu
1

<210> SEQ ID NO 449
<211> LENGTH: 11
<212> TYPE: PRT
<213> ORGANISM: Artificial
<220> FEATURE:
<223> OTHER INFORMATION: Humanized antibody sequence

<400> SEQUENCE: 449

Trp Gly Pro Gly Thr Leu Val Thr Val Ser Ser
1               5                   10

<210> SEQ ID NO 450
<211> LENGTH: 330
<212> TYPE: PRT
<213> ORGANISM: Artificial
<220> FEATURE:
<223> OTHER INFORMATION: Humanized antibody sequence

<400> SEQUENCE: 450

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 451
<211> LENGTH: 1317
<212> TYPE: DNA
<213> ORGANISM: Artificial
<220> FEATURE:
<223> OTHER INFORMATION: Humanized antibody sequence

<400> SEQUENCE: 451
cagtcggtgg aggagtccgg gggtcgcctg gtcacgcctg gacacccct gacactcacc      60 tgcacagtct ctggaatcga cctcagtagc tactacatga gctgggtccg ccaggctcca     120
gggaaggggc tggaatggat cggattcatt gatactgatg gtagcgcata ctacgcgacc     180
tgggcgaaag gccgattcac catctccaaa acctcgacca cggtggatct gaaaatcacc     240
agtccgacaa ccgaggacac ggccacctat ttctgtgcca gagatcttga cttgtggggc     300
ccgggcaccc tcgtcaccgt ctcgagcgcc tccaccaagg gcccatcggt cttcccctg      360 gcaccctcct ccaagagcac ctctgggggc acagcggccc tgggctgcct ggtcaaggac     420
tacttccccg aaccggtgac ggtgtcgtgg aactcaggcg ccctgaccag cggcgtgcac     480
accttcccgg ctgtcctaca gtcctcagga ctctactccc tcagcagcgt ggtgaccgtg     540
ccctccagca gcttgggcac ccagacctac atctgcaacg tgaatcacaa gcccagcaac     600
accaaggtgg acaagaaagt tgagcccaaa tcttgtgaca aaactcacac atgcccaccg     660
tgcccagcac ctgaactcct ggggggaccg tcagtcttcc tcttcccccc aaaacccaag     720
gacaccctca tgatctcccg gacccctgag gtcacatgcg tggtggtgga cgtgagccac     780
gaagaccctg aggtcaagtt caactggtac gtggacggcg tggaggtgca taatgccaag     840
acaaagccgc gggaggagca gtacgccagc acgtaccgtg tggtcagcgt cctcaccgtc     900
ctgcaccagg actggctgaa tggcaaggag tacaagtgca aggtctccaa caaagccctc     960
ccagccccca tcgagaaaac catctccaaa gccaaagggc agccccgaga accacaggtg    1020
tacaccctgc ccccatcccg ggaggagatg accaagaacc aggtcagcct gacctgcctg    1080
gtcaaaggct tctatcccag cgacatcgcc gtggagtggg agagcaatgg gcagccggag    1140
aacaactaca agaccacgcc tcccgtgctg gactccgacg gctccttctt cctctacagc    1200
aagctcaccg tggacaagag caggtggcag caggggaacg tcttctcatg ctccgtgatg    1260
catgaggctc tgcacaacca ctacacgcag aagagcctct ccctgtctcc gggtaaa      1317

<210> SEQ ID NO 452
<211> LENGTH: 327
<212> TYPE: DNA
<213> ORGANISM: Artificial
<220> FEATURE:
```

<223> OTHER INFORMATION: Humanized antibody sequence

<400> SEQUENCE: 452

| | |
|---|---|
| cagtcggtgg aggagtccgg gggtcgcctg gtcacgcctg ggacacccct gacactcacc | 60 |
| tgcacagtct ctggaatcga cctcagtagc tactacatga gctgggtccg ccaggctcca | 120 |
| gggaagggc tggaatggat cggattcatt gatactgatg gtagcgcata ctacgcgacc | 180 |
| tgggcgaaag gccgattcac catctccaaa acctcgacca cggtggatct gaaaatcacc | 240 |
| agtccgacaa ccgaggacac ggccacctat ttctgtgcca gagatcttga cttgtgggc | 300 |
| ccgggcaccc tcgtcaccgt ctcgagc | 327 |

<210> SEQ ID NO 453
<211> LENGTH: 87
<212> TYPE: DNA
<213> ORGANISM: Oryctolagus cuniculus

<400> SEQUENCE: 453

| | |
|---|---|
| cagtcggtgg aggagtccgg gggtcgcctg gtcacgcctg ggacacccct gacactcacc | 60 |
| tgcacagtct ctggaatcga cctcagt | 87 |

<210> SEQ ID NO 454
<211> LENGTH: 15
<212> TYPE: DNA
<213> ORGANISM: Oryctolagus cuniculus

<400> SEQUENCE: 454

| | |
|---|---|
| agctactaca tgagc | 15 |

<210> SEQ ID NO 455
<211> LENGTH: 42
<212> TYPE: DNA
<213> ORGANISM: Oryctolagus cuniculus

<400> SEQUENCE: 455

| | |
|---|---|
| tgggtccgcc aggctccagg gaaggggctg gaatggatcg ga | 42 |

<210> SEQ ID NO 456
<211> LENGTH: 48
<212> TYPE: DNA
<213> ORGANISM: Oryctolagus cuniculus

<400> SEQUENCE: 456

| | |
|---|---|
| ttcattgata ctgatggtag cgcatactac gcgacctggg cgaaaggc | 48 |

<210> SEQ ID NO 457
<211> LENGTH: 90
<212> TYPE: DNA
<213> ORGANISM: Oryctolagus cuniculus

<400> SEQUENCE: 457

| | |
|---|---|
| cgattcacca tctccaaaac ctcgaccacg gtggatctga aaatcaccag tccgacaacc | 60 |
| gaggacacgg ccacctattt ctgtgccaga | 90 |

<210> SEQ ID NO 458
<211> LENGTH: 12
<212> TYPE: DNA
<213> ORGANISM: Oryctolagus cuniculus

<400> SEQUENCE: 458

| | |
|---|---|
| gatcttgact tg | 12 |

<210> SEQ ID NO 459
<211> LENGTH: 33
<212> TYPE: DNA
<213> ORGANISM: Artificial
<220> FEATURE:
<223> OTHER INFORMATION: Humanized antibody sequence

<400> SEQUENCE: 459

```
tggggcccgg gcaccctcgt caccgtctcg agc                                    33
```

<210> SEQ ID NO 460
<211> LENGTH: 990
<212> TYPE: DNA
<213> ORGANISM: Artificial
<220> FEATURE:
<223> OTHER INFORMATION: Humanized antibody sequence

<400> SEQUENCE: 460

```
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcggaggga gcagtacgcc      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggaggag      720
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                       990
```

<210> SEQ ID NO 461
<211> LENGTH: 216
<212> TYPE: PRT
<213> ORGANISM: Artificial
<220> FEATURE:
<223> OTHER INFORMATION: Humanized antibody sequence

<400> SEQUENCE: 461

```
Ala Ala Val Leu Thr Gln Thr Pro Ser Pro Val Ser Ala Val Gly
1               5                   10                  15

Gly Thr Val Ser Ile Ser Cys Gln Ser Ser Glu Ser Val Tyr Ser Asn
            20                  25                  30

Tyr Leu Ala Trp Phe Gln Gln Lys Pro Gly Gln Pro Pro Lys Phe Leu
        35                  40                  45

Ile Tyr Glu Ala Ser Lys Leu Ala Ser Gly Val Pro Ser Arg Phe Lys
    50                  55                  60
```

```
Gly Ser Gly Ser Gly Thr Gln Phe Thr Leu Thr Ile Ser Asp Val Gln
65                  70                  75                  80

Cys Asp Asp Ala Gly Thr Tyr Tyr Cys Ala Gly Gly Tyr Ser Ser Glu
                85                  90                  95

Gly Val Ala Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 462
<211> LENGTH: 110
<212> TYPE: PRT
<213> ORGANISM: Artificial
<220> FEATURE:
<223> OTHER INFORMATION: Humanized antibody sequence

<400> SEQUENCE: 462

Ala Ala Val Leu Thr Gln Thr Pro Ser Pro Val Ser Ala Ala Val Gly
1               5                   10                  15

Gly Thr Val Ser Ile Ser Cys Gln Ser Ser Glu Ser Val Tyr Ser Asn
            20                  25                  30

Tyr Leu Ala Trp Phe Gln Gln Lys Pro Gly Gln Pro Pro Lys Phe Leu
        35                  40                  45

Ile Tyr Glu Ala Ser Lys Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Gly Thr Tyr Tyr Cys Ala Gly Gly Tyr Ser Ser Glu
                85                  90                  95

Gly Val Ala Phe Gly Gly Gly Thr Glu Val Val Val Lys Arg
            100                 105                 110

<210> SEQ ID NO 463
<211> LENGTH: 23
<212> TYPE: PRT
<213> ORGANISM: Oryctolagus cuniculus

<400> SEQUENCE: 463

Ala Ala Val Leu Thr Gln Thr Pro Ser Pro Val Ser Ala Ala Val Gly
1               5                   10                  15

Gly Thr Val Ser Ile Ser Cys
            20

<210> SEQ ID NO 464
<211> LENGTH: 12
<212> TYPE: PRT
```

<213> ORGANISM: Oryctolagus cuniculus

<400> SEQUENCE: 464

Gln Ser Ser Glu Ser Val Tyr Ser Asn Tyr Leu Ala
1               5                   10

<210> SEQ ID NO 465
<211> LENGTH: 15
<212> TYPE: PRT
<213> ORGANISM: Oryctolagus cuniculus

<400> SEQUENCE: 465

Trp Phe Gln Gln Lys Pro Gly Gln Pro Pro Lys Phe Leu Ile Tyr
1               5                   10                  15

<210> SEQ ID NO 466
<211> LENGTH: 7
<212> TYPE: PRT
<213> ORGANISM: Oryctolagus cuniculus

<400> SEQUENCE: 466

Glu Ala Ser Lys Leu Ala Ser
1               5

<210> SEQ ID NO 467
<211> LENGTH: 32
<212> TYPE: PRT
<213> ORGANISM: Oryctolagus cuniculus

<400> SEQUENCE: 467

Gly Val Pro Ser Arg Phe Lys Gly Ser Gly Ser Gly Thr Gln Phe Thr
1               5                   10                  15

Leu Thr Ile Ser Asp Val Gln Cys Asp Asp Ala Gly Thr Tyr Tyr Cys
            20                  25                  30

<210> SEQ ID NO 468
<211> LENGTH: 10
<212> TYPE: PRT
<213> ORGANISM: Oryctolagus cuniculus

<400> SEQUENCE: 468

Ala Gly Gly Tyr Ser Ser Glu Gly Val Ala
1               5                   10

<210> SEQ ID NO 469
<211> LENGTH: 11
<212> TYPE: PRT
<213> ORGANISM: Artificial
<220> FEATURE:
<223> OTHER INFORMATION: Humanized antibody sequence

<400> SEQUENCE: 469

Phe Gly Gly Gly Thr Glu Val Val Val Lys Arg
1               5                   10

<210> SEQ ID NO 470
<211> LENGTH: 106
<212> TYPE: PRT
<213> ORGANISM: Artificial
<220> FEATURE:
<223> OTHER INFORMATION: Humanized antibody sequence

<400> SEQUENCE: 470

Thr Val Ala Ala Pro Ser Val Phe Ile Phe Pro Pro Ser Asp Glu Gln
1               5                   10                  15

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 471
<211> LENGTH: 648
<212> TYPE: DNA
<213> ORGANISM: Artificial
<220> FEATURE:
<223> OTHER INFORMATION: Humanized antibody sequence

<400> SEQUENCE: 471

```
gccgccgtgc tgacccagac tccatctccc gtgtctgcag ctgtgggagg cacagtcagc      60
atcagttgcc agtccagtga gagtgtttat agtaactact tagcctggtt tcagcagaaa     120
ccagggcagc ctcctaagtt cttgatctac gaagcatcca actggcatc tggggtccca     180
tcgcggttca aaggcagtgg atctgggaca cagttcactc tcaccatcag cgacgtgcag     240
tgtgacgatg ctggcactta ctactgtgca ggcggctata gtagtgaagg tgttgctttc     300
ggcggaggga ccgaggtggt ggtcaaacgt acggtagcgg ccccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648
```

<210> SEQ ID NO 472
<211> LENGTH: 330
<212> TYPE: DNA
<213> ORGANISM: Artificial
<220> FEATURE:
<223> OTHER INFORMATION: Humanized antibody sequence

<400> SEQUENCE: 472

```
gccgccgtgc tgacccagac tccatctccc gtgtctgcag ctgtgggagg cacagtcagc      60
atcagttgcc agtccagtga gagtgtttat agtaactact tagcctggtt tcagcagaaa     120
ccagggcagc ctcctaagtt cttgatctac gaagcatcca actggcatc tggggtccca     180
tcgcggttca aaggcagtgg atctgggaca cagttcactc tcaccatcag cgacgtgcag     240
tgtgacgatg ctggcactta ctactgtgca ggcggctata gtagtgaagg tgttgctttc     300
ggcggaggga ccgaggtggt ggtcaaacgt                                      330
```

<210> SEQ ID NO 473
<211> LENGTH: 69
<212> TYPE: DNA
<213> ORGANISM: Oryctolagus cuniculus

```
<400> SEQUENCE: 473
gccgccgtgc tgacccagac tccatctccc gtgtctgcag ctgtgggagg cacagtcagc    60
atcagttgc                                                            69

<210> SEQ ID NO 474
<211> LENGTH: 36
<212> TYPE: DNA
<213> ORGANISM: Oryctolagus cuniculus

<400> SEQUENCE: 474
cagtccagtg agagtgttta tagtaactac ttagcc                              36

<210> SEQ ID NO 475
<211> LENGTH: 45
<212> TYPE: DNA
<213> ORGANISM: Oryctolagus cuniculus

<400> SEQUENCE: 475
tggtttcagc agaaaccagg gcagcctcct aagttcttga tctac                    45

<210> SEQ ID NO 476
<211> LENGTH: 21
<212> TYPE: DNA
<213> ORGANISM: Oryctolagus cuniculus

<400> SEQUENCE: 476
gaagcatcca aactggcatc t                                              21

<210> SEQ ID NO 477
<211> LENGTH: 96
<212> TYPE: DNA
<213> ORGANISM: Oryctolagus cuniculus

<400> SEQUENCE: 477
ggggtcccat cgcggttcaa aggcagtgga tctgggacac agttcactct caccatcagc    60
gacgtgcagt gtgacgatgc tggcacttac tactgt                              96

<210> SEQ ID NO 478
<211> LENGTH: 30
<212> TYPE: DNA
<213> ORGANISM: Oryctolagus cuniculus

<400> SEQUENCE: 478
gcaggcggct atagtagtga aggtgttgct                                     30

<210> SEQ ID NO 479
<211> LENGTH: 33
<212> TYPE: DNA
<213> ORGANISM: Artificial
<220> FEATURE:
<223> OTHER INFORMATION: Humanized antibody sequence

<400> SEQUENCE: 479
ttcggcggag ggaccgaggt ggtggtcaaa cgt                                 33

<210> SEQ ID NO 480
<211> LENGTH: 318
<212> TYPE: DNA
<213> ORGANISM: Artificial
<220> FEATURE:
<223> OTHER INFORMATION: Humanized antibody sequence

<400> SEQUENCE: 480
```

```
acggtagcgg ccccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgt                                                 318
```

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

```
<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501
```

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
000

<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523
<400> SEQUENCE: 523
000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558
<400> SEQUENCE: 558
000

<210> SEQ ID NO 559
<400> SEQUENCE: 559
000

<210> SEQ ID NO 560
<400> SEQUENCE: 560
000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564
<400> SEQUENCE: 564
000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
000

<210> SEQ ID NO 568
<400> SEQUENCE: 568
000

<210> SEQ ID NO 569

```
<400> SEQUENCE: 569
000

<210> SEQ ID NO 570
<400> SEQUENCE: 570
000

<210> SEQ ID NO 571
<400> SEQUENCE: 571
000

<210> SEQ ID NO 572
<400> SEQUENCE: 572
000

<210> SEQ ID NO 573
<400> SEQUENCE: 573
000

<210> SEQ ID NO 574
<400> SEQUENCE: 574
000

<210> SEQ ID NO 575
<400> SEQUENCE: 575
000

<210> SEQ ID NO 576
<400> SEQUENCE: 576
000

<210> SEQ ID NO 577
<400> SEQUENCE: 577
000

<210> SEQ ID NO 578
<400> SEQUENCE: 578
000

<210> SEQ ID NO 579
<400> SEQUENCE: 579
000

<210> SEQ ID NO 580
<400> SEQUENCE: 580
```

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

-continued

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615
<400> SEQUENCE: 615
000

<210> SEQ ID NO 616
<400> SEQUENCE: 616
000

<210> SEQ ID NO 617
<400> SEQUENCE: 617
000

<210> SEQ ID NO 618
<400> SEQUENCE: 618
000

<210> SEQ ID NO 619
<400> SEQUENCE: 619
000

<210> SEQ ID NO 620
<400> SEQUENCE: 620
000

<210> SEQ ID NO 621
<400> SEQUENCE: 621
000

<210> SEQ ID NO 622
<400> SEQUENCE: 622
000

<210> SEQ ID NO 623
<400> SEQUENCE: 623
000

<210> SEQ ID NO 624
<400> SEQUENCE: 624
000

<210> SEQ ID NO 625
<400> SEQUENCE: 625
000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660
<400> SEQUENCE: 660
000

<210> SEQ ID NO 661
<400> SEQUENCE: 661
000

<210> SEQ ID NO 662
<400> SEQUENCE: 662
000

<210> SEQ ID NO 663
<400> SEQUENCE: 663
000

<210> SEQ ID NO 664
<400> SEQUENCE: 664
000

<210> SEQ ID NO 665
<400> SEQUENCE: 665
000

<210> SEQ ID NO 666
<400> SEQUENCE: 666
000

<210> SEQ ID NO 667
<400> SEQUENCE: 667
000

<210> SEQ ID NO 668
<400> SEQUENCE: 668
000

<210> SEQ ID NO 669
<400> SEQUENCE: 669
000

<210> SEQ ID NO 670
<400> SEQUENCE: 670
000

<210> SEQ ID NO 671
<400> SEQUENCE: 671
000

<210> SEQ ID NO 672
<400> SEQUENCE: 672
000

<210> SEQ ID NO 673
<400> SEQUENCE: 673
000

<210> SEQ ID NO 674
<400> SEQUENCE: 674
000

<210> SEQ ID NO 675
<400> SEQUENCE: 675
000

<210> SEQ ID NO 676
<400> SEQUENCE: 676
000

<210> SEQ ID NO 677
<400> SEQUENCE: 677
000

<210> SEQ ID NO 678
<400> SEQUENCE: 678
000

<210> SEQ ID NO 679
<400> SEQUENCE: 679
000

<210> SEQ ID NO 680
<400> SEQUENCE: 680
000

<210> SEQ ID NO 681
<400> SEQUENCE: 681
000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

-continued

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

-continued

<210> SEQ ID NO 750
<400> SEQUENCE: 750
000

<210> SEQ ID NO 751
<400> SEQUENCE: 751
000

<210> SEQ ID NO 752
<400> SEQUENCE: 752
000

<210> SEQ ID NO 753
<400> SEQUENCE: 753
000

<210> SEQ ID NO 754
<400> SEQUENCE: 754
000

<210> SEQ ID NO 755
<400> SEQUENCE: 755
000

<210> SEQ ID NO 756
<400> SEQUENCE: 756
000

<210> SEQ ID NO 757
<400> SEQUENCE: 757
000

<210> SEQ ID NO 758
<400> SEQUENCE: 758
000

<210> SEQ ID NO 759
<400> SEQUENCE: 759
000

<210> SEQ ID NO 760
<400> SEQUENCE: 760
000

<210> SEQ ID NO 761

```
<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772
```

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801

<400> SEQUENCE: 801

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

```
<400> SEQUENCE: 806
000

<210> SEQ ID NO 807
<400> SEQUENCE: 807
000

<210> SEQ ID NO 808
<400> SEQUENCE: 808
000

<210> SEQ ID NO 809
<400> SEQUENCE: 809
000

<210> SEQ ID NO 810
<400> SEQUENCE: 810
000

<210> SEQ ID NO 811
<400> SEQUENCE: 811
000

<210> SEQ ID NO 812
<400> SEQUENCE: 812
000

<210> SEQ ID NO 813
<400> SEQUENCE: 813
000

<210> SEQ ID NO 814
<400> SEQUENCE: 814
000

<210> SEQ ID NO 815
<400> SEQUENCE: 815
000

<210> SEQ ID NO 816
<400> SEQUENCE: 816
000

<210> SEQ ID NO 817
<400> SEQUENCE: 817
```

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829
<400> SEQUENCE: 829
000

<210> SEQ ID NO 830
<400> SEQUENCE: 830
000

<210> SEQ ID NO 831
<400> SEQUENCE: 831
000

<210> SEQ ID NO 832
<400> SEQUENCE: 832
000

<210> SEQ ID NO 833
<400> SEQUENCE: 833
000

<210> SEQ ID NO 834
<400> SEQUENCE: 834
000

<210> SEQ ID NO 835
<400> SEQUENCE: 835
000

<210> SEQ ID NO 836
<400> SEQUENCE: 836
000

<210> SEQ ID NO 837
<400> SEQUENCE: 837
000

<210> SEQ ID NO 838
<400> SEQUENCE: 838
000

<210> SEQ ID NO 839
<400> SEQUENCE: 839
000

<210> SEQ ID NO 840

<400> SEQUENCE: 840

000

<210> SEQ ID NO 841
<211> LENGTH: 439
<212> TYPE: PRT
<213> ORGANISM: Artificial
<220> FEATURE:
<223> OTHER INFORMATION: Humanized antibody sequence

<400> SEQUENCE: 841

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Tyr
                20                  25                  30

Met Thr Trp Val Arg Gln Ala Pro Gly Lys Gly Leu Glu Trp Val Gly
            35                  40                  45

Phe Ile Asp Ala Gly Gly Ser Ala Tyr Tyr Ala Thr Trp Ala Lys Gly
    50                  55                  60

Arg Phe Thr Ile Ser Lys Ala Ser Thr Thr Val Asp Leu Lys Ile Thr
65                  70                  75                  80

Ser Pro Thr Thr Glu Asp Thr Ala Thr Tyr Phe Cys Ala Arg Asp Leu
                85                  90                  95

Asp Leu Trp Gly Pro Gly Thr Leu Val Thr Val Ser Ser Ala Ser Thr
            100                 105                 110

Lys Gly Pro Ser Val Phe Pro Leu Ala Pro Ser Ser Lys Ser Thr Ser
    115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
    195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
    275                 280                 285

Ala Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Glu Glu Met Thr Lys
```

```
                    340                 345                 350
Asn Gln Val Ser Leu Thr Cys Leu Val Lys Gly Phe Tyr Pro Ser Asp
            355                 360                 365
Ile Ala Val Glu Trp Glu Ser Asn Gly Gln Pro Glu Asn Asn Tyr Lys
        370                 375                 380
Thr Thr Pro Pro Val Leu Asp Ser Asp Gly Ser Phe Phe Leu Tyr Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro Gly Lys
        435

<210> SEQ ID NO 842
<211> LENGTH: 109
<212> TYPE: PRT
<213> ORGANISM: Artificial
<220> FEATURE:
<223> OTHER INFORMATION: Humanized antibody sequence

<400> SEQUENCE: 842

Gln Ser Val Glu Glu Ser Gly Gly Arg Leu Val Thr Pro Gly Thr Pro
1               5                   10                  15
Leu Thr Leu Thr Cys Thr Val Ser Gly Ile Asp Leu Ser Ser Tyr Tyr
            20                  25                  30
Met Thr Trp Val Arg Gln Ala Pro Gly Lys Gly Leu Glu Trp Val Gly
        35                  40                  45
Phe Ile Asp Ala Gly Gly Ser Ala Tyr Tyr Ala Thr Trp Ala Lys Gly
    50                  55                  60
Arg Phe Thr Ile Ser Lys Ala Ser Thr Thr Val Asp Leu Lys Ile Thr
65                  70                  75                  80
Ser Pro Thr Thr Glu Asp Thr Ala Thr Tyr Phe Cys Ala Arg Asp Leu
                85                  90                  95
Asp Leu Trp Gly Pro Gly Thr Leu Val Thr Val Ser Ser
            100                 105

<210> SEQ ID NO 843
<211> LENGTH: 29
<212> TYPE: PRT
<213> ORGANISM: Oryctolagus cuniculus

<400> SEQUENCE: 843

Gln Ser Val Glu Glu Ser Gly Gly Arg Leu Val Thr Pro Gly Thr Pro
1               5                   10                  15
Leu Thr Leu Thr Cys Thr Val Ser Gly Ile Asp Leu Ser
            20                  25

<210> SEQ ID NO 844
<211> LENGTH: 5
<212> TYPE: PRT
<213> ORGANISM: Oryctolagus cuniculus

<400> SEQUENCE: 844

Ser Tyr Tyr Met Thr
1               5

<210> SEQ ID NO 845
<211> LENGTH: 14
```

```
<212> TYPE: PRT
<213> ORGANISM: Oryctolagus cuniculus

<400> SEQUENCE: 845

Trp Val Arg Gln Ala Pro Gly Lys Gly Leu Glu Trp Val Gly
1               5                   10

<210> SEQ ID NO 846
<211> LENGTH: 16
<212> TYPE: PRT
<213> ORGANISM: Oryctolagus cuniculus

<400> SEQUENCE: 846

Phe Ile Asp Ala Gly Gly Ser Ala Tyr Tyr Ala Thr Trp Ala Lys Gly
1               5                   10                  15

<210> SEQ ID NO 847
<211> LENGTH: 30
<212> TYPE: PRT
<213> ORGANISM: Oryctolagus cuniculus

<400> SEQUENCE: 847

Arg Phe Thr Ile Ser Lys Ala Ser Thr Thr Val Asp Leu Lys Ile Thr
1               5                   10                  15

Ser Pro Thr Thr Glu Asp Thr Ala Thr Tyr Phe Cys Ala Arg
            20                  25                  30

<210> SEQ ID NO 848
<211> LENGTH: 4
<212> TYPE: PRT
<213> ORGANISM: Oryctolagus cuniculus

<400> SEQUENCE: 848

Asp Leu Asp Leu
1

<210> SEQ ID NO 849
<211> LENGTH: 11
<212> TYPE: PRT
<213> ORGANISM: Artificial
<220> FEATURE:
<223> OTHER INFORMATION: Humanized antibody sequence

<400> SEQUENCE: 849

Trp Gly Pro Gly Thr Leu Val Thr Val Ser Ser
1               5                   10

<210> SEQ ID NO 850
<211> LENGTH: 330
<212> TYPE: PRT
<213> ORGANISM: Artificial
<220> FEATURE:
<223> OTHER INFORMATION: Humanized antibody sequence

<400> SEQUENCE: 850

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 851
<211> LENGTH: 1317
<212> TYPE: DNA
<213> ORGANISM: Artificial
<220> FEATURE:
<223> OTHER INFORMATION: Humanized antibody sequence

<400> SEQUENCE: 851
cagtcggtgg aggagtccgg gggtcgcctg gtcacgcctg gacacccct  gacactcacc        60 tgcacagtct ctggaatcga cctcagtagc tactacatga cctgggtccg ccaggctcca      120
gggaaggggc tggaatgggt cggattcatt gatgctggtg gtagcgcata ctacgcgacc      180
tgggcaaaag gccgattcac catctccaaa gcctcgacca cggtggatct gaaaatcacc      240
agtccgacaa ccgaggacac ggccacctat ttctgtgcca gagatcttga cttgtggggc      300
ccgggcaccc tggtcaccgt ctcgagcgcc tccaccaagg gcccatcggt cttccccctg      360
gcaccctcct ccaagagcac ctctgggggc acagcggccc tgggctgcct ggtcaaggac      420
tacttccccg aaccggtgac ggtgtcgtgg aactcaggcg ccctgaccag cggcgtgcac      480
accttcccgg ctgtcctaca gtcctcagga ctctactccc tcagcagcgt ggtgaccgtg      540
```

```
ccctccagca gcttgggcac ccagacctac atctgcaacg tgaatcacaa gcccagcaac      600
accaaggtgg acaagaaagt tgagcccaaa tcttgtgaca aaactcacac atgcccaccg      660
tgcccagcac ctgaactcct ggggggaccg tcagtcttcc tcttccccc aaaacccaag      720 gacacc ctca tgatctcccg gacccctgag gtcacatgcg tggtggtgga cgtgagccac      780
gaagaccctg aggtcaagtt caactggtac gtggacggcg tggaggtgca taatgccaag      840
acaaagccgc gggaggagca gtacgccagc acgtaccgtg tggtcagcgt cctcaccgtc      900
ctgcaccagg actggctgaa tggcaaggag tacaagtgca aggtctccaa caaagccctc      960
ccagccccca tcgagaaaac catctccaaa gccaaagggc agccccgaga accacaggtg     1020
tacaccctgc ccccatcccg ggaggagatg accaagaacc aggtcagcct gacctgcctg     1080
gtcaaaggct tctatcccag cgacatcgcc gtggagtggg agagcaatgg gcagccggag     1140
aacaactaca agaccacgcc tcccgtgctg gactccgacg gctccttctt cctctacagc     1200
aagctcaccg tggacaagag caggtggcag caggggaacg tcttctcatg ctccgtgatg     1260
catgaggctc tgcacaacca ctacacgcag aagagcctct ccctgtctcc gggtaaa        1317
```

```
<210> SEQ ID NO 852
<211> LENGTH: 327
<212> TYPE: DNA
<213> ORGANISM: Artificial
<220> FEATURE:
<223> OTHER INFORMATION: Humanized antibody sequence

<400> SEQUENCE: 852
cagtcggtgg aggagtccgg gggtcgcctg gtcacgcctg ggacacccct gacactcacc       60
tgcacagtct ctggaatcga cctcagtagc tactacatga cctgggtccg ccaggctcca      120 gggaagggc tggaatgggt cggattcatt gatgctggtg gtagcgcata ctacgcgacc      180
tgggcaaaag gccgattcac catctccaaa gcctcgacca cggtggatct gaaaatcacc      240
agtccgacaa ccgaggacac ggccacctat ttctgtgcca gagatcttga cttgtggggc      300
ccgggcaccc tggtcaccgt ctcgagc                                          327
```

```
<210> SEQ ID NO 853
<211> LENGTH: 87
<212> TYPE: DNA
<213> ORGANISM: Oryctolagus cuniculus

<400> SEQUENCE: 853
cagtcggtgg aggagtccgg gggtcgcctg gtcacgcctg ggacacccct gacactcacc       60
tgcacagtct ctggaatcga cctcagt                                           87
```

```
<210> SEQ ID NO 854
<211> LENGTH: 15
<212> TYPE: DNA
<213> ORGANISM: Oryctolagus cuniculus

<400> SEQUENCE: 854
agctactaca tgacc                                                        15
```

```
<210> SEQ ID NO 855
<211> LENGTH: 42
<212> TYPE: DNA
<213> ORGANISM: Oryctolagus cuniculus

<400> SEQUENCE: 855
tgggtccgcc aggctccagg gaaggggctg gaatgggtcg ga                          42
```

<210> SEQ ID NO 856
<211> LENGTH: 48
<212> TYPE: DNA
<213> ORGANISM: Oryctolagus cuniculus

<400> SEQUENCE: 856
ttcattgatg ctggtggtag cgcatactac gcgacctggg caaaaggc          48

<210> SEQ ID NO 857
<211> LENGTH: 90
<212> TYPE: DNA
<213> ORGANISM: Oryctolagus cuniculus

<400> SEQUENCE: 857
cgattcacca tctccaaagc ctcgaccacg gtggatctga aaatcaccag tccgacaacc     60
gaggacacgg ccacctattt ctgtgccaga                                     90

<210> SEQ ID NO 858
<211> LENGTH: 12
<212> TYPE: DNA
<213> ORGANISM: Oryctolagus cuniculus

<400> SEQUENCE: 858
gatcttgact tg                                                        12

<210> SEQ ID NO 859
<211> LENGTH: 33
<212> TYPE: DNA
<213> ORGANISM: Artificial
<220> FEATURE:
<223> OTHER INFORMATION: Humanized antibody sequence

<400> SEQUENCE: 859
tggggcccgg gcaccctggt caccgtctcg agc                                 33

<210> SEQ ID NO 860
<211> LENGTH: 990
<212> TYPE: DNA
<213> ORGANISM: Artificial
<220> FEATURE:
<223> OTHER INFORMATION: Humanized antibody sequence

<400> SEQUENCE: 860
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcggagga gcagtacgcc     540 agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720

```
atgaccaaga accaggtcag cctgacctgc ctggtcaaag gcttctatcc cagcgacatc        780
gccgtggagt gggagagcaa tgggcagccg gagaacaact acaagaccac gcctcccgtg        840
ctggactccg acggctcctt cttcctctac agcaagctca ccgtggacaa gagcaggtgg        900
cagcagggga acgtcttctc atgctccgtg atgcatgagg ctctgcacaa ccactacacg        960
cagaagagcc tctccctgtc tccgggtaaa                                         990
```

<210> SEQ ID NO 861
<211> LENGTH: 216
<212> TYPE: PRT
<213> ORGANISM: Artificial
<220> FEATURE:
<223> OTHER INFORMATION: Humanized antibody sequence

<400> SEQUENCE: 861

```
Ala Ala Val Leu Thr Gln Thr Pro Ser Pro Val Ser Ala Ala Val Gly
1               5                   10                  15

Gly Thr Val Ser Ile Ser Cys Lys Ser Ser Glu Ser Val Tyr Gly Asp
            20                  25                  30

Tyr Leu Ala Trp Phe Gln Gln Lys Pro Gly Gln Pro Pro Lys Gln Leu
        35                  40                  45

Ile Tyr Asp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Gly Tyr Val Ser Ala
                85                  90                  95

Gly Val Ala Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 862
<211> LENGTH: 110
<212> TYPE: PRT
<213> ORGANISM: Artificial
<220> FEATURE:
<223> OTHER INFORMATION: Humanized antibody sequence

<400> SEQUENCE: 862

```
Ala Ala Val Leu Thr Gln Thr Pro Ser Pro Val Ser Ala Ala Val Gly
1               5                   10                  15

Gly Thr Val Ser Ile Ser Cys Lys Ser Ser Glu Ser Val Tyr Gly Asp
            20                  25                  30

Tyr Leu Ala Trp Phe Gln Gln Lys Pro Gly Gln Pro Pro Lys Gln Leu
```

```
                35                  40                  45
Ile Tyr Asp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Gly Tyr Val Ser Ala
                85                  90                  95

Gly Val Ala Phe Gly Gly Gly Thr Glu Val Val Val Lys Arg
            100                 105                 110

<210> SEQ ID NO 863
<211> LENGTH: 23
<212> TYPE: PRT
<213> ORGANISM: Oryctolagus cuniculus

<400> SEQUENCE: 863

Ala Ala Val Leu Thr Gln Thr Pro Ser Pro Val Ser Ala Ala Val Gly
1               5                   10                  15

Gly Thr Val Ser Ile Ser Cys
            20

<210> SEQ ID NO 864
<211> LENGTH: 12
<212> TYPE: PRT
<213> ORGANISM: Oryctolagus cuniculus

<400> SEQUENCE: 864

Lys Ser Ser Glu Ser Val Tyr Gly Asp Tyr Leu Ala
1               5                   10

<210> SEQ ID NO 865
<211> LENGTH: 15
<212> TYPE: PRT
<213> ORGANISM: Oryctolagus cuniculus

<400> SEQUENCE: 865

Trp Phe Gln Gln Lys Pro Gly Gln Pro Pro Lys Gln Leu Ile Tyr
1               5                   10                  15

<210> SEQ ID NO 866
<211> LENGTH: 7
<212> TYPE: PRT
<213> ORGANISM: Oryctolagus cuniculus

<400> SEQUENCE: 866

Asp Ala Ser Thr Leu Ala Ser
1               5

<210> SEQ ID NO 867
<211> LENGTH: 32
<212> TYPE: PRT
<213> ORGANISM: Oryctolagus cuniculus

<400> SEQUENCE: 867

Gly Val Pro Ser Arg Phe Lys Gly Ser Gly Ser Gly Thr Gln Phe Thr
1               5                   10                  15

Leu Thr Ile Ser Gly Val Gln Cys Asp Asp Ala Ala Thr Tyr Tyr Cys
            20                  25                  30

<210> SEQ ID NO 868
<211> LENGTH: 10
<212> TYPE: PRT
```

<213> ORGANISM: Oryctolagus cuniculus

<400> SEQUENCE: 868

Ala Gly Gly Tyr Val Ser Ala Gly Val Ala
1               5                   10

<210> SEQ ID NO 869
<211> LENGTH: 11
<212> TYPE: PRT
<213> ORGANISM: Artificial
<220> FEATURE:
<223> OTHER INFORMATION: Humanized antibody sequence

<400> SEQUENCE: 869

Phe Gly Gly Gly Thr Glu Val Val Val Lys Arg
1               5                   10

<210> SEQ ID NO 870
<211> LENGTH: 106
<212> TYPE: PRT
<213> ORGANISM: Artificial
<220> FEATURE:
<223> OTHER INFORMATION: Humanized antibody sequence

<400> SEQUENCE: 870

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 871
<211> LENGTH: 648
<212> TYPE: DNA
<213> ORGANISM: Artificial
<220> FEATURE:
<223> OTHER INFORMATION: Humanized antibody sequence

<400> SEQUENCE: 871
gccgccgtgc tgacccagac tccatctccc gtgtctgcag ctgtgggagg cacagtcagc      60
atcagttgca agtccagtga gagcgtttat ggtgactact agcctggtt tcagcagaaa     120 ccagggcagc ctcccaagca actgatctat gatgcatcca ctctggcatc tggggtccca     180
tcgcggttca aaggcagtgg atctgggaca cagttcactc tcaccatcag cggcgtgcag     240
tgtgacgatg ctgccactta ctactgtgca ggcggttatg ttagtgcagg tgttgctttc     300
ggcggaggga ccgaggtggt ggtcaaacgt acggtagcgg ccccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540

```
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 872
<211> LENGTH: 330
<212> TYPE: DNA
<213> ORGANISM: Artificial
<220> FEATURE:
<223> OTHER INFORMATION: Humanized antibody sequence

<400> SEQUENCE: 872

```
gccgccgtgc tgacccagac tccatctccc gtgtctgcag ctgtgggagg cacagtcagc    60
atcagttgca agtccagtga gagcgtttat ggtgactact tagcctggtt tcagcagaaa   120
ccagggcagc ctcccaagca actgatctat gatgcatcca ctctggcatc tggggtccca   180
tcgcggttca aaggcagtgg atctgggaca cagttcactc tcaccatcag cggcgtgcag   240
tgtgacgatg ctgccactta ctactgtgca ggcggttatg ttagtgcagg tgttgctttc   300
ggcggaggga ccgaggtggt ggtcaaacgt                                    330
```

<210> SEQ ID NO 873
<211> LENGTH: 69
<212> TYPE: DNA
<213> ORGANISM: Oryctolagus cuniculus

<400> SEQUENCE: 873

```
gccgccgtgc tgacccagac tccatctccc gtgtctgcag ctgtgggagg cacagtcagc    60
atcagttgc                                                            69
```

<210> SEQ ID NO 874
<211> LENGTH: 36
<212> TYPE: DNA
<213> ORGANISM: Oryctolagus cuniculus

<400> SEQUENCE: 874

```
aagtccagtg agagcgttta tggtgactac ttagcc                              36
```

<210> SEQ ID NO 875
<211> LENGTH: 45
<212> TYPE: DNA
<213> ORGANISM: Oryctolagus cuniculus

<400> SEQUENCE: 875

```
tggtttcagc agaaaccagg gcagcctccc aagcaactga tctat                    45
```

<210> SEQ ID NO 876
<211> LENGTH: 21
<212> TYPE: DNA
<213> ORGANISM: Oryctolagus cuniculus

<400> SEQUENCE: 876

```
gatgcatcca ctctggcatc t                                              21
```

<210> SEQ ID NO 877
<211> LENGTH: 96
<212> TYPE: DNA
<213> ORGANISM: Oryctolagus cuniculus

<400> SEQUENCE: 877

```
ggggtcccat cgcggttcaa aggcagtgga tctgggacac agttcactct caccatcagc    60
ggcgtgcagt gtgacgatgc tgccacttac tactgt                              96
```

<210> SEQ ID NO 878
<211> LENGTH: 30
<212> TYPE: DNA
<213> ORGANISM: Oryctolagus cuniculus

<400> SEQUENCE: 878
gcaggcggtt atgttagtgc aggtgttgct                                      30

<210> SEQ ID NO 879
<211> LENGTH: 33
<212> TYPE: DNA
<213> ORGANISM: Artificial
<220> FEATURE:
<223> OTHER INFORMATION: Humanized antibody sequence

<400> SEQUENCE: 879
ttcggcggag ggaccgaggt ggtggtcaaa cgt                                  33

<210> SEQ ID NO 880
<211> LENGTH: 318
<212> TYPE: DNA
<213> ORGANISM: Artificial
<220> FEATURE:
<223> OTHER INFORMATION: Humanized antibody sequence

<400> SEQUENCE: 880
acggtagcgg ccccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgt                                                  318

<210> SEQ ID NO 881
<211> LENGTH: 442
<212> TYPE: PRT
<213> ORGANISM: Artificial
<220> FEATURE:
<223> OTHER INFORMATION: Humanized antibody sequence

<400> SEQUENCE: 881

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Asp Phe Ser Ser Asn
            20                  25                  30

Ala Met Cys Trp Val Arg Gln Ala Pro Gly Lys Gly Leu Glu Trp Ile
        35                  40                  45

Gly Ser Ile Tyr Asn Ala Asp Gly Lys Asn Tyr Tyr Ala Ile Trp Ala
    50                  55                  60

Lys Gly Arg Phe Thr Ile Ser Arg Thr Ser Thr Thr Val Thr Leu
65                  70                  75                  80

Gln Met Thr Ser Leu Thr Ala Ala Asp Thr Ala Thr Tyr Phe Cys Ala
            85                  90                  95

Arg Asp Phe Asp Leu Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Ala
        195                 200                 205

Arg Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Ala Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 882
<211> LENGTH: 112
<212> TYPE: PRT
<213> ORGANISM: Artificial
<220> FEATURE:
<223> OTHER INFORMATION: Humanized antibody sequence

<400> SEQUENCE: 882

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Asp Phe Ser Ser Asn
            20                  25                  30

Ala Met Cys Trp Val Arg Gln Ala Pro Gly Lys Gly Leu Glu Trp Ile
        35                  40                  45

```
Gly Ser Ile Tyr Asn Ala Asp Gly Lys Asn Tyr Tyr Ala Ile Trp Ala
        50                  55                  60

Lys Gly Arg Phe Thr Ile Ser Arg Thr Ser Ser Thr Val Thr Leu
65                  70                  75                  80

Gln Met Thr Ser Leu Thr Ala Ala Asp Thr Ala Thr Tyr Phe Cys Ala
                85                  90                  95

Arg Asp Phe Asp Leu Trp Gly Gln Gly Thr Leu Val Thr Val Ser Ser
            100                 105                 110
```

<210> SEQ ID NO 883
<211> LENGTH: 30
<212> TYPE: PRT
<213> ORGANISM: Oryctolagus cuniculus

<400> SEQUENCE: 883

```
Gln Glu Gln Leu Val Glu Ser Gly Gly Leu Val Gln Pro Glu Gly
1               5                   10                  15

Ser Leu Thr Leu Thr Cys Thr Ala Ser Gly Phe Asp Phe Ser
                20                  25                  30
```

<210> SEQ ID NO 884
<211> LENGTH: 5
<212> TYPE: PRT
<213> ORGANISM: Oryctolagus cuniculus

<400> SEQUENCE: 884

```
Ser Asn Ala Met Cys
1               5
```

<210> SEQ ID NO 885
<211> LENGTH: 14
<212> TYPE: PRT
<213> ORGANISM: Oryctolagus cuniculus

<400> SEQUENCE: 885

```
Trp Val Arg Gln Ala Pro Gly Lys Gly Leu Glu Trp Ile Gly
1               5                   10
```

<210> SEQ ID NO 886
<211> LENGTH: 17
<212> TYPE: PRT
<213> ORGANISM: Oryctolagus cuniculus

<400> SEQUENCE: 886

```
Ser Ile Tyr Asn Ala Asp Gly Lys Asn Tyr Tyr Ala Ile Trp Ala Lys
1               5                   10                  15

Gly
```

<210> SEQ ID NO 887
<211> LENGTH: 31
<212> TYPE: PRT
<213> ORGANISM: Oryctolagus cuniculus

<400> SEQUENCE: 887

```
Arg Phe Thr Ile Ser Arg Thr Ser Ser Thr Val Thr Leu Gln Met
1               5                   10                  15

Thr Ser Leu Thr Ala Ala Asp Thr Ala Thr Tyr Phe Cys Ala Arg
                20                  25                  30
```

<210> SEQ ID NO 888
<211> LENGTH: 4
<212> TYPE: PRT

<213> ORGANISM: Oryctolagus cuniculus

<400> SEQUENCE: 888

Asp Phe Asp Leu
1

<210> SEQ ID NO 889
<211> LENGTH: 11
<212> TYPE: PRT
<213> ORGANISM: Artificial
<220> FEATURE:
<223> OTHER INFORMATION: Humanized antibody sequence

<400> SEQUENCE: 889

Trp Gly Gln Gly Thr Leu Val Thr Val Ser Ser
1               5                   10

<210> SEQ ID NO 890
<211> LENGTH: 330
<212> TYPE: PRT
<213> ORGANISM: Artificial
<220> FEATURE:
<223> OTHER INFORMATION: Humanized antibody sequence

<400> SEQUENCE: 890

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn

Asn Tyr Lys Thr Thr Pro Pro Val Leu Asp Ser Asp Gly Ser Phe Phe
            260                 265                 270
    275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 891
<211> LENGTH: 1326
<212> TYPE: DNA
<213> ORGANISM: Artificial
<220> FEATURE:
<223> OTHER INFORMATION: Humanized antibody sequence

<400> SEQUENCE: 891

| | | |
|---|---|---|
| caggagcagc tggtggagtc cggggggaggc ctggtccagc ctgagggatc cctgacactc | 60 |
| acctgcacag cctctggatt cgacttcagt agcaatgcaa tgtgctgggt ccgccaggct | 120 |
| ccagggaagg gcctggagtg gatcggatcc atttataatg ctgatggtaa gaattattac | 180 |
| gcgatttggg cgaaaggccg attcaccatc tccagaacct cgtcgaccac ggtgactctg | 240 |
| caaatgacca gtctgacagc cgcggacacg gccacctatt tctgtgcgag agactttgac | 300 |
| ttgtggggcc agggcaccct cgtcaccgtc tcgagcgcct ccaccaaggg cccatcggtc | 360 |
| ttccccctgg cacccctcctc caagagcacc tctgggggca gcggccct gggctgcctg | 420 |
| gtcaaggact acttccccga accggtgacg gtgtcgtgga actcaggcgc cctgaccagc | 480 |
| ggcgtgcaca ccttcccggc tgtcctacag tcctcaggac tctactccct cagcagcgtg | 540 |
| gtgaccgtgc cctccagcag cttgggcacc cagacctaca tctgcaacgt gaatcacaag | 600 |
| cccagcaaca ccaaggtgga cgcgagagtt gagcccaaat cttgtgacaa aactcacaca | 660 |
| tgcccaccgt gcccagcacc tgaactcctg ggggaccgt cagtcttcct cttccccccca | 720 |
| aaacccaagg acaccctcat gatctcccgg acccctgagg tcacatgcgt ggtggtggac | 780 |
| gtgagccacg aagaccctga ggtcaagttc aactggtacg tggacggcgt ggaggtgcat | 840 |
| aatgccaaga caaagccgcg ggaggagcag tacgccagca cgtaccgtgt ggtcagcgtc | 900 |
| ctcaccgtcc tgcaccagga ctggctgaat ggcaaggagt acaagtgcaa ggtctccaac | 960 |
| aaagccctcc cagcccccat cgagaaaacc atctccaaag ccaaagggca gccccgagaa | 1020 |
| ccacaggtgt acaccctgcc cccatcccgg gaggagatga ccaagaacca ggtcagcctg | 1080 |
| acctgcctgg tcaaaggctt ctatcccagc gacatcgccg tggagtggga gagcaatggg | 1140 |
| cagccggaga acaactacaa gaccacgcct cccgtgctgg actccgacgg ctccttcttc | 1200 |
| ctctacagca agctcaccgt ggacaagagc aggtggcagc aggggaacgt cttctcatgc | 1260 |
| tccgtgatgc atgaggctct gcacaaccac tacacgcaga gagcctctc cctgtctccg | 1320 |
| ggtaaa | 1326 |

<210> SEQ ID NO 892
<211> LENGTH: 336
<212> TYPE: DNA
<213> ORGANISM: Artificial
<220> FEATURE:
<223> OTHER INFORMATION: Humanized antibody sequence

<400> SEQUENCE: 892

```
caggagcagc tggtggagtc cgggggaggc ctggtccagc ctgagggatc cctgacactc    60
acctgcacag cctctggatt cgacttcagt agcaatgcaa tgtgctgggt ccgccaggct   120
ccagggaagg gcctggagtg gatcggatcc atttataatg ctgatggtaa gaattattac   180
gcgatttggg cgaaaggccg attcaccatc tccagaacct cgtcgaccac ggtgactctg   240
caaatgacca gtctgacagc cgcggacacg gccacctatt tctgtgcgag agactttgac   300
ttgtggggcc agggcaccct cgtcaccgtc tcgagc                             336
```

<210> SEQ ID NO 893
<211> LENGTH: 90
<212> TYPE: DNA
<213> ORGANISM: Oryctolagus cuniculus

<400> SEQUENCE: 893

```
caggagcagc tggtggagtc cgggggaggc ctggtccagc ctgagggatc cctgacactc    60
acctgcacag cctctggatt cgacttcagt                                     90
```

<210> SEQ ID NO 894
<211> LENGTH: 15
<212> TYPE: DNA
<213> ORGANISM: Oryctolagus cuniculus

<400> SEQUENCE: 894

```
agcaatgcaa tgtgc                                                     15
```

<210> SEQ ID NO 895
<211> LENGTH: 42
<212> TYPE: DNA
<213> ORGANISM: Oryctolagus cuniculus

<400> SEQUENCE: 895

```
tgggtccgcc aggctccagg gaagggcctg gagtggatcg ga                       42
```

<210> SEQ ID NO 896
<211> LENGTH: 51
<212> TYPE: DNA
<213> ORGANISM: Oryctolagus cuniculus

<400> SEQUENCE: 896

```
tccatttata atgctgatgg taagaattat tacgcgattt gggcgaaagg c             51
```

<210> SEQ ID NO 897
<211> LENGTH: 93
<212> TYPE: DNA
<213> ORGANISM: Oryctolagus cuniculus

<400> SEQUENCE: 897

```
cgattcacca tctccagaac ctcgtcgacc acggtgactc tgcaaatgac cagtctgaca    60
gccgcggaca cggccaccta tttctgtgcg aga                                 93
```

<210> SEQ ID NO 898
<211> LENGTH: 12
<212> TYPE: DNA
<213> ORGANISM: Oryctolagus cuniculus

<400> SEQUENCE: 898

```
gactttgact tg                                                        12
```

<210> SEQ ID NO 899

<211> LENGTH: 33
<212> TYPE: DNA
<213> ORGANISM: Artificial
<220> FEATURE:
<223> OTHER INFORMATION: Humanized antibody sequence

<400> SEQUENCE: 899
tggggccagg gcaccctcgt caccgtctcg agc            33

<210> SEQ ID NO 900
<211> LENGTH: 990
<212> TYPE: DNA
<213> ORGANISM: Artificial
<220> FEATURE:
<223> OTHER INFORMATION: Humanized antibody sequence

<400> SEQUENCE: 900
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacgcgag agttgagccc     300
aaatcttgtg acaaaactca cacatgccca ccgtgcccag cacctgaact cctggggggga    360
ccgtcagtct tcctcttccc cccaaaaccc aaggacaccc tcatgatctc ccggaccct      420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 901
<211> LENGTH: 219
<212> TYPE: PRT
<213> ORGANISM: Artificial
<220> FEATURE:
<223> OTHER INFORMATION: Humanized antibody sequence

<400> SEQUENCE: 901

Ala Ala Val Leu Thr Gln Thr Pro Ser Pro Val Ser Ala Ala Val Gly
1               5                   10                  15

Gly Thr Val Thr Ile Asn Cys Gln Ser Ser Gln Ser Val Tyr Asp Asn
            20                  25                  30

Asp Trp Leu Ala Trp Phe Gln Gln Lys Pro Gly Gln Pro Pro Lys Leu
        35                  40                  45

Leu Ile Tyr Leu Thr Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

```
Gln Cys Asp Asp Ala Ala Thr Tyr Tyr Cys Leu Gly Gly Tyr Asp Glu
                85                  90                  95

Asp Gly Asp Thr His Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 902
<211> LENGTH: 113
<212> TYPE: PRT
<213> ORGANISM: Artificial
<220> FEATURE:
<223> OTHER INFORMATION: Humanized antibody sequence

<400> SEQUENCE: 902

Ala Ala Val Leu Thr Gln Thr Pro Ser Pro Val Ser Ala Ala Val Gly
1               5                   10                  15

Gly Thr Val Thr Ile Asn Cys Gln Ser Ser Gln Ser Val Tyr Asp Asn
            20                  25                  30

Asp Trp Leu Ala Trp Phe Gln Gln Lys Pro Gly Gln Pro Pro Lys Leu
        35                  40                  45

Leu Ile Tyr Leu Thr Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Glu
                85                  90                  95

Asp Gly Asp Thr His Val Phe Gly Gly Gly Thr Glu Val Val Val Lys
            100                 105                 110

Arg

<210> SEQ ID NO 903
<211> LENGTH: 23
<212> TYPE: PRT
<213> ORGANISM: Oryctolagus cuniculus

<400> SEQUENCE: 903

Ala Ala Val Leu Thr Gln Thr Pro Ser Pro Val Ser Ala Ala Val Gly
1               5                   10                  15

Gly Thr Val Thr Ile Asn Cys
            20

<210> SEQ ID NO 904
<211> LENGTH: 13
<212> TYPE: PRT
<213> ORGANISM: Oryctolagus cuniculus
```

```
<400> SEQUENCE: 904

Gln Ser Ser Gln Ser Val Tyr Asp Asn Asp Trp Leu Ala
1               5                   10

<210> SEQ ID NO 905
<211> LENGTH: 15
<212> TYPE: PRT
<213> ORGANISM: Oryctolagus cuniculus

<400> SEQUENCE: 905

Trp Phe Gln Gln Lys Pro Gly Gln Pro Pro Lys Leu Leu Ile Tyr
1               5                   10                  15

<210> SEQ ID NO 906
<211> LENGTH: 7
<212> TYPE: PRT
<213> ORGANISM: Oryctolagus cuniculus

<400> SEQUENCE: 906

Leu Thr Ser Thr Leu Ala Ser
1               5

<210> SEQ ID NO 907
<211> LENGTH: 32
<212> TYPE: PRT
<213> ORGANISM: Oryctolagus cuniculus

<400> SEQUENCE: 907

Gly Val Pro Ser Arg Phe Ser Gly Ser Gly Ser Gly Thr Gln Phe Thr
1               5                   10                  15

Leu Thr Ile Ser Gly Val Gln Cys Asp Asp Ala Ala Thr Tyr Tyr Cys
                20                  25                  30

<210> SEQ ID NO 908
<211> LENGTH: 12
<212> TYPE: PRT
<213> ORGANISM: Oryctolagus cuniculus

<400> SEQUENCE: 908

Leu Gly Gly Tyr Asp Glu Asp Gly Asp Thr His Val
1               5                   10

<210> SEQ ID NO 909
<211> LENGTH: 11
<212> TYPE: PRT
<213> ORGANISM: Artificial
<220> FEATURE:
<223> OTHER INFORMATION: Humanized antibody sequence

<400> SEQUENCE: 909

Phe Gly Gly Gly Thr Glu Val Val Val Lys Arg
1               5                   10

<210> SEQ ID NO 910
<211> LENGTH: 106
<212> TYPE: PRT
<213> ORGANISM: Artificial
<220> FEATURE:
<223> OTHER INFORMATION: Humanized antibody sequence

<400> SEQUENCE: 910

Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
        20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 911
<211> LENGTH: 657
<212> TYPE: DNA
<213> ORGANISM: Artificial
<220> FEATURE:
<223> OTHER INFORMATION: Humanized antibody sequence

<400> SEQUENCE: 911

```
gcagccgtgc tgacccagac accatcgccc gtgtctgcag ctgtgggagg cacagtcacc      60
atcaattgcc agtccagtca gagtgtttat gataacgact ggttagcctg gttccagcag     120
aaaccagggc agcctcccaa gctcctgatc tatctgacat ccactctggc atctggagtc     180
ccatcgcggt tcagcggcag tggatctggg acacagttca ctctcaccat cagtggtgtg     240
cagtgtgacg atgctgccac ttactactgt ctaggcggct atgatgaaga tggtgatacg     300
catgttttcg gcggagggac cgaggtggtg gtcaaacgta cggtagcggc cccatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt        657
```

<210> SEQ ID NO 912
<211> LENGTH: 339
<212> TYPE: DNA
<213> ORGANISM: Artificial
<220> FEATURE:
<223> OTHER INFORMATION: Humanized antibody sequence

<400> SEQUENCE: 912

```
gcagccgtgc tgacccagac accatcgccc gtgtctgcag ctgtgggagg cacagtcacc      60
atcaattgcc agtccagtca gagtgtttat gataacgact ggttagcctg gttccagcag     120
aaaccagggc agcctcccaa gctcctgatc tatctgacat ccactctggc atctggagtc     180
ccatcgcggt tcagcggcag tggatctggg acacagttca ctctcaccat cagtggtgtg     240
cagtgtgacg atgctgccac ttactactgt ctaggcggct atgatgaaga tggtgatacg     300
catgttttcg gcggagggac cgaggtggtg gtcaaacgt                            339
```

<210> SEQ ID NO 913
<211> LENGTH: 69
<212> TYPE: DNA
<213> ORGANISM: Oryctolagus cuniculus

<400> SEQUENCE: 913

```
gcagccgtgc tgacccagac accatcgccc gtgtctgcag ctgtgggagg cacagtcacc    60
atcaattgc                                                             69
```

<210> SEQ ID NO 914
<211> LENGTH: 39
<212> TYPE: DNA
<213> ORGANISM: Oryctolagus cuniculus

<400> SEQUENCE: 914

```
cagtccagtc agagtgttta tgataacgac tggttagcc                            39
```

<210> SEQ ID NO 915
<211> LENGTH: 45
<212> TYPE: DNA
<213> ORGANISM: Oryctolagus cuniculus

<400> SEQUENCE: 915

```
tggttccagc agaaaccagg gcagcctccc aagctcctga tctat                     45
```

<210> SEQ ID NO 916
<211> LENGTH: 21
<212> TYPE: DNA
<213> ORGANISM: Oryctolagus cuniculus

<400> SEQUENCE: 916

```
ctgacatcca ctctggcatc t                                               21
```

<210> SEQ ID NO 917
<211> LENGTH: 96
<212> TYPE: DNA
<213> ORGANISM: Oryctolagus cuniculus

<400> SEQUENCE: 917

```
ggagtcccat cgcggttcag cggcagtgga tctgggacac agttcactct caccatcagt    60
ggtgtgcagt gtgacgatgc tgccacttac tactgt                              96
```

<210> SEQ ID NO 918
<211> LENGTH: 36
<212> TYPE: DNA
<213> ORGANISM: Oryctolagus cuniculus

<400> SEQUENCE: 918

```
ctaggcggct atgatgaaga tggtgatacg catgtt                              36
```

<210> SEQ ID NO 919
<211> LENGTH: 33
<212> TYPE: DNA
<213> ORGANISM: Artificial
<220> FEATURE:
<223> OTHER INFORMATION: Humanized antibody sequence

<400> SEQUENCE: 919

```
ttcggcggag ggaccgaggt ggtggtcaaa cgt                                  33
```

<210> SEQ ID NO 920
<211> LENGTH: 318
<212> TYPE: DNA
<213> ORGANISM: Artificial
<220> FEATURE:
<223> OTHER INFORMATION: Humanized antibody sequence

<400> SEQUENCE: 920

```
acggtagcgg cccatctgt cttcatcttc ccgccatctg atgagcagtt gaaatctgga      60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgt                                                  318
```

```
<210> SEQ ID NO 921
<211> LENGTH: 447
<212> TYPE: PRT
<213> ORGANISM: Artificial
<220> FEATURE:
<223> OTHER INFORMATION: Humanized antibody sequence

<400> SEQUENCE: 921

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
                20                  25                  30

Met Ser Trp Val Arg Gln Ala Pro Gly Lys Gly Leu Glu Trp Ile Gly
            35                  40                  45

Ile Met Gly Val Asn Asp Ile Thr Tyr Tyr Ala Ser Trp Ala Lys Gly
        50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Thr Arg Glu Ile
                85                  90                  95

Arg Asp Asp Gly Asp Ser Ser Asp Lys Leu Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Ala Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300
```

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 922
<211> LENGTH: 117
<212> TYPE: PRT
<213> ORGANISM: Artificial
<220> FEATURE:
<223> OTHER INFORMATION: Humanized antibody sequence

<400> SEQUENCE: 922

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Val Arg Gln Ala Pro Gly Lys Gly Leu Glu Trp Ile Gly
        35                  40                  45

Ile Met Gly Val Asn Asp Ile Thr Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Thr Arg Glu Ile
            85                  90                  95

Arg Asp Asp Gly Asp Ser Ser Asp Lys Leu Trp Gly Pro Gly Thr Leu
            100                 105                 110

Val Thr Val Ser Ser
        115

<210> SEQ ID NO 923
<211> LENGTH: 29
<212> TYPE: PRT
<213> ORGANISM: Oryctolagus cuniculus

<400> SEQUENCE: 923

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn
            20                  25

<210> SEQ ID NO 924
<211> LENGTH: 5
<212> TYPE: PRT

<213> ORGANISM: Oryctolagus cuniculus

<400> SEQUENCE: 924

Asn Tyr Ala Met Ser
1               5

<210> SEQ ID NO 925
<211> LENGTH: 14
<212> TYPE: PRT
<213> ORGANISM: Oryctolagus cuniculus

<400> SEQUENCE: 925

Trp Val Arg Gln Ala Pro Gly Lys Gly Leu Glu Trp Ile Gly
1               5                   10

<210> SEQ ID NO 926
<211> LENGTH: 16
<212> TYPE: PRT
<213> ORGANISM: Oryctolagus cuniculus

<400> SEQUENCE: 926

Ile Met Gly Val Asn Asp Ile Thr Tyr Tyr Ala Ser Trp Ala Lys Gly
1               5                   10                  15

<210> SEQ ID NO 927
<211> LENGTH: 30
<212> TYPE: PRT
<213> ORGANISM: Oryctolagus cuniculus

<400> SEQUENCE: 927

Arg Phe Thr Ile Ser Lys Thr Ser Thr Thr Val Asp Leu Lys Met Thr
1               5                   10                  15

Ser Leu Thr Thr Glu Asp Thr Ala Thr Tyr Phe Cys Thr Arg
            20                  25                  30

<210> SEQ ID NO 928
<211> LENGTH: 12
<212> TYPE: PRT
<213> ORGANISM: Oryctolagus cuniculus

<400> SEQUENCE: 928

Glu Ile Arg Asp Asp Gly Asp Ser Ser Asp Lys Leu
1               5                   10

<210> SEQ ID NO 929
<211> LENGTH: 11
<212> TYPE: PRT
<213> ORGANISM: Artificial
<220> FEATURE:
<223> OTHER INFORMATION: Humanized antibody sequence

<400> SEQUENCE: 929

Trp Gly Pro Gly Thr Leu Val Thr Val Ser Ser
1               5                   10

<210> SEQ ID NO 930
<211> LENGTH: 330
<212> TYPE: PRT
<213> ORGANISM: Artificial
<220> FEATURE:
<223> OTHER INFORMATION: Humanized antibody sequence

<400> SEQUENCE: 930

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 931
<211> LENGTH: 1341
<212> TYPE: DNA
<213> ORGANISM: Artificial
<220> FEATURE:
<223> OTHER INFORMATION: Humanized antibody sequence

<400> SEQUENCE: 931
cagtcggtgg aggagtccgg gggtcgcctg gtcacgcctg ggacacccct gacactcacc    60
tgcaccgtct ctggattctc cctcaataac tatgcaatga gctgggtccg ccaggctcca   120
gggaaggggc tggaatggat cggaatcatg ggtgttaatg atatcacata ctacgcgagc   180
tgggcgaaag gccgattcac catctcccaaa acctcgacca cggtggatct gaaaatgacc   240

```
agtctgacaa ccgaggacac ggccacctat ttctgtacta gagagatccg tgatgatggt      300
gatagttctg ataagttgtg gggcccgggc accctcgtca ccgtctcgag cgcctccacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacgcga gagttgagcc caaatcttgt      660
gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacgc cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag      1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca gagcaggtg gcagcagggg     1260
aacgtcttct catgctccgt gatgcatgag gctctgcaca accactacac gcagaagagc     1320
ctctcctgt ctccgggtaa a                                                1341

<210> SEQ ID NO 932
<211> LENGTH: 351
<212> TYPE: DNA
<213> ORGANISM: Artificial
<220> FEATURE:
<223> OTHER INFORMATION: Humanized antibody sequence

<400> SEQUENCE: 932
cagtcggtgg aggagtccgg gggtcgcctg gtcacgcctg ggacacccct gacactcacc       60
tgcaccgtct ctggattctc cctcaataac tatgcaatga gctgggtccg ccaggctcca      120
gggaaggggc tggaatggat cggaatcatg ggtgttaatg atatcacata ctacgcgagc      180
tgggcgaaag gccgattcac catctccaaa acctcgacca cggtggatct gaaaatgacc      240
agtctgacaa ccgaggacac ggccacctat ttctgtacta gagagatccg tgatgatggt      300
gatagttctg ataagttgtg gggcccgggc accctcgtca ccgtctcgag c               351

<210> SEQ ID NO 933
<211> LENGTH: 87
<212> TYPE: DNA
<213> ORGANISM: Oryctolagus cuniculus

<400> SEQUENCE: 933
cagtcggtgg aggagtccgg gggtcgcctg gtcacgcctg ggacacccct gacactcacc       60
tgcaccgtct ctggattctc cctcaat                                          87

<210> SEQ ID NO 934
<211> LENGTH: 15
<212> TYPE: DNA
<213> ORGANISM: Oryctolagus cuniculus

<400> SEQUENCE: 934
```

```
aactatgcaa tgagc                                                       15

<210> SEQ ID NO 935
<211> LENGTH: 42
<212> TYPE: DNA
<213> ORGANISM: Oryctolagus cuniculus

<400> SEQUENCE: 935
tgggtccgcc aggctccagg gaagggctg gaatggatcg ga                          42

<210> SEQ ID NO 936
<211> LENGTH: 48
<212> TYPE: DNA
<213> ORGANISM: Oryctolagus cuniculus

<400> SEQUENCE: 936
atcatgggtg ttaatgatat cacatactac gcgagctggg cgaaaggc                   48

<210> SEQ ID NO 937
<211> LENGTH: 90
<212> TYPE: DNA
<213> ORGANISM: Oryctolagus cuniculus

<400> SEQUENCE: 937
cgattcacca tctccaaaac ctcgaccacg gtggatctga aaatgaccag tctgacaacc      60
gaggacacgg ccacctattt ctgtactaga                                       90

<210> SEQ ID NO 938
<211> LENGTH: 36
<212> TYPE: DNA
<213> ORGANISM: Oryctolagus cuniculus

<400> SEQUENCE: 938
gagatccgtg atgatggtga tagttctgat aagttg                                36

<210> SEQ ID NO 939
<211> LENGTH: 33
<212> TYPE: DNA
<213> ORGANISM: Artificial
<220> FEATURE:
<223> OTHER INFORMATION: Humanized antibody sequence

<400> SEQUENCE: 939
tggggcccgg gcaccctcgt caccgtctcg agc                                   33

<210> SEQ ID NO 940
<211> LENGTH: 990
<212> TYPE: DNA
<213> ORGANISM: Artificial
<220> FEATURE:
<223> OTHER INFORMATION: Humanized antibody sequence

<400> SEQUENCE: 940
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacgcgag agttgagccc     300
aaatcttgtg acaaaactca cacatgccca ccgtgcccag cacctgaact cctggggga     360
```

```
ccgtcagtct tcctcttccc cccaaaaccc aaggacaccc tcatgatctc ccggaccoct    420 gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacgcc    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 941
<211> LENGTH: 219
<212> TYPE: PRT
<213> ORGANISM: Artificial
<220> FEATURE:
<223> OTHER INFORMATION: Humanized antibody sequence

<400> SEQUENCE: 941

```
Ala Ile Lys Met Thr Gln Thr Pro Ser Ser Val Ser Ala Ala Val Gly
1               5                   10                  15

Gly Thr Val Thr Ile Asn Cys Gln Ala Ser Glu Asp Ile Tyr Thr Asn
            20                  25                  30

Leu Ala Trp Tyr Gln Gln Lys Pro Gly Gln Pro Pro Asn Leu Leu Ile
        35                  40                  45

Tyr Asp Ala Ser Asp Leu Ala Ser Gly Val Pro Ser Arg Phe Ser Gly
    50                  55                  60

Ser Gly Asp Gly Thr Gln Phe Thr Leu Thr Ile Ser Ala Val Gln Cys
65                  70                  75                  80

Glu Asp Ala Ala Thr Tyr Tyr Cys Gln Gly Val Ala Trp Ser Ser Asn
                85                  90                  95

Thr Gly Tyr Gly Ser Ala Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 942
<211> LENGTH: 113
<212> TYPE: PRT
<213> ORGANISM: Artificial
<220> FEATURE:
<223> OTHER INFORMATION: Humanized antibody sequence

<400> SEQUENCE: 942

Ala Ile Lys Met Thr Gln Thr Pro Ser Ser Val Ser Ala Ala Val Gly
1               5                   10                  15

Gly Thr Val Thr Ile Asn Cys Gln Ala Ser Glu Asp Ile Tyr Thr Asn
            20                  25                  30

Leu Ala Trp Tyr Gln Gln Lys Pro Gly Gln Pro Pro Asn Leu Leu Ile
        35                  40                  45

Tyr Asp Ala Ser Asp Leu Ala Ser Gly Val Pro Ser Arg Phe Ser Gly
    50                  55                  60

Ser Gly Asp Gly Thr Gln Phe Thr Leu Thr Ile Ser Ala Val Gln Cys
65                  70                  75                  80

Glu Asp Ala Ala Thr Tyr Tyr Cys Gln Gly Val Ala Trp Ser Ser Asn
                85                  90                  95

Thr Gly Tyr Gly Ser Ala Phe Gly Gly Gly Thr Glu Val Val Val Lys
            100                 105                 110

Arg

<210> SEQ ID NO 943
<211> LENGTH: 23
<212> TYPE: PRT
<213> ORGANISM: Oryctolagus cuniculus

<400> SEQUENCE: 943

Ala Ile Lys Met Thr Gln Thr Pro Ser Ser Val Ser Ala Ala Val Gly
1               5                   10                  15

Gly Thr Val Thr Ile Asn Cys
            20

<210> SEQ ID NO 944
<211> LENGTH: 11
<212> TYPE: PRT
<213> ORGANISM: Oryctolagus cuniculus

<400> SEQUENCE: 944

Gln Ala Ser Glu Asp Ile Tyr Thr Asn Leu Ala
1               5                   10

<210> SEQ ID NO 945
<211> LENGTH: 15
<212> TYPE: PRT
<213> ORGANISM: Oryctolagus cuniculus

<400> SEQUENCE: 945

Trp Tyr Gln Gln Lys Pro Gly Gln Pro Pro Asn Leu Leu Ile Tyr
1               5                   10                  15

<210> SEQ ID NO 946
<211> LENGTH: 7
<212> TYPE: PRT
<213> ORGANISM: Oryctolagus cuniculus

<400> SEQUENCE: 946

Asp Ala Ser Asp Leu Ala Ser
1               5

<210> SEQ ID NO 947
<211> LENGTH: 32
<212> TYPE: PRT

<213> ORGANISM: Oryctolagus cuniculus

<400> SEQUENCE: 947

```
Gly Val Pro Ser Arg Phe Ser Gly Ser Gly Asp Gly Thr Gln Phe Thr
1               5                   10                  15

Leu Thr Ile Ser Ala Val Gln Cys Glu Asp Ala Ala Tyr Tyr Cys
            20                  25                  30
```

<210> SEQ ID NO 948
<211> LENGTH: 14
<212> TYPE: PRT
<213> ORGANISM: Oryctolagus cuniculus

<400> SEQUENCE: 948

```
Gln Gly Val Ala Trp Ser Ser Asn Thr Gly Tyr Gly Ser Ala
1               5                   10
```

<210> SEQ ID NO 949
<211> LENGTH: 11
<212> TYPE: PRT
<213> ORGANISM: Artificial
<220> FEATURE:
<223> OTHER INFORMATION: Humanized antibody sequence

<400> SEQUENCE: 949

```
Phe Gly Gly Gly Thr Glu Val Val Val Lys Arg
1               5                   10
```

<210> SEQ ID NO 950
<211> LENGTH: 106
<212> TYPE: PRT
<213> ORGANISM: Artificial
<220> FEATURE:
<223> OTHER INFORMATION: Humanized antibody sequence

<400> SEQUENCE: 950

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 951
<211> LENGTH: 657
<212> TYPE: DNA
<213> ORGANISM: Artificial
<220> FEATURE:
<223> OTHER INFORMATION: Humanized antibody sequence

<400> SEQUENCE: 951

```
gccatcaaaa tgacccagac tccatcctcc gtgtctgcag ctgtgggagg cacagtcacc    60
atcaattgcc aggccagtga ggacatttac accaatttag cctggtatca gcagaaacca   120
```

```
gggcagcctc caacctcct gatctatgat gcatccgatc tggcatctgg ggtcccgtcg    180
cggttcagcg gcagtggaga tgggacacag ttcactctca ccatcagcgc cgtgcagtgt    240
gaagatgctg ccacttacta ctgtcaaggt gttgcttgga gtagtaatac tggttatggt    300
tccgctttcg gcggagggac cgaggtggtg gtcaaacgta cggtagcggc cccatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt       657
```

<210> SEQ ID NO 952
<211> LENGTH: 339
<212> TYPE: DNA
<213> ORGANISM: Artificial
<220> FEATURE:
<223> OTHER INFORMATION: Humanized antibody sequence

<400> SEQUENCE: 952

```
gccatcaaaa tgacccagac tccatcctcc gtgtctgcag ctgtgggagg cacagtcacc     60
atcaattgcc aggccagtga ggacatttac accaatttag cctggtatca gcagaaacca    120
gggcagcctc caacctcct gatctatgat gcatccgatc tggcatctgg ggtcccgtcg    180
cggttcagcg gcagtggaga tgggacacag ttcactctca ccatcagcgc cgtgcagtgt    240
gaagatgctg ccacttacta ctgtcaaggt gttgcttgga gtagtaatac tggttatggt    300
tccgctttcg gcggagggac cgaggtggtg gtcaaacgt                           339
```

<210> SEQ ID NO 953
<211> LENGTH: 69
<212> TYPE: DNA
<213> ORGANISM: Oryctolagus cuniculus

<400> SEQUENCE: 953

```
gccatcaaaa tgacccagac tccatcctcc gtgtctgcag ctgtgggagg cacagtcacc     60
atcaattgc                                                             69
```

<210> SEQ ID NO 954
<211> LENGTH: 33
<212> TYPE: DNA
<213> ORGANISM: Oryctolagus cuniculus

<400> SEQUENCE: 954

```
caggccagtg aggacattta caccaattta gcc                                  33
```

<210> SEQ ID NO 955
<211> LENGTH: 45
<212> TYPE: DNA
<213> ORGANISM: Oryctolagus cuniculus

<400> SEQUENCE: 955

```
tggtatcagc agaaaccagg gcagcctccc aacctcctga tctat                     45
```

<210> SEQ ID NO 956
<211> LENGTH: 21
<212> TYPE: DNA
<213> ORGANISM: Oryctolagus cuniculus

<400> SEQUENCE: 956

```
gatgcatccg atctggcatc t                                              21
```

<210> SEQ ID NO 957
<211> LENGTH: 96
<212> TYPE: DNA
<213> ORGANISM: Oryctolagus cuniculus

<400> SEQUENCE: 957

```
ggggtcccgt cgcggttcag cggcagtgga gatgggacac agttcactct caccatcagc   60
gccgtgcagt gtgaagatgc tgccacttac tactgt                             96
```

<210> SEQ ID NO 958
<211> LENGTH: 42
<212> TYPE: DNA
<213> ORGANISM: Oryctolagus cuniculus

<400> SEQUENCE: 958

```
caaggtgttg cttggagtag taatactggt tatggttccg ct                       42
```

<210> SEQ ID NO 959
<211> LENGTH: 33
<212> TYPE: DNA
<213> ORGANISM: Artificial
<220> FEATURE:
<223> OTHER INFORMATION: Humanized antibody sequence

<400> SEQUENCE: 959

```
ttcggcggag ggaccgaggt ggtggtcaaa cgt                                 33
```

<210> SEQ ID NO 960
<211> LENGTH: 318
<212> TYPE: DNA
<213> ORGANISM: Artificial
<220> FEATURE:
<223> OTHER INFORMATION: Humanized antibody sequence

<400> SEQUENCE: 960

```
acggtagcgg cccatctgt cttcatcttc ccgccatctg atgagcagtt gaaatctgga    60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                 318
```

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

```
<210> SEQ ID NO 975
<400> SEQUENCE: 975
000

<210> SEQ ID NO 976
<400> SEQUENCE: 976
000

<210> SEQ ID NO 977
<400> SEQUENCE: 977
000

<210> SEQ ID NO 978
<400> SEQUENCE: 978
000

<210> SEQ ID NO 979
<400> SEQUENCE: 979
000

<210> SEQ ID NO 980
<400> SEQUENCE: 980
000

<210> SEQ ID NO 981
<400> SEQUENCE: 981
000

<210> SEQ ID NO 982
<400> SEQUENCE: 982
000

<210> SEQ ID NO 983
<400> SEQUENCE: 983
000

<210> SEQ ID NO 984
<400> SEQUENCE: 984
000

<210> SEQ ID NO 985
<400> SEQUENCE: 985
000

<210> SEQ ID NO 986
```

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

```
<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000
```

-continued

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

-continued

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077
<400> SEQUENCE: 1077
000

<210> SEQ ID NO 1078
<400> SEQUENCE: 1078
000

<210> SEQ ID NO 1079
<400> SEQUENCE: 1079
000

<210> SEQ ID NO 1080
<400> SEQUENCE: 1080
000

<210> SEQ ID NO 1081
<400> SEQUENCE: 1081
000

<210> SEQ ID NO 1082
<400> SEQUENCE: 1082
000

<210> SEQ ID NO 1083
<400> SEQUENCE: 1083
000

<210> SEQ ID NO 1084
<400> SEQUENCE: 1084
000

<210> SEQ ID NO 1085
<400> SEQUENCE: 1085
000

<210> SEQ ID NO 1086
<400> SEQUENCE: 1086
000

<210> SEQ ID NO 1087
<400> SEQUENCE: 1087
000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111

<400> SEQUENCE: 1111

000

<210> SEQ ID NO 1112

<400> SEQUENCE: 1112

000

<210> SEQ ID NO 1113

<400> SEQUENCE: 1113

000

<210> SEQ ID NO 1114

<400> SEQUENCE: 1114

000

<210> SEQ ID NO 1115

<400> SEQUENCE: 1115

000

<210> SEQ ID NO 1116

<400> SEQUENCE: 1116

000

<210> SEQ ID NO 1117

<400> SEQUENCE: 1117

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131

<400> SEQUENCE: 1131

000

<210> SEQ ID NO 1132

<400> SEQUENCE: 1132

000

```
<210> SEQ ID NO 1133
<400> SEQUENCE: 1133
000

<210> SEQ ID NO 1134
<400> SEQUENCE: 1134
000

<210> SEQ ID NO 1135
<400> SEQUENCE: 1135
000

<210> SEQ ID NO 1136
<400> SEQUENCE: 1136
000

<210> SEQ ID NO 1137
<400> SEQUENCE: 1137
000

<210> SEQ ID NO 1138
<400> SEQUENCE: 1138
000

<210> SEQ ID NO 1139
<400> SEQUENCE: 1139
000

<210> SEQ ID NO 1140
<400> SEQUENCE: 1140
000

<210> SEQ ID NO 1141
<400> SEQUENCE: 1141
000

<210> SEQ ID NO 1142
<400> SEQUENCE: 1142
000

<210> SEQ ID NO 1143
<400> SEQUENCE: 1143
000

<210> SEQ ID NO 1144
```

-continued

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156
<400> SEQUENCE: 1156
000

<210> SEQ ID NO 1157
<400> SEQUENCE: 1157
000

<210> SEQ ID NO 1158
<400> SEQUENCE: 1158
000

<210> SEQ ID NO 1159
<400> SEQUENCE: 1159
000

<210> SEQ ID NO 1160
<400> SEQUENCE: 1160
000

<210> SEQ ID NO 1161
<400> SEQUENCE: 1161
000

<210> SEQ ID NO 1162
<400> SEQUENCE: 1162
000

<210> SEQ ID NO 1163
<400> SEQUENCE: 1163
000

<210> SEQ ID NO 1164
<400> SEQUENCE: 1164
000

<210> SEQ ID NO 1165
<400> SEQUENCE: 1165
000

<210> SEQ ID NO 1166
<400> SEQUENCE: 1166
000

<210> SEQ ID NO 1167
<400> SEQUENCE: 1167
000

<210> SEQ ID NO 1168
<400> SEQUENCE: 1168
000

<210> SEQ ID NO 1169
<400> SEQUENCE: 1169
000

<210> SEQ ID NO 1170
<400> SEQUENCE: 1170
000

<210> SEQ ID NO 1171
<400> SEQUENCE: 1171
000

<210> SEQ ID NO 1172
<400> SEQUENCE: 1172
000

<210> SEQ ID NO 1173
<400> SEQUENCE: 1173
000

<210> SEQ ID NO 1174
<400> SEQUENCE: 1174
000

<210> SEQ ID NO 1175
<400> SEQUENCE: 1175
000

<210> SEQ ID NO 1176
<400> SEQUENCE: 1176
000

<210> SEQ ID NO 1177
<400> SEQUENCE: 1177
000

<210> SEQ ID NO 1178

```
<400> SEQUENCE: 1178
000

<210> SEQ ID NO 1179
<400> SEQUENCE: 1179
000

<210> SEQ ID NO 1180
<400> SEQUENCE: 1180
000

<210> SEQ ID NO 1181
<400> SEQUENCE: 1181
000

<210> SEQ ID NO 1182
<400> SEQUENCE: 1182
000

<210> SEQ ID NO 1183
<400> SEQUENCE: 1183
000

<210> SEQ ID NO 1184
<400> SEQUENCE: 1184
000

<210> SEQ ID NO 1185
<400> SEQUENCE: 1185
000

<210> SEQ ID NO 1186
<400> SEQUENCE: 1186
000

<210> SEQ ID NO 1187
<400> SEQUENCE: 1187
000

<210> SEQ ID NO 1188
<400> SEQUENCE: 1188
000

<210> SEQ ID NO 1189
<400> SEQUENCE: 1189
```

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

-continued

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218

000

<210> SEQ ID NO 1219

<400> SEQUENCE: 1219

000

<210> SEQ ID NO 1220

<400> SEQUENCE: 1220

000

<210> SEQ ID NO 1221

<400> SEQUENCE: 1221

000

<210> SEQ ID NO 1222

<400> SEQUENCE: 1222

000

<210> SEQ ID NO 1223

<400> SEQUENCE: 1223

000

<210> SEQ ID NO 1224

<400> SEQUENCE: 1224

000

<210> SEQ ID NO 1225

<400> SEQUENCE: 1225

000

<210> SEQ ID NO 1226

<400> SEQUENCE: 1226

000

<210> SEQ ID NO 1227

<400> SEQUENCE: 1227

000

<210> SEQ ID NO 1228

<400> SEQUENCE: 1228

000

<210> SEQ ID NO 1229

<400> SEQUENCE: 1229

000

<210> SEQ ID NO 1230

<400> SEQUENCE: 1230

000

<210> SEQ ID NO 1231

<400> SEQUENCE: 1231

000

<210> SEQ ID NO 1232

<400> SEQUENCE: 1232

000

<210> SEQ ID NO 1233

<400> SEQUENCE: 1233

000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 1241

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 1242
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 1242

His Ser Asp Gly Ile Phe Thr Asp Ser Tyr Ser Arg Tyr Arg Lys Gln
1               5                   10                  15

-continued

Met Ala Val Lys Lys Tyr Leu Ala Ala Val Leu
            20                  25

<210> SEQ ID NO 1243
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: AMIDATION

<400> SEQUENCE: 1243

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 1244
<211> LENGTH: 330
<212> TYPE: PRT
<213> ORGANISM: Artificial
<220> FEATURE:
<223> OTHER INFORMATION: Humanized antibody sequence

<400> SEQUENCE: 1244

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1245
<211> LENGTH: 330
<212> TYPE: PRT
<213> ORGANISM: Artificial
<220> FEATURE:
<223> OTHER INFORMATION: Humanized antibody sequence

<400> SEQUENCE: 1245

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 1246
<211> LENGTH: 330
<212> TYPE: PRT
<213> ORGANISM: Artificial
<220> FEATURE:
<223> OTHER INFORMATION: Humanized antibody sequence

<400> SEQUENCE: 1246

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
                325             330
```